(12) United States Patent
Yu et al.

(10) Patent No.: US 11,345,679 B2
(45) Date of Patent: May 31, 2022

(54) QUATERNARY LACTAM COMPOUND AND PHARMACEUTICAL USE THEREOF

(71) Applicant: SHANGHAI MEIYUE BIOTECH DEVELOPMENT CO., LTD., Shanghai (CN)

(72) Inventors: Shanghai Yu, Shanghai (CN); Yan Feng, Shanghai (CN); Shiqiang Li, Shanghai (CN); Xiaolin Wang, Shanghai (CN); Zhilong Hu, Shanghai (CN); Yawen Ding, Shanghai (CN); Feihong Dai, Shanghai (CN); Qian He, Shanghai (CN); Chaodong Wang, Shanghai (CN)

(73) Assignee: SHANGHAI MEIYUE BIOTECH DEVELOPMENT CO., LTD., Shanghai (CN)

( * ) Notice: Subject to any disclaimer, the term of this patent is extended or adjusted under 35 U.S.C. 154(b) by 0 days.

(21) Appl. No.: 16/968,118

(22) PCT Filed: Mar. 29, 2019

(86) PCT No.: PCT/CN2019/080549
§ 371 (c)(1),
(2) Date: Aug. 6, 2020

(87) PCT Pub. No.: WO2019/185046
PCT Pub. Date: Oct. 3, 2019

(65) Prior Publication Data
US 2021/0032219 A1    Feb. 4, 2021

(30) Foreign Application Priority Data

Mar. 30, 2018  (CN) .......................... 201810276765.6

(51) Int. Cl.
| | |
|---|---|
| *C07D 401/14* | (2006.01) |
| *C07D 407/14* | (2006.01) |
| *C07D 413/14* | (2006.01) |
| *C07D 487/04* | (2006.01) |
| *A61K 45/06* | (2006.01) |

(52) U.S. Cl.
CPC .......... *C07D 401/14* (2013.01); *C07D 407/14* (2013.01); *C07D 413/14* (2013.01); *C07D 487/04* (2013.01); *A61K 45/06* (2013.01)

(58) Field of Classification Search
CPC ........................... C07D 401/14; C07D 487/04
USPC ...................................... 514/210.02
See application file for complete search history.

(56) References Cited

U.S. PATENT DOCUMENTS

| | | |
|---|---|---|
| 2004/0147502 A1 | 7/2004 | Bisacchi et al. |
| 2004/0180855 A1 | 9/2004 | Schumacher et al. |

FOREIGN PATENT DOCUMENTS

| | | |
|---|---|---|
| CN | 106029064 A | 10/2016 |
| WO | 2006108039 A2 | 10/2006 |

OTHER PUBLICATIONS

Banker et al. "Modern Pharmaceutics", 3rd Ed. p. 596 (1996). (Year: 1996).*
Burger's Medicinal Chemistry,, edited by Manfred E.Wolf, 5th Ed. Part 1, pp. 975-977 (1995). (Year: 1995).*
Wei et al. Molecules 23, 2002, p. 1-23. (Year: 2018).*

* cited by examiner

*Primary Examiner* — Kahsay Habte
(74) *Attorney, Agent, or Firm* — Novick, Kim & Lee, PLLC; Allen Xue

(57) ABSTRACT

A quaternary lactam compound of formula (I). The compound is used in the manufacture of a medicament for the treatment and/or prevention of thrombotic or thromboembolic disorders.

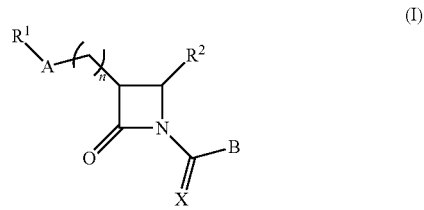

14 Claims, No Drawings

QUATERNARY LACTAM COMPOUND AND PHARMACEUTICAL USE THEREOF

CROSS-REFERENCE TO RELATED APPLICATIONS

This application is the national stage application of International Application No. PCT/CN2019/080549, filed Mar. 29, 2019, which claims the benefit of priority to Chinese Patent Application No. 201810276765.6, filed Mar. 30, 2018, the content of which is incorporated herein by reference in its entirety.

FIELD OF THE INVENTION

The invention belongs to the technical field of pharmaceutical chemistry, and particularly relates to a quaternary lactam compound and the use thereof in the manufacture of a medicament for the treatment and/or prevention of thrombotic or thromboembolic disorders.

BACKGROUND OF THE INVENTION

Blood coagulation is the result of the coordinated activation of various plasma proteins, cofactors and platelets. This cascade is divided into endogenous (contact activation) pathway, exogenous (tissue factor activation) pathway and common pathway (prothrombin and thrombin production). The most important physiological process in the process of blood coagulation is the activation of tissue factor. The tissue factor forms a complex with factor VIIa, which catalyzes the activation of Factor X (FX), and then the activated FXa cleaves prothrombin to produce activated thrombin (FIIa). The activated thrombin (FIIa) as the central catalytic enzyme in the coagulation process catalyzes the cleavage of fibrinogen into fibrin, which plays a role in blood coagulation. This exogenous pathway involves a small number of enzymes, and has a quick effect. The endogenous pathway is the inherent coagulation pathway of the body; and in this pathway, Factor XIIa (FXIIa), Factor XIa (FXIa), Factor IXa (FIXa) and Factor VIIIa (FVIIIa) are activated through a cascade reaction, and then Factor Xa (FXa) and the downstream central thrombin (FIIa) are activated. Thrombin in turn activates Factor XIa (FXIa), which produces an amplification effect and accelerates blood coagulation. In the endogenous pathway, more enzymes are involved in blood coagulation, all of which come from the blood. The endogenous has a relative slower effect.

In the whole coagulation process, FXa plays a very critical role. As a downstream co-regulator of the exogenous and endogenous coagulation pathways, the antagonists of FXa are widely used in the prevention and treatment of various thromboses. Many antagonists have been marketed and occupied the cardiovascular drug market owning to their remarkable efficacy. However, they also show a bigger probability of occurrence of side effects, and the most prominent side effect is the risk of bleeding. To solve the problem of bleeding, Factor XIa in the endogenous pathway (FXIa) has become a research hotspot of major companies and institutions.

The potential of FXIa as a safer anticoagulation target is manifested in patients with hemophilia C. FXIa-deficient patients with hemophilia C do not have active bleeding; and to the distinct contrary, patients with Factor IX-deficient hemophilia A and Factor IX-deficient hemophilia B are easy to bleeding. Although a study of limited sample size (115 patients) showed that FXIa deficiency cannot protect patients from acute myocardial ischemia, it found that these patients have lower incidence of ischemic stroke and deep vein thrombosis.

Gene knockout experiments in mice have found that the selective gene knockout of the common pathway factors (Factors X, V and II) and exogenous factors (tissue factor and Factor VII) in mice can cause prenatal or perinatal lethality. Although Factor VIII and Factor IX gene knockout mice can survive, they are often accompanied by severe bleeding, which is similar to hemophilia A and B in humans where the lack of Factors VIII and IX can cause serious bleeding risk. Mice can reproduce normally after the selective knockout of Factor XI. Moreover, the lack of Factor XI can protect mice from the formation of arterial thrombosis induced by ferric chloride. At the same time, the absence of Factor XI does not affect the bleeding and hemostasis function of mice. Therefore, the experiments showed that inhibiting factor XI not only prevents thrombosis, but is also safely tolerated.

Many antibodies, small molecules and antisense nucleotides against FXIa have also been proven in animals or clinically that inhibiting FXIa can effectively prevent thrombosis. Moreover, compared with existing antithrombotic drugs (such as enoxaparin), the risk of bleeding is greatly reduced. The above shows that FXIa is closely related to human thrombotic diseases, and inhibition of FXIa has a significant anticoagulant effect, but no obvious bleeding tendency, which can greatly reduce the risk of bleeding during clinical anticoagulation.

Therefore, the development of compounds with good anticoagulant effect and low side effects has important research significance.

SUMMARY OF THE INVENTION

To solve the above technical problems, the invention provides a quaternary lactam cyclic compound of the following formula (I), the isomer, solvate, prodrug thereof or mixtures thereof, and pharmaceutically acceptable salts thereof,

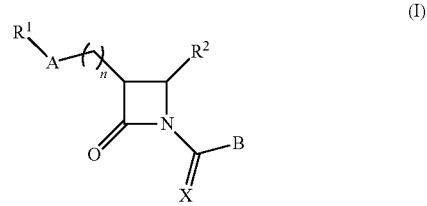

wherein, $R^1$ is selected from the group consisting of hydrogen, halogen, $C_{1-10}$ alkyl, $C_{3-10}$ cycloalkyl, heterocyclyl, aryl, heteroaryl, —$(CH_2)_t NR^6R^7$, —$COR^{5a}$, —$COOR^{5b}$, —$C(O)_m(CH_2)_t NR^6R^7$, —$(CH_2)_t NHC(O)_m C_{1-10}$ alkyl, —$NHC(O)_m(CH_2)_n C(O)_m C_{1-6}$ alkyl, —$S(O)_m(CH_2)_t NR^6R^7$, —$NH(CH_2)_t S(O)_m R^{5a}$, —$NH(CH_2)_t S(O)_m$—$OR^{5b}$, —$OR^{5b}$, —$SR^{5b}$, —$(CH_2)_t CN$, and —$O(CH_2)_n NR^6R^7$;

$R^2$ is selected from the group consisting of hydrogen, halogen, hydroxyl, $C_{1-10}$ alkyl, $C_{1-10}$ alkoxy, —$(CH_2)_t X$ $(CH_2)_n NR^6R^7$, —$(CH_2)_t CN$, —$(CH_2)_t COR^{5a}$, —$(CH_2)_t COOR^{5b}$, —$(CH_2)_t NR^6R^7$, —$C(O)_m(CH_2)_t NR^6R^7$, —$C(O)_m(CH_2)_t$-aryl, —$C(O)_m(CH_2)_t$-heteroaryl, —$CONH$ $(CH_2)_t$-heterocyclyl, —$CONHS(O)_m R^{5a}$, and —$CONHS$ $(O)_m$—$OR^{5b}$;

X is selected from the group consisting of O and S:

A is aryl, heteroaryl, $C_{3-10}$cycloalkyl or heterocyclyl;

B is heterocyclyl containing nitrogen, wherein the nitrogen atom is linked to CX, and the heterocyclyl may be optionally further substituted with 1 to 3 $R^3$; wherein each $R^3$ is the same or different and is independently selected from the group consisting of hydrogen, oxo, halogen, hydroxyl, —$(CH_2)_tCN$, —$(CH_2)_tNR^6R^7$, —$(CH_2)_t$ $CONR^6R^7$, —$(CH_2)_tNHC(O)C_{1-10}$ alkyl, $C_{1-10}$ alkyl, $C_{1-10}$ alkoxy, halogenated $C_{1-10}$ alkyl, halogenated $C_{1-10}$ alkoxy, $C_{3-10}$ to cycloalkyl, $C_{3-10}$ cycloalkyloxy, heterocyclyl, benzoheterocyclyl, aryl or heteroaryl; and when B is substituted with $R^3$, at least one $R^3$ is $C_{3-10}$ cycloalkyl, aryl, benzoheterocyclyl or heterocyclyl; the $R^3$ may be optionally substituted with 1 to 3 $R^{4a}$;

or B is fused bicyclic group containing nitrogen, wherein the nitrogen atom is linked to CX, and the fused bicyclic group may be optionally further substituted with 1 to 3 $R^{4b}$;

the $R^{4a}$ and $R^{4b}$ are the same or different and are independently selected from the group consisting of hydrogen, oxo, halogen, —$(CH_2)_tCN$, $C_{1-10}$ alkyl, $C_{1-10}$ alkoxy, halogenated $C_{1-10}$ alkyl, halogenated $C_{1-10}$ alkoxy, $C_{3-10}$ cycloalkyl, $C_{3-10}$ cycloalkyloxy, heterocyclyl, heterocyclyloxy, aryl, amino, nitro, —$(CH_2)_tNR^6R^7$, —$(CH_2)_tNHC(O)_m$ $C_{1-10}$ alkyl, —$(CH_2)_tCONR^6R^7$, —$(CH_2)_tCOR^{5a}$, —$(CH_2)_t$ $COOR^{5b}$, —$SR^{5b}$, and —$OR^{5b}$; further, the $R^{4a}$ and $R^{4b}$ are optionally substituted with one or more of the following groups: hydrogen, =O, halogen, $C_{1-10}$ alkyl, $C_{1-10}$ alkoxy or aryl;

in the above groups, each $R^{5a}$ is the same or different and is independently selected from the group consisting of hydrogen, halogen, $C_{1-10}$ alkyl, halogenated $C_{1-10}$ alkyl, $C_{3-10}$ cycloalkyl, heterocyclyl, aryl, and heteroaryl;

in the above groups, $R^{5b}$, $R^6$ and $R^7$ are the same or different and are independently selected from the group consisting of hydrogen, $C_{1-10}$ alkyl, halogenated $C_{1-10}$ alkyl, $C_{3-10}$ cycloalkyl, heterocyclyl, aryl, and heteroaryl;

in the above groups, each n is the same or different and is independently selected from the integers from 1 to 10;

in the above groups, each m is the same or different and is independently an integer of 1 or 2;

in the above groups, each t is the same or different and is independently selected from the integers from 0 to 10.

In some embodiments, B is 3- to 10-membered heterocyclyl containing nitrogen (for example, 3-, 4-, 5-, 6-, 7-, 8-, 9- or 10-membered heterocyclyl containing nitrogen) optionally substituted with 1 to 3 $R^3$.

In some embodiments, B is the following group optionally substituted with 1 to 3 $R^3$:

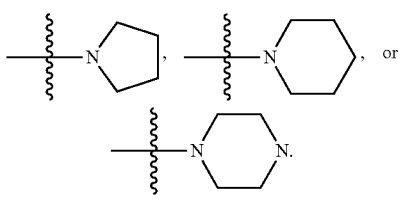

In some embodiments, B is 5- to 12-membered fused bicyclic group containing nitrogen (for example, 5-, 6-, 7-, 8-, 9-, 10-, 11- or 12-membered fused bicyclic group containing nitrogen), which further may be optionally substituted with 1 to 3 $R^{4b}$, and for example the fused bicyclic group containing nitrogen includes but is not limited to: benzopyrrolidinyl, benzopiperidinyl, benzopiperazinyl, or triazolopiperazinyl.

In some embodiments, B is the following group optionally substituted with 1 to 3 $R^{4b}$:

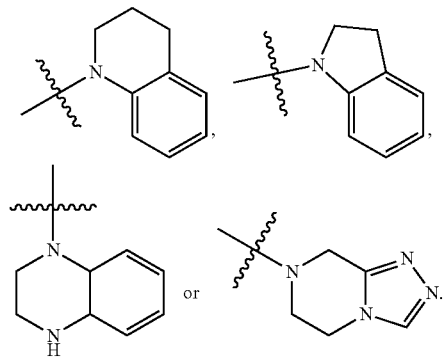

In some embodiments, B is

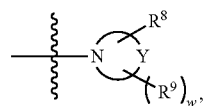

wherein, Y is C, S, O or N,

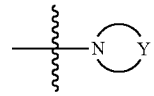

represents 3- to 10-membered heterocyclyl, $R^8$ is $C_{3-10}$ cycloalkyl, aryl, heteroaryl or benzoheterocyclyl; and the $R^8$ may be optionally substituted with 1 to 3 $R^{10}$, wherein the $R^{10}$ is hydrogen, oxo, halogen, —$(CH_2)_tCN$, $C_{1-10}$ alkyl, $C_{1-10}$ alkoxy, halogenated $C_{1-10}$ alkyl, halogenated $C_{1-10}$ alkoxy, $C_{3-10}$ cycloalkyl, $C_{3-10}$ cycloalkoxy, heterocyclyl, aryl, amino, nitro, —$(CH_2)_tNR^6R^7$, —$(CH_2)NHC(O)_mC_{1-10}$ alkyl, —$(CH_2)_tCONR^6R^7$, —$(CH_2)_tCOR^{5a}$, —$(CH_2)_t$ $COOR^{5b}$, —$SR^{5b}$, or —$OR^{5b}$; the substituent $R^{10}$ may be optionally substituted with one or more of the following groups: hydrogen, =O, halogen, $C_{1-10}$ alkyl, $C_{1-10}$ alkoxy or aryl. Each $R^9$ is the same or different and is independently selected from the group consisting of hydrogen, oxo, halogen, hydroxyl, —$(CH_2)_tCN$, —$(CH_2)_tNR^6R^7$, —$(CH_2)$ $CONR^6R^7$, —$(CH_2)_tNHC(O)_mC_{1-10}$ alkyl, $C_{1-10}$ alkyl, $C_{1-10}$ alkoxy, halogenated $C_{1-10}$ alkyl, halogenated $C_{1-10}$ alkoxy. $C_{3-10}$ cycloalkyl, $C_{3-10}$ cycloalkoxy, heterocyclyl, aryl, heteroaryl; the above $R^9$ may be optionally substituted with 1 to 3 the following group $R^{11}$: hydrogen, oxo, halogen, —$(CH_2)_tCN$, $C_{1-10}$ alkyl, $C_{1-10}$ alkoxy, halogenated $C_{1-10}$ alkyl, halogenated $C_{1-10}$ alkoxy, $C_{3-10}$ cycloalkyl, $C_{3-10}$ cycloalkoxy, heterocyclyl, aryl, amino, nitro, —$(CH_2)_t$ $NR^6R^7$, —$(CH_2)_tNHC(O)_mC_{1-10}$ alkyl, —$(CH_2)_t$ $CONR^6R^7$, —$(CH_2)_tCOR^{5a}$, —$(CH_2)_tCOOR^{5b}$, —$SR^{5b}$, or —$OR^{5b}$; w is 1 or 2.

In some embodiments, $R^8$ is selected from the group consisting of $C_{3-10}$ cycloalkyl, aryl, heteroaryl, and benzoheterocyclyl; the $R^8$ may be optionally substituted with the following group: hydrogen, oxo, halogen, —$(CH_2)_tCN$, $C_{1-10}$ alkyl, $C_{1-10}$ alkoxy, halogenated $C_{1-10}$ alkyl, halogenated $C_{1-10}$ alkoxy, $C_{3-10}$ cycloalkyl, $C_{3-10}$ cycloalkoxy, heterocyclyl, heterocyclyloxy, oxoheterocyclyl, $C_{1-10}$ alkyl-oxoheterocyclyl, aryl, aryloxy, amino, nitro, —$(CH_2)_t$NR$^6$R$^7$, —NHCOOC$_{1-10}$ alkyl, —NHCOC$_{1-10}$ alkyl, CONR$^6$R$^7$, COR$^{5a}$, COOR$^{5b}$, —SR$^{5b}$, or —OH.

In some embodiments, R$^1$ is selected from the group consisting of hydrogen, halogen, $C_{1-10}$ alkyl, $C_{1-10}$ alkoxy, $C_{3-10}$ cycloalkyl, $C_{3-10}$ cycloalkyloxy, aryl, —$(CH_2)_t$NR$^6$R$^7$, —COR$^{5a}$, —COOR$^{5b}$, —C(O)(CH$_2$)$_t$NR$^6$R$^7$, —$(CH_2)_t$ NHC(O)$_m$C$_{1-10}$ alkyl, —NHC(O)$_m$(CH$_2$)$_n$C(O)$_m$C$_{1-6}$ alkyl, —S(O)$_m$(CH$_2$)$_t$NR$^6$R$^7$, —NH(CH$_2$)$_t$S(O)$_m$R$^{5a}$, —SR$^{5b}$, —(CH$_2$)$_t$CN, and —O(CH$_2$)$_n$NR$^6$R$^7$.

In some embodiments, A is aryl or heteroaryl, and phenyl or pyridyl is preferred.

In some embodiments, R$^2$ is selected from the group consisting of —(CH$_2$)$_t$X(CH$_2$)$_n$NR$^6$R$^7$, —(CH$_2$)$_t$CN, —(CH$_2$)$_t$NR$^6$R$^7$, —(CH$_2$)$_t$COR$^{5a}$, —(CH$_2$)$_t$COOR$^{5b}$—C(O)$_m$(CH$_2$)$_t$NR$^6$R$^7$, —C(O)$_m$(CH$_2$)$_t$-aryl, —C(O)$_m$(CH$_2$)$_t$-heteroaryl, —CONH(CH$_2$)$_t$-heterocyclyl, and —CONHS(O)$_m$R$^{5a}$.

In some embodiments, X is O.

In some embodiments, each n is the same or different and is independently an integer of 1, 2, 3, 4, 5, 6, 7, 8, 9 or 10.

In some embodiments, each m is the same or different and is independently an integer of 1 or 2.

In some embodiments, each t is the same or different and is independently an integer of 0, 1, 2, 3, 4, 5, 6, 7, 8, 9 or 10.

In some embodiments, each R$^{5a}$ is the same or different and is independently selected from the group consisting of hydrogen, halogen, $C_{1-4}$ alkyl, halogenated $C_{1-4}$ alkyl, $C_{3-6}$ cycloalkyl, heterocyclyl, aryl, and heteroaryl:

In some embodiments, R$^{5b}$, R$^6$ and R$^7$ are the same or different and are independently selected from the group consisting of hydrogen, $C_{1-4}$ alkyl, halogenated $C_{1-4}$ alkyl, $C_{3-6}$ cycloalkyl, heterocyclyl, aryl, and heteroaryl;

In some embodiments, the invention provides a quaternary lactam cyclic compound of the following formula (IA), the isomer, solvate, prodrug thereof or mixtures thereof, and pharmaceutically acceptable salts thereof, (IA)

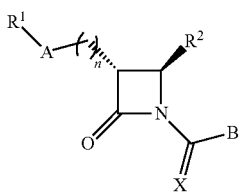

each group has the definition as defined above.

As examples, the compounds of formula (I) (or formula (IA)) include but are not limited to the following compounds, the isomers, solvates, prodrugs thereof or mixtures thereof, and pharmaceutically acceptable salts thereof (when a pharmaceutically acceptable salt exists, trifluoroacetate or hydrochloride is preferred),

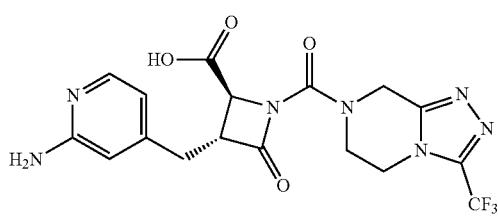

-continued

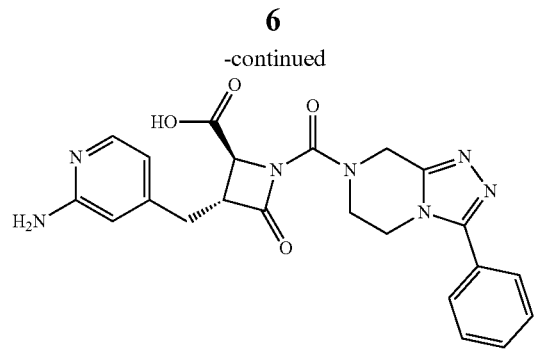

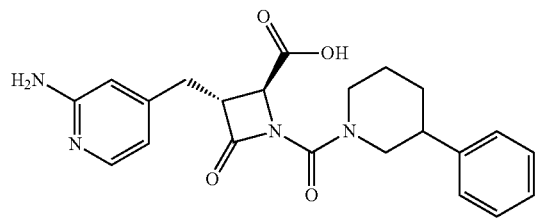

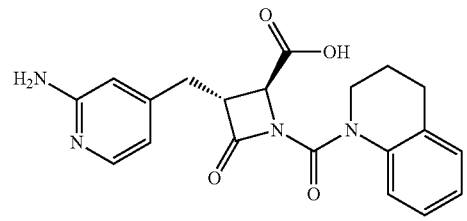

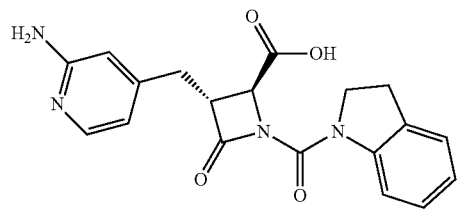

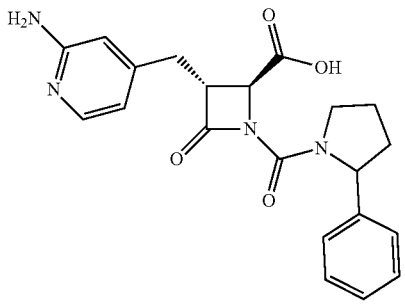

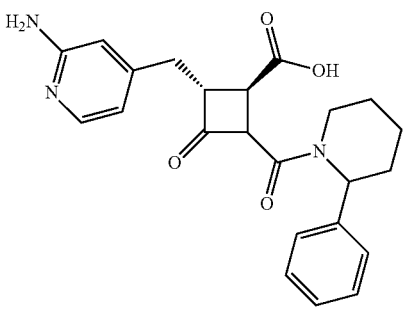

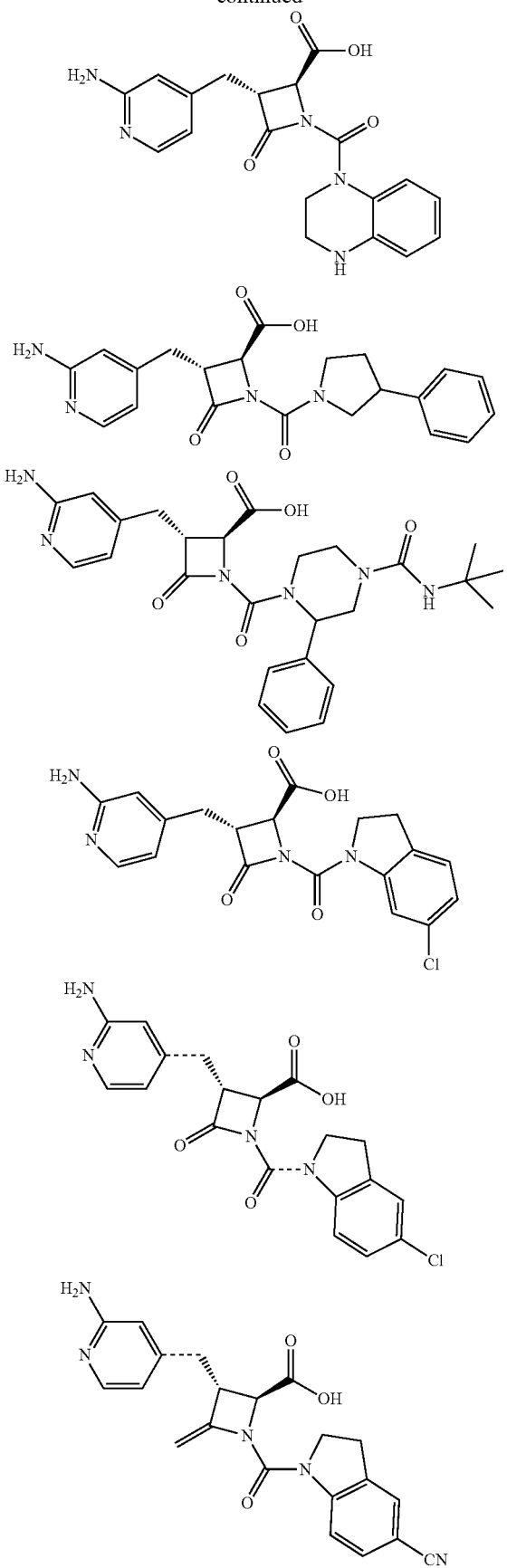
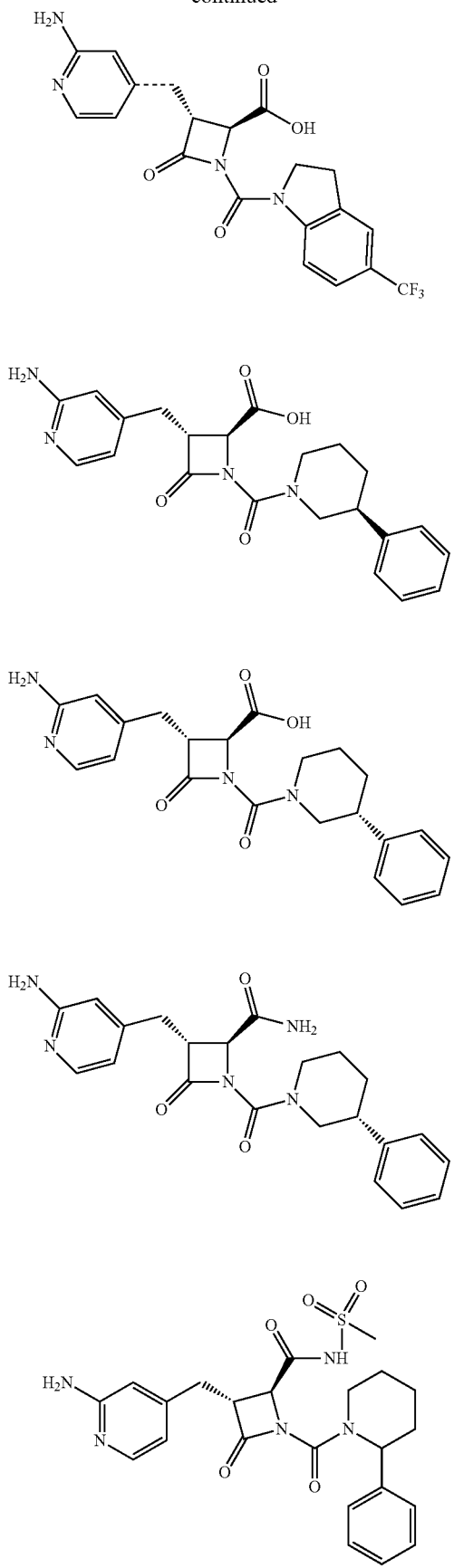

9
-continued
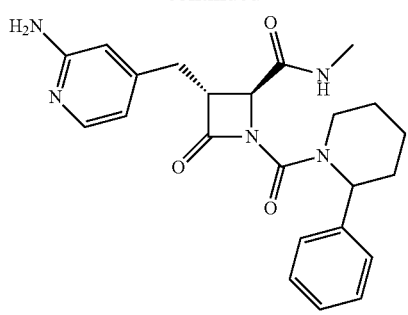
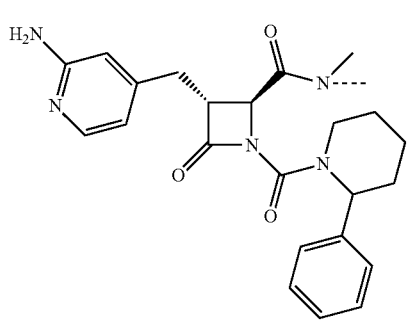
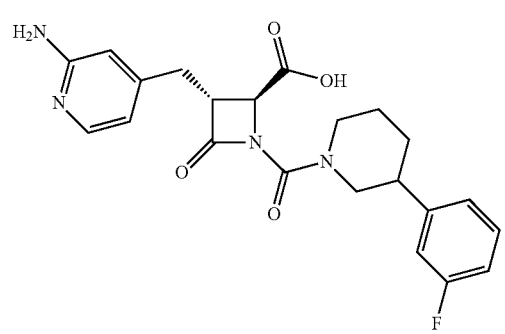
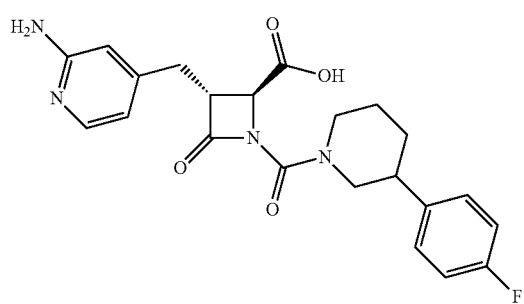
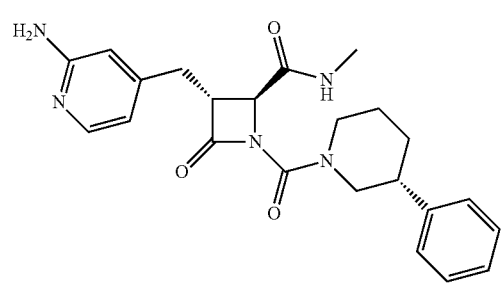
10
-continued
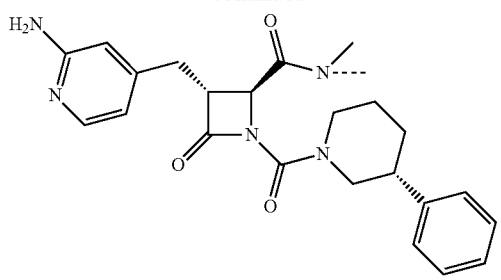
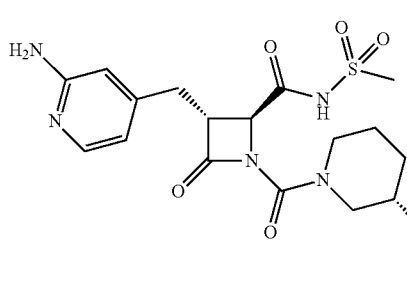
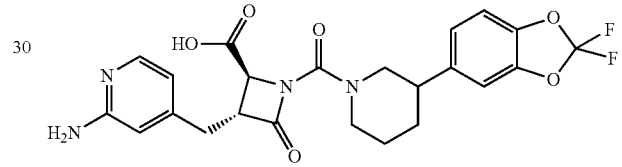
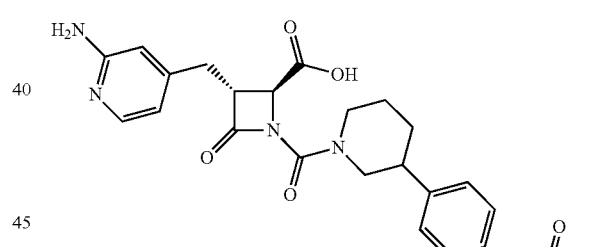
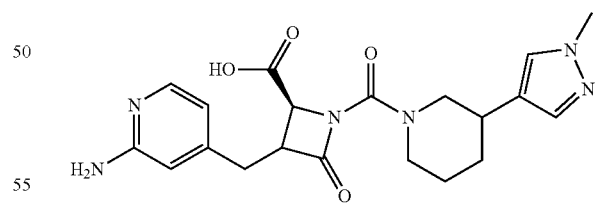
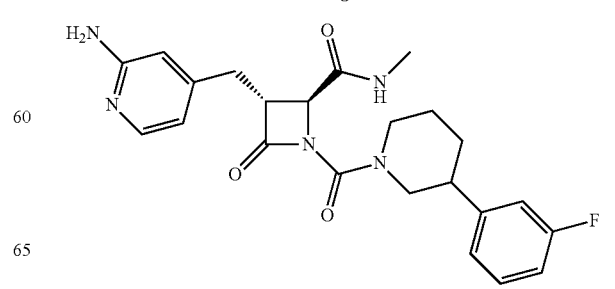

-continued
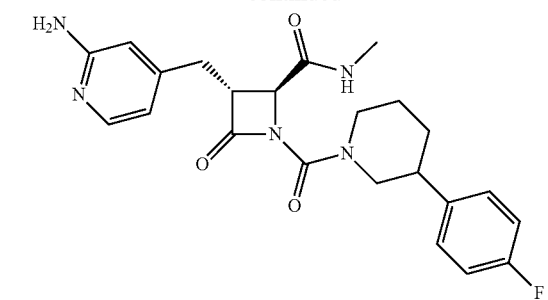
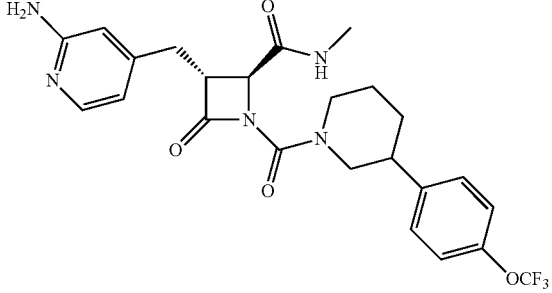
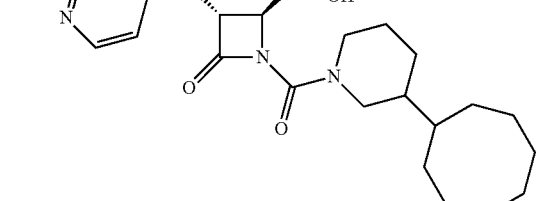
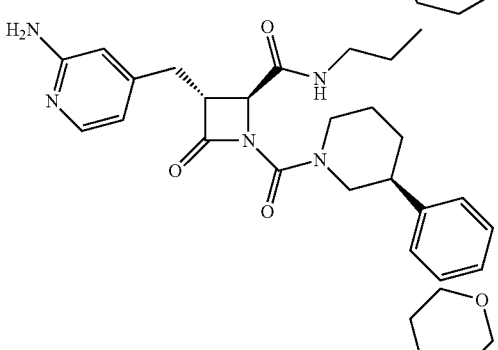
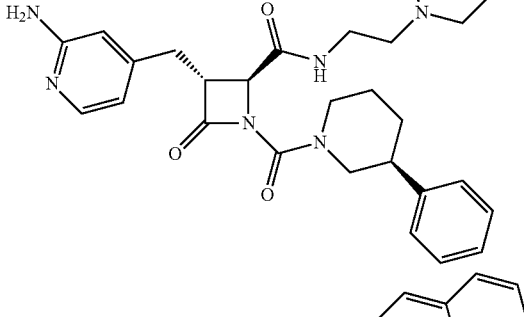
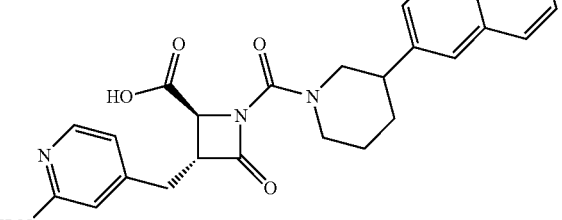
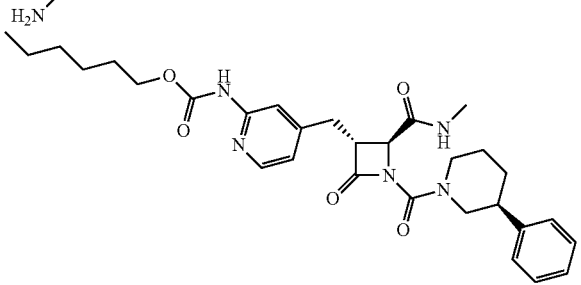

-continued
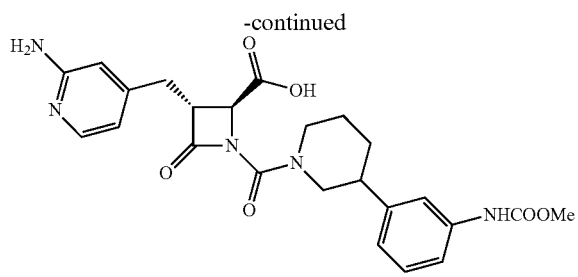
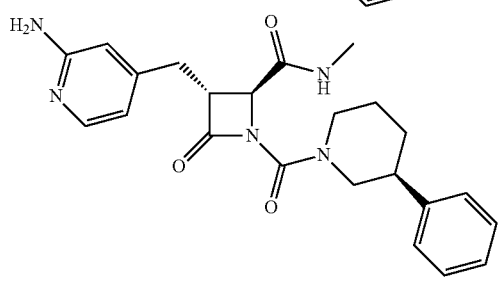
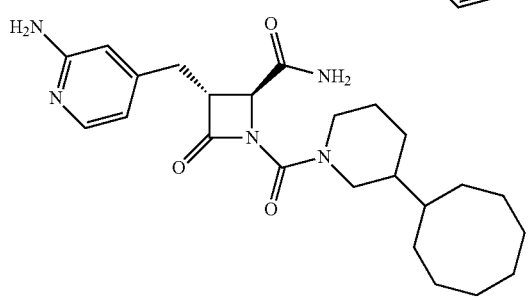
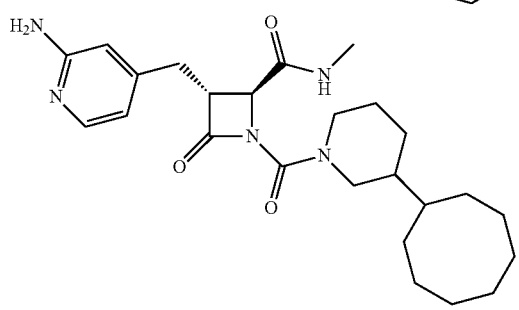
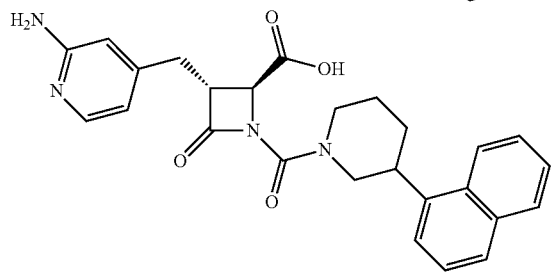
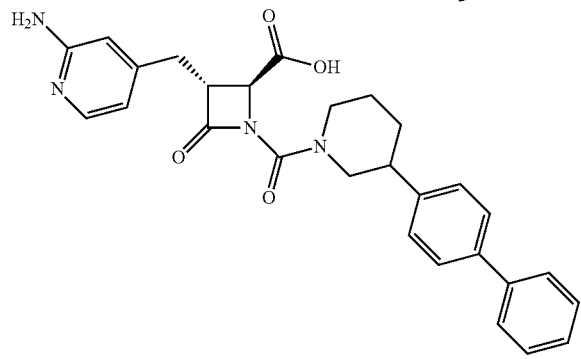
-continued
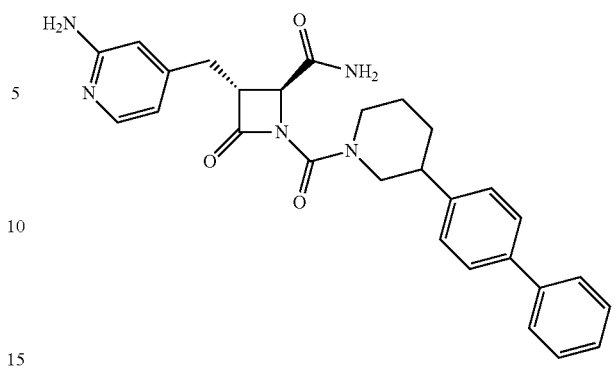
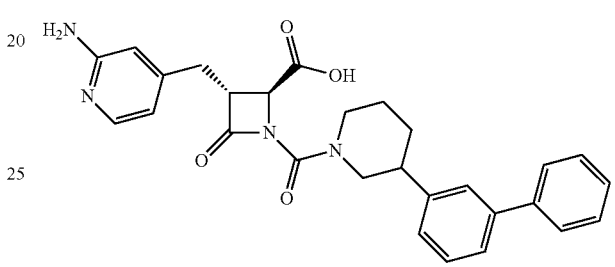
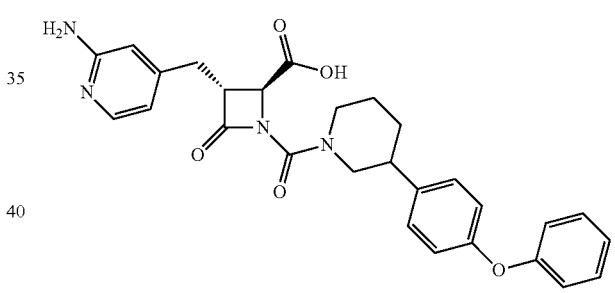
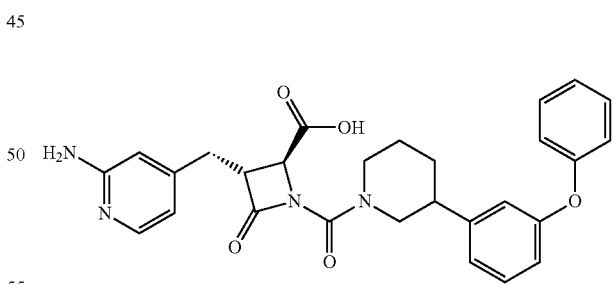
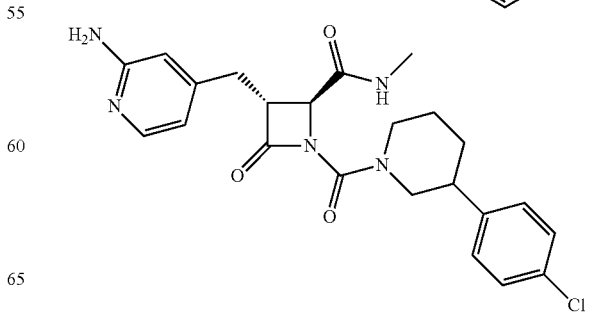

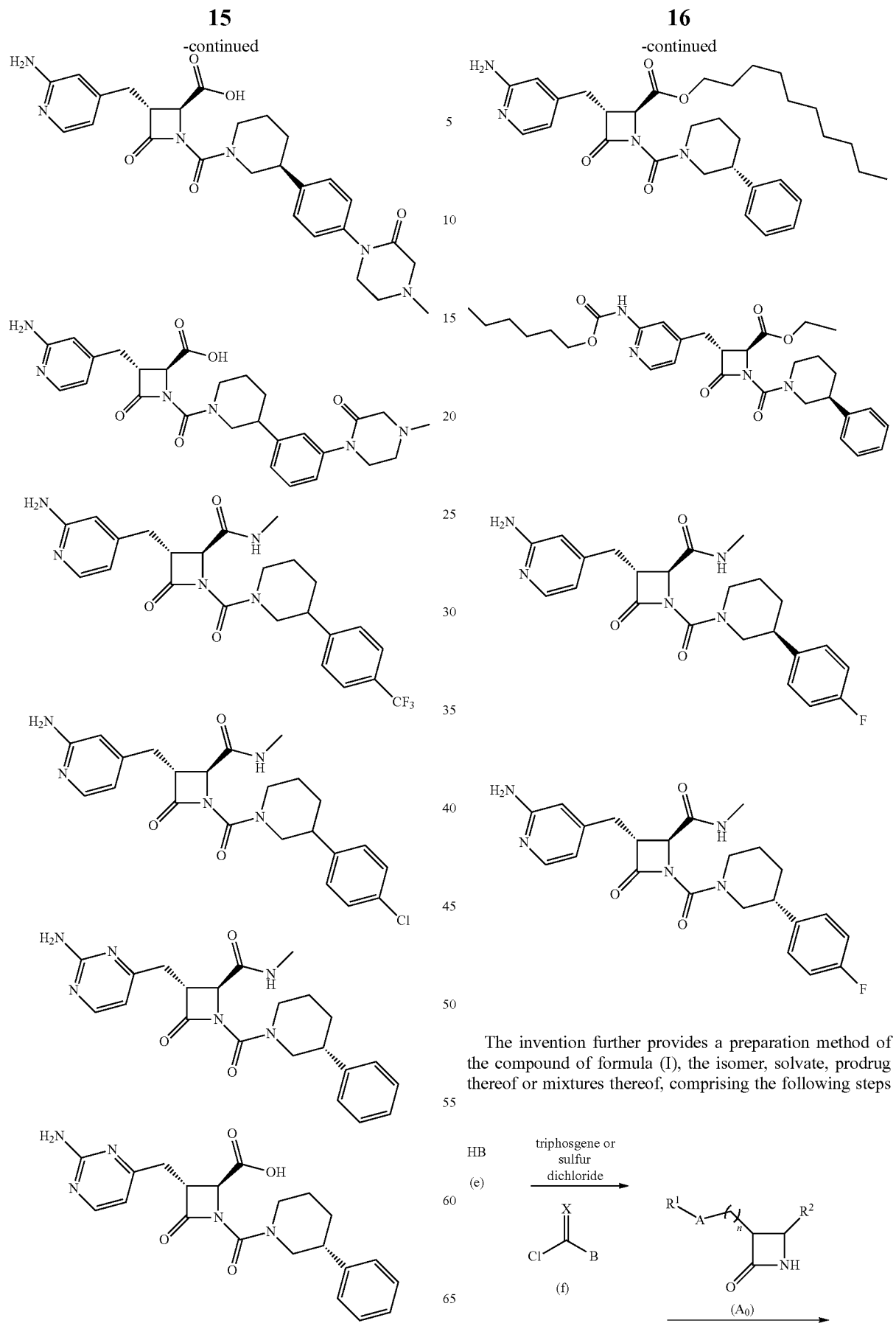
The invention further provides a preparation method of the compound of formula (I), the isomer, solvate, prodrug thereof or mixtures thereof, comprising the following steps -continued

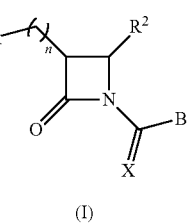

(I)

1) reacting compound (e) with triphosgene or sulfur dichloride under alkaline condition to obtain compound (f);
2) reacting compound (f) with compound ($A_0$) under alkaline condition to obtain compound (I);
wherein, $R_1$, $R_2$, A, B, X, and n have the definitions as defined above.

According to the invention, in step 2), the reagents used to provide the alkaline condition include but are not limited to triethylamine, diisopropylethylamine, N,N-dimethylaminopyridine, sodium hydroxide and the like.

According to the invention, the compound ($A_0$) in step 2) may be prepared by the following method, comprising the following steps:

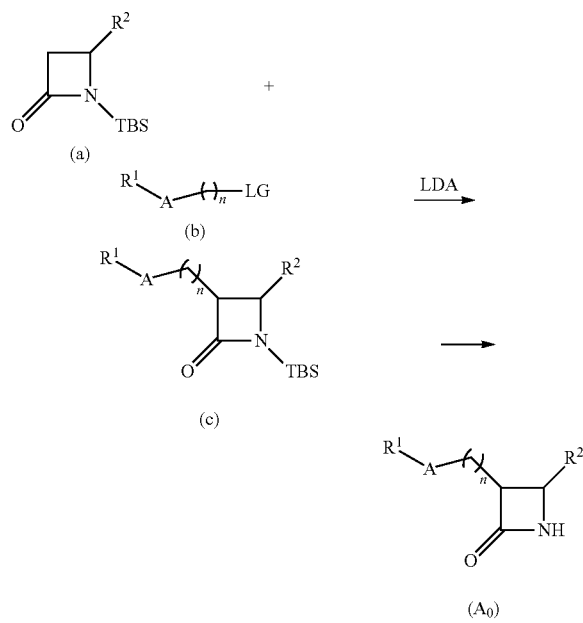

A) reacting compound (a) with compound (b) in the presence of LDA to obtain compound (c);
B) deprotecting of compound (c) to obtain compound ($A_0$);
wherein, $R_1$, $R_2$, A, and n have the definitions as defined above; LG is a leaving group.

Any group in compound (a), compound (b), compound (c), compound (e), compound (f), and compound ($A_0$) can be protected with a protecting group, if necessary. After the reaction was completed, the protecting group is removed by an appropriate method.

The invention also provides a pharmaceutical composition, comprising at least one selected from the group consisting of the compound of formula (I) (or formula (IA)) as mentioned above, the isomer, solvate, prodrug thereof or mixtures thereof, and pharmaceutically acceptable salts thereof, and the optionally pharmaceutically acceptable carrier and/or excipient.

The invention further provides use of the compound of formula (I) as mentioned above, the isomer, solvate, prodrug thereof or mixtures thereof, and pharmaceutically acceptable salts thereof, or the pharmaceutical composition as mentioned above in the manufacture of a medicament for the treatment and/or prevention of disorders related to thrombosis or thromboembolism; or in the manufacture of a medicament of thrombin inhibitor.

The disorders related to thrombosis or thromboembolism include, but are not limited to, for example, arterial cardiovascular thromboembolic disorders, venous cardiovascular thromboembolic disorders, thromboembolic disorders in the cardiac chamber or peripheral circulation, unstable angina, acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, renal embolism, pulmonary embolism, and thrombosis due to medical implants, devices, or processes in which blood is exposed to artificial surfaces that promote thrombosis.

The invention also provides a pharmaceutical preparation, comprising the above-mentioned pharmaceutical composition, wherein, the pharmaceutical preparation includes but is not limited to tablet, pill, granule, capsule, injection, suspension, drop, extract, ointment, patch, emulsion, film, suppository, paste, gel, or spray.

The invention further provides a combined preparation, comprising the above-mentioned pharmaceutical composition with at least one of other anticoagulant drugs, antithrombotic drugs or antivenous thromboembolic drugs; wherein the anticoagulant drugs, antithrombotic drugs or antivenous thromboembolic drugs include but are not limited to: heparin, low molecular weight heparin LMWH, enoxaparin, warfarin, rivaroxaban, apixaban, edoxaban, betrixaban, omisaraban, aspirin, ticlopidine, clopidogrel, tirofiban, coumarin, urokinase, platelet protein IIb/IIIa receptor antagonist.

The invention also provides a method for the treatment and/or prevention of disorders related to thrombosis or thromboembolis, comprising administering the above-mentioned pharmaceutical composition or pharmaceutical preparation or combined preparation to a subject in need thereof.

The disorders related to thrombosis or thromboembolism have the definitions as defined above.

Definitions of Terms

Unless otherwise stated, the meanings of terms used in the specification and claims are defined as follows.

The term "$C_{1-10}$ alkyl" refers to a linear and/or branched saturated aliphatic hydrocarbon group, for example, the aliphatic hydrocarbon group may include 1-10 carbon atoms, 1-6 carbon atoms, 1-4 carbon atoms, 1-3 carbon atoms, 1 or 2 carbon atoms, etc. Examples of alkyl groups include but are not limited to methyl, ethyl, n-propyl, isopropyl, n-butyl, isobutyl, sec-butyl, tert-butyl, n-pentyl, neopentyl, n-hexyl, etc. The adjacent carbon atoms of the alkyl group are optionally separated by one or more heteroatoms selected from the group consisting of O, S or N for example, propyl, i.e., $CH_3CH_2CH_2$— may be $CH_3$—O—$CH_2CH_2$— or $CH_3CH_2$—O—$CH_2$— after being interrupted by O, and so on.

The term "$C_{1-10}$ alkoxy" refers to $C_{1-10}$ alkyl-oxy, such as $C_{1-10}$ alkyloxy, $C_{1-6}$ alkyloxy, $C_{1-4}$ alkyloxy, and the alkyl is defined as above. Representative examples of alkoxy include but are not limited to methoxy, ethoxy, propoxy, butoxy, etc.

The term "$C_{3-10}$ cycloalkyl" refers to a saturated or partially unsaturated 3-10 membered all-carbon monocyclic ring. Examples of $C_{3-10}$ cycloalkyl include, but are not limited to, cyclopropyl, cyclobutyl, cyclopentyl, cyclopentenyl, cyclohexyl, cyclohexadienyl, adamantyl, cycloheptyl, cyclooctyl, etc. Further, the "$C_{3-10}$ cycloalkyl" may be optionally substituted by one or more substituents selected from the following: halogen, —(CH$_2$)$_t$CN, linear or branched $C_{1-10}$ alkyl or $C_{1-10}$ alkoxy, halogenated $C_{1-10}$ alkyl, halogenated $C_{1-10}$ alkoxy, $C_{3-10}$ cycloalkyl, $C_{3-10}$ cycloalkoxy, a saturated or partially unsaturated 3-10 membered heterocyclic group having 1-3 ring heteroatoms independently selected from the group consisting of nitrogen, oxygen and sulfur, aryl, amino, nitro, —(CH$_2$)$_t$NR$^6$R$^7$, —(CH$_2$)$_t$NHC(O)$_m$C$_{1-10}$ alkyl, —(CH$_2$)$_t$CONR$^6$R$^7$, —(CH$_2$)$_t$C(O)$_m$R$^{5a}$, —SR$^{5b}$, —OR$^{5b}$, or —(CH$_2$)$_t$COOH.

The term "$C_{3-10}$ cycloalkoxy" or "cycloalkyloxy" refers to $C_{3-10}$ cycloalkyl-oxy, and the $C_{3-10}$ cycloalkyl is defined as above, oxy refers to —O— group. Examples of $C_{3-10}$ cycloalkyloxy include, but are not limited to, cyclopropoxy, cyclobutoxy, cyclopentyloxy, cyclopentenyloxy, cyclohexyloxy, cyclohexadienyloxy, adamantoxy, cycloheptyloxy, cyclooctyloxy, etc. Further, the "$C_{3-10}$ cycloalkoxy" may be optionally substituted with one or more substituents selected from the group consisting of: halogen, —(CH$_2$)$_t$CN, linear or branched $C_{1-10}$ alkyl or $C_{1-10}$ alkoxy, halogenated $C_{1-10}$ alkyl, halogenated $C_{1-10}$ alkoxy, $C_{3-10}$ cycloalkyl, $C_{3-10}$ cycloalkoxy, a saturated or partially unsaturated 3-10 membered heterocyclic group having 1-3 ring heteroatoms independently selected from the group consisting of nitrogen, oxygen and sulfur, aryl, amino, nitro, —(CH$_2$)$_t$NR$^6$R$^7$, —(CH$_2$)$_t$NHC(O)$_m$C$_{1-10}$ alkyl, —(CH$_2$)$_t$CONR$^6$R$^7$, —(CH$_2$)$_t$C(O)$_m$R$^{5a}$, —SR$^{5b}$, —OR$^{5b}$, and —(CH$_2$)$_t$COOH.

The term "heterocyclyl" or "heterocyclic group" refers to a monocyclic ring system containing 3 to 10 atoms, wherein 1, 2, 3, 4 or 5 ring atoms are selected from heteroatoms such as nitrogen, sulfur or oxygen. The heterocyclic ring may be fully saturated or contain one or more unsaturated bonds, but have no aromaticity; and the heteroxyclic ring links to other molecules via one or more sites, and unless otherwise stated, it may link via carbon or nitrogen. In the heterocyclyl or heterocyclic group, the —CH$_2$— group may be optionally replaced by —C(O)—. Examples of the "heterocyclyl" or "heterocyclic group" include, but are not limited to, a single ring composed of 3-10 atoms, which contains 1-5, preferably 1-3, heteroatoms selected from N, O, or S. For example, a 3-10 membered monocyclic ring having 1-3 ring heteroatoms independently selected from nitrogen, oxygen, or sulfur. Examples include but are not limited to epoxyethyl, epithioethyl, aziridinyl, oxocyclopropyl, azacyclopropyl, thiocyclopropyl, oxetanyl, thietanyl, azetidinyl, pyrrolidinyl, piperidinyl, piperazinyl, morpholinyl, thiomorpholinyl, homopiperazinyl,

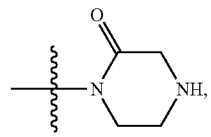 [SMILES: *N1CCNCC1=O]

etc.; further, the "heterocyclyl" or "heterocyclic group" may be optionally substituted with one or more substituents selected from the group consisting of: halogen, —(CH$_2$)$_t$CN, linear or branched $C_{1-10}$ alkyl or $C_{1-10}$ alkoxy, halogenated $C_{1-10}$ alkyl, halogenated $C_{1-10}$ alkoxy, $C_{3-10}$ cycloalkyl, $C_{3-10}$ cycloalkoxy, a saturated or partially unsaturated 3-10 membered heterocyclic group having 1-3 ring heteroatoms independently selected from the group consisting of nitrogen, oxygen and sulfur, aryl, amino, nitro, —(CH$_2$)$_t$NR$^6$R$^7$, —(CH$_2$)$_t$NHC(O)$_m$C$_{1-10}$ alkyl, —(CH$_2$)$_t$CONR$^6$R$^7$, —(CH$_2$)$_t$C(O)R$^5$, —SR$^{5b}$, —OR$^{5b}$, and —(CH$_2$)$_t$COOH.

The term "benzoheterocyclyl" refers to a group formed by the fusion of phenyl and heterocyclyl, wherein phenyl and heterocyclyl share a pair of adjacent ring atoms, and the heterocyclyl is defined as above. Specific examples of the "benzoheterocyclic group" include, but are not limited to:

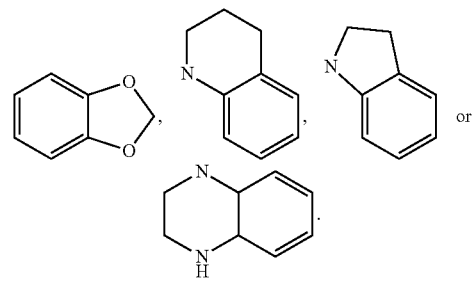

Further, the benzoheterocyclyl may be optionally substituted with 1 to 3 R$^{4a}$, wherein each R$^{4a}$ is the same or different and is independently selected from the group consisting of halogen, —(CH$_2$)$_t$CN, linear or branched $C_{1-6}$ alkyl or $C_{1-6}$ alkoxy, halogenated $C_{1-6}$ alkyl, and halogenated $C_{1-6}$ alkoxy.

The term "fused bicyclic group containing nitrogen" refers to a bicyclic ring system having 6 to 20 ring atoms, wherein 1, 2, 3, 4 or 5 ring atoms are selected from heteroatoms such as nitrogen, sulfur or oxygen; and in the bicyclic ring system, at least one ring contains at least one nitrogen heteroatom, and one ring in the bicyclic system shares a pair of adjacent ring atoms with the other ring; moreover, one ring may contain one or more double bonds, but the entire bicyclic system does not have Pi-electronic system with complete conjugation. The "fused bicyclic group containing nitrogen" includes 6-membered/6-membered, 6-membered/5-membered, 6-membered/4-membered fused bicyclic rings, and specific examples include but are not limited to:

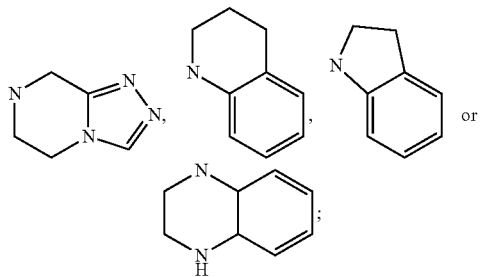

further, the fused bicyclic group containing nitrogen may be optionally substituted with 1 to 3 R$^{4b}$, wherein each R$^{4b}$ is the same or different and is independently selected from the group consisting of halogen, —(CH$_2$)$_t$CN, linear or branched $C_{1-6}$ alkyl or $C_{1-6}$ alkoxy, halogenated $C_{1-6}$ alkyl, halogenated $C_{1-6}$ alkoxy, $C_{3-10}$ cycloalkyl, $C_{3-10}$ cycloalkoxy, a saturated or partially unsaturated 3-10 membered heterocyclic group having 1-3 ring heteroatoms independently selected from the group consisting of nitrogen, oxygen and sulfur, aryl, amino, nitro, —(CH$_2$)$_t$NR$^6$R$^7$, —(CH$_2$)$_t$NHC(O)$_m$C$_{1-10}$ alkyl, —(CH$_2$)$_t$CONR$^6$R$^7$, —(CH$_2$)C(O)$_m$R$^{5a}$, —SR$^{5b}$, —OR$^{5b}$, and —(CH$_2$)$_t$COOH.

The term "aryl" refers to a group having 6-20 carbon atoms in the molecular structure and containing at least one aromatic ring, that is, having a conjugated pi-electron system. In the invention, the aryl group may be either an independent aryl group or a combined group of aryl and other groups, such as arylalkyl, alkylaryl, etc. Examples of aryl groups include but are not limited to phenyl, naphthyl, anthracenyl, phenylalkyl, alkylphenyl, alkylenephenylene, alkylidenephenyl, or benzyl.

The term "heteroaryl" refers to an aromatic heterocyclic group having at least one ring heteroatom (eg, sulfur, oxygen, or nitrogen). The heteroaryl includes monocyclic and polycyclic systems (e.g., having 2, 3, or 4 fused rings). Preferably, the heteroaryl contains 5-20 ring atoms and 1-3 ring heteroatoms independently selected from the group consisting of nitrogen, oxygen and sulfur, more preferably the heteroaryl is 5-membered heteroaryl ring or 6-membered containing 1-3 ring heteroatoms. Examples of heteroaryl include but are not limited to furyl, thienyl, pyridyl, pyrrolyl, pyrimidinyl, pyrazinyl, imidazolyl, phthalazinyl, piperidinyl, piperazinyl, morpholinyl, quinolinyl, pterdinyl,

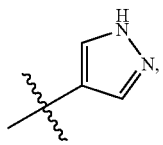

etc.

The term "halogen" refers to fluorine, chlorine, bromine, iodine, preferably fluorine or chlorine.

The term "halogenated C$_{1-10}$ alkyl" refers to a group formed by the substitution of one or more hydrogen atoms of C$_{1-10}$ alkyl by the same/different halogen atoms. Representative examples include but are not limited to chloromethyl, trifluoromethyl, 1-chloroethyl, 3-bromopropyl, etc.

The term "halogenated C$_{1-10}$ alkoxy" refers to a group formed by the substitution of one or more hydrogen atoms of C$_{1-10}$ alkoxy by the same/different halogen atoms. Representative examples include but are not limited to: chloromethoxy, trifluoromethoxy, 1-chloroethoxy, 3-bromopropoxy, etc.

The term "amino" refers to —NH$_2$ group.

The term "acyl" refers to —C(O)R$^{5a}$ group.

The term "acylamino" refers to —C(O)NR$^6$R$^7$ group, and representative examples of acylamino include such as —CO—NH$_2$ group.

The term "sulfonamido" refers to a group having structure of —S(O)$_m$NR$^6$R$^7$ or —NHS(O)$_m$R$^{5a}$; wherein, the t, m, R$^{5a}$, R$^{5b}$, R$^6$, and R$^7$ have the definitions as described above.

The term "cyano" refers to —C≡N group.

The term "hydroxyl" refers to —OH group.

The term "carboxyl" refers to —COOH group.

The term "mercapto" refers to —SH group.

The term "oxo" refers to ═O group.

Unless otherwise specified, when a substituent or group defined or described herein has multiple sites capable of linking to the substituted structure, the corresponding chemical structures include all the forms where the substituent or group links to the substituted structure at all of these sites. For example, C$_{1-4}$ alkylamino includes a form where —C$_{1-4}$ alkylamino or C$_{1-4}$ alkylamino- is linked to the substituted site.

The term "optional", "optional". "optionally" refers to occasions where the event or environment described subsequently may, but does not necessarily occur, that is, the event or environment may occurs or may not occur. For example, "optionally substituted alkyl" refers to that the alkyl may be but not necessarily is substituted by a substituent, that is, it includes both unsubstituted alkyl and substituted alkyl.

The term "isomer" is an abbreviation of isomer having the same molecular formula, which refers to compounds that have the same chemical formula and the same chemical bond but different atomic arrangements. Compounds that have the same molecular formula but different structural formulas are called isomers, such as ethanol and ether. Isomers include structural isomers, stereoisomers, geometric isomers, optical isomers. The "isomer" used in the invention is preferably a stereoisomer.

The term "solvate" refers to a compound containing a solvent, in which the solvent molecule can be connected to other parts by a coordinate bond or can be combined by a covalent bond. The solvent is a known solvent, such as water, alcohols, ethers, benzenes, esters, aliphatic hydrocarbons, alicyclic hydrocarbons, ketones and others. Examples of solvents include but are not limited to water, methanol, ethanol, isopropanol, ether, propylene oxide, benzene, toluene, xylene, methyl acetate, ethyl acetate, pentane, hexane, octane, cyclohexane, cyclohexanone, acetone, methyl butanone, methyl isobutyl ketone, acetonitrile, pyridine, phenol, carbon tetrachloride, etc.

The term "prodrug" is also known as precursor drug. It refers to a drug that has been chemically modified to be inactive or less active in vitro, but releases active drug after enzymatic or non-enzymatic conversion in vivo so as to exert efficacy.

The term "pharmaceutically acceptable salts" refers to those salts obtained by reacting a compound in free state with a non-toxic inorganic or organic base, or a non-toxic inorganic or organic acid. Suitable acid addition salts include, but are not limited to, formate, acetate, trifluoroacetate, ethanesulfonate, 2-hydroxyethanesulfonate, glycolate, propionate, 3-phenyl propionate, malonate, butyrate, pivalate, hexanoate, adipate, enanthate, alginate, aspartate, benzoate, benzenesulfonate, bisulfate, citrate, camphorate, camphorsulfonate, digluconate, dodecyl sulfate, fumarate, glucoheptanoate, sulfate, thiocyanate, hemisulfate, persulfate, hydrochloride, nitrate, phosphate, hydrobromide, hydroiodide, lactate, maleate, methanesulfonate, 2-naphthalensulfonate, nicotinate, palmitate, pectate, picrate, salicylate, succinate, tartrate, tosylate and undecanoate; suitable base addition salts include alkali metal salts (such as sodium salt, potassium salt, lithium salt, etc.), alkaline earth metal salts (such as calcium salt, magnesium salt, etc.), other metal salts (such as iron salt, copper salt, cobalt salt, etc.), organic alkali salts (such as ammonium salt, triethylamine salt, pyridinium salt, picoline salt, 2,6-lutidine salt, ethanolamine salt, diethanolamine salt, triethanolamine salt, cyclohexylamine salt, ethylenediamine salt, guanidinium salt, isopropylamine salt, trimethylamine salt, tripropylamine salt, dimethylethanolamine salt, dicyclohexylamine salt, caffeine salt, procaine salt, choline salt, betaine salt, benethamine salt, glucosamine salt, N-methylglucosamine salt, theobromine salt, tromethamine salt, purine salt, piperazine salt, morpholine salt, piperidine salt, N-ethylpiperidine salt, tetramethylamine salt, dibenzylamine salt and salt of phenylglycine alkyl ester) and inorganic ammonium salt.

The term "combined preparation" refers to a pharmaceutical preparation containing at least two preparations (active ingredients), one of which may be administered (optionally repeatable) before, after, and/or simultaneously with the administration of other preparations. In the context of the invention, "simultaneous administration" includes administration within 48 hours of the previous administration, such as within 24 hours.

The term "pharmaceutically acceptable carrier or excipient" refers to any type of solvent, dispersion medium, coating material, surfactant, antioxidant, preservative (e.g., antifungal agent, antibacterial agent), isotonic agents, absorption delay agents, drug stabilizers, binders, excipients, disintegrating agents, lubricants, sweeteners, flavoring agents, dyes, etc. or combinations thereof well known in the field of pharmaceutical preparation). Any conventional carriers or excipients may be comprised in the pharmaceutical composition of the invention, unless the carriers or excipients are incompatible to the active ingredients.

It should be noted that the compounds, compositions and combined preparations provided in the invention can be formulated into various suitable dosage forms according to the route of administration. The use of one or more pharmaceutically acceptable carriers or excipients will facilitate the process of the active ingredient into a clinically usable dosage form. The appropriate dosage form depends on the selected route of administration and can be prepared according to common knowledge well known in the art.

It should also be understood that the compounds, compositions, and combined preparations provided in the invention may be administered orally, parenterally (e.g., by injection), or topically. Pharmaceutical preparations that can be taken orally include capsules and tablets, etc. When the patient has difficulty in swallowing, sublingual tablets or other non-swallowing routes can also be used for the administration. The compounds, compositions and combined preparations provided in the invention can also be formulated into dosages forms suitable for parenteral administration, transdermal administration, mucosal administration, or administration by means of suppositories or implants. Those skilled in the art will understand that the compounds of the invention can be delivered via a suitable drug delivery system to obtain more advantageous effects.

In addition, it should be noted that the dosage and usage of the compounds, compositions and combined preparations provided in the invention depend on many factors, including the age, weight, gender, natural health status and nutritional status of the patients, active strength, administration time and metabolic rate of the compounds, severity of illness and subjective judgment of the clinician.

Beneficial Effects

The inventors unexpectedly found that the compounds of formula (I), isomers, hydrates, solvates, prodrugs or mixtures thereof, and pharmaceutically acceptable salts thereof, as well as pharmaceutical compositions containing the compounds have excellent thrombin inhibitory activity.

DETAILED DESCRIPTION OF THE INVENTION

The invention will be further illustrated below in conjunction with specific examples. It should be understood that these examples are only used to illustrate the invention and are not intended to limit the scope of the invention. In addition, it should be understood that after reading the contents described in the invention, those skilled in the art can make various changes or modifications to the invention, and these equivalent forms also fall within the scope defined by the invention.

EXAMPLES

The structures of all compounds were identified by nuclear magnetic resonance ($^1$HNMR) and/or mass spectrometry (MS). The nuclear magnetic resonance chemical shift (δ) was recorded in ppm ($10^{-6}$).

Compound Abbreviations:

TBSCl: tert-butyldimethylchlorosilane; LDA: lithium diisopropylamine; DCC: dicyclohexylcarbodiimide; DMSO: dimethylsulfoxide; CDI: N,N-carbonyl-diimidazole; DMF: dimethylformamide; DIEA: N,N-diisopropylethylamine; DMAP: 4-dimethylaminopyridine; CDCl$_3$: deuterated chloroform; PE/EA: petroleum ether/ethyl acetate; HATU: 2-(7-azabenzotriazolyl)-N,N,N',N'-tetramethyluronium hexafluorophosphate; TFA: trifluoroacetic acid; DCM: dichloromethane; EDCI: 1-ethyl-(3-dimethylaminopropyl) carbodiimide; THF: tetrahydrofuran; Boc: tert-butyloxycarbonyl; HOBT: 1-hydroxyl benzotriazole; Xantphos: 4,5-bis (diphenylphosphino)-9,9-dimethylxanthene; Pd(amphos)$_2$Cl$_2$: bis[di-tert-butyl-(4-dimethylaminophenyl)phosphine] palladium(II)dichloride.

Preparation of Intermediate A

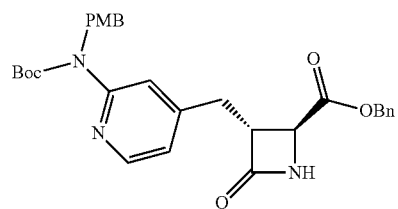

The intermediate A was prepared according to the following scheme and method.

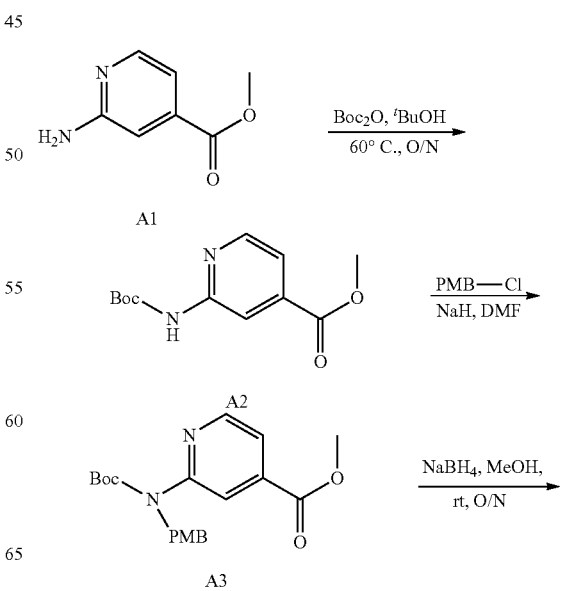

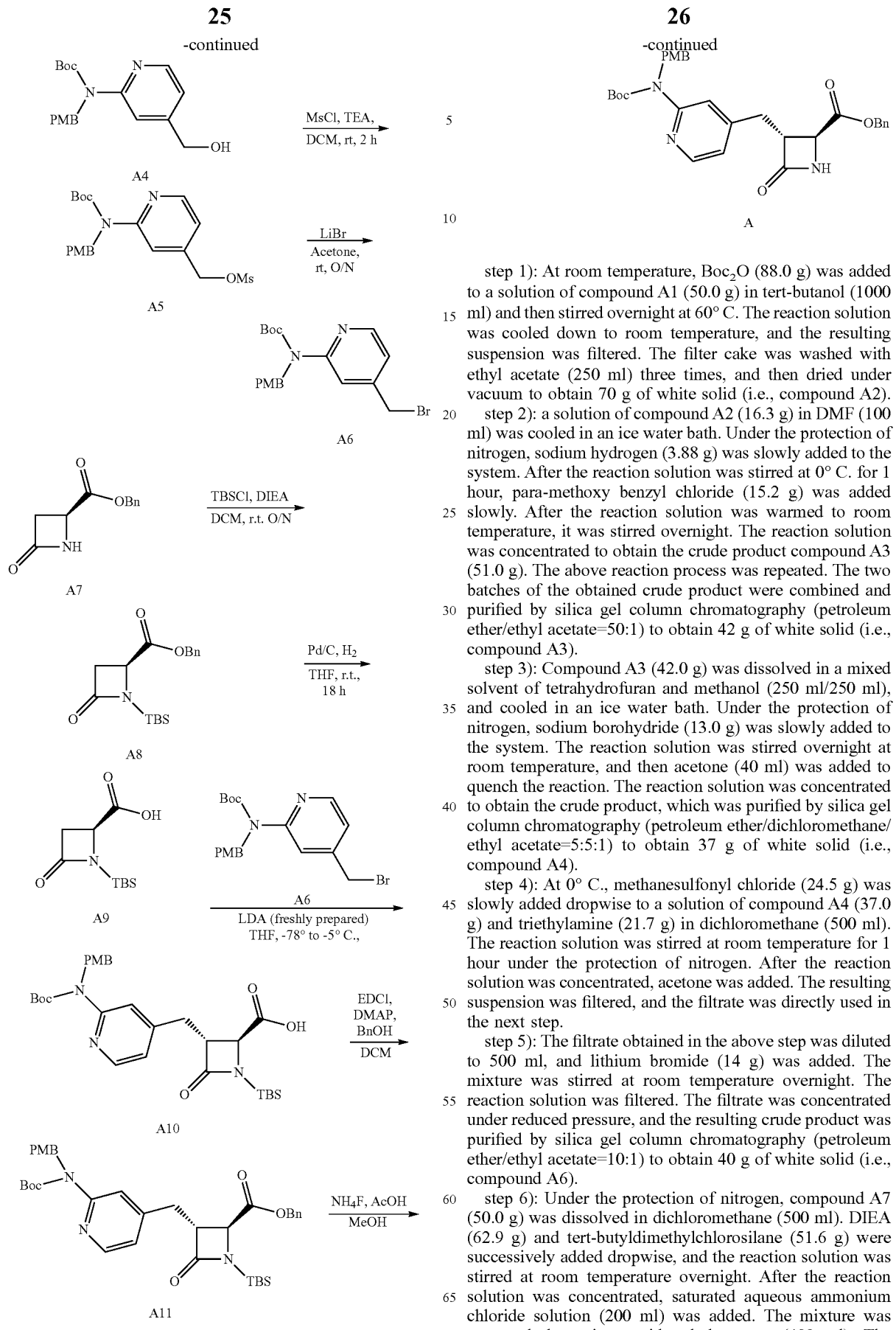

step 1): At room temperature, Boc$_2$O (88.0 g) was added to a solution of compound A1 (50.0 g) in tert-butanol (1000 ml) and then stirred overnight at 60° C. The reaction solution was cooled down to room temperature, and the resulting suspension was filtered. The filter cake was washed with ethyl acetate (250 ml) three times, and then dried under vacuum to obtain 70 g of white solid (i.e., compound A2).

step 2): a solution of compound A2 (16.3 g) in DMF (100 ml) was cooled in an ice water bath. Under the protection of nitrogen, sodium hydrogen (3.88 g) was slowly added to the system. After the reaction solution was stirred at 0° C. for 1 hour, para-methoxy benzyl chloride (15.2 g) was added slowly. After the reaction solution was warmed to room temperature, it was stirred overnight. The reaction solution was concentrated to obtain the crude product compound A3 (51.0 g). The above reaction process was repeated. The two batches of the obtained crude product were combined and purified by silica gel column chromatography (petroleum ether/ethyl acetate=50:1) to obtain 42 g of white solid (i.e., compound A3).

step 3): Compound A3 (42.0 g) was dissolved in a mixed solvent of tetrahydrofuran and methanol (250 ml/250 ml), and cooled in an ice water bath. Under the protection of nitrogen, sodium borohydride (13.0 g) was slowly added to the system. The reaction solution was stirred overnight at room temperature, and then acetone (40 ml) was added to quench the reaction. The reaction solution was concentrated to obtain the crude product, which was purified by silica gel column chromatography (petroleum ether/dichloromethane/ethyl acetate=5:5:1) to obtain 37 g of white solid (i.e., compound A4).

step 4): At 0° C., methanesulfonyl chloride (24.5 g) was slowly added dropwise to a solution of compound A4 (37.0 g) and triethylamine (21.7 g) in dichloromethane (500 ml). The reaction solution was stirred at room temperature for 1 hour under the protection of nitrogen. After the reaction solution was concentrated, acetone was added. The resulting suspension was filtered, and the filtrate was directly used in the next step.

step 5): The filtrate obtained in the above step was diluted to 500 ml, and lithium bromide (14 g) was added. The mixture was stirred at room temperature overnight. The reaction solution was filtered. The filtrate was concentrated under reduced pressure, and the resulting crude product was purified by silica gel column chromatography (petroleum ether/ethyl acetate=10:1) to obtain 40 g of white solid (i.e., compound A6).

step 6): Under the protection of nitrogen, compound A7 (50.0 g) was dissolved in dichloromethane (500 ml). DIEA (62.9 g) and tert-butyldimethylchlorosilane (51.6 g) were successively added dropwise, and the reaction solution was stirred at room temperature overnight. After the reaction solution was concentrated, saturated aqueous ammonium chloride solution (200 ml) was added. The mixture was extracted three times with ethyl acetate (400 ml). The organic phases were combined, dried over anhydrous sodium sulfate, filtered and concentrated. The crude product was purified by silica gel column chromatography (petroleum ether/ethyl acetate=15:1~7/1) to obtain 76 g of yellow oil (i.e., compound A8).

step 7): 10 wt % palladium carbon (7.2 g) was added to a solution of compound A8 (35 g) in tetrahydrofuran (150 ml). After the addition was completed, the system was pumped and ventilated three times and charged with hydrogen, and the mixed system was stirred overnight at room temperature under hydrogen atmosphere. After the completion of the reaction, the reaction mixture was subjected to suction filtration. The filtrate was concentrated to obtain 23.6 g of white solid (i.e., compound A9).

step 8): After cooling a solution of diisopropylamine (24.7 g) in tetrahydrofuran (120 ml) to −78° C., a 2.5 M solution of n-butyllithium in n-hexane (98 ml) was added. The reaction solution was slowly warmed to 0° C. and further stirred for 1 hour. This solution was cooled down to −78° C. again, a solution of compound A9 (20.0 g) in tetrahydrofuran (100 ml) was added dropwise and the addition was completed within 45 minutes. The reaction solution was stirred at −65° C. for 30 minutes, and then raised to −20° C. and further stirred for 30 minutes. At this temperature, a solution of compound A6 (46.1 g) in tetrahydrofuran (100 ml) was slowly added and then stirred at −10~−15° C. for 1 hour. After the reaction was completed, saturated ammonium chloride was added to quench the reaction. The reaction solution was extracted three times with ethyl acetate. The organic phases were combined, washed with saturated brine, dried over anhydrous sodium sulfate, filtered and concentrated to obtain 60.7 g of crude product (i.e., compound A10), which was directly used in the next step reaction.

step 9): Compound A10 (58.8 g, crude product) was dissolved in dichloromethane (500 ml), and EDCI (21.0 g), DMAP (1.03 g) and benzyl alcohol (11.0 g) were added sequentially at room temperature. Under the protection of nitrogen, the reaction solution was stirred overnight at room temperature. After being quenched with water, the reaction solution was concentrated. The crude product was purified by silica gel column chromatography (petroleum ether/ethyl acetate=4/1) to obtain 26.1 g of yellow oil (i.e., compound A11). This crude product was directly used for the next step.

step 10): Ammonium fluoride (1.54 g) and acetic acid (7.48 g) were added to a solution of compound A11 (26.8 g) in methanol, and stirred at room temperature for 1 hour. After concentration, the reaction solution was diluted with ethyl acetate (200 ml), and then washed with saturated aqueous sodium bicarbonate solution and brine. The organic phase was dried over anhydrous sodium sulfate, filtered and concentrated. The crude product was purified by silica gel column chromatography (petroleum ether/ethyl acetate=4/1~dichloromethane/methanol=50/1) to obtain 17.1 g of white solid (i.e., intermediate A).

$^1$HNMR (400 MHz, CDCl$_3$): δ 8.25 (d, J=4.8 Hz, 1H), 7.55 (s, 1H), 7.36-7.33 (m, 3H), 7.23-7.22 (m, 2H), 7.20 (d, J=8.8 Hz, 2H), 6.91 (d, J=3.6 Hz, 1H), 6.78 (d, J=8.8 Hz, 2H), 602 (brs, 1H), 5.12 (s, 2H), 5.09 (s, 2H), 3.91 (d, J=2.4 Hz, 1H), 3.75 (s, 3H), 3.58 (m, 1H), 3.15 (J=14.8, 5.6 Hz, 1H), 3.03 (J=14.8, 8.0 Hz, 1H), 1.41 (s, 9H).

LCMS: Rt=1.939 min, [M+H$^+$]=532.0.

Example 1 Preparation of Compound I-001 Trifluoroacetate

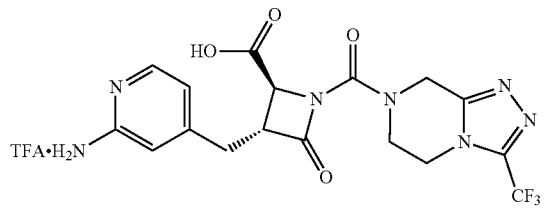

Compound I-001 trifluoroacetate was prepared according to the following scheme and method.

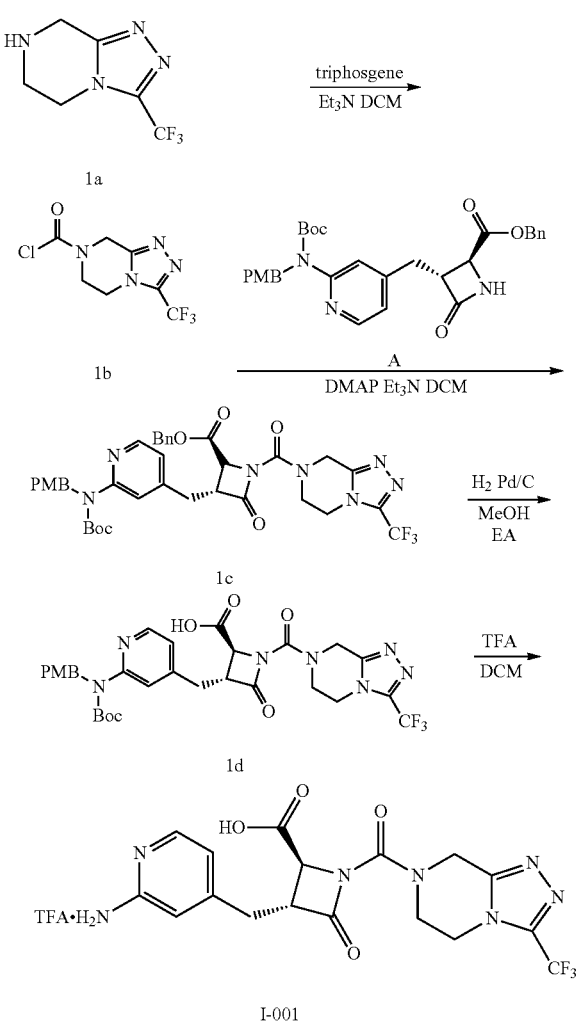

step 1): Compound 1a (400 mg) was dissolved in 10.0 mL of dichloromethane, and triethylamine (631 mg) was added. The mixture was cooled down with ice-salt bath to 0° C., and triphosgene (309 mg) was added. The mixture was allowed to react at room temperature for 1 h. The reaction solution was poured into ice water, extracted with dichloromethane (60 mL×3). The combined extract liquor was washed with saturated brine, dried over anhydrous sodium sulfate, and dried under reduced pressure to obtain a crude compound 1b (430 mg).

step 2): Intermediate A (300 mg) was dissolved in 6 mL of dichloromethane, triethylamine (171 mg) was added, and a solution of compound 1b (430 mg) in dichloromethane was added dropwise. The reaction mixture was stirred at room temperature for 1 h. The reaction solution was directly subjected to rotary evaporation to dryness, and then purified by silica gel column chromatography to obtain compound 1c (240 mg).

step 3): Compound 1c (240 mg) was dissolved in 5 mL of methanol, and 5 mL of ethyl acetate was added. Palladium on carbon (3.4 mg) was added, and the mixture was allowed to react at room temperature under hydrogen atmosphere for 2 h. The reaction solution was filtered and purified by reverse-phase preparative HPLC to obtain Compound 1d (120 mg).

step 4): Compound 1d (120 mg) was dissolved in 2 mL of dichloromethane, and after cooling down to 0° C., 3 mL of trifluoroacetic acid was added. The mixture was warmed to room temperature and stirred overnight. The reaction solution was directly subjected to rotary evaporation to dryness and purified by reverse-phase preparative HPLC to obtain compound I-001 trifluoroacetate (28 mg).

$^1$H-NMR (400 MHz, DMSO-$d_6$): (13.36 (s, 1H), 8.29-8.00 (m, 3H), 7.00-6.73 (m, 2H), 4.94 (s, 2H), 4.53-4.16 (m, 3H), 4.10-4.04 (m, 1H), 3.99-3.85 (m, 1H), 3.80-70 (m 1H), 3.20-3.10 (m, 2H).

LCMS: Rt=1.105 min, [M+H]$^+$=554.1.

Example 2 Preparation of Compound I-002 Trifluoroacetate

Compound I-002 trifluoroacetate was prepared according to the following scheme and method.

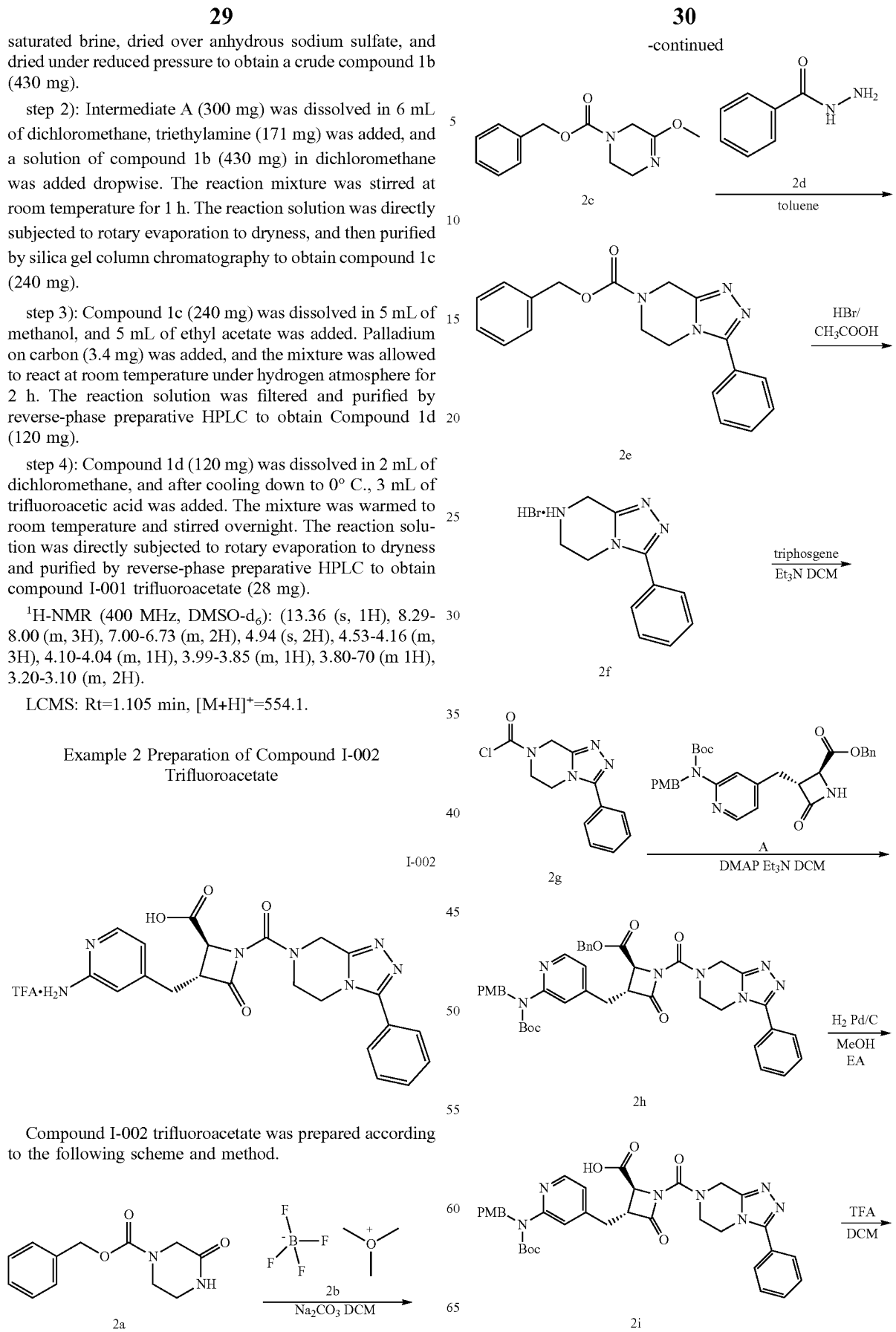

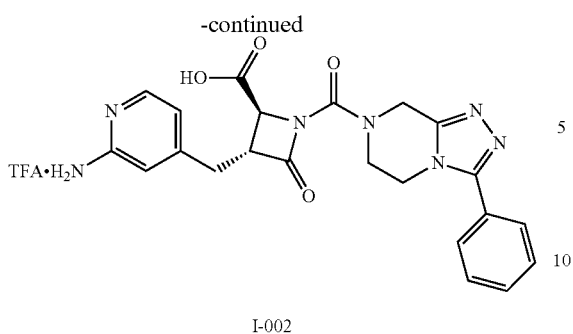

I-002 and then purified by reverse-phase preparative HPLC to obtain compound I-002 trifluoroacetate (28 mg).

[M+H]⁺=448.1.

Example 3 Preparation of Compound I-003 Trifluoroacetate

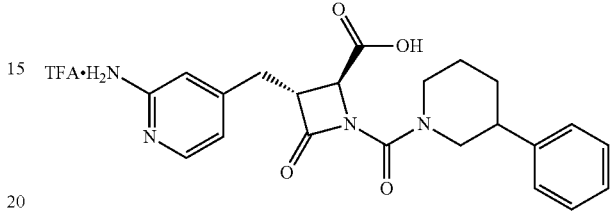

I-003

Compound I-003 trifluoroacetate was prepared according to the following scheme and method.

step 1): Compound 2a (2.5 g) was dissolved in 80.0 mL of dichloromethane, and after cooling down to 0° C., sodium carbonate (22.6 g) was added. After stirring for 10 min. compound 2b (5.5 g) was added. Under the protection of nitrogen, the reaction solution was warmed to room temperature and allowed to react for 6 h. The reaction solution was poured into water and extracted with dichloromethane (80 mL×3). The combined extract liquor was washed with saturated brine, dried over anhydrous sodium sulfate, and dried under reduced pressure to obtain compound 2c (2.1 g).

step 2): Compound 2c (2.1 g) was dissolved in 50 mL of toluene, compound 2d (1.15 g) was added, and a water separator was installed. The mixture was heated to 130° C. and refluxed overnight. The reaction solution was directly subjected to rotary evaporation to dryness, slurried with ethyl acetate, and filtered to obtain compound 2e (2 g).

step 3): Compound 2e (2 g) was dissolved in 20.0 mL of 30% hydrobromic acid acetic acid solution and reacted at room temperature for 3 hours under the protection of nitrogen. The reaction solution was directly subjected to rotary evaporation to dryness, and slurried with ethyl acetate to obtain compound 2f (1.6 g).

step 4): Compound 2f (400 mg) was dissolved in 3.0 mL of dichloromethane, and triethylamine (721 mg) was added. The mixture was cooled down in ice salt bath to 0° C., and triphosgene (212 mg) was added. The mixture was allowed to react at room temperature for 1 h. The reaction solution was poured into ice water, and extracted with dichloromethane (30 mL×3). The combined extract liquor was washed with saturated brine, dried over anhydrous sodium sulfate, and dried under reduced pressure to obtain a crude compound 2g (410 mg).

step 5): Compound 2g (100 mg) was dissolved in 3 mL of dichloromethane, triethylamine (57.1 mg) was added, and a solution of intermediate A (410 mg) in dichloromethane was added dropwise. After being stirred at room temperature for 1 h, the reaction solution was directly subjected to rotary evaporation to dryness, and then purified by silica gel column chromatography to obtain compound 2h (60 mg).

step 6): Compound 2h (60 mg) was dissolved in 3 mL of methanol and 3 mL of ethyl acetate was added. Palladium carbon (0.9 mg) was added and the mixture was allowed to react at room temperature for 2 hours under hydrogen atmosphere. The reaction solution was filtered to obtain compound 2i (50 mg, 94.6%).

step 7): Compound 2i (50 mg) was dissolved in 2 mL of dichloromethane, and after cooling down to 0° C., 3 mL of trifluoroacetic acid was added. The mixture was warmed to room temperature and stirred overnight. The reaction solution was directly subjected to rotary evaporation to dryness

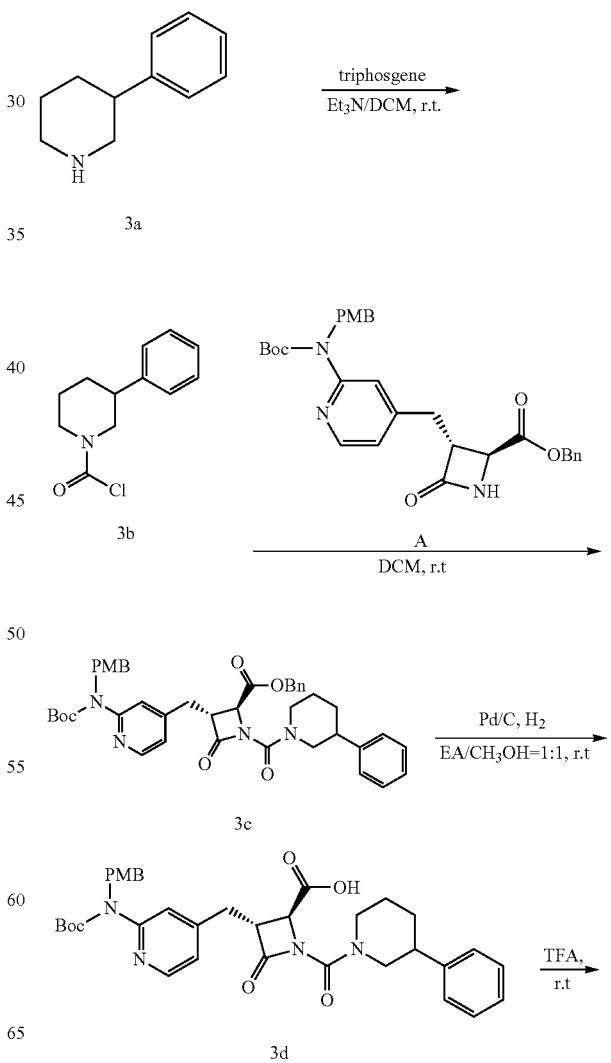

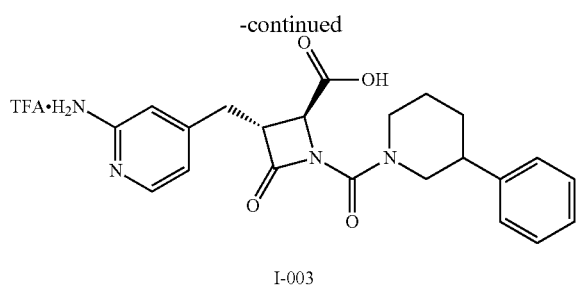

I-003 step 1): Compound 3a (200 mg) was dissolved in 10.0 mL of dichloromethane, and triethylamine (377 mg) was added. After cooling down to 0° C. in ice-salt bath, triphosgene (185 mg) was added, and the mixture was allowed to react at room temperature for 2 hours. After the reaction was completed, the reaction solution was washed with ice water, extracted with DCM, and concentrated to obtain 120 mg of crude product (i.e., compound 3b).

step 2): Intermediate A (100 mg) was dissolved in 10 mL of dichloromethane, and triethylamine (377 mg) was added. The mixture was added dropwise to a solution of compound 3b in dichloromethane, and then stirred at room temperature for 1 h. The reaction solution was directly subjected to rotary evaporation to dryness, and purified by silica gel column chromatography to obtain compound 3c (120 mg).

step 3): Compound 3c (120 mg) was dissolved in 5 mL of methanol, and 5 mL of ethyl acetate was added. Palladium carbon (0.8 mg) was added, and the mixture was allowed to react at room temperature for 1 h under hydrogen atmosphere. The reaction solution was filtered to obtain compound 3d (80 mg).

step 4): Compound 3d (80 mg) was dissolved in 2 mL of dichloromethane and cooled down to 0° C. 3 mL of trifluoroacetic acid was added and the mixture was allowed to react at room temperature overnight. The reaction solution was directly subjected to rotary evaporation to dryness and purified by reverse-phase preparative HPLC to obtain compound I-003 trifluoroacetate (10.29 mg).

$^1$H-NMR (400 MHz, DMSO-$d_6$): (13.50 (s, 1H), 7.86 (m, 1H), 7.41-7.21 (m, 7H), 6.75-6.73 (m, 2H), 4.28-4.23 (m, 1H), 4.07-3.98 (m, 2H), 3.69-3.67 (m, 1H), 3.07-2.77 (m, 4H), 2.67-2.61 (m, 1H), 1.93-1.87 (m, 4H).

LCMS: Rt=0.250 min, [M+H]$^+$=409.

Example 4 Preparation of Compound I-004 Trifluoroacetate

Compound I-004 trifluoroacetate was prepared according to the following scheme and method.

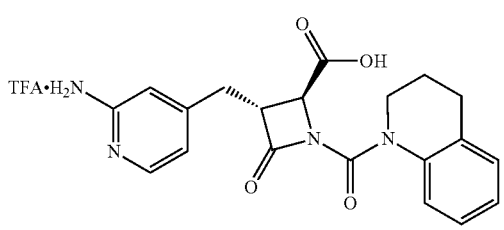

I-004

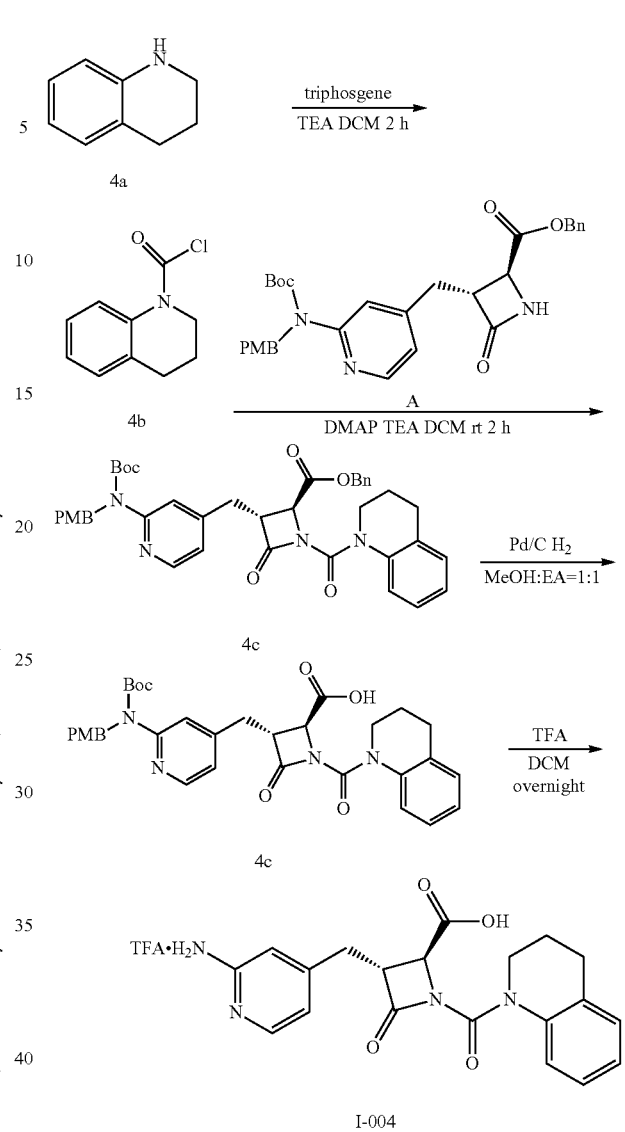

I-004 step 1): Compound 4a (100 mg) was dissolved in 10.0 mL of dichloromethane, and triethylamine (239 mg) was added. After cooling down in an ice water bath to 0° C., triphosgene (87.9 mg) was added, and the mixture was allowed to react at room temperature for 2 hours. The reaction solution was directly used in the next step.

step 2): Compound 4b (100 mg) was dissolved in 10 mL of dichloromethane, and triethylamine (57.1 mg) was added. The mixture was added dropwise to a solution of intermediate A in dichloromethane, and stirred at room temperature overnight. The reaction solution was directly subjected to rotary evaporation to dryness, and then purified by silica gel column chromatography to obtain compound 4c (90 mg).

step 3): Compound 4c (90 mg) was dissolved in 5 mL of methanol, and 5 mL of ethyl acetate was added. Palladium on carbon (0.8 mg) was added, and the mixture was allowed to react at room temperature for 1 h under hydrogen atmosphere. The reaction solution was filtered to obtain compound 4d (70 mg).

step 4): Compound 4d (70 mg) was dissolved in 5 mL of dichloromethane and the solution was cooled down to 0° C. 3 mL of trifluoroacetic acid was added and the mixture was allowed to react at room temperature overnight. The reaction solution was directly subjected to rotary evaporation to dryness and purified by reverse-phase preparative HPLC to obtain compound I-004 trifluoroacetate (17.2 mg).

$^1$H-NMR (400 MHz, DMSO-$d_6$): (13.50 (s, 1H), 7.87 (d, 1H), 7.56 (s, 2H), 7.42 (d, 1H), 7.17-7.01 (m, 3H), 6.78-6.76 (m, 2H), 4.28 (d, 1H), 3.96-3.92 (m, 1H), 3.70-3.66 (m, 1H), 3.47-3.33 (m, 1H), 3.08-3.05 (m, 2H), 2.80-2.65 (m, 2H), 1.97-1.93 (m, 1H), 1.87-1.82 (m, 1H).

LCMS: Rt=1.131 min, [M+H]$^+$=381.1.

Example 5 Preparation of Compound I-005 Trifluoroacetate

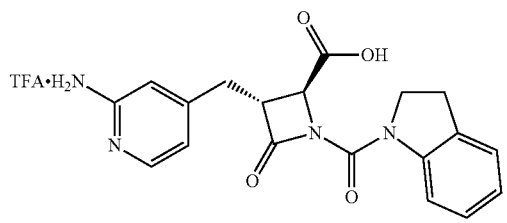

I-005

Compound I-005 trifluoroacetate was prepared according to the following scheme and method.

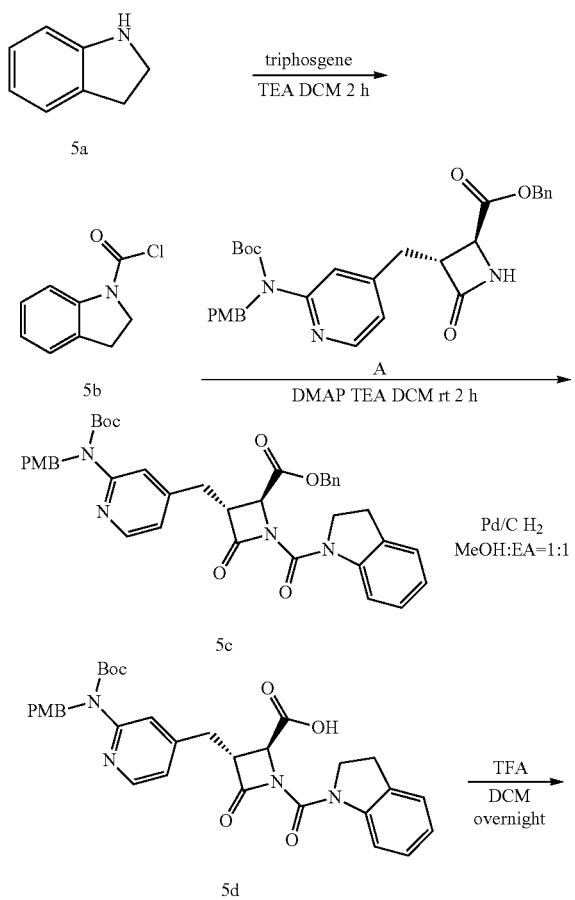

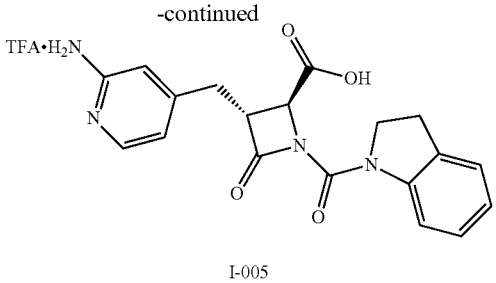

I-005 step 1): Compound 5a (300 mg) was dissolved in 10.0 mL of dichloromethane, and triethylamine (239 mg) was added. After cooling down in an ice water bath to 0° C. triphosgene (87.9 mg) was added, and the mixture was allowed to react at room temperature for 2 hours. The reaction solution was directly used in the next step.

step 2): Compound 5b was dissolved in 10 mL of dichloromethane, and triethylamine (57.1 mg) was added. The mixture was added dropwise to a solution of intermediate A in dichloromethane, and stirred at room temperature overnight. The reaction solution was directly subjected to rotary evaporation to dryness and purified by silica gel column chromatography to obtain Compound 5c (85 mg).

step 3): Compound 5c (85 mg) was dissolved in 5 mL of methanol, and 5 mL of ethyl acetate was added. Palladium carbon (0.8 mg) was added, and the mixture was allowed to react at room temperature for 1 h under hydrogen atmosphere. The reaction solution was filtered to obtain compound 5d (67 mg).

step 4): Compound 5d (67 mg) was dissolved in 10 mL of dichloromethane and the solution was cooled down to 0° C. 3 mL of trifluoroacetic acid was added and the mixture was allowed to react at room temperature overnight. The reaction solution was directly subjected to rotary evaporation to dryness and purified by reverse-phase preparative HPLC to obtain compound I-005 trifluoroacetate (18.6 mg).

$^1$H-NMR (400 MHz, DMSO-$d_6$): (13.50 (m, 1H), 7.89 (d, 1H), 7.82 (s, 1H), 7.68 (d, 1H), 7.28 (d, 1H), 7.20 (t, 1H), 7.05 (t, 1H), 6.89 (m, 2H), 4.46-4.39 (m, 2H), 4.14-4.11 (m, 1H), 3.81-3.77 (m, 1H), 3.25-3.13 (m, 4H).

LCMS: Rt=1.167 min, [M+H]$^+$=367.1.

Example 6 Preparation of Compound I-006 Trifluoroacetate

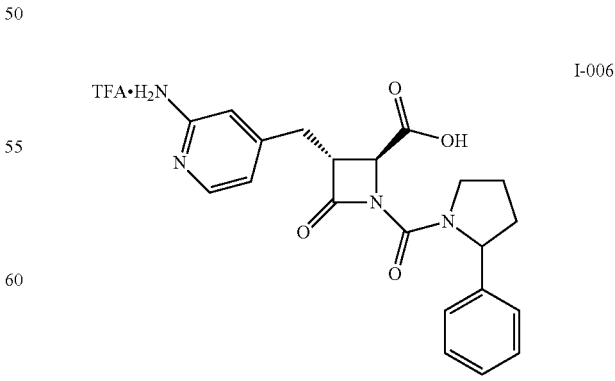

I-006

Compound I-006 trifluoroacetate was prepared according to the following scheme and method.

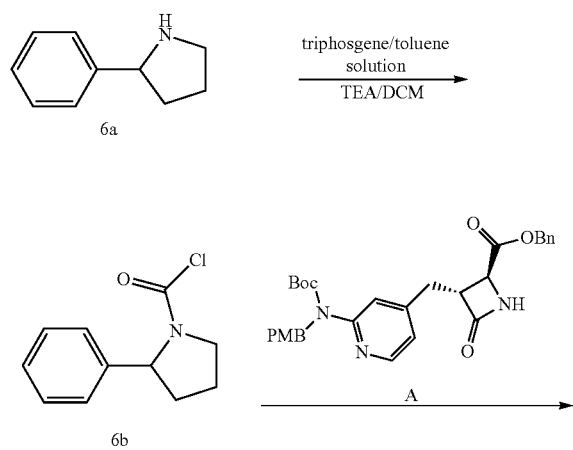

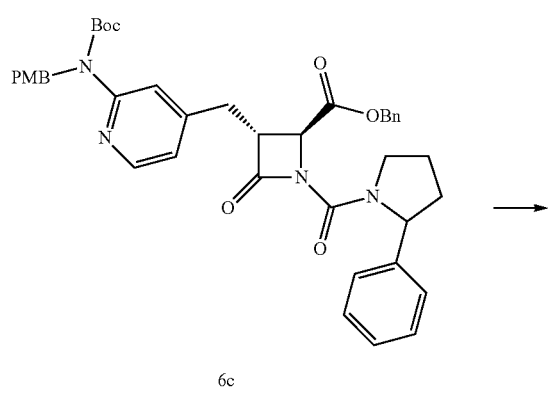

step 1): Compound 6a (300 mg) was dissolved in 10.0 mL of dichloromethane, and triethylamine (606 mg) was added. After cooling down in an ice water bath to 0° C., triphosgene (302 mg) was added, and the mixture was allowed to react at room temperature for 2 h. After the reaction was completed, the reaction solution was washed with water, extracted with DCM, and concentrated to obtain 280 mg of crude product (i.e., compound 6b).

step 2): Intermediate A (324 mg) was dissolved in 10 mL of dichloromethane, and triethylamine (123 mg) was added. The mixture was added dropwise to a solution of 6b (280 mg) in dichloromethane, and stirred at room temperature for 1 h. The reaction solution was directly subjected to rotary evaporation to dryness, and purified by silica gel column chromatography to obtain compound 6c (175 mg).

step 3): Compound 6c (175 mg) was dissolved in 5 mL of methanol, and 5 mL of ethyl acetate was added. Palladium carbon (0.2 mg) was added, and the mixture was allowed to react at room temperature for 1 h under hydrogen atmosphere. The reaction solution was filtered to obtain compound 6d (160 mg).

step 4): Compound 6d (160 mg) was dissolved in 2 mL of dichloromethane and the solution was cooled down to 0° C. 3 mL of trifluoroacetic acid was added and the mixture was allowed to react at room temperature overnight. The reaction solution was directly subjected to rotary evaporation to dryness and purified by reverse-phase preparative HPLC to obtain compound I-006 trifluoroacetate (60 mg).

$^1$H-NMR (400 MHz, DMSO-$d_6$): (13.41 (s, 1H), 8.08 (s, 2H), 7.95-7.88 m, 1H), 7.33-7.14 (m, 7H), 6.87-6.85 (m, 2H), 4.97-4.92 (m, 1H), 4.27 (s, 1H), 3.99-3.92 (m, 1H), 3.90-3.89 (m, 2H), 3.12 (m, 2H), 2.40-2.25 (m, 1H), 1.99-1.65 (m, 4H).

LCMS: Rt=0.892 min, [M+H]$^+$=395.25.

Example 7 Preparation of Compound I-007 Trifluoroacetate

Compound I-007 trifluoroacetate was prepared according to the following scheme and method.

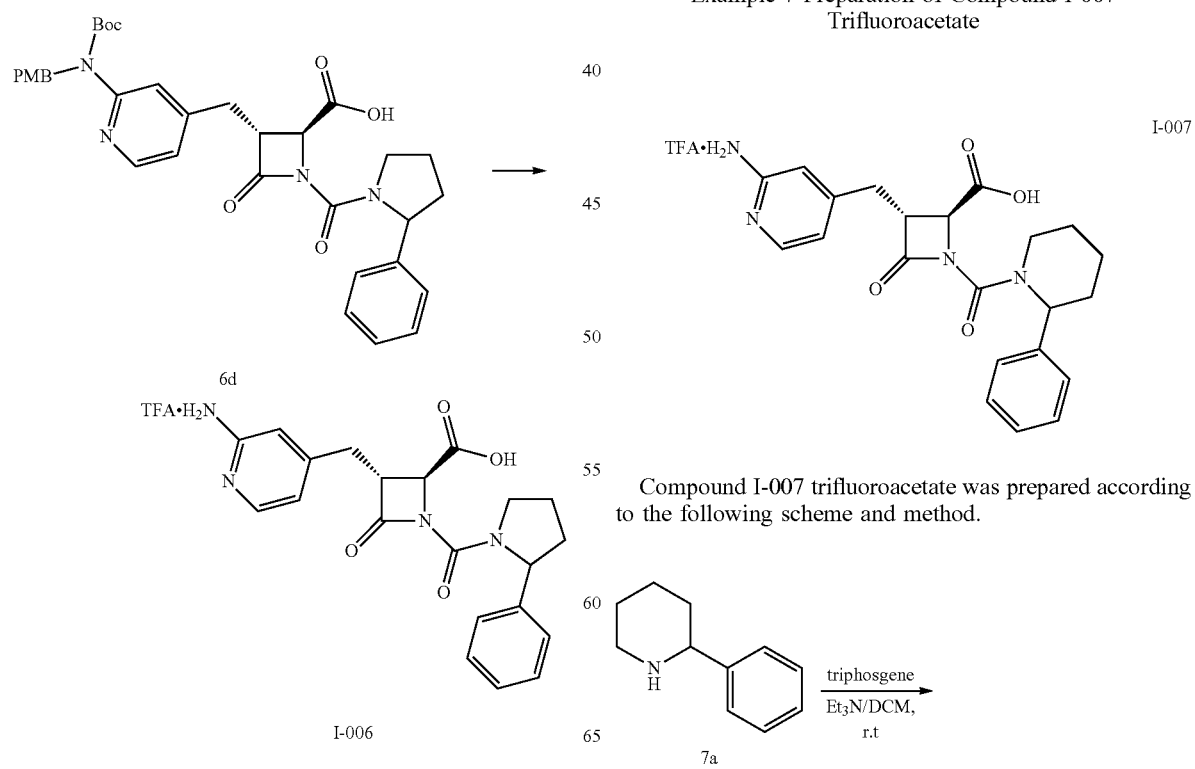

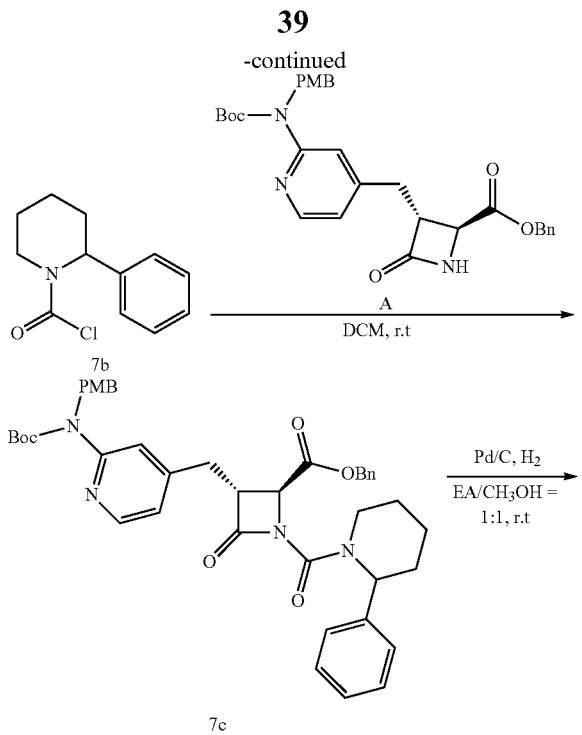

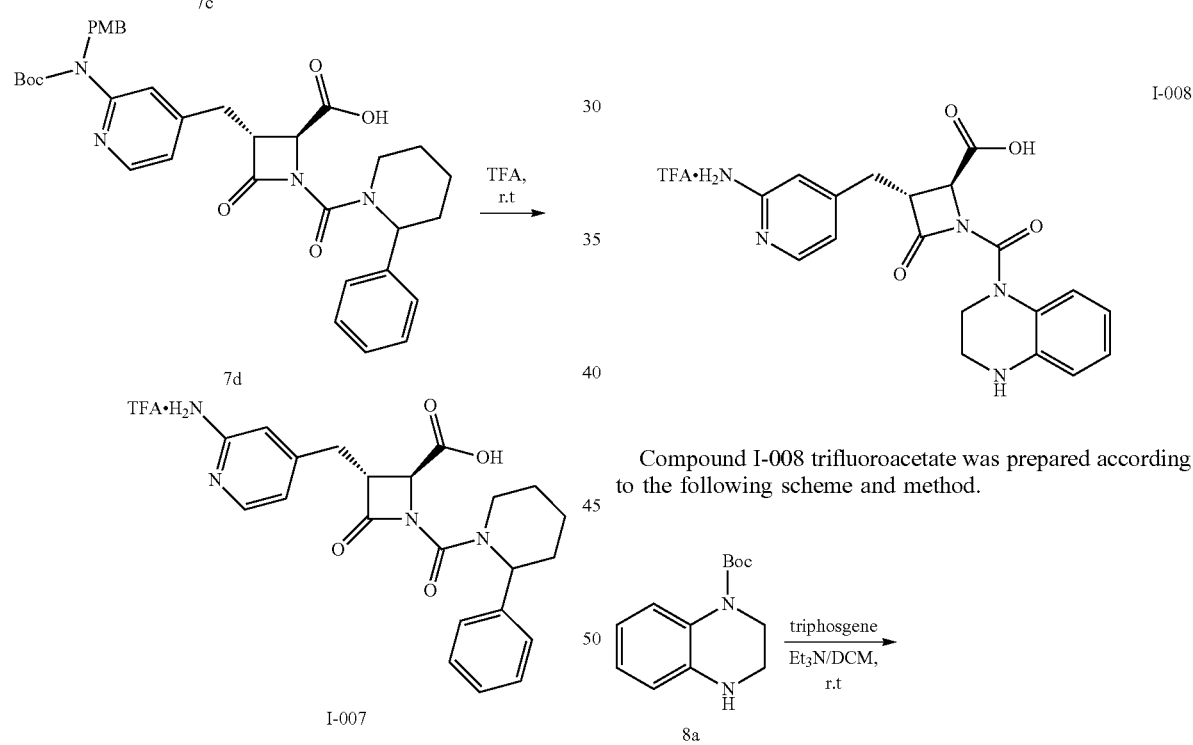

1 h. The reaction solution was directly subjected to rotary evaporation to dryness, and purified by silica gel column chromatography to obtain compound 7c (90 mg).

step 3): Compound 7c (90 mg) was dissolved in 5 mL of methanol, and 5 mL of ethyl acetate was added. Palladium carbon (0.8 mg) was added, and the mixture was allowed to react at room temperature for 1 h under hydrogen atmosphere. The reaction solution was filtered to obtain compound 7d (70 mg).

step 4): Compound 7d (70 mg) was dissolved in 2 mL of dichloromethane and the solution was cooled down to 0° C. 3 mL of trifluoroacetic acid was added and the mixture was allowed to react at room temperature overnight. The reaction solution was directly subjected to rotary evaporation to dryness and purified by reverse-phase preparative HPLC to obtain compound I-007 trifluoroacetate (9.53 mg).

$^1$H-NMR (400 MHz, DMSO-$d_6$): (13.40 (s, 1H), 7.84 (d, 1H), 7.39-7.24 (m, 5H), 6.72-6.69 (m, 2H), 5.47 (m, 1H), 4.34-4.30 (m, 1H), 3.92 (m, 1H), 3.82 (m, 1H), 3.07 (m, 2H), 2.48-2.40 (m, 1H), 1.98-1.80 (m, 2H), 1.71-1.41 (m, 4H).

LCMS: Rt=1.158 min, [M+H]$^+$=409.2.

Example 8 Preparation of Compound I-008 Trifluoroacetate

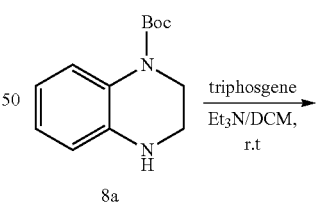

Compound I-008 trifluoroacetate was prepared according to the following scheme and method.

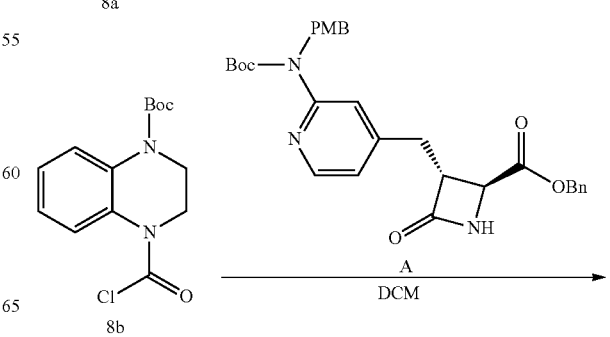

step 1): Compound 7a (200 mg) was dissolved in 10.0 mL of dichloromethane, and triethylamine (377 mg) was added. After cooling down in a nice water bath to 0° C., triphosgene (185 mg) was added, and the mixture was allowed to react at room temperature for 2 hours. After the reaction was completed, the reaction solution was washed with ice water, extracted with DCM, and concentrated to obtain 100 mg of crude product (i.e. compound 7b).

step 2): Intermediate A (100 mg) was dissolved in 10 mL of dichloromethane, and triethylamine (377 mg) was added. The mixture was added dropwise to a solution of compound 7b in dichloromethane, and stirred at room temperature for

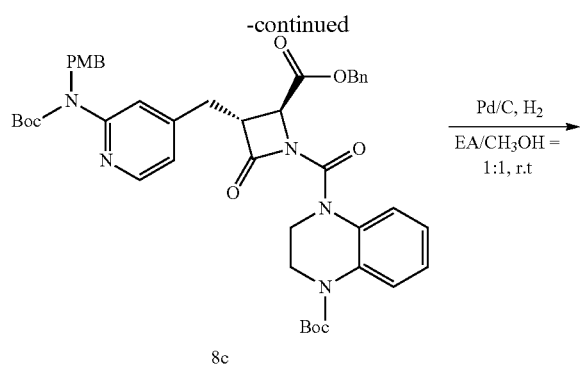

solution was directly subjected to rotary evaporation to dryness and purified by reverse-phase preparative HPLC to obtain compound I-008 trifluoroacetate (23.98 mg).

$^1$H-NMR (400 MHz, DMSO-$d_6$): (13.15 (s, 1H), 7.87 (d, 1H), 7.56 (s, 2H), 7.20 (d, 1H), 6.84-6.81 (m, 1H), 6.75 (s, 2H), 6.58 (d, 1H), 6.44-6.40 (m, 2H), 6.14 (s, 1H), 4.25 (d, 1H), 4.10-4.07 (m, 1H), 3.71-3.67 (m, 1H), 3.42-3.16 (m, 3H), 3.06 (m, 2H).

LCMS: Rt=1.099 min, [M+H]$^+$=482.1.

Example 9 Preparation of Compound I-009 Trifluoroacetate

Compound I-009 trifluoroacetate was prepared according to the following scheme and method.

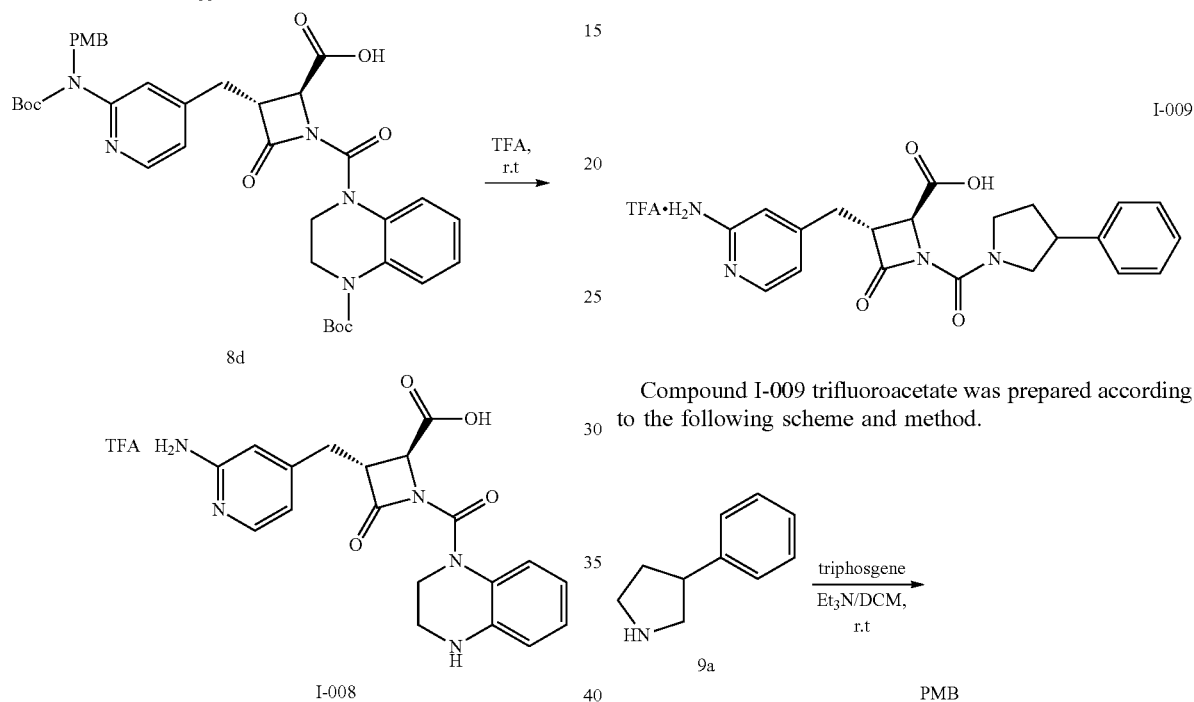

step 1): Compound 8a (200 mg) was dissolved in 10.0 mL of dichloromethane, and triethylamine (377 mg) was added. After cooling down in an ice water bath to 0° C., triphosgene (185 mg) was added, and the mixture was allowed to react at room temperature for 2 hours. After the reaction was completed, the reaction solution was washed with ice water, extracted with DCM, and concentrated to obtain 150 mg of crude product (i.e., compound 8b).

step 2): Intermediate A (100 mg) was dissolved in 10 mL of dichloromethane, and triethylamine (377 mg) was added. The mixture was added dropwise to a solution of compound 8b in dichloromethane, and stirred at room temperature for 1 h. The reaction solution was directly subjected to rotary evaporation to dryness, and purified by silica gel column chromatography to obtain compound 8c (150 mg).

step 3): Compound 8c (150 mg) was dissolved in 5 mL of methanol, and 5 mL of ethyl acetate was added. Palladium carbon (0.8 mg) was added, and the mixture was allowed to react at room temperature for 1 h under hydrogen atmosphere. The reaction solution was filtered to obtain compound 8d (120 mg).

step 4): Compound 8d (120 mg) was dissolved in 2 mL of dichloromethane and the solution was cooled down to 0° C. 3 mL of trifluoroacetic acid was added and the mixture was allowed to react at room temperature overnight. The reaction

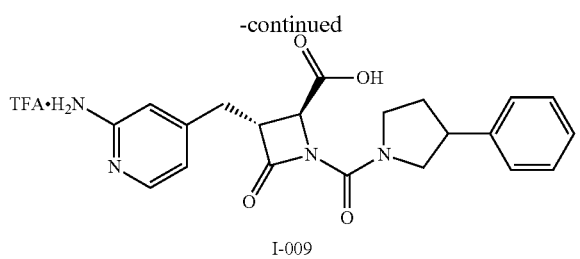

I-009 step 1): Compound 9a (250 mg) was dissolved in 10.0 mL of dichloromethane, and triethylamine (377 mg) was added. After cooling down in an ice water bath to 0° C., triphosgene (185 mg) was added, and the mixture was allowed to react at room temperature for 2 hours. After the reaction was completed, the reaction solution was washed with ice water, extracted with DCM, and concentrated to obtain 250 mg of crude product (i.e., compound 9b).

step 2): Intermediate A (150 mg) was dissolved in 10 mL of dichloromethane, and triethylamine (377 mg) was added. The mixture was added dropwise to a solution of compound 9b in dichloromethane, and stirred at room temperature for 1 h. The reaction solution was directly subjected to rotary evaporation to dryness, and purified by silica gel column chromatography to obtain compound 9c (350 mg).

step 3): Compound 9c (350 mg) was dissolved in 5 mL of methanol, and 5 mL of ethyl acetate was added. Palladium carbon (0.8 mg) was added, and the mixture was allowed to react at room temperature for 1 h under hydrogen atmosphere. The reaction solution was filtered to obtain compound 9d (280 mg).

step 4): Compound 9d (280 mg) was dissolved in 2 mL of dichloromethane and the solution was cooled down to 0° C. 3 mL of trifluoroacetic acid was added and the mixture was allowed to react at room temperature overnight. The reaction solution was directly subjected to rotary evaporation to dryness and purified by reverse-phase preparative HPLC to obtain compound I-009 trifluoroacetate (50 mg).

¹H-NMR (400 MHz, MeOD): (7.76 (d, 1H), 7.34-7.21 (m, 5H), 6.98 (s, 1H), 6.89 (d, 1H), 4.37-4.33 (m, 1H), 3.69-3.60 (m, 2H), 3.48-3.42 (m, 2H), 3.24-3.18 (m, 2H), 2.33 (m, 1H), 2.15-2.05 (m, 1H).

MS: m/z=395.2 [M+1].

Example 10 Preparation of Compound I-010 Trifluoroacetate

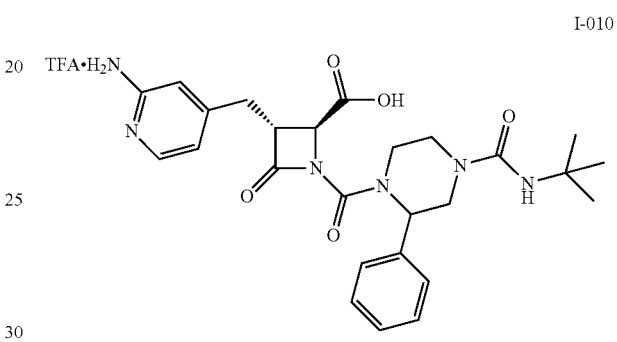

I-010

Compound I-010 trifluoroacetic was prepared according to the following scheme and method.

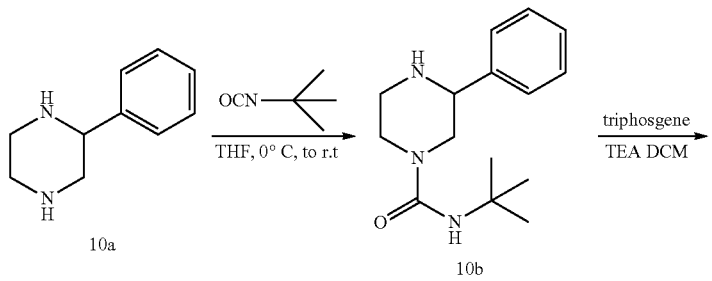

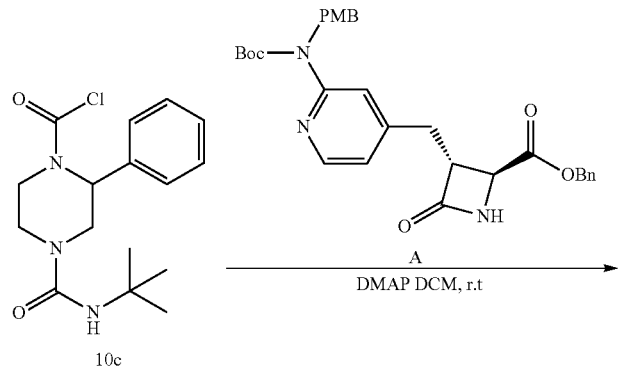

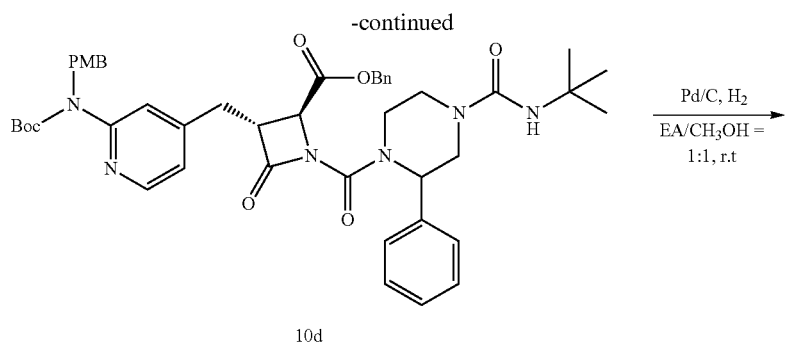

10d

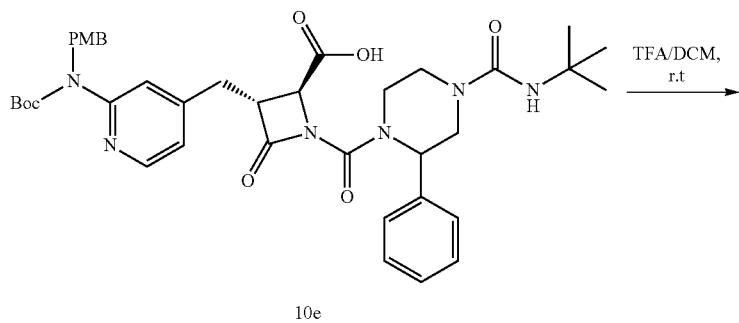

10e

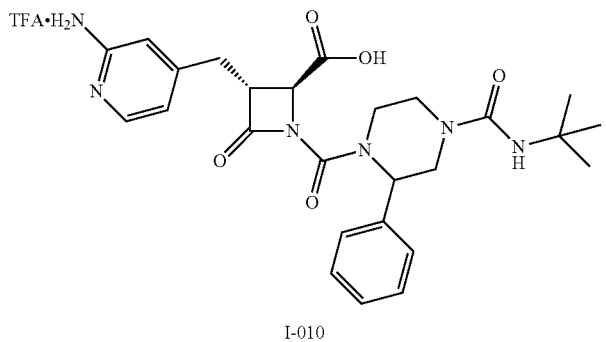

I-010 step 1): Compound 10a (200 mg) was dissolved in 10 mL of THF, and after cooling down to 0° C., tert-butyl isocyanate (122.22 mg) was added. After stirring at room temperature for 2 h, the reaction solution was purified and used in the next step (Compound 10b).

step 2): Compound 10b (200 mg) was dissolved in 10.0 mL of dichloromethane, and triethylamine (239 mg) was added. After cooling down in a nice water bath to 0° C., triphosgene (87.9 mg) was added, and the mixture was allowed to react at room temperature for 2 hours. The reaction solution was directly used in the next step (compound 10c).

step 3): Compound 10c was dissolved in 10 mL of dichloromethane, and triethylamine (57.1 mg) was added. The mixture was added dropwise to a solution of intermediate A in dichloromethane, and stirred at room temperature overnight. The reaction solution was directly subjected to rotary evaporation to dryness and purified by silica gel column chromatography to obtain Compound 10d (102 mg).

step 4): Compound 10d (112 mg) was dissolved in 10 mL of a mixed solution of ethyl acetate and methanol. Palladium carbon (0.8 mg) was added and the mixture was allowed to react at room temperature under hydrogen atmosphere for 0.5 h. The reaction solution was filtered to obtain compound 10e (85 mg).

step 5): Compound 10e (86 mg) was dissolved in 5 mL of dichloromethane, and the solution was cooled down to 0° C. 3 mL of trifluoroacetic acid was added and the mixture was allowed to react at room temperature overnight. The reaction solution was directly subjected to rotary evaporation to dryness and purified by reverse-phase preparative HPLC to obtain compound I-010 trifluoroacetate (2.5 mg).

$^1$H-NMR (400 MHz, DMSO-$d_6$): (13.50 (s, 1H), 7.95-7.88 (m, 3H), 7.37-7.26 (m, 5H), 6.91-6.88 (m, 2H), 5.76 (d, 1H), 5.32 (s, 1H), 4.39-4.38 (m, 1H), 3.88-3.76 (m, 3H), 3.21-3.16 (m, 2H), 2.99-2.87 (m, 2H), 2.67-2.50 (m, 2H), 1.25-1.20 (m, 9H).

MS: m/z=509.3 [M+1].

Example 11 Preparation of Compound I-011 Trifluoroacetate

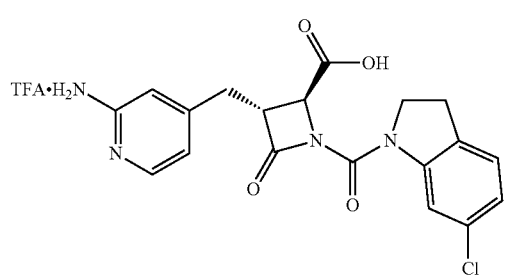

I-011

Compound I-011 trifluoroacetate was prepared according to the following scheme and method.

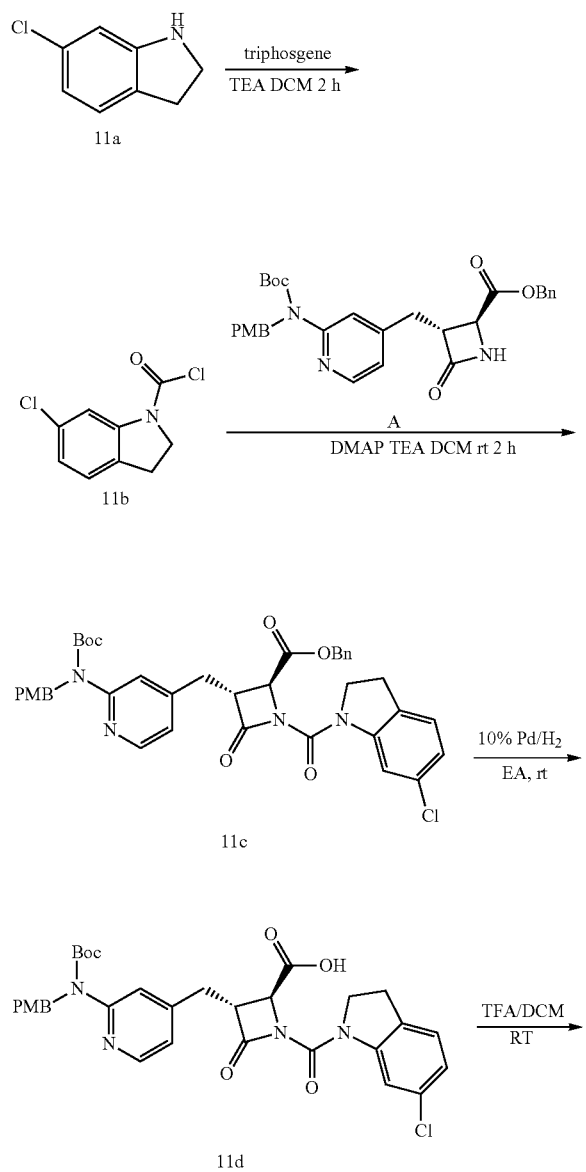

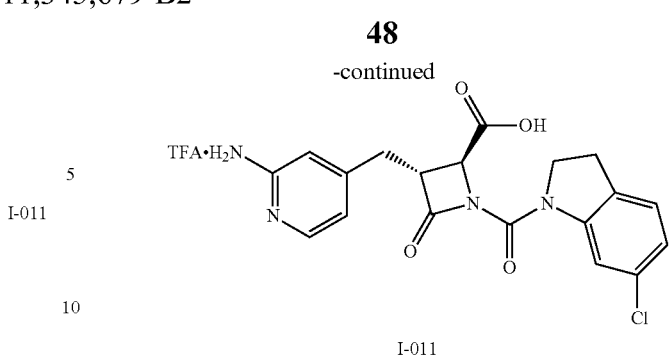

I-011 step 1): Compound 11a (600 mg) was dissolved in 10.0 mL of dichloromethane, and triethylamine (239 mg) was added. After cooling down in an ice water bath to 0° C., triphosgene (87.9 mg) was added, and the mixture was allowed to react at room temperature for 2 hours. The reaction solution (containing compound 11b) was directly used in the next step.

step 2): Compound 11b was dissolved in 10 mL of dichloromethane, and triethylamine (57.1 mg) was added. The mixture was added dropwise to a solution of intermediate A in dichloromethane, and stirred at room temperature overnight. The reaction solution was directly subjected to rotary evaporation to dryness and purified by silica gel column chromatography to obtain Compound 11c (180 mg).

step 3): Compound 11c (180 mg) was dissolved in 10 mL of ethyl acetate. Palladium on carbon (0.8 mg) was added and the mixture was allowed to react at room temperature for 0.5 h under hydrogen atmosphere. The reaction solution was filtered to obtain compound 11d (150 mg).

step 4): Compound 11d (150 mg) was dissolved in 10 mL of dichloromethane and the solution was cooled down to 0° C. 3 mL of trifluoroacetic acid was added and the mixture was allowed to react at room temperature overnight. The reaction solution was directly subjected to rotary evaporation to dryness and purified by reverse-phase preparative HPLC to obtain compound I-011 trifluoroacetate (40 mg).

$^1$H-NMR (400 MHz, DMSO-$d_6$): (13.20 (s, 1H), 7.88 (d, 1H), 7.69-7.68 (m, 3H), 7.30 (d, 1H), 7.10 (m, 1H), 6.86-6.84 (m, 2H), 4.51-4.39 (m, 1H), 4.38-4.37 (m, 1H), 4.18-4.17 (d, 1H), 3.80-3.79 (m, 1H), 3.20-3.15 (m, 4H).

MS: m/z=401.3 [M+1].

Example 12 Preparation of Compound I-012 Trifluoroacetate

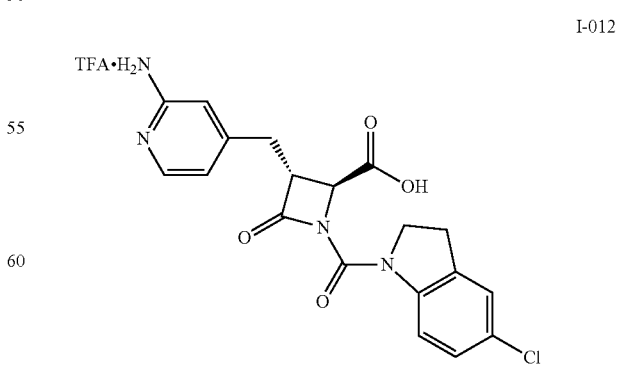

I-012

Compound I-012 trifluoroacetate was prepared according to the following scheme and method.

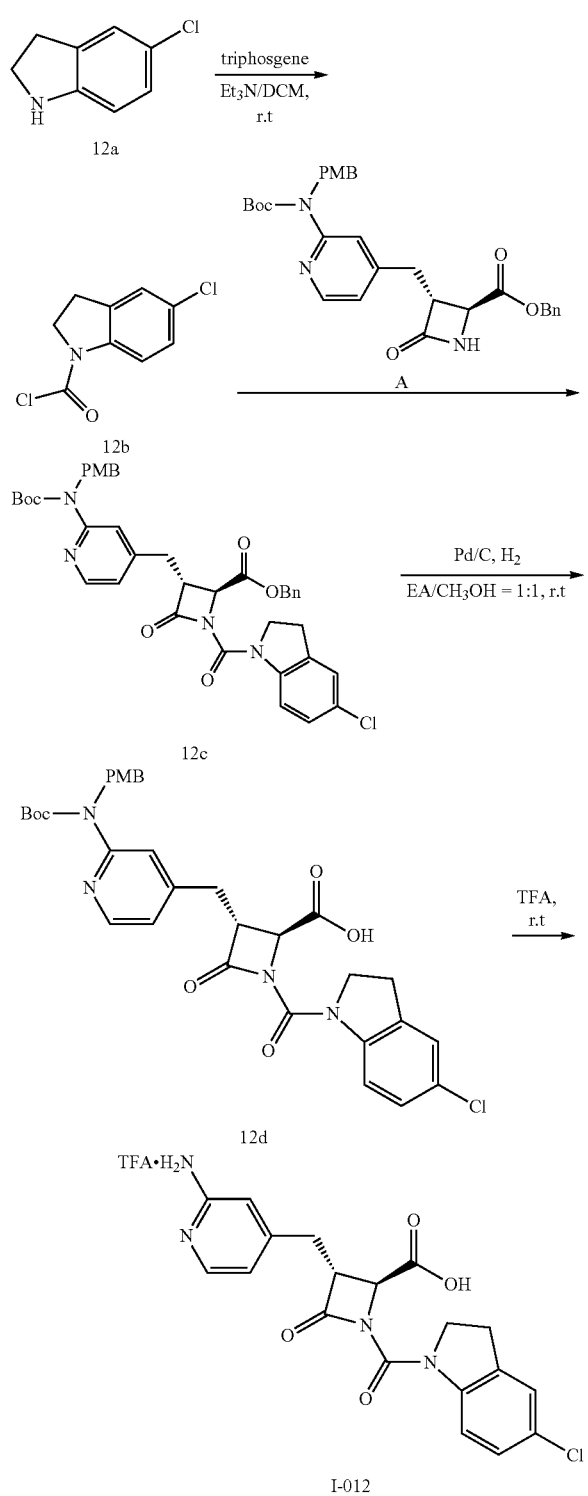

step 2): Intermediate A (176 mg) was dissolved in 10 mL of dichloromethane, and triethylamine (101 mg) was added. The mixture was added dropwise to a solution of compound 12b (240 mg) in dichlormethane, and stirred at room temperature for 1 h. The reaction solution was directly subjected to rotary evaporation to dryness, and purified by silica gel column chromatography to obtain compound 12c (220 mg).

step 3): Compound 12c (170 mg) was dissolved in 5 mL of methanol, and 5 mL of ethyl acetate was added. Palladium carbon (0.2 mg) was added, and the mixture was allowed to react at room temperature for 1 h under hydrogen atmosphere. The reaction solution was filtered to obtain compound 12d (120 mg).

step 4): Compound 12d (120 mg) was dissolved in 2 mL of dichloromethane and the solution was cooled down to 0° C. 3 mL of trifluoroacetic acid was added and the mixture was allowed to react at room temperature overnight. The reaction solution was directly subjected to rotary evaporation to dryness and purified by reverse-phase preparative HPLC to obtain compound I-012 trifluoroacetate (20 mg).

$^1$H-NMR (400 MHz, DMSO-$d_6$): (13.50 (s, 1H), 8.23-8.22 (m, 2H), 8.17 (d, 1H), 7.91-7.90 (d, 1H), 7.67-7.65 (m, 1H), 7.36-7.24 (m, 1H), 6.97-6.85 (m, 2H), 4.51-4.39 (m, 2H), 4.23-4.22 (m, 1H), 3.92 (m, 1H), 3.61-3.20 (m, 4H). MS: m/z=401.3 [M+1].

Example 13 Preparation of Compound I-013 Trifluoroacetate

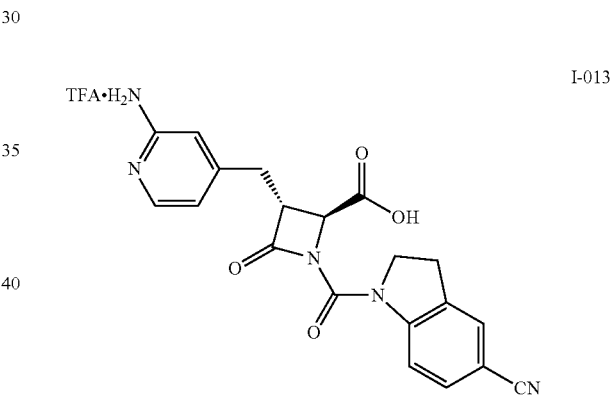

Compound I-013 trifluoroacetate was prepared according to the following scheme and method.

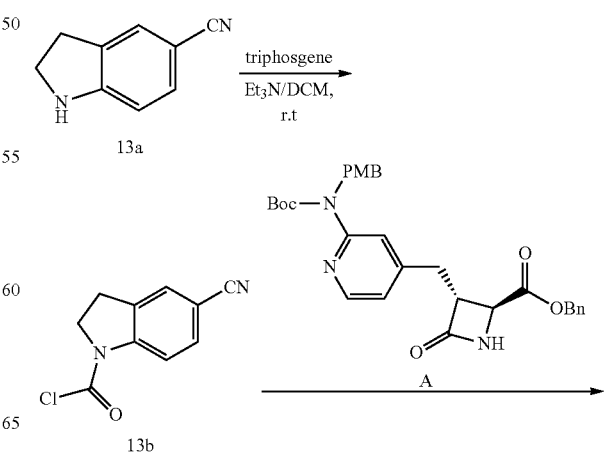

step 1): Compound 12a (200 mg) was dissolved in 10.0 mL of dichloromethane, and triethylamine (396 mg) was added. After cooling down in an ice water bath to 0° C., triphosgene (194 mg) was added, and the mixture was allowed to react at room temperature for 2 ht. After the reaction was completed, the reaction solution was washed with ice-water, extracted with DCM, and concentrated to obtain 240 mg of crude product (i.e., compound 12b).

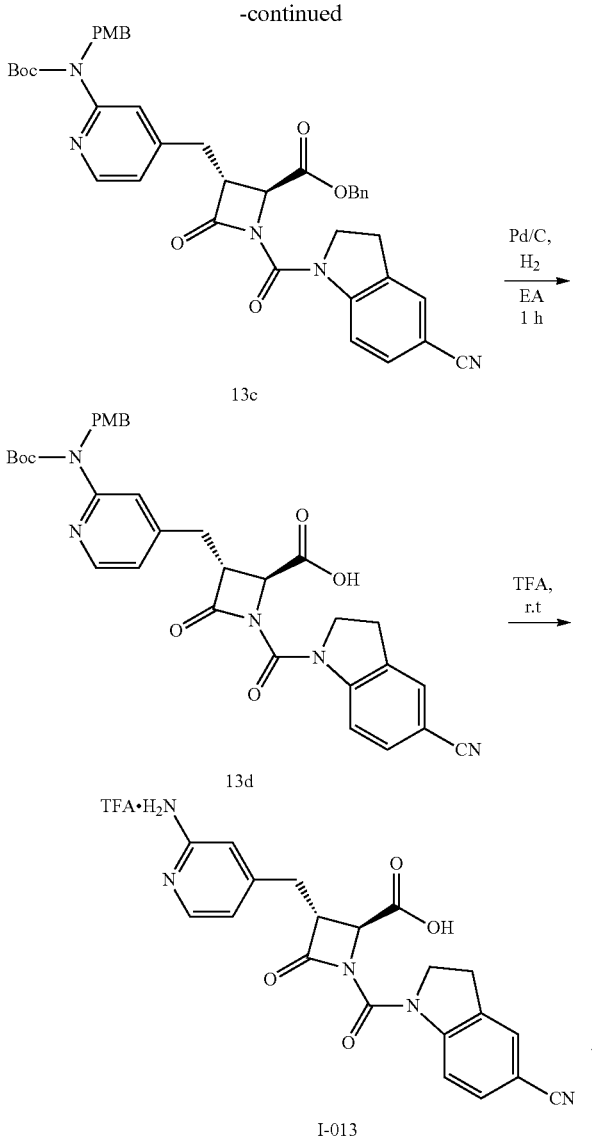

13c

13d

I-013 step 1): Compound 13a (200 mg) was dissolved in 10.0 mL of dichloromethane, and triethylamine (239 mg) was added. After cooling down in an ice water bath to 0° C., triphosgene (87.9 mg) was added, and the mixture was allowed to react at room temperature for 2 hours. The reaction solution (containing compound 13b) was directly used in the next step.

step 2): Compound 13b was dissolved in 10 mL of dichloromethane, and triethylamine (57.1 mg) was added. The mixture was added dropwise to a solution of intermediate A in dichloromethane, and stirred at room temperature overnight. The reaction solution was directly subjected to rotary evaporation to dryness and purified by silica gel column chromatography to obtain Compound 3c (130 mg).

step 3): Compound 13c (130 mg) was dissolved in 10 mL of ethyl acetate. Palladium carbon (0.8 mg) was added and the mixture was allowed to react at room temperature for 0.5 h under hydrogen atmosphere. The reaction solution was filtered to obtain compound 13d (90 mg).

step 4): Compound 13d (70 mg) was dissolved in 5 mL of dichloromethane and the solution was cooled down to 0° C. 3 mL of trifluoroacetic acid was added and the mixture was allowed to react at room temperature overnight. The reaction solution was directly subjected to rotary evaporation to dryness and purified by reverse-phase preparative HPLC to obtain compound I-013 trifluoroacetate (18 mg).

$^1$H-NMR (400 MHz, DMSO-$d_6$): (13.20 (m, 1H), 7.88 (d, 1H), 7.86-7.78 (m, 2H), 7.76-7.69 (m, 1H), 7.45 (s, 2H), 6.78-6.76 (m, 2H), 4.50-4.43 (m, 1H), 4.39-4.38 (d, 1H), 4.18-4.17 (m, 1H), 3.82-3.78 (m, 1H), 3.25-3.23 (m, 2H), 3.15-3.13 (m, 2H).

MS: m/z=392.2 [M+1].

Example 14 Preparation of Compound I-014 Trifluoroacetate

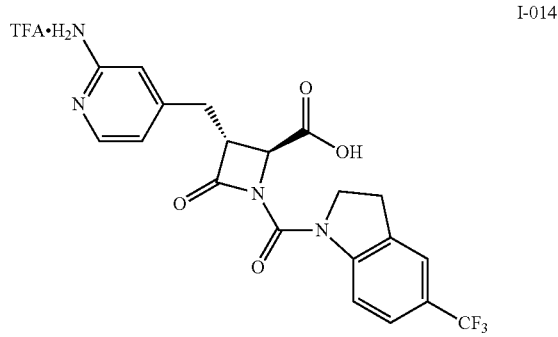

I-014

Compound I-014 trifluoroacetate was re d according to the following scheme and method.

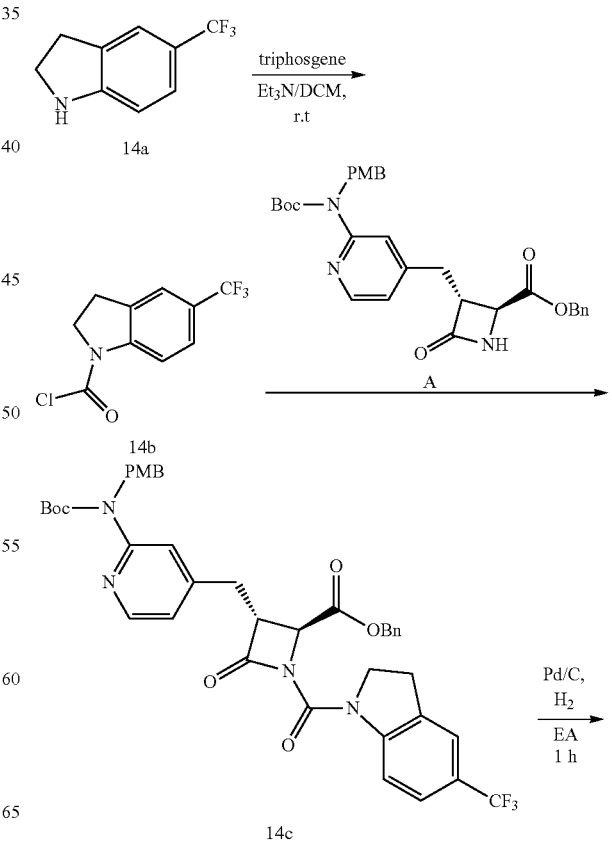

14a

14b

14c

-continued

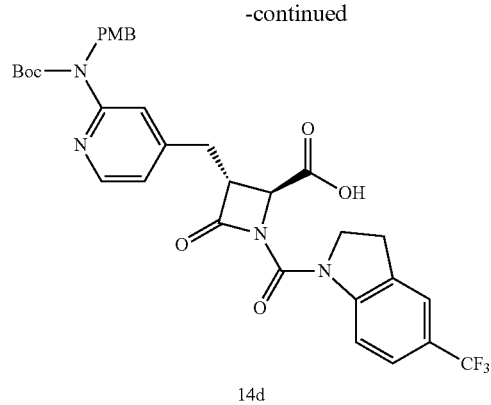

14d

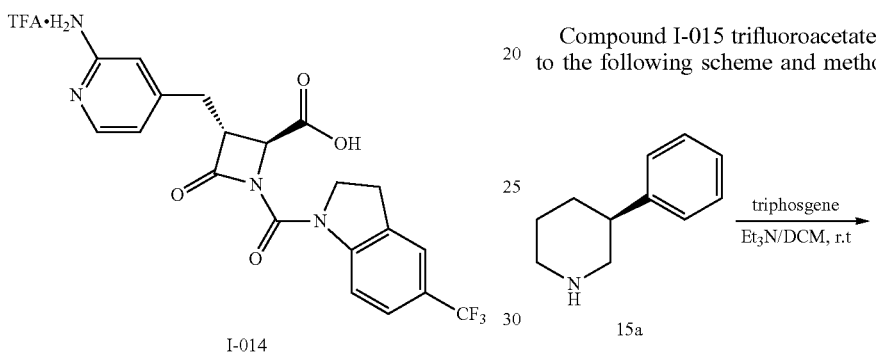

I-014

Example 15 Preparation of Compound I-015 Trifluoroacetate

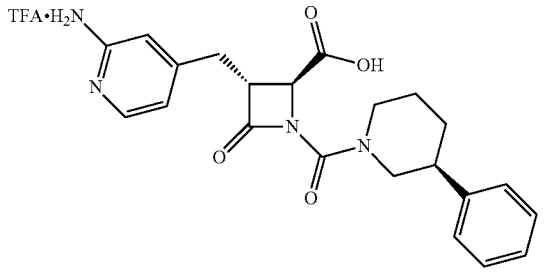

I-015

Compound I-015 trifluoroacetate was prepared according to the following scheme and method.

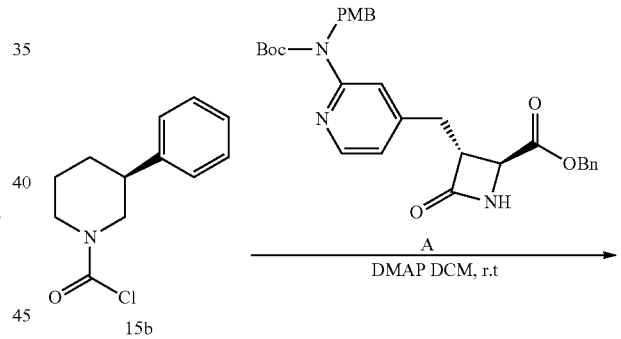

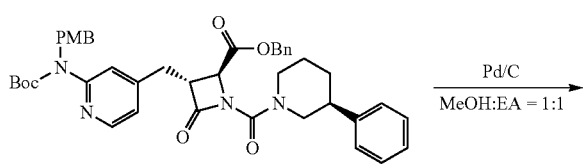

15c

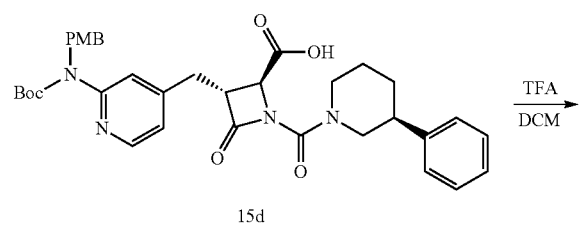

15d step 1): Compound 14a (200 mg) was dissolved in 10.0 mL of dichloromethane, and triethylamine (239 mg) was added. After cooling down in an ice water bath to 0° C., triphosgene (87.9 mg) was added, and the mixture was allowed to react at room temperature for 2 hours. The reaction solution (containing compound 14b) was directly used in the next step.

step 2): Compound 14b was dissolved in 10 mL of dichloromethane, and triethylamine (57.1 mg) was added. The mixture was added dropwise to a solution of intermediate A in dichloromethane, and stirred at room temperature overnight. The reaction solution was directly subjected to rotary evaporation to dryness and purified by silica gel column chromatography to obtain Compound 14c (98 mg).

step 3): Compound 14c (98 mg) was dissolved in 10 mL of ethyl acetate. Palladium carbon (0.8 mg) was added and the mixture was allowed to react at room temperature for 0.5 h under hydrogen atmosphere. The reaction solution was filtered to obtain compound 14d (70 mg).

step 4): Compound 14d (70 mg) was dissolved in 5 mL of dichloromethane, and the solution was cooled down to 0° C. 3 mL of trifluoroacetic acid was added and the mixture was allowed to react at room temperature overnight. The reaction solution was directly subjected to rotary evaporation to dryness and purified by reverse-phase preparative HPLC to obtain compound I-014 trifluoroacetate (8 mg).

$^1$H-NMR (400 MHz, DMSO-$d_6$): (13.20 (m, 1H), 7.88 (s, 1H), 7.81 (d, 1H), 7.65 (s, 1H), 7.59-7.53 (m, 4H), 6.81-6.79 (m, 2H), 4.52 (m, 1H), 4.39 (d, 1H), 4.18 (m, 1H), 3.80 (m, 1H), 3.25-3.23 (m, 2H), 3.15-3.13 (m, 2H).

MS: m/z=435.2 [M+1].

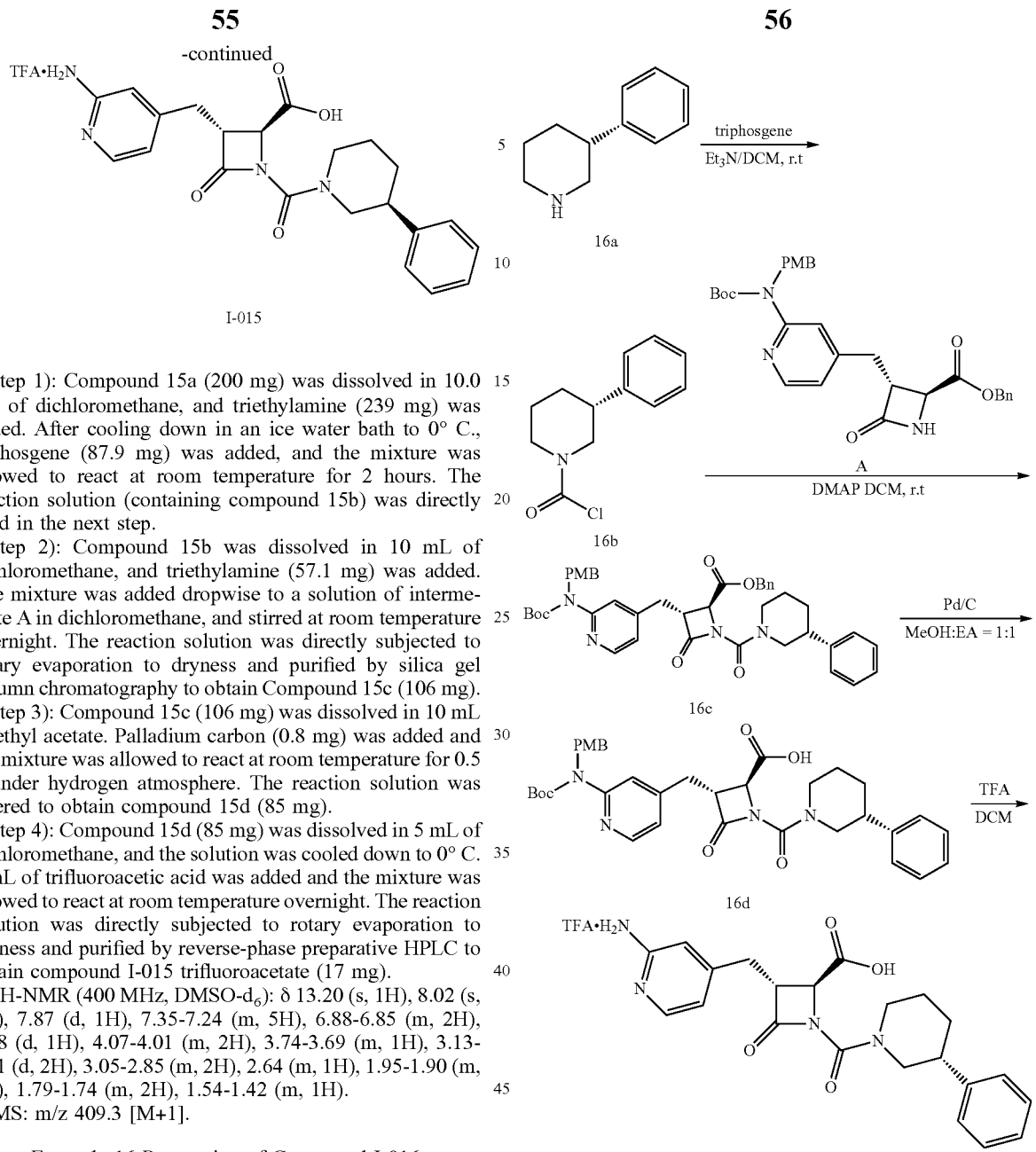

step 1): Compound 15a (200 mg) was dissolved in 10.0 mL of dichloromethane, and triethylamine (239 mg) was added. After cooling down in an ice water bath to 0° C., triphosgene (87.9 mg) was added, and the mixture was allowed to react at room temperature for 2 hours. The reaction solution (containing compound 15b) was directly used in the next step.

step 2): Compound 15b was dissolved in 10 mL of dichloromethane, and triethylamine (57.1 mg) was added. The mixture was added dropwise to a solution of intermediate A in dichloromethane, and stirred at room temperature overnight. The reaction solution was directly subjected to rotary evaporation to dryness and purified by silica gel column chromatography to obtain Compound 15c (106 mg).

step 3): Compound 15c (106 mg) was dissolved in 10 mL of ethyl acetate. Palladium carbon (0.8 mg) was added and the mixture was allowed to react at room temperature for 0.5 h under hydrogen atmosphere. The reaction solution was filtered to obtain compound 15d (85 mg).

step 4): Compound 15d (85 mg) was dissolved in 5 mL of dichloromethane, and the solution was cooled down to 0° C. 3 mL of trifluoroacetic acid was added and the mixture was allowed to react at room temperature overnight. The reaction solution was directly subjected to rotary evaporation to dryness and purified by reverse-phase preparative HPLC to obtain compound I-015 trifluoroacetate (17 mg).

$^1$H-NMR (400 MHz, DMSO-$d_6$): δ 13.20 (s, 1H), 8.02 (s, 2H), 7.87 (d, 1H), 7.35-7.24 (m, 5H), 6.88-6.85 (m, 2H), 4.28 (d, 1H), 4.07-4.01 (m, 2H), 3.74-3.69 (m, 1H), 3.13-3.11 (d, 2H), 3.05-2.85 (m, 2H), 2.64 (m, 1H), 1.95-1.90 (m, 1H), 1.79-1.74 (m, 2H), 1.54-1.42 (m, 1H).

MS: m/z 409.3 [M+1].

Example 16 Preparation of Compound I-016 Trifluoroacetate

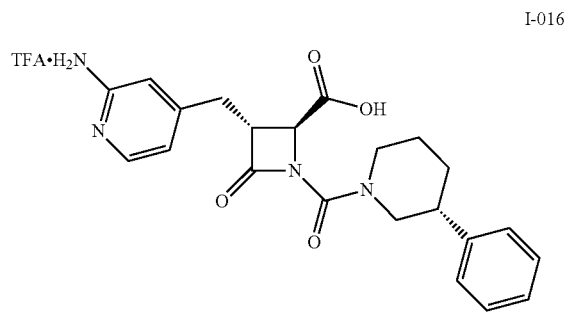

I-016

Compound I-016 trifluoroacetate was prepared according to the following scheme and method.

step 1): Compound 16a (200 mg) was dissolved in 10.0 mL of dichloromethane, and triethylamine (239 mg) was added. After cooling down in an ice water bath to 0° C., triphosgene (87.9 mg) was added, and the mixture was allowed to react at room temperature for 2 hours. The reaction solution (containing compound 16b) was directly used in the next step.

step 2): Compound 16b was dissolved in 10 mL of dichloromethane, and triethylamine (57.1 mg) was added. The mixture was added dropwise to a solution of intermediate A in dichloromethane, and stirred at room temperature overnight. The reaction solution was directly subjected to rotary evaporation to dryness and purified by silica gel column chromatography to obtain Compound 16c (106 mg).

step 3): Compound 16c (106 mg) was dissolved in 10 mL of ethyl acetate. Palladium carbon (0.8 mg) was added and the mixture was allowed to react at room temperature for 0.5 h under hydrogen atmosphere. The reaction solution was filtered to obtain compound 16d (85 mg).

step 4): Compound 16d (85 mg) was dissolved in 5 mL of dichloromethane and the solution was cooled down to 0° C. 3 mL of trifluoroacetic acid was added and the mixture was allowed to react at room temperature overnight. The reaction solution was directly subjected to rotary evaporation to dryness and purified by reverse-phase preparative HPLC to obtain compound I-016 trifluoroacetate (15 mg).

$^1$H-NMR (400 MHz, DMSO-d$_6$): (13.50 (s, 1H), 7.85 (d, 1H), 7.56 (brs, 2H), 7.35-7.24 (m, 5H), 6.78 (d, 2H), 4.25 (d, 1H), 4.04 (t, 2H), 3.70 (m, 1H), 3.08 (d, 2H), 3.08-2.90 (m, 1H), 2.67-2.61 (m, 2H), 1.91 (d, 1H), 1.80-1.73 (m, 2H), 1.70-1.54 (m, 1H).

MS: m/z=409.2 [M+1].

Example 17 Preparation of Compound I-017 Trifluoroacetate

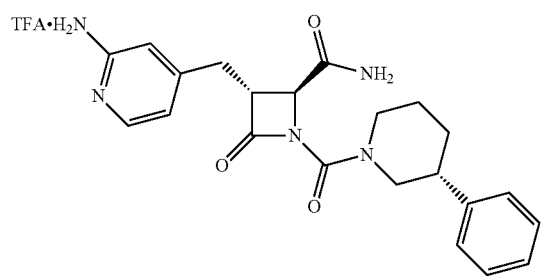

I-017

Compound I-017 trifluoroacetate was reared according to the following scheme and method.

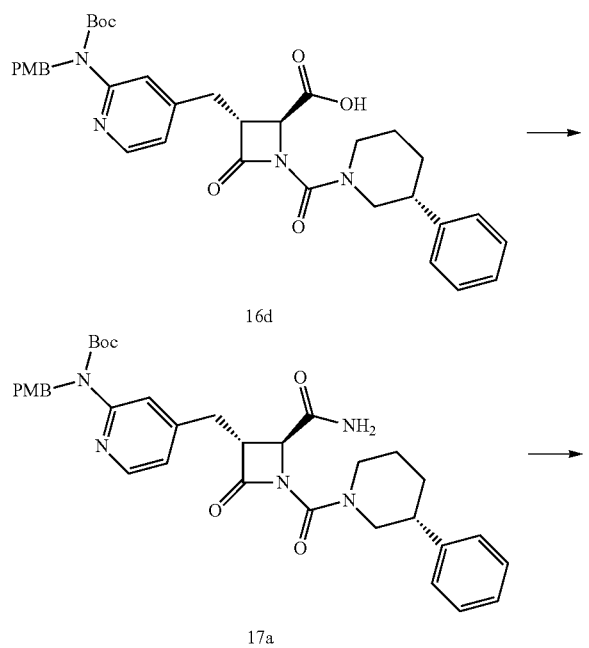

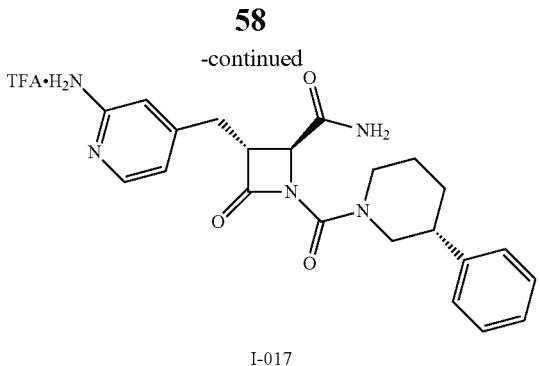

I-017

Under the protection of nitrogen, diisopropylethylamine (128 mg) and HATU (250 mg) were added to a solution of compound 16d (220 mg crude product) in dichloromethane (5 ml). After stirring at 0° C. for 1 hour, ammonium chloride (53 mg) was added. The reaction solution was further stirred at 0° C. for 2 hours. Saturated aqueous sodium bicarbonate solution (10 ml) was added to quench the reaction, and the organic phase was separated, dried and concentrated. The crude product was purified by silica gel column chromatography (petroleum ether/ethyl acetate=1/2) to obtain 140 mg of white solid (compound 17a).

Compound 17a (140 mg) was added to a solution of TFA/DCM (3 ml/1.5 ml) and the mixture was stirred at 25° C. for 6 hours. After the reaction was completed as detected by LC MS, the reaction solution was concentrated at room temperature. After concentration, the residue was purified by reverse-phase preparative HPLC to obtain 45.9 mg of white solid (compound I-017 trifluoroacetate).

$^1$H NMR (400 MHz, DMSO-d$_6$): (13.45 (brs, 1H), 7.98 (brs, 2H), 7.86 (d, J=7.6 Hz, 1H), 7.72 (brs, 1H), 7.35-7.23 (m, 6H), 6.87-6.86 (m, 2H), 4.19 (d, J=3.2 Hz, 1H), 4.08-4.01 (m, 2H), 3.53-3.48 (m, 1H), 3.13-3.11 (m, 2H), 3.03-2.86 (m, 2H), 2.69-2.61 (m, 1H), 1.94-1.88 (m, 1H), 1.79-1.69 (m, 2H), 1.64-1.55 (m, 1H).

LCMS: Rt=3.198 min, [M+H]$^+$=408.3.

Example 18 Preparation of Compound I-018 Trifluoroacetate

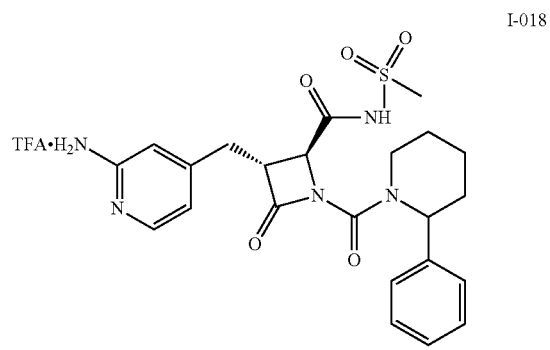

I-018

Compound I-018 trifluoroacetate was prepared according to the following scheme and method.

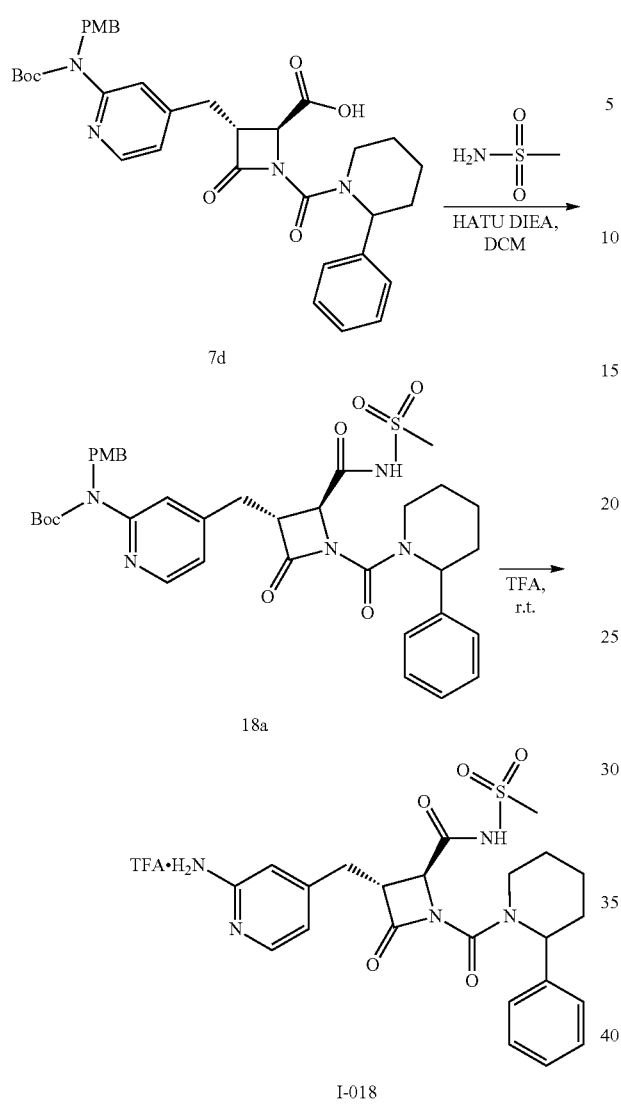

7d

18a

I-018 step 1): Compound 7d (220 mg) was dissolved in 2 mL of dichloromethane, and the solution was cooled down to 0° C. Methanesulfonamide (48 mg), HATU (190 mg), and DIEA (68 mg) were added sequentially, and the mixture was allowed to react at room temperature overnight. The reaction solution was directly subjected to rotary evaporation to dryness and purified to obtain compound 18a (170 mg).

step 2): Compound 18a (170 mg) was dissolved in 2 mL of dichloromethane, and the solution was cooled down to 0° C. 2 mL of trifluoroacetic acid was added and the mixture was allowed to react at room temperature overnight. The reaction solution was directly subjected to rotary evaporation to dryness and purified by silica gel column chromatography to obtain compound I-018 trifluoroacetate (10 mg).

$^1$H-NMR (400 MHz, CD$_3$OD): (7.78-7.77 (m, 1H), 7.37-7.23 (m, 5H), 6.97-6.89 (m, 2H), 5.36-5.47 (m, 1H), 4.39-4.32 (m, 1H), 4.04-4.01 (m, 1H), 3.75-3.72 (m, 1H), 3.31-3.24 (m, 3H), 3.22-3.20 (m, 2H), 3.03-2.97 (m, 1H), 2.48-2.45 (m, 1H), 2.03-1.99 (m, 1H), 1.65-1.51 (m, 4H), 1.29 (m, 1H).

MS: m/z=486.17 [M+1].

Example 19 Preparation of Compound I-019 Trifluoroacetate

Compound I-019 trifluoroacetate was prepared according to the following scheme and method.

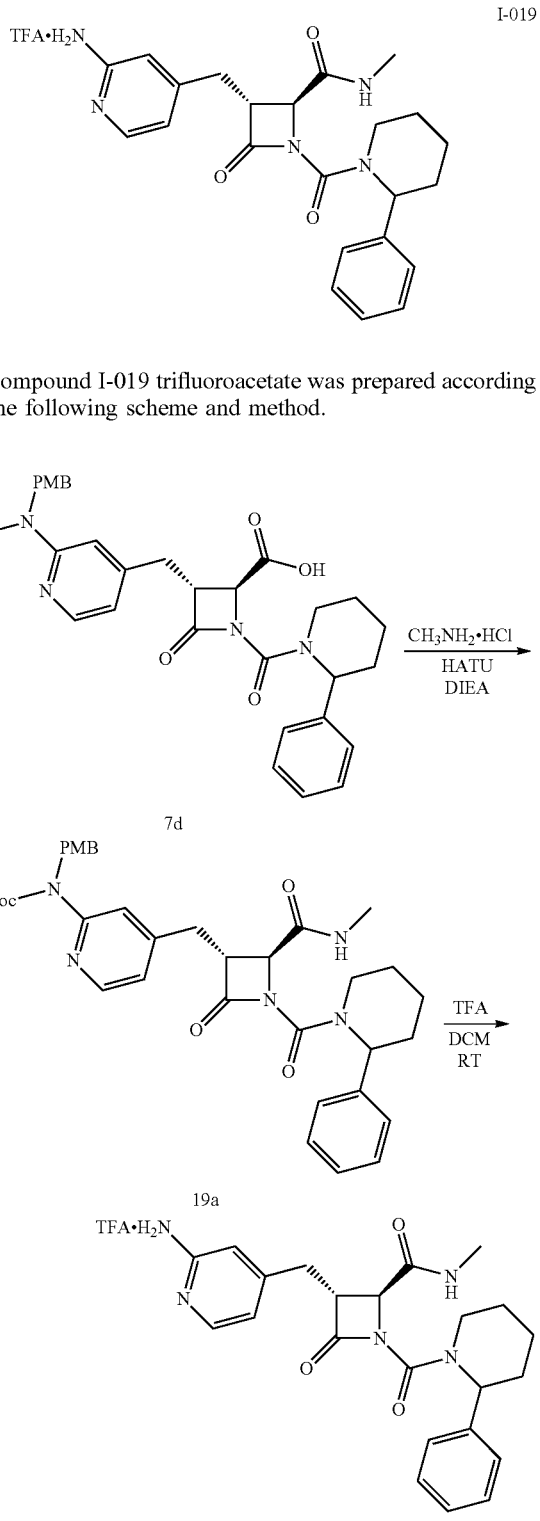

7d

19a

I-019 step 1): Compound 7d (70 mg) was dissolved in 5 mL of dichloromethane, and methylamine hydrochloride (10.6 mg), DIEA (20.0 mg), and HATU (50.0 mg) were added sequentially. The mixture was stirred at room temperature for 1 h. The reaction solution was directly subjected to rotary evaporation to dryness and purified by silica gel column chromatography to obtain compound 19a (80 mg).

step 2): Compound 19a (75 mg) was dissolved in 1 mL of dichloromethane and the solution was cooled down to 0° C. 1 mL of trifluoroacetic acid was added and the mixture was allowed to react at room temperature overnight. The reaction solution was directly subjected to rotary evaporation to dryness and purified by reverse-phase preparative HPLC to obtain compound I-019 trifluoroacetate (6.8 mg).

$^1$H-NMR (400 MHz, CD$_3$OD): (8.21 (m, 1H), 8.09 (s, 2H), 7.89-7.88 (m, 1H), 7.40-7.24 (m, 5H), 6.87-6.83 (m, 2H), 5.47 (s, 1H), 4.28-4.27 (m, 1H), 3.94-3.91 (m, 1H), 3.58-3.53 (m, 2H) 3.17-3.15 (m, 2H), 2.62 (m, 3H), 2.40 (d, 1H), 1.87 (m, 1H), 1.60-1.58 (m, 2H), 1.46-1.23 (m, 2H).

MS: m/z=422.20 [M+1].

Example 20 Preparation of Compound I-020 Trifluoroacetate

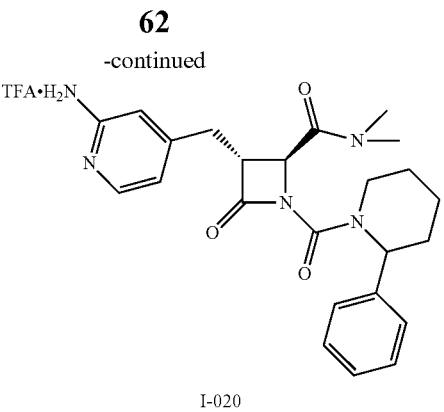

I-020

Compound I-020 trifluoroacetate was prepared according to the following scheme and method.

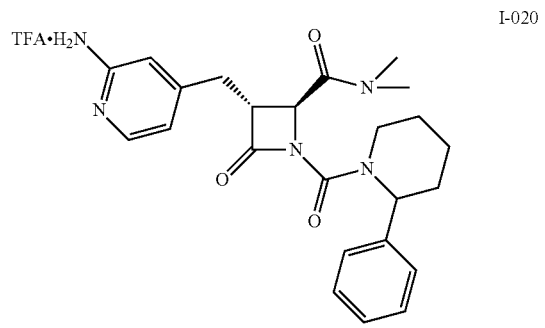

7d

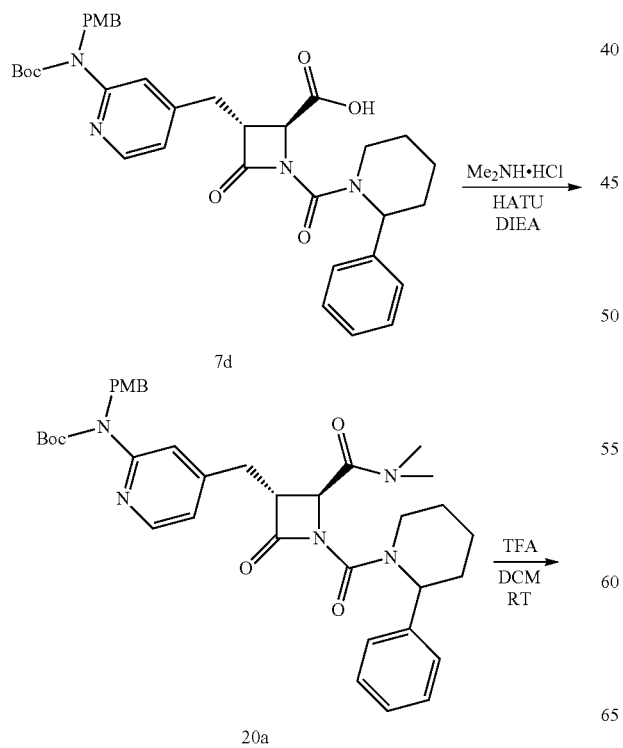

20a step 1): Compound 7d (70 mg) was dissolved in 5 mL of dichloromethane, and dimethylamine hydrochloride (10.6 mg), DIEA (20.0 mg), and HATU (50.0 mg) were added sequentially. The mixture was stirred at room temperature for 1 h. The reaction solution was directly subjected to rotary evaporation to dryness and purified by gel column chromatography to obtain compound 20a (75 mg).

step 2): Compound 20a (75 mg) was dissolved in 1 mL of dichloromethane and the solution was cooled down to 0° C. 1 mL of trifluoroacetic acid was added and the mixture was allowed to react at room temperature overnight. The reaction solution was directly subjected to rotary evaporation to dryness and purified by reverse-phase preparative HPLC to obtain compound I-020 trifluoroacetate (5.0 mg).

$^1$H-NMR (400 MHz, DMSO-d): 88.17 (brs, 2H), 7.91 (d, 1H), 7.40-7.24 (m, 5H), 6.93-6.87 (m, 2H), 5.47 (m, 1H), 4.90-4.88 (m, 1H), 3.92-3.88 (m, 1H), 3.28-3.17 (m, 2H), 2.99 (s, 3H), 2.90 (m, 1H), 2.87 (m, 3H), 2.42-2.38 (m, 1H), 1.87 (m, 1H), 1.59-1.46 (m, 2H), 1.35-1.24 (m, 2H).

MS: m/z 436.3 [M+1].

Example 21 Preparation of Compound I-021 Trifluoroacetate

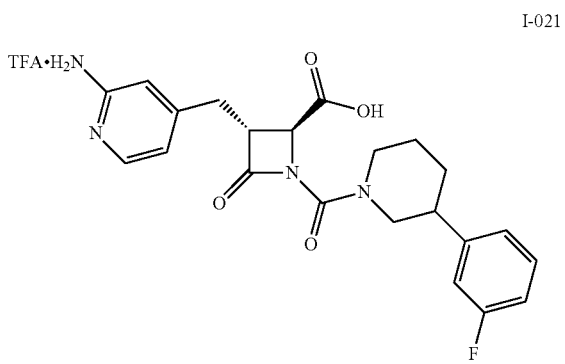

I-021

Compound I-021 trifluoroacetate was prepared according to the following scheme and method.

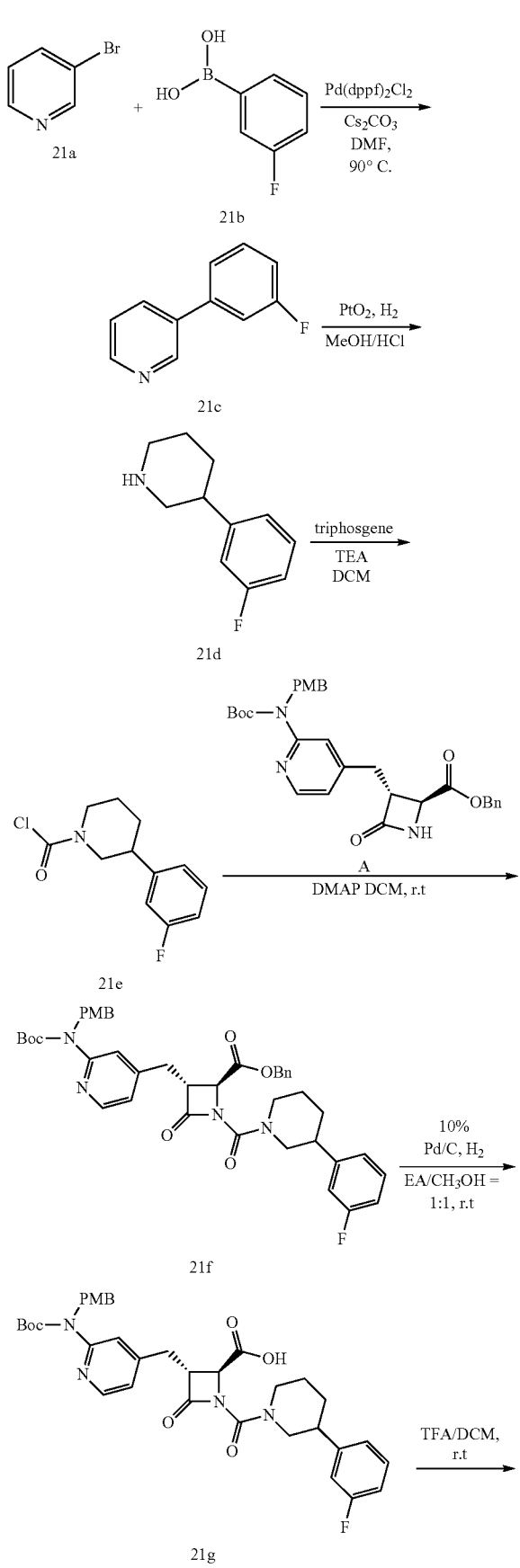
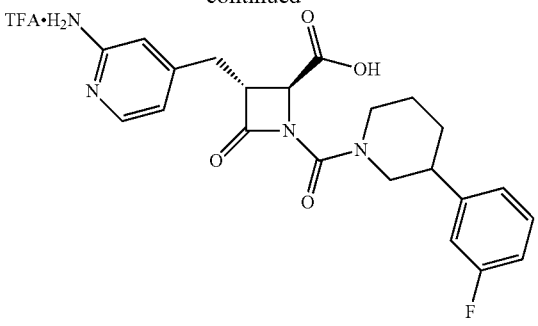

step 1): Compound 21a (7.05 g), compound 21b (4.8 g), Pd(dppf)Cl$_2$ (249 mg) and cesium carbonate (22.4 g) were added to 1,4-dioxane (140 ml) at room temperature. After the addition was completed, the mixture was pumped and ventilated with argon three times and stirred overnight at 90° C. under the protection of argon. After cooling down, the reaction solution was quenched with water, and extracted with ethyl acetate. The organic phase was dried, concentrated, and purified by silica gel column chromatography to obtain a yellow liquid. The obtained yellow liquid was dried over magnesium sulfate to obtain 5.1 g of yellow solid (i.e., compound 21c).

step 2): Compound 21c (5.3 g), PtO$_2$ (0.70 g), and concentrated HCl (9.2 mL) were charged into a hydrogenation reactor containing methanol (77 mL). The reactor was closed after the addition was completed. The mixture was pumped and ventilated with hydrogen three times and then stirred at room temperature for 6 hours under hydrogen (400 psi) atmosphere. PtO$_2$ was filtered out through celite. The reaction solution was concentrated under reduced pressure, and the residue was dissolved in ethyl acetate, washed with water three times, and dried over anhydrous magnesium sulfate to obtain 3.7 g of yellow solid (i.e., compound 21d).

step 3): Triethylamine (508 mg) was added to a solution of compound 21d (300 mg) in dichloromethane (10 mL). After cooling down to 0° C., triphosgene (249 mg) was added, and the mixture was stirred at room temperature under the protection of argon for about 1 hour (the reaction was completed as detected by LC MS). The reaction solution was then washed with ice water (10 mL) three times, and dried over anhydrous magnesium sulfate. Subsequently, triethylamine (79 mg), catalytic amount of DMAP and intermediate A (150 mg) were added. After the addition was completed, the mixture was stirred at room temperature for about 4 hours under the protection of argon. After the reaction was completed as detected by LC MS, 20 ml of water was added to the reaction system, and then the reaction mixture was extracted three times with ethyl acetate (20 mL). The combined organic phase was washed three times with water and dried over anhydrous sodium sulfate. The residue was purified by preparative silica gel chromatography (petroleum ether/ethyl acetate=10:1) to obtain 90 mg of white solid (i.e., compound 21f).

step 4): Pd/C (58 mg, w/w=50%, 10%) was added to a solution of compound 21f (105 mg) in ethyl acetate/methanol (3/3 mL). After the addition was completed, the mixture was pumped and ventilated three times and charged with hydrogen. The mixed system was stirred under hydrogen atmosphere for 2 hours. After the reaction was completed, the reaction solution was subjected to suction filtration and then concentrated to obtain 88 mg of white solid (i.e., compound 21g).

step 5): Compound 21g (100 mg) was added to a solution of TFA/DCM (3/3 mL) and the mixture was stirred at room temperature for about 3 hours. After the reaction was completed as detected by LC MS, the reaction solution was concentrated at room temperature and purified by reverse-phase preparative HPLC to obtain 26 mg of white solid (i.e., compound I-021 trifluoroacetate).

$^1$H NMR (400 MHz, DMSO-d): (7.87-7.86 (d, J=6.4, 1H), 7.52 (s, 2H), 7.38-7.36 (s, 1H), 7.16-7.14 (d, J=7.6, 2H), 7.09-7.06 (t, J=8.8, 1H), 6.79-6.78 (m, 2H), 4.29-4.24 (m, 1H), 4.06-3.98 (m, 2H), 3.71-3.67 (m, 1H), 3.10-3.08 (d, J=8.4, 2H), 3.03-2.93 (m, 2H), 2.84 (m, 1H), 2.68-2.61 (m, 1H), 1.95-1.92 (m, 1H), 1.79-1.73 (m, 2H), 1.50-1.47 (m, 1H).

LCMS: Rt=1.315 min, [M+H]$^+$=427.2.

Example 22 Preparation of Compound I-022 Trifluoroacetate

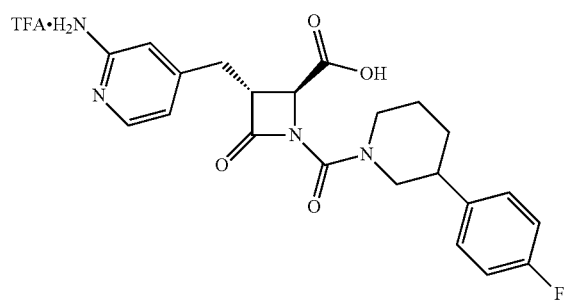

I-022

According to the method of Example 21, compound 21b was used instead of compound 21b to obtain 23 mg of white solid (i.e., compound I-022 trifluoroacetate).

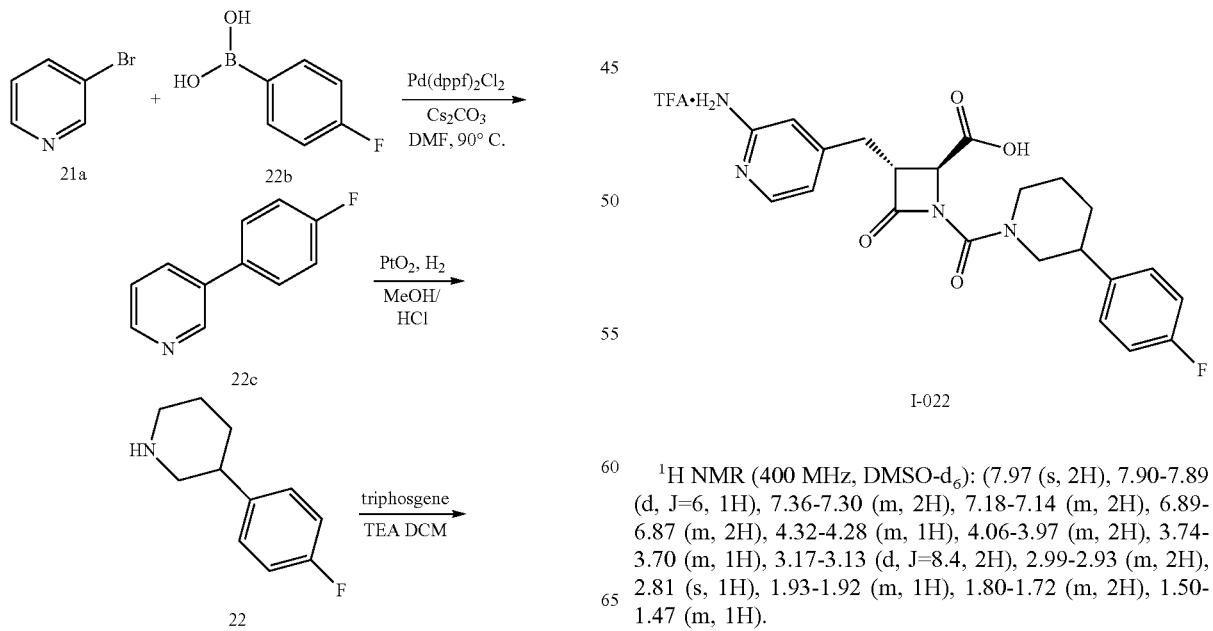

$^1$H NMR (400 MHz, DMSO-d$_6$): (7.97 (s, 2H), 7.90-7.89 (d, J=6, 1H), 7.36-7.30 (m, 2H), 7.18-7.14 (m, 2H), 6.89-6.87 (m, 2H), 4.32-4.28 (m, 1H), 4.06-3.97 (m, 2H), 3.74-3.70 (m, 1H), 3.17-3.13 (d, J=8.4, 2H), 2.99-2.93 (m, 2H), 2.81 (s, 1H), 1.93-1.92 (m, 1H), 1.80-1.72 (m, 2H), 1.50-1.47 (m, 1H).

LCMS: Rt=1.318 min, [M+H]$^+$=427.2.

Example 23 Preparation of Compound I-023 Trifluoroacetate

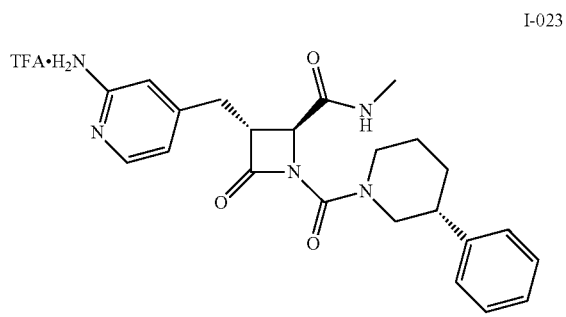

Compound I-023 trifluoroacetate was prepared according to the following scheme and method.

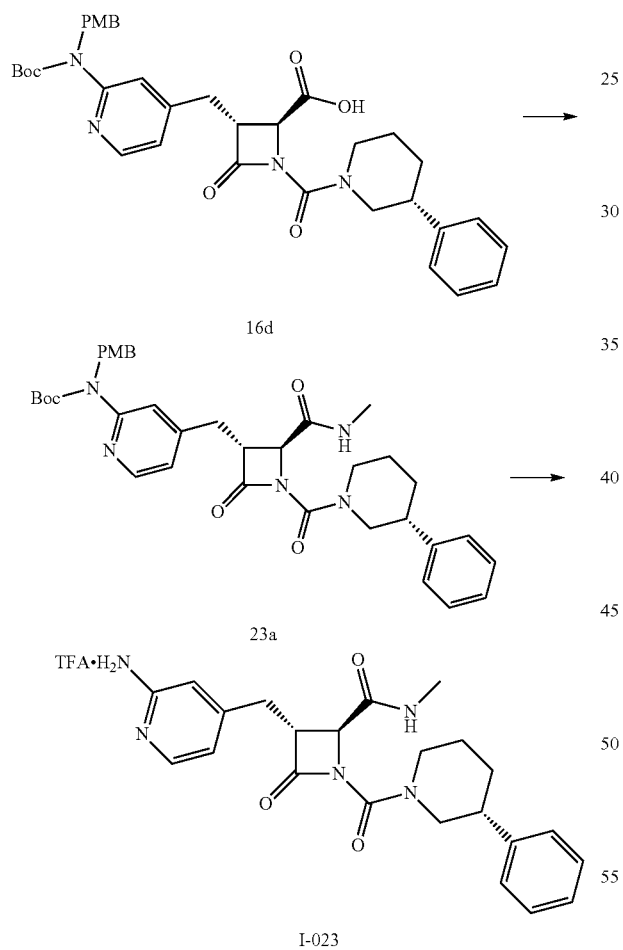

Under the protection of nitrogen, diisopropylethylamine (1.48 g) and HATU (2.72 g) were added to a solution (20 mL) of compound 16d (1.78 g) in dichloromethane. After stirring for 10 min in an ice water bath, a 2M solution of methylamine in tetrahydrofuran was added (2.86 mL). The mixture was stirred at this temperature for 2 hours. The reaction was quenched with water, and extracted with dichloromethane. The organic phase was concentrated and purified by normal-phase silica gel column chromatography (methanol/dichloromethane=1:100~1/50), and the resulting product was further purified by reverse-phase C-18 silica gel column chromatography (acetonitrile/water=30-95%) to obtain a 1.51 g of white solid (compound 23a).

Compound 23a (1.5 g) was added to a solution of TFA/DCM (30 mL/15 mL) and the mixture was stirred at 25° C. for 5 hours. The reaction was completed as detected by LCMS, and the reaction solution was concentrated at room temperature. The crude product was purified by C-18 reverse-phase column chromatography (5-95% acetonitrile/water (containing 0.1% TFA)) to obtain 1.17 of white solid (compound I-023 trifluoroacetate).

$^1$H NMR (400 MHz, DMSO-$d_6$): (13.51 (brs, 1H), 8.27-8.23 (m, 1H), 8.00 (brs, 2H) 7.87-7.85 (m, 1H), 7.35-7.31 (m, 2H), 7.29-7.22 (m, 3H), 6.84-6.83 (m, 2H), 4.19 (d, J=3.2 Hz, 1H), 4.07-4.00 (m, 2H), 3.54-3.49 (m, 1H), 3.13-3.11 (m, 2H), 3.02-2.95 (m, 1H), 2.93-2.88 (m, 1H), 2.67-2.64 (m, 1H), 2.62 (d, J=4.4 Hz, 3H), 1.95-1.87 (m, 1H), 1.79-1.68 (m, 2H), 1.64-1.54 (m, 1H).

LCMS: Rt=3.018 min, [M+H]$^+$=422.1.

Example 24 Preparation of Compound I-024 Trifluoroacetate

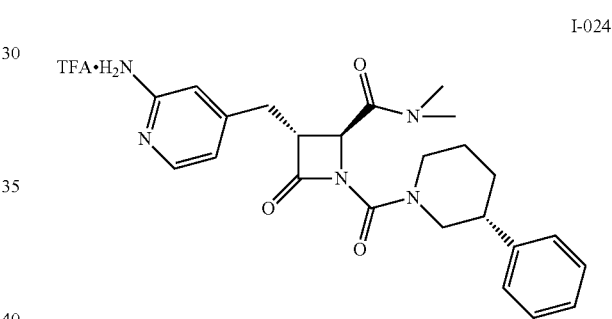

Compound I-024 trifluoroacetate was prepared according to the following scheme and method.

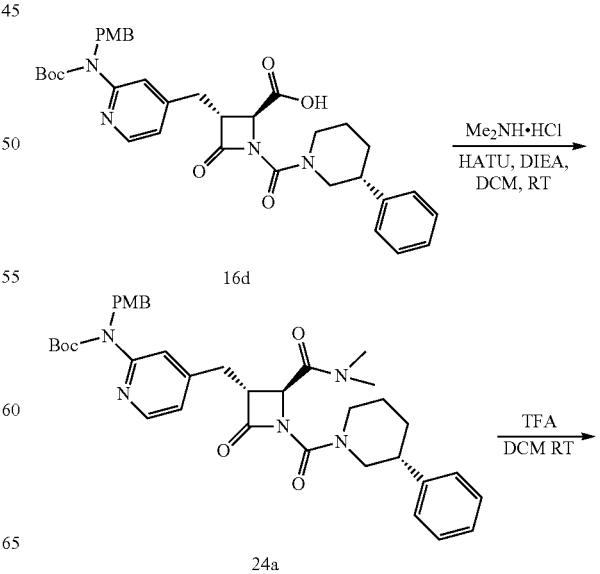

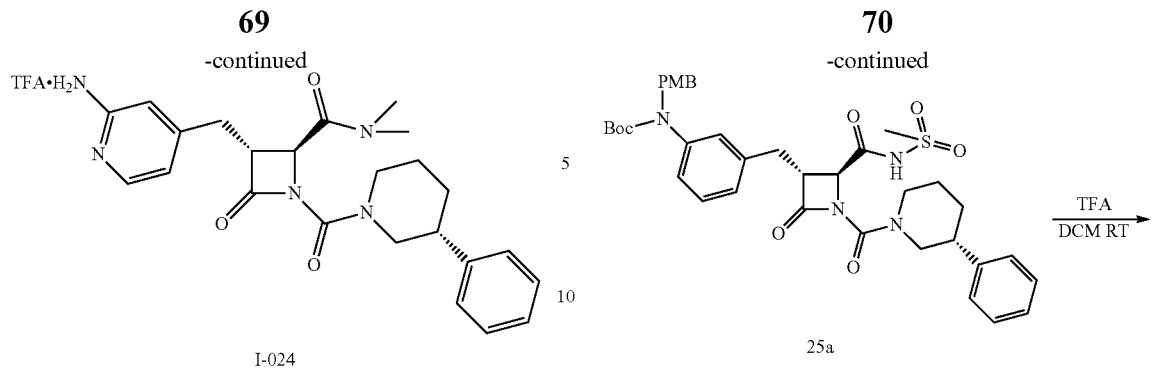

I-024 step 1): DIEA (54 mg), and HATU (82 mg) were added to a solution (20 mL) of compound 16d (90 mg) in dichloromethane. After stirring for 10 min, dimethylamine hydrochloride was added, and the mixture was stirred at room temperature for 1 hour. Then the reaction solution was concentrated and purified on a silica gel preparation plate to obtain 73 mg of colorless solid (i.e., compound 24a).

step 2): Compound 24a (73 mg) was added to a solution of TFA/DCM (3/3 mL) and the mixture was stirred at room temperature for about 3 hours. After the reaction was completed as detected by LC MS, the reaction solution was concentrated at room temperature and purified by reverse-phase preparative HPLC to obtain 35 mg of white solid (i.e., compound I-024 trifluoroacetate).

$^1$H NMR (400 MHz, CD$_3$OD): (7.79-7.77 (d, J=6.8, 1H), 7.29-7.28 (m, 4H), 7.27-7.20 (m, 1H), 6.95 (s, 1H), 6.90-6.88 (d, J=6.8, 1H), 4.21-4.16 (m, 2H), 3.65-3.61 (m, 1H), 3.31-3.30 (m, 2H), 3.19 (s, 3H), 3.00-2.91 (m, 7H), 2.03-2.00 (m, 1H), 1.90-1.78 (m, 2H), 1.65 (m, 1H).

LCMS: Rt=1.137 min, [M+H]$^+$=436.3.

Example 25 Preparation of Compound I-025 Trifluoroacetate

I-025

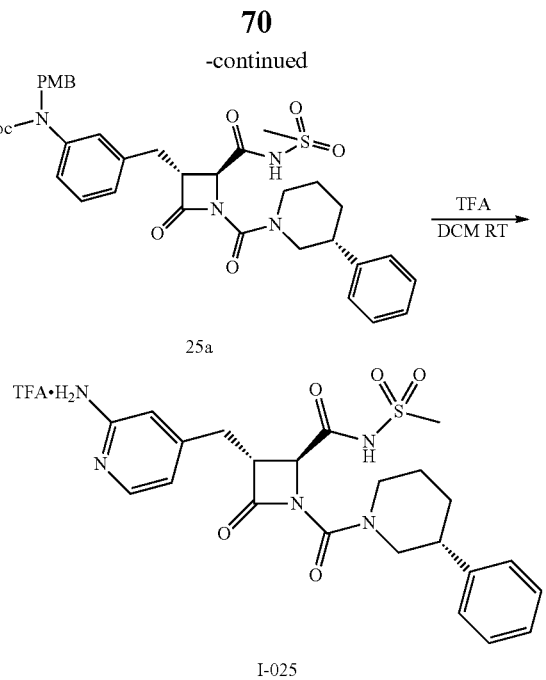

Compound I-025 trifluoroacetate was prepared according to the following scheme and method.

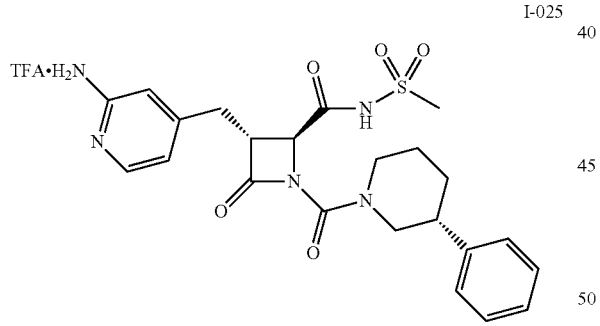

16d

I-025 step 1): DIEA (54 mg) and HATU (82 mg) were added to solution (20 mL) of compound 16d (90 mg) in dichloromethane. After stirring for 10 min, methylsulfonamide was added, and the mixture was stirred at room temperature for 1 hour. The reaction solution was concentrated and purified on a silica gel preparation plate to obtain 60 mg of colorless solid (i.e., compound 25a)

step 2): Compound 25a (60 mg) was added to a solution of TFA/DCM (3/3 mL) and the mixture was stirred at room temperature for about 3 hours. After the reaction was completed as detected by LC MS, the reaction solution was concentrated at room temperature and purified by reverse-phase preparative HPLC to obtain 27 mg of white solid (i.e., compound I-025 trifluoroacetate).

$^1$H NMR (400 MHz, CD$_3$OD): (7.78-7.76 (d, J=6.8, 1H), 7.29-7.28 (m, 4H), 7.23-7.20 (m, 1H), 6.95 (s, 1H), 6.90-6.88 (d, J=6.8, 1H), 4.34-4.33 (d, J=3.2, 1H), 4.23-4.17 (m, 2H), 3.72-3.70 (m, 1H), 3.30-3.22 (m, 5H), 3.00-2.85 (m, 4H), 2.00 (m, 1H), 1.86-1.80 (m, 2H), 1.66 (m, 1H).

LCMS: Rt=1.229 min, [M+H]$^+$=486.2.

Example 26 Preparation of Compound I-026 Hydrochloride

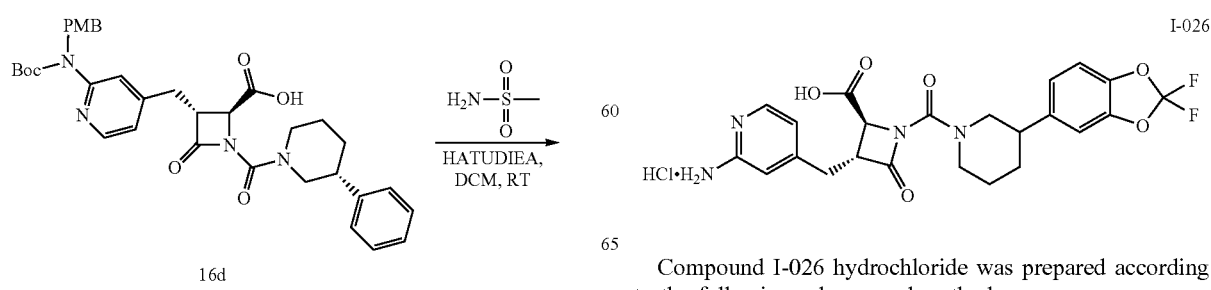

I-026

Compound I-026 hydrochloride was prepared according to the following scheme and method.

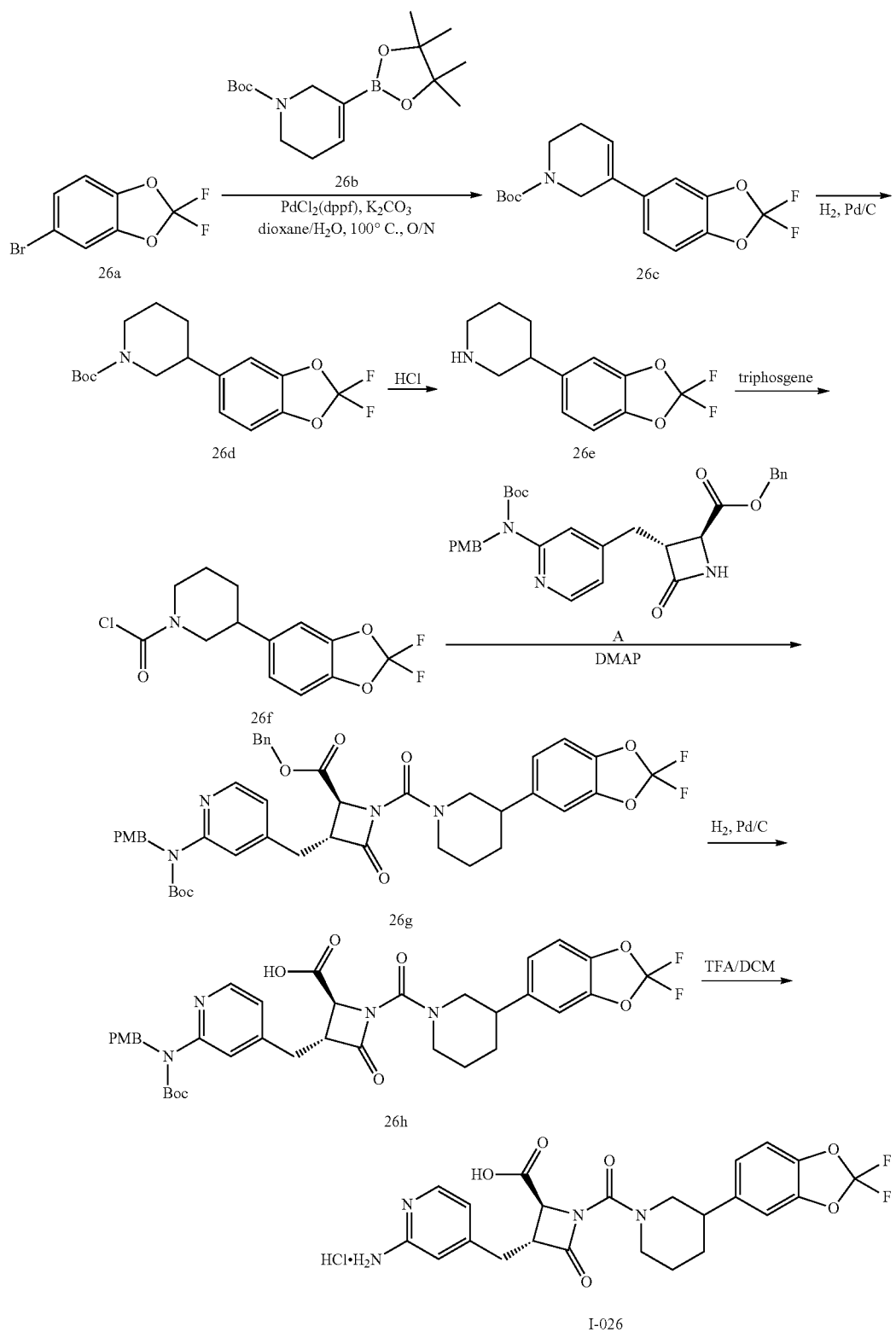

step 1): Compound 26a (1.46 g), compound 26b (2.0 g) and potassium carbonate (1.70 g) were dissolved in 20 mL of a mixed solvent of dioxane and water (10/1), and Pd(dppf)Cl₂ (450 mg) was added under the protection of nitrogen. The mixture was stirred in an oil bath at 80° C. for 90 minutes. The reaction solution was concentrated under reduced pressure. The resulting crude product was purified by silica gel column chromatography (petroleum ether/ethyl acetate=30:1-20:1) to obtain 1.86 g of yellow oil (compound 26c).

step 2): Pd/C (1 g, 10% wet) was added to a solution of compound 26c (1.86 g) in methanol (20 mL). After the addition was completed, the system was pumped and ventilated three times and charged with hydrogen. The reaction solution was stirred overnight at room temperature in hydrogen atmosphere. After the reaction was completed, the reaction solution was subjected to suction filtration and then concentrated to obtain 1.76 g of white solid (Compound 26d).

step 3): Compound 26d was dissolved in 5 mL of a solution of HCl in dioxane. The mixture was stirred at room temperature for 2 hours, and concentrated under reduced pressure. The resulting solid was diluted with 20 mL of ethyl acetate, washed with saturated aqueous sodium bicarbonate solution (3 mL) and brine (3 mL) successively. The organic phase was dried over anhydrous sodium sulfate and filtered. The filtrate was concentrated under reduced pressure to obtain 1.2 g of white solid (Compound 26e).

step 4): Diisopropylethylamine (642 mg) was added to a solution of compound 26e (400 mg) in dichloromethane (20 mL). After cooling down to 0° C., triphosgene (197 mg) was added in one portion. The mixture was stirred overnight at room temperature under the protection of nitrogen. Then, the reaction solution was washed three times with saturated aqueous sodium bicarbonate solution (5 mL), dried over anhydrous sodium sulfate, and directly used in the next step.

step 5): Diisopropylethylamine (146 mg), DMAP (46 mg) and intermediate A (200 mg) were added to the reaction solution obtained by the above post-treatment. After the addition was completed, the mixture was stirred at room temperature for 3 hours under the protection of argon. After the reaction was completed as detected by LC MS, 40 ml of water was added to the reaction system, the organic phase was separated, and the aqueous phase was extracted with dichloromethane (30 mL). The organic phases were combined, dried over anhydrous sodium sulfate, filtered, and concentrated under reduced pressure. The resulting crude product was purified by silica gel column chromatography (petroleum ether/ethyl acetate=2:1) to obtain 280 mg of white solid (compound 26g).

step 6): Pd/C (90 mg, 10% wet) was added to a solution of compound 26g (280 mg) in ethyl acetate/methanol (10 mL/10 mL). After the addition was completed, the mixture was pumped and ventilated with hydrogen three times and charged with hydrogen. Then, the reaction solution was stirred for 1 hour under hydrogen atmosphere. After the reaction was completed, the reaction solution was subjected to suction filtration, and the filtrate was concentrated to obtain 240 mg of white solid (Compound 26h).

step 7): Compound 26h (50 mg) was added to a solution of TFA/DCM (2 mL/2 mL), and the mixture was stirred at 25° C. for 3 hours. After the reaction was completed as detected by LC MS, the reaction solution was concentrated at room temperature. The resulting crude product was purified by C-18 Reverse-phase column chromatography (5-95% acetonitrile/water (containing 0.02% HCl)) to obtain 14.8 mg of white solid (i.e., compound I-026 hydrochloride).

$^1$H NMR (400 MHz, DMSO-$d_6$) δ 7.90-7.87 (m, 3H), 7.39-7.34 (m, 2H), 7.15-7.09 (m, 1H), 6.90-6.80 (m, 2H), 4.29 (dd, J=15.1, 3.4 Hz, 1H), 4.05-3.98 (m, 2H), 3.71 (d, J=2.9 Hz, 1H), 3.12 (dd, J=7.7, 4.0 Hz, 1H), 2.99-2.76 (m, 4H), 2.68-2.66 (m, 1H), 1.90-1.88 (m, 1H), 1.78-1.72 (m, 1H), 1.64-1.36 (m, 1H).

LCMS: Rt=3.761 min, [M+H]$^+$=488.9.

Example 27 Preparation of Compound I-027

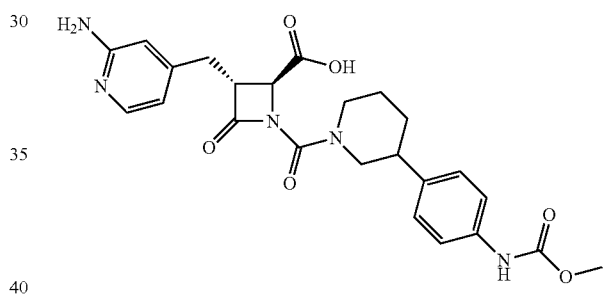

Compound I-027 was prepared according to the following scheme and method.

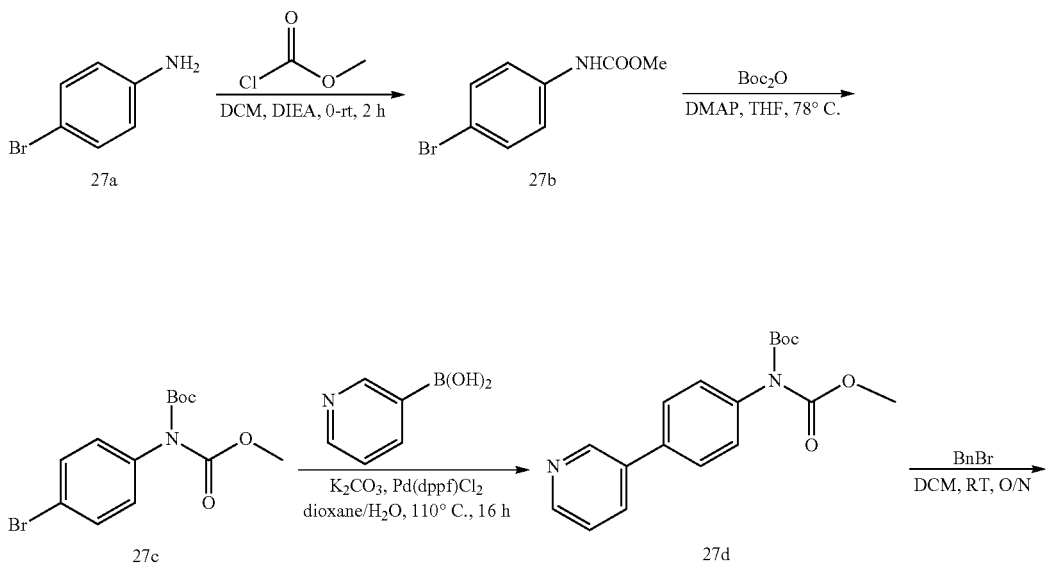

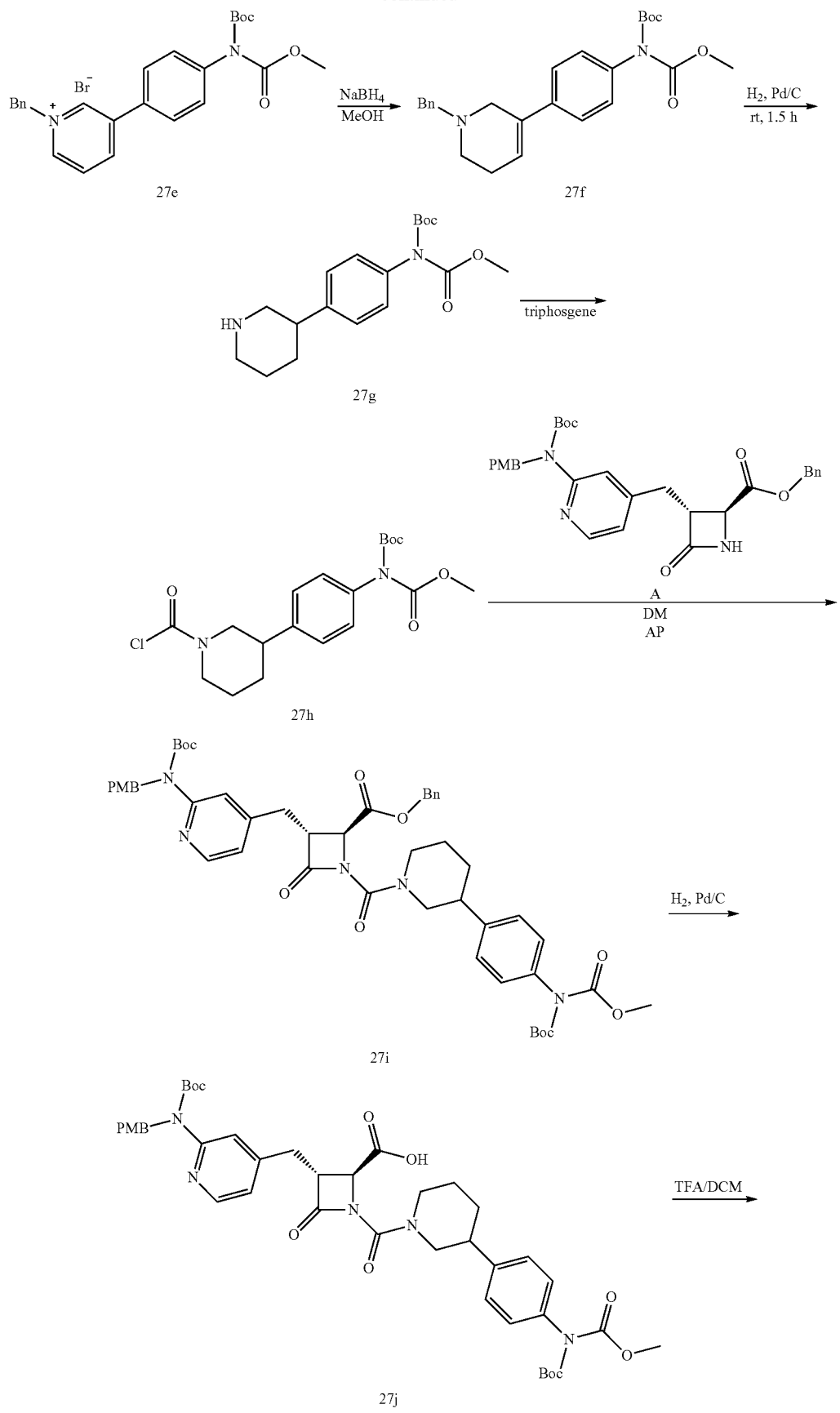

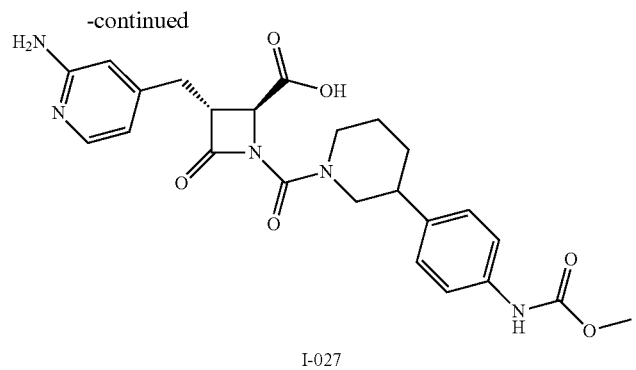

I-027 step 1): Compound 27a (3.44 g) was dissolved in 25 mL of anhydrous dichloromethane. A solution of methyl chloroformate (2.46 g) in dichloromethane (5 mL) was added dropwise at 0° C. under the protection of nitrogen. The reaction solution was stirred at room temperature for 1.5 hours. The reaction was quenched with water (30 mL) and extracted with dichloromethane (20 mL). The organic phase was washed with brine (30 mL), dried over anhydrous sodium sulfate, filtered, and concentrated under reduced pressure to obtain 6.01 g of light yellow solid (crude product, compound 27b).

step 2): Boc$_2$O (6.56 g) and DMAP (3.63 g) was added in sequence to a solution of compound 27b (5.77 g, crude) in tetrahydrofuran (125 mL). Under the protection of nitrogen, the mixture was stirred at 78° C. for 2 hours. The reaction solution was concentrated under reduced pressure, and the crude product was purified by silica gel column chromatography (petroleum ether/ethyl acetate=100:1~20:1) to obtain 4.4 g of pale yellow solid (compound 27c).

step 3): Compound 27c (5.0 g) compound pyridine-3-boronic acid (2.24 g) and potassium carbonate (3.13 g) was dissolved in a mixed solvent of dioxane and water (30 mL/3 mL). Pd(dppf)Cl$_2$ (260 g) was added under the protection of nitrogen. The mixture was stirred in an oil bath at 110° C. overnight. The reaction solution was filtered, and the filtrate was concentrated under reduced pressure. The crude product was purified by silica gel column chromatography (petroleum ether/ethyl acetate=20:1~) 3/1) to obtain 4.85 g of brown oil (compound 27d).

step 4): Compound 27d (3.2 g) was dissolved in 10 mL of anhydrous dichloromethane, benzyl bromide (4.16 g) was added under the protection of nitrogen, and the mixture was stirred overnight at room temperature. The reaction solution was concentrated under reduced pressure, and the resulting solid was dissolved in dichloromethane (20 mL). The organic phase was washed twice with water (50 mL), and the aqueous phase was freeze-dried to obtain 880 mg of yellow solid (compound 27e).

step 5): Sodium borohydride (160 mg) was added to a solution of compound 27e (880 mg, crude) in methanol (16 mL). The mixture was stirred at room temperature for 2 hours under the protection of nitrogen. The reaction solution was concentrated, diluted with water, and extracted with dichloromethane (30 mL) three times. The organic phases were combined, washed with brine (50 mL), dried over anhydrous sodium sulfate and filtered, and the filtrate was concentrated to obtain 586 mg of yellow oil. The resulting oil was dissolved in 10 mL of tetrahydrofuran, and Boc$_2$O (384 mg) and DMAP (215 mg) were added sequentially. The reaction solution was stirred at 78° C. for 2.5 hours. The reaction solution was concentrated, diluted with water, and extracted with dichloromethane (50 mL). The organic phase was washed with brine, dried over anhydrous sodium sulfate and filtered. The filtrate was concentrated under reduced pressure. The crude product was purified by silica gel column chromatography (dichloromethane/methanol=50:1~20:1) to obtain 620 mg of yellow solid (compound 27f).

step 6): Pd/C (350 mg, 10% wet) was added to a solution of compound 27f (720 mg) in methanol (15 mL). After the addition was completed, the system was pumped and ventilated three times and charged with hydrogen. The mixed system was stirred in hydrogen atmosphere at 30° C. for 1.5 hours. After the reaction was completed, the reaction solution was subjected to suction filtration, and the filtrate was concentrated to obtain 550 mg of yellow oil (compound 27g).

step 7): Diisopropylethylamine (139 mg) was added to a solution of compound 27g (120 mg) in dichloromethane (7 mL). After cooling down to 0° C., triphosgene (51 mg) was added in one portion. The mixture was stirred at room temperature under the protection of nitrogen for 3 hours. The reaction solution was washed once with saturated aqueous sodium bicarbonate solution (4 mL) which was cooled with ice water, dried over anhydrous sodium sulfate and filtered, and the filtrate was directly used in the next step.

step 8): Diisopropylethylamine (28 mg), DMAP (9 mg) and intermediate A (74 mg) was added to the reaction solution obtained by the above post-treatment. After the addition was completed, the mixture was stirred at room temperature under the protection of argon overnight. The reaction was completed as detected by LC MS. Then, the reaction was quenched with water (3 mL), and extracted with dichloromethane (4 mL) three times. The organic phases were combined, dried over anhydrous sodium sulfate, filtered, and concentrated under reduced pressure. The above two steps were repeated by using intermediate A (149 mg). The two batches of the obtained crude product were combined and purified by silica gel column chromatography (petroleum ether/ethyl acetate=2:1) to obtain 570 mg of white solid (compound 27i).

step 9): Pd/C (115 mg, 10% wet) was added to a solution of compound 27i (330 mg) in ethyl acetate/methanol (5 mL/5 mL). After the addition was completed, the mixed system was pumped and ventilated three times and charged with hydrogen, stirred under hydrogen atmosphere for 3 hours. After the reaction was completed, the reaction mixture was subjected to suction filtration and concentrated to obtain 270 mg of white solid (compound 27j).

step 10): Compound 27j (250 mg) was added to a solution of TFA/DCM (5 mL/2.5 mL), and the mixture was stirred for 3 hours at 25° C. After the reaction was completed as detected by LC MS, the reaction solution was concentrated at room temperature. The crude product was purified by reverse-phase preparative HPLC (5-95% acetonitrile/water) to obtain 58.1 mg of white solid (i.e., compound I-027).

$^1$H NMR (400 MHz, DMSO-d$_6$): (9.59 (s, 1H), 7.79-7.76 (m, 1H), 7.38 (d, J=8.0 Hz, 2H), 7.20-7.16 (m, 2H), 6.44-6.41 (m, 1H), 6.34 (s, 1H), 5.95 (s, 2H), 4.13 (d, J=18.4 Hz, 1H), 4.03-3.94 (m, 2H), 3.65 (s, 3H), 3.55-3.50 (m, 1H), 2.88-2.84 (m, 4H), 2.72-2.59 (m, 1H), 1.88-1.86 (m, 1H), 1.76-1.67 (m, 2H), 1.57-1.46 (m, 1H).

LCMS: Rt=2.779 min, [M+H]$^+$=482.0.

Example 28 Preparation of Compound I-028 Hydrochloride

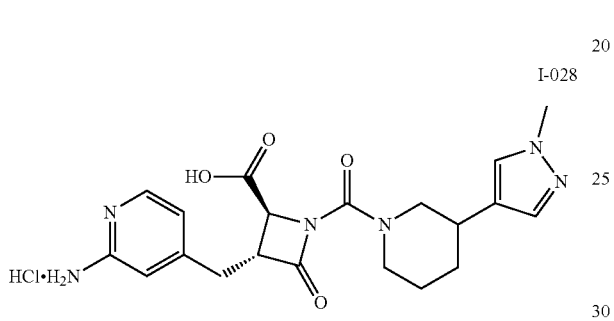
I-028

Compound I-028 hydrochloride was prepared according to the following scheme and method.

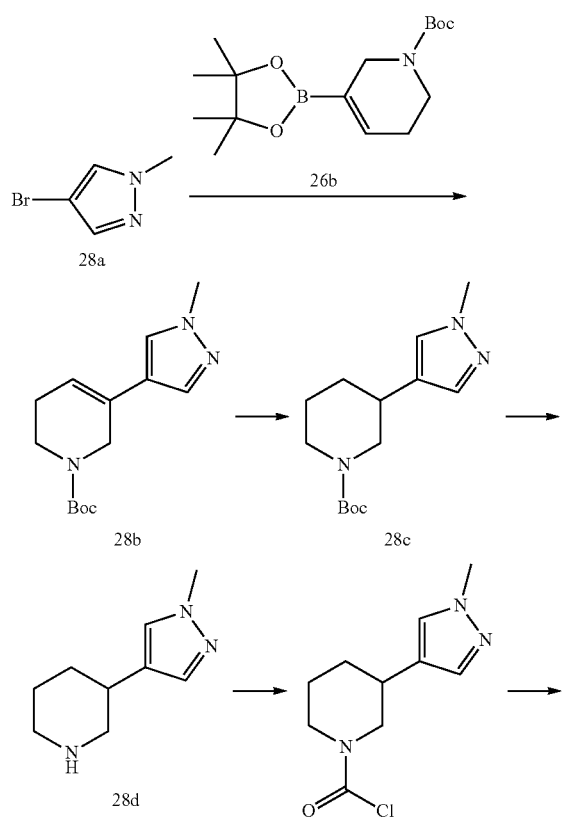

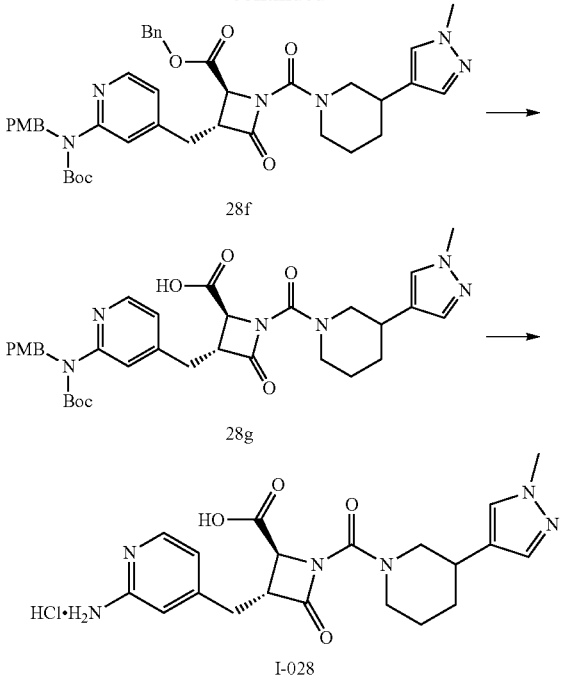

step 1): Compound 28a (868 mg), compound 26b (2.0 g) and potassium carbonate (1.08 g) was dissolved in 11 mL of mixed solvent of dioxane and water (10/1). Pd(dppf)Cl$_2$ (120 mg) was added, and the reaction solution was stirred overnight at 110° C. under the protection of nitrogen. The reaction solution was concentrated under reduced pressure, and the resulting crude product was purified by silica gel column chromatography (petroleum ether/ethyl acetate=4:1) to obtain a pale yellow oil 1.26 g (Compound 28b).

step 2): Pd/C (1.0 g, 10% wet) was added to a solution of compound 28b (1.59 g) in methanol (20 mL). After the addition was completed, the system was pumped and ventilated three times and charged with hydrogen. The mixed system was stirred at room temperature under hydrogen atmosphere. After the reaction was completed, the reaction mixture was subjected to suction filtration, and the filtrate was concentrated to obtain 1.41 g of light yellow oil (compound 28c).

step 3): Compound 28c (1.41 g) was dissolved in a solution of HCl (2N, 5 mL) in dioxane. The mixture was stirred at room temperature for 3 hours and concentrated under reduced pressure. The solid was diluted with ethyl acetate and washed with dilute ammonia solution to pH>8. The organic phase was dried over anhydrous sodium sulfate and filtered. The filtrate was concentrated under reduced pressure to obtain 800 mg of light yellow oil (Compound 28d).

step 4): Diisopropylethylamine (469 mg) was added to a solution of compound 28d (200 mg) in dichloromethane (10 mL). After cooling down to 0° C., triphosgene (180 mg) was added. Under the protection of nitrogen, the reaction mixture was stirred at room temperature overnight. The reaction solution was washed four times with saturated sodium bicarbonate aqueous solution (10 mL), dried over sodium sulfate and filtered. The filtrate was directly used in the next step.

step 5): Diisopropylethylamine (155 mg), DMAP (44 mg) and intermediate A (191 mg) was added to the reaction solution obtained by the above post-treatment. After the addition was completed, the mixture was stirred at room temperature for 2 hours under the protection of nitrogen. The reaction was completed as detected by LC MS. 10 ml of water was added to the reaction system. The organic phase was separated, and the aqueous phase was extracted with dichloromethane. The organic phases were combined, dried over anhydrous sodium sulfate, filtered, and concentrated under reduced pressure. The resulting crude product was purified by silica gel column chromatography (petroleum ether/ethyl acetate=1:1) to obtain 199 mg of white solid (compound 28f).

step 6): Pd/C (60 mg, 10% wet) was added to a solution of compound 28f (199 mg) in ethyl acetate/methanol (4 mL/4 mL). After the addition was completed, the mixed system was pumped and ventilated three times and charged with hydrogen, and was stirred at room temperature for 1 hour under hydrogen atmosphere. After the reaction was completed, the reaction mixture was subjected to suction filtration, and the filtrate was concentrated to obtain 135 mg of a white solid (compound 28g).

step 7): Compound 28g (65 mg) was added to a solution of TFA/DCM (8 mL/2 mL), and the mixture was stirred at 30° C. for 2 hours. After the reaction was completed as detected by LC MS, the reaction solution was concentrated at room temperature, and purified by C-18 reverse-phase column chromatography (5-95% acetonitrile/water (containing 0.02% HCl)) to obtain 40 mg of white solid (i.e., compound I-028 hydrochloride).

$^1$H NMR (400 MHz, DMSO-d$_6$): (14.04 (s, 1H), 8.19 (s, 2H), 7.92 (d, J=5.6 Hz, 1H), 7.56 (s, 1H), 7.33 (s, 1H), 6.94 (s, 1H), 6.88 (d, J=6.4 Hz, 1H), 4.32-4.27 (m, 1H), 4.05 (s, 2H), 3.78 (s, 3H), 3.71 (d, J=9.2 Hz, 1H), 3.14 (d, J=7.2 Hz, 2H), 2.97-2.68 (m, 2H), 2.57 (s, 1H), 1.99-1.96 (m, 1H), 1.76-1.73 (m, 1H), 1.58-1.56 (m, 2H).

LCMS: Rt=2.475 min. [M+H]$^+$=413.

Example 29 Preparation of Compound I-029 Trifluoroacetate

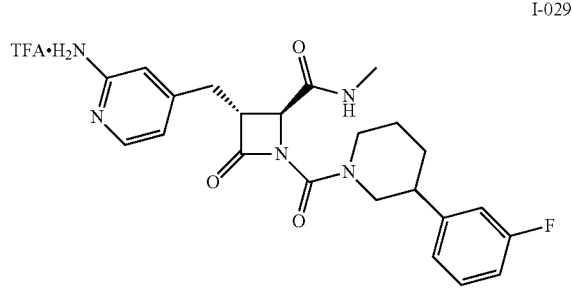

I-029

Compound I-029 trifluoroacetate was prepared according to the following scheme and method.

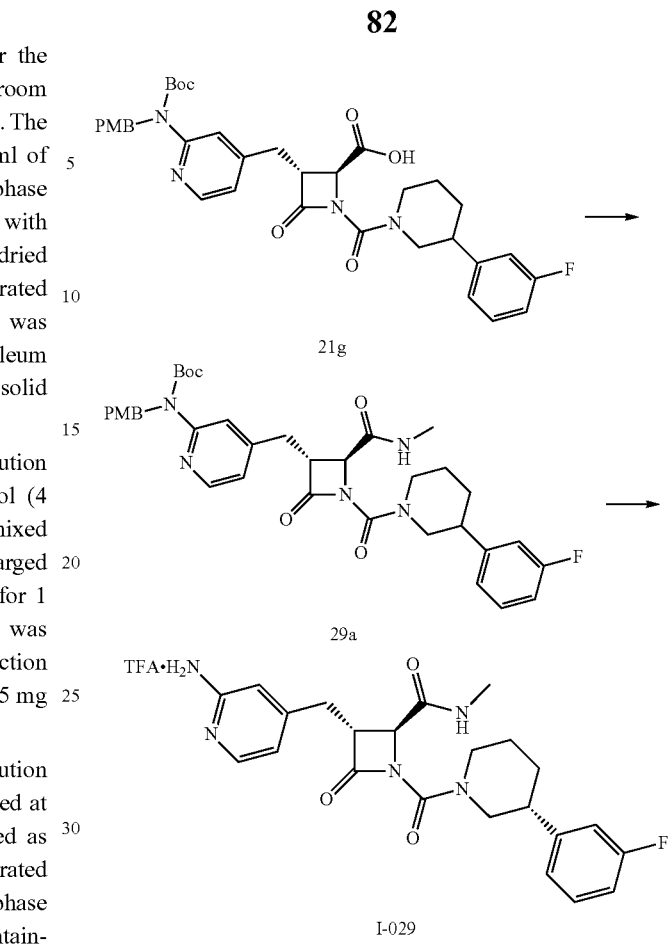

step 1): DIEA (174 mg) and HATU (215 mg) were added to a solution (3 mL) of compound 21g (290 mg, crude product) in dichloromethane. The mixture was stirred at 0° C. for 20 min, and a solution (0.45 mL) of methylamine in tetrahydrofuran was added. The reaction solution was further stirred at 0° C. for 6 hours. The reaction solution was diluted with dichloromethane (20 mL), and then washed successively with saturated aqueous ammonium chloride solution (10 mL) and saturated brine (10 mL). The organic phase was dried over anhydrous sodium sulfate and filtered. The filtrate was concentrated under reduced pressure, and the resulting crude product was purified by silica gel column chromatography (methanol/dichloromethane=1:25) to obtain 149 mg of white solid (Compound 29a).

step 2): Compound 29a (149 mg) was added to a solution of TFA/DCM (3 mL/1.5 mL). After being stirred at room temperature for about 2 hours, the reaction was completed as detected by LC MS. The reaction solution was concentrated at room temperature, and the resulting crude product was purified by reverse-phase preparative HPLC to obtain 78 mg of white solid (i.e., compound I-029 trifluoroacetate).

$^1$H NMR (400 MHz, DMSO-d$_6$): (13.41 (brs, 1H), 8.26-8.20 (m, 1H), 7.98 (s, 2H), 7.88-7.85 (m, 1H), 7.40-7.35 (m, 1H), 7.16-7.14 (m, 2H), 7.09-7.05 (m, 1H), 6.86-6.84 (m, 2H), 4.21-4.19 (m, 1H), 4.19-4.01 (m, 2H), 3.54-3.50 (m, 1H), 3.14-3.11 (m, 2H), 2.98-2.87 (m, 2.6H), 2.86-2.73 (m, 0.4H), 2.61 (dd, J=12.8, 4.8 Hz, 3H), 1.94-1.91 (m, 1H), 1.82-1.69 (m, 2H), 1.64-1.42 (m, 1H).

LCMS: Rt=3.196 min, [M+H]$^+$=440.2.

Example 30 Preparation of Compound I-030

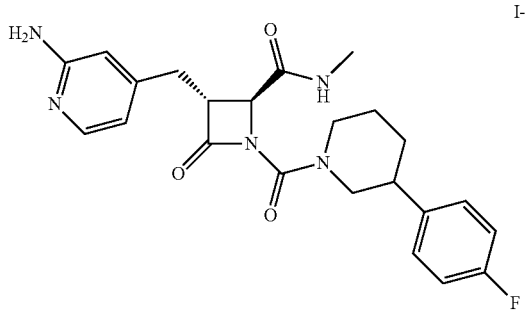

Compound I-030 was prepared according to the following scheme and method.

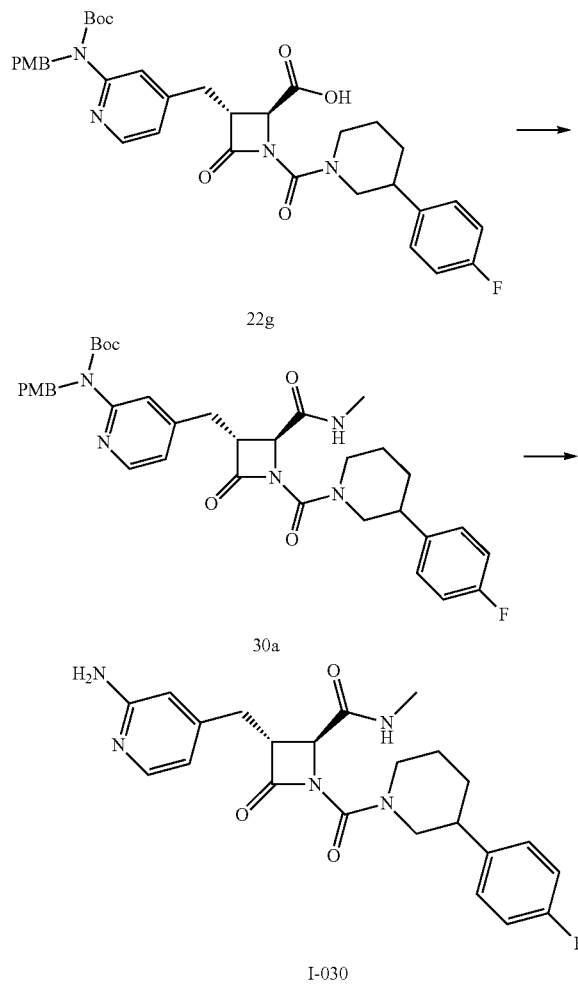

step 1): DIEA (81 mg) and HATU (120 mg) was added to a solution of compound 22g (136 mg) in dichloromethane (3 mL), and the mixture was stirred at 0° C. for 30 min. A solution (0.21 mL) of methylamine in tetrahydrofuran was added. The reaction solution was stirred at 0° C. for 2 hours, and then quenched with water. The organic phase was separated, dried over anhydrous sodium sulfate and filtered, and the filtrate was concentrated under reduced pressure. The resulting crude product was purified by silica gel column chromatography (methanol/dichloromethane=1:20) to obtain 106 mg of white solid (compound 30a).

step 2): Compound 30a (106 mg) was added to a solution of TFA/DCM (6 mL/2 mL), and the mixture was stirred at room temperature for about 2 hours. After the reaction was completed as detected by LC MS, the reaction solution was concentrated at room temperature, and purified by a C-18 reverse-phase column chromatography (5-95% acetonitrile/water) to obtain 31.4 mg of white solid (compound I-030).

$^1$H NMR (400 MHz, DMSO-$d_6$): (8.26-8.21 (m, 1H), 7.81 (t, J=6.0 Hz, 1H), 7.35-7.31 (m, 2H), 7.15 (t, J=8.8 Hz, 2H), 6.57 (t, J=5.6 Hz, 3H), 6.49 (d, J=4.4 Hz, H), 4.19-4.16 (m, 1H), 4.05-3.97 (m, 2H), 3.42-3.40 (m, 1H), 2.97-2.80 (m, 4H), 2.66 (s, 1H), 2.63-2.58 (m, 3H), 1.89-1.87 (m, 1H), 1.81-1.69 (m, 2H), 1.57-1.46 (m, 1H).

LCMS: Rt=2.772 min, [M+H]$^+$=440.

Example 31 Preparation of Compound I-031

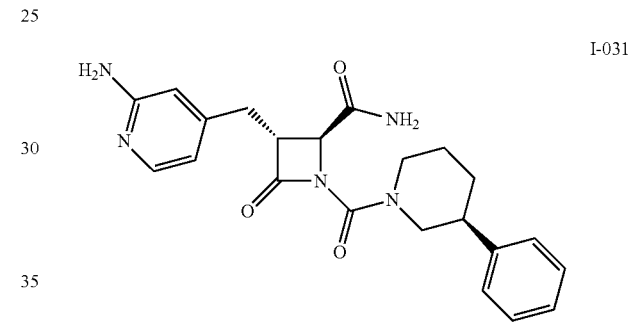

Compound I-031 was prepared according to the following scheme and method.

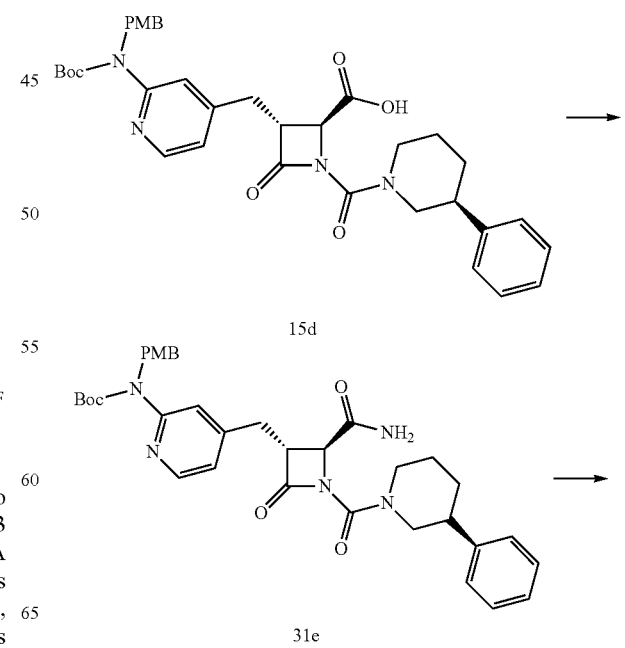

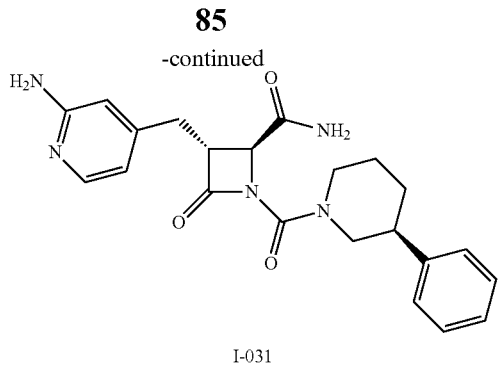

I-031 step 1): Under the protection of nitrogen, diisopropylethylamine (69.7 mg) and HATU (90.7 mg) were added to a solution (10 mL) of compound 15d (100 mg) in dichloromethane. The mixture was stirred at 0° C. for 10 min and then ammonium chloride (17.0 mg) was added. The reaction solution was further stirred at 0° C. for 2 hours. The reaction was quenched with 2 mL of water and extracted three times with dichloromethane (4 mL). The organic phases were combined and concentrated, and then purified by C-18 reverse-phase column chromatography (50-90% acetonitrile/water) to obtain 62 mg of white solid (compound 31e).

step 2): Compound 31e (62 mg) was added to a solution of TFA/DCM (2 mL/1 mL), and the mixture was stirred for 2 hours at 25° C. After the reaction was completed as detected by LC MS, the reaction solution was concentrated at room temperature, and the residue was dissolved in 1 mL of DMF and then purified by C-18 reverse-phase column chromatography (5-95% acetonitrile/water) to obtain 13.1 mg of white solid (compound I-031).

$^1$H NMR (400 MHz, DMSO-d$_6$): (7.79 (d, J=5.2 Hz, 1H), 7.67 (s, 1H), 7.35-7.29 (m, 5H), 7.25-7.20 (m, 1H), 6.45 (d, J=5.2 Hz, 1H), 6.35 (s, 1H), 5.89 (s, 2H), 4.18 (d, J=3.2 Hz, 1H), 4.03 (t, 2H), 3.37-3.35 (m, 1H), 2.94-2.87 (m, 4H), 2.83-2.74 (m, 1H), 1.92-1.89 (m, 1H), 1.81-1.68 (m, 2H), 1.53-1.43 (m, 1H).

LCMS: Rt=3.835 min, [M+H]$^+$=408.1.

Example 32 Preparation of Compound I-032 Hydrochloride

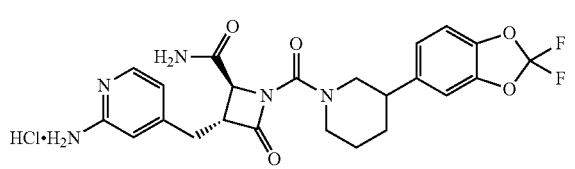

I-032

Compound I-032 hydrochloride was prepared according to the following scheme and method.

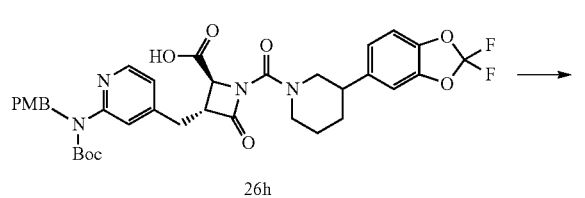

26h

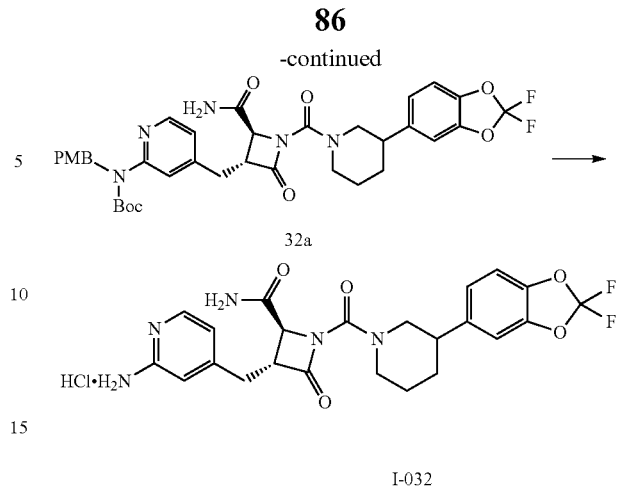

32a

I-032 step 1): Under the protection of nitrogen, diisopropylethylamine (51.9 mg) and HATU (76.4 mg) were added to a solution of compound 26h (95 mg) in dichloromethane (5 mL). After stirring at 0° C. for 10 min, chlorination ammonium (14.3 mg) was added. The mixture was stirred at 0° C. for 2 hours. The reaction was quenched with saturated aqueous sodium bicarbonate, and then water was added. The reaction mixture was extracted with dichloromethane. The organic phases were combined and concentrated, and then purified by silica gel column chromatography (methanol/dichloromethane=1/20) to obtain 90 mg of white solid (compound 32a).

step 2): Compound 32a (90 mg) was added to a solution of TFA/DCM (4 mL/2 mL), and the mixture was stirred at 20° C. for about 3 hours. After the reaction was completed as detected by LC MS, the reaction solution was concentrated at room temperature, and purified by C-18 reverse-phase column chromatography (5-95% acetonitrile/0.02% aqueous hydrochloric acid) to obtain 59 mg of white solid (i.e., compound I-032 hydrochloride).

$^1$H NMR (400 MHz, DMSO-d$_6$) δ 13.63-13.46 (m, 1H), 8.01 (s, 2H), 7.88 (d, J=3.8 Hz, 1H), 7.80-7.68 (m, 1H), 7.40 (d, J=1.6 Hz, 1H), 7.36 (d, J=8.3 Hz, 1H), 7.31 (d, J=12.5 Hz, 1H), 7.18-7.07 (m, 1H), 6.87 (dd, J=6.1, 1.8 Hz, 2H), 4.20 (t, J=3.1 Hz, 1H), 4.04-3.98 (m, 2H), 3.50 (d, J=3.4 Hz, 1H), 3.13 (dd, J=7.6, 3.2 Hz, 2H), 3.02-2.81 (m, 2H), 2.77-2.60 (m, 1H), 1.98-1.83 (m, 1H), 1.79-1.71 (m, 2H), 1.62-1.38 (m, 1H).

LCMS: Rt=2.985. [M+H]$^+$=487.9.

Example 33 Preparation of Compound I-033

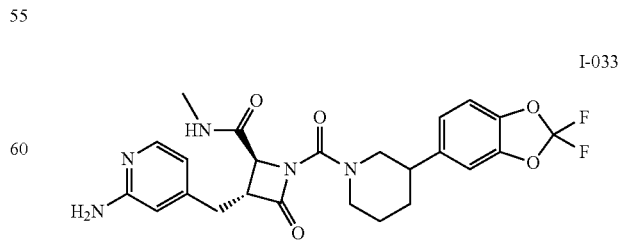

I-033

Compound I-033 was prepared according to the following scheme and method.

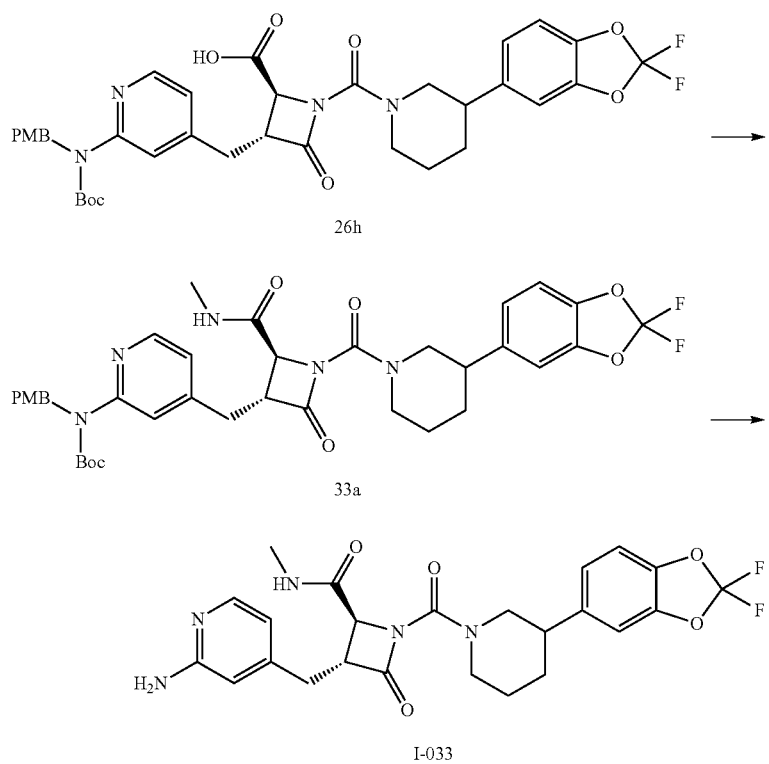

step 1): Under the protection of nitrogen, dinitropropylethylamine (51.9 mg) and HATU (76.4 mg) were added to a solution (5 mL) of compound 26h (95 mg) in dichloromethane, and the mixture was stirred at 0° C. for 10 min. A solution (0.134 mL) of methylamine in tetrahydrofuran was diluted with 0.5 mL of anhydrous dichloromethane, and then added to the reaction system at 0° C. The mixture was stirred at this temperature for 2 hours. The reaction was quenched with saturated aqueous sodium bicarbonate solution, and then water was added. The reaction mixture was extracted with dichloromethane. The organic phase were combined, concentrated, and purified by silica gel column chromatography (methanol/dichloromethane=1/20) to obtain 60 mg of colorless transparent solid (compound 33a).

step 2): Compound 33a (60 mg) was added to a solution of TFA/DCM (4 mL/2 mL), and the mixture was stirred for 3 hours at 20° C. After the reaction was completed as detected by LC MS, the reaction solution was concentrated at room temperature, and the residue was dissolved in 1 mL of DMF and purified by C18 reverse-phase column chromatography (5-95% acetonitrile/water) to obtain 28.1 mg of white solid (i.e., compound I-033).

$^1$H NMR (400 MHz, DMSO-d$_6$) δ 8.31-8.17 (m, 1H), 7.85-7.71 (m, 1H), 7.39-7.34 (m, 2H), 7.19-7.06 (m, 1H), 6.53-6.42 (m, 1H), 6.43 (d, J=1.6 Hz, H), 6.6.18 (brs, 2H), 4.23-4.15 (m, 1H), 4.09-3.89 (m, 2H), 3.44-3.36 (m, 1H), 3.03-2.75 (m, 4H), 2.78-2.754 (m, 1H), 2.61 (dd, J=11.7, 4.5 Hz, 3H), 2.00-1.82 (m, 1H), 1.88-1.78 (m, 2H), 1.62-1.37 (m, 1H).

LCMS: Rt=3.050 min, [M+H]$^+$=502.0.

Example 34 Preparation of Compound I-034 Trifluoroacetate

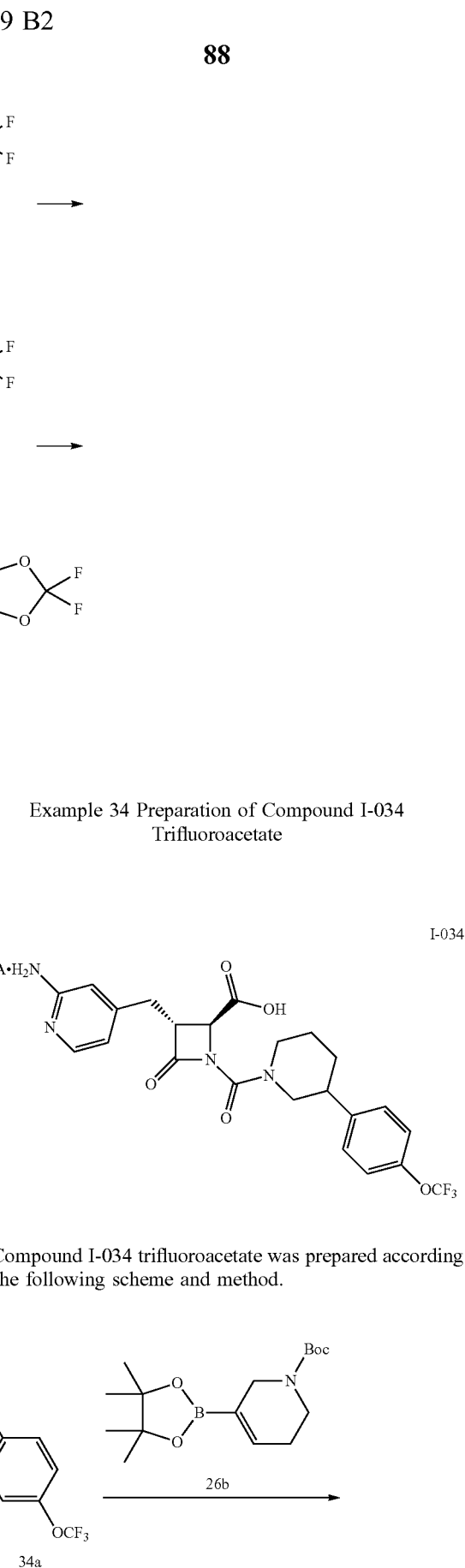

Compound I-034 trifluoroacetate was prepared according to the following scheme and method.

89

-continued

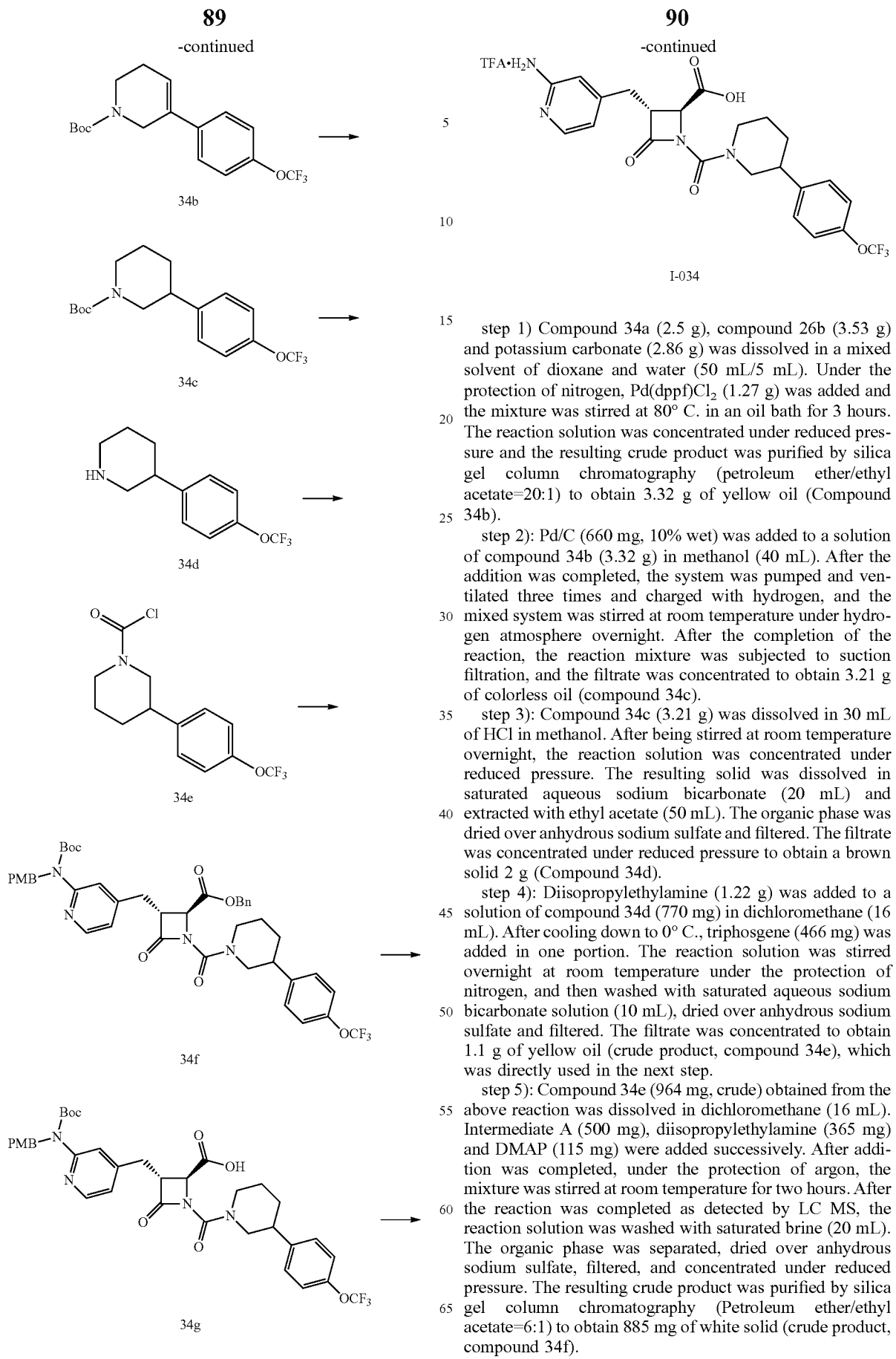

34b

34c

34d

34e

34f

34g

90

-continued

I-034 step 1) Compound 34a (2.5 g), compound 26b (3.53 g) and potassium carbonate (2.86 g) was dissolved in a mixed solvent of dioxane and water (50 mL/5 mL). Under the protection of nitrogen, Pd(dppf)Cl$_2$ (1.27 g) was added and the mixture was stirred at 80° C. in an oil bath for 3 hours. The reaction solution was concentrated under reduced pressure and the resulting crude product was purified by silica gel column chromatography (petroleum ether/ethyl acetate=20:1) to obtain 3.32 g of yellow oil (Compound 34b).

step 2): Pd/C (660 mg, 10% wet) was added to a solution of compound 34b (3.32 g) in methanol (40 mL). After the addition was completed, the system was pumped and ventilated three times and charged with hydrogen, and the mixed system was stirred at room temperature under hydrogen atmosphere overnight. After the completion of the reaction, the reaction mixture was subjected to suction filtration, and the filtrate was concentrated to obtain 3.21 g of colorless oil (compound 34c).

step 3): Compound 34c (3.21 g) was dissolved in 30 mL of HCl in methanol. After being stirred at room temperature overnight, the reaction solution was concentrated under reduced pressure. The resulting solid was dissolved in saturated aqueous sodium bicarbonate (20 mL) and extracted with ethyl acetate (50 mL). The organic phase was dried over anhydrous sodium sulfate and filtered. The filtrate was concentrated under reduced pressure to obtain a brown solid 2 g (Compound 34d).

step 4): Diisopropylethylamine (1.22 g) was added to a solution of compound 34d (770 mg) in dichloromethane (16 mL). After cooling down to 0° C., triphosgene (466 mg) was added in one portion. The reaction solution was stirred overnight at room temperature under the protection of nitrogen, and then washed with saturated aqueous sodium bicarbonate solution (10 mL), dried over anhydrous sodium sulfate and filtered. The filtrate was concentrated to obtain 1.1 g of yellow oil (crude product, compound 34e), which was directly used in the next step.

step 5): Compound 34e (964 mg, crude) obtained from the above reaction was dissolved in dichloromethane (16 mL). Intermediate A (500 mg), diisopropylethylamine (365 mg) and DMAP (115 mg) were added successively. After addition was completed, under the protection of argon, the mixture was stirred at room temperature for two hours. After the reaction was completed as detected by LC MS, the reaction solution was washed with saturated brine (20 mL). The organic phase was separated, dried over anhydrous sodium sulfate, filtered, and concentrated under reduced pressure. The resulting crude product was purified by silica gel column chromatography (Petroleum ether/ethyl acetate=6:1) to obtain 885 mg of white solid (crude product, compound 34f).

step 6): Pd/C (310 mg, 10% wet) was added to a solution of compound 34f (885 mg, crude) in ethyl acetate/methanol (5 mL/5 mL). After the addition was completed, the system was pumped and ventilated three times and charged with hydrogen. The mixed system was stirred under hydrogen atmosphere for 1 hour. After the reaction was completed, the reaction mixture was subjected to suction filtration. The filtrate was concentrated to obtain 827 mg of white solid (crude product, compound 34g).

step 7): Compound 34g (150 mg, crude) was added to a solution of TFA/DCM (3 mL/1.5 mL), and the mixture was stirred for 2 hours at 30° C. After the reaction was completed as detected by LC MS, the reaction solution was concentrated at room temperature. The crude product was purified by reverse-phase preparative HPLC to obtain 56 mg of white solid (i.e., compound I-034 trifluoroacetate)

$^1$H NMR (400 MHz, DMSO-$d_6$) δ 13.4 (brs, 1H), 7.95 (s, 2H), 7.90-7.87 (m, 1H), 7.45-7.40 (m, 2H), 7.34-7.32 (m, 2H), 6.88-6.86 (m, 2H), 4.30 (dd, J=16.0, 3.2 Hz, 1H), 4.07-3.96 (m, 2H), 3.75-3.70 (m, 1H), 3.15-3.07 (m, 2H), 2.97-2.83 (m, 2.5H), 2.75-2.67 (m, 0.5H), 1.96-1.84 (m, 1H), 1.76-1.69 (m, 2H), 1.66-1.57 (m, 1H).

LCMS: Rt=2.881 min, [M+H]$^+$=493.1.

Example 35 Preparation of Compound I-035 Trifluoroacetate

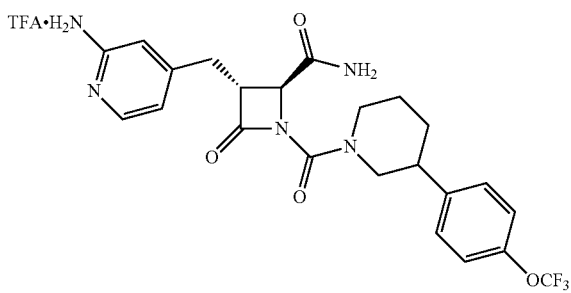

I-035

Compound I-035 trifluoroacetate was prepared according to the following scheme and method.

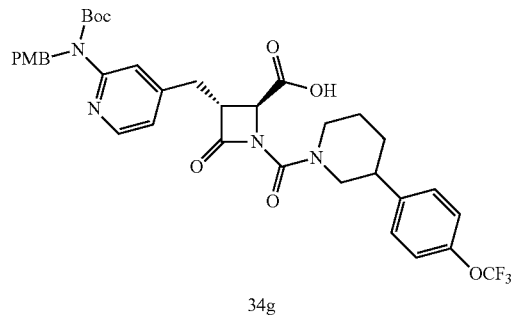

34g

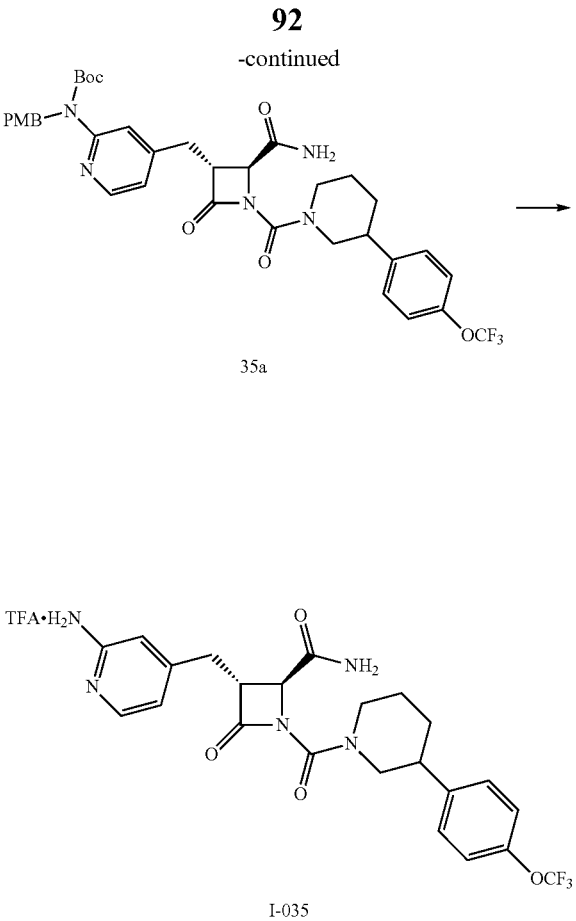

35a

I-035 step 1): Under the protection of nitrogen, diisopropylethylamine (109 mg) and HATU (213 mg) were added to a solution of compound 34g (200 mg, crude) in dichloromethane (4 mL). After stirring at 0° C. for 30 min, ammonium chloride (45 mg) was added, and the mixture was stirred at 0° C. for 2 hours. The reaction was quenched with aqueous ammonium chloride solution (10 mL), and extracted with dichloromethane. The organic phases were combined, concentrated and purified by silica gel column chromatography (methanol/dichloromethane=1/20) to obtain 228 mg of white solid (crude product, compound 35a).

step 2): Compound 35a (228 mg, crude) was added to a solution of TFA/DCM (3 mL/1.5 mL), and the mixture was stirred for 3 hours at 30° C. After the reaction was completed as detected by LC MS, the reaction solution was concentrated at room temperature. The crude product was purified by reversed-phase preparative HPLC to obtain 40.3 mg of white solid (i.e., compound I-035 trifluoroacetate).

$^1$H NMR (400 MHz, DMSO-$d_6$) δ 13.38 (brs, 1H), 7.98 (s, 2H), 7.88-7.85 (m, 1H), 7.70 (d, J=16.8 Hz, 1H), 7.44-7.41 (m, 2H), 7.34-7.29 (m, 3H), 6.88-6.86 (m, 2H), 4.21-4.19 (m, 1H), 4.08-4.01 (m, 2H), 3.53-3.48 (m, 1H), 3.14-3.11 (m, 2H), 2.97-2.86 (m, 3H), 2.75-2.66 (m, 1H), 1.95-1.83 (m, 1H), 1.83-1.69 (m, 2H), 1.64-1.45 (m, 1H).

LCMS: Rt=3.356 min, [M+H]$^+$=492.0.

Example 36 Preparation of Compound I-036 Trifluoroacetate

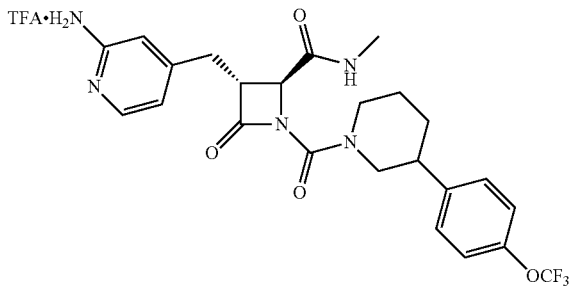

I-036

Compound I-036 trifluoroacetate was prepared according to the following scheme and method.

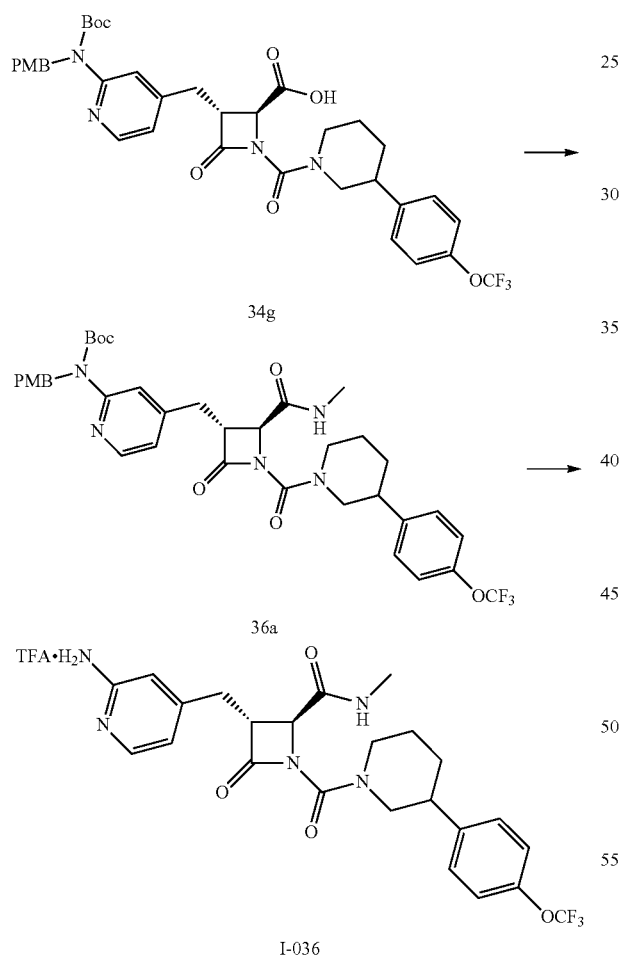

step 1): Under the protection of nitrogen, diisopropylethylamine (108 mg) and HATU (202 mg) were added to a solution of compound 34g (200 mg, crude) in dichloromethane (4 mL). After stirring at 0° C. for 30 min, a solution of methylamine in tetrahydrofuran (2.0 M, 0.28 mL) was added. The mixture was further stirred for 3 hours at 0° C. The reaction was quenched with aqueous ammonium chloride solution (10 mL), and extracted with dichloromethane. The organic phases were combined, concentrated and purified by silica gel column chromatography (methanol/dichloromethane=1/25) to obtain 247 mg of white solid (crude product, compound 36a).

step 2): Compound 36a (247 mg, crude product) was added to a solution of TFA/DCM (3 mL/1.5 mL), and the mixture was stirred at 30° C. for 3 hours. After the reaction was completed as detected by LC MS, the reaction solution was concentrated at room temperature. The crude product was purified by reverse-phase preparative HPLC to obtain 58.2 mg of white solid (i.e., compound I-036 trifluoroacetate).

$^1$H NMR (400 MHz, DMSO-$d_6$) δ 13.39 (brs, 1H), 8.27-8.18 (m, 1H), 7.97 (s, 2H), 7.88-7.85 (m, 1H), 7.44-7.41 (m, 2H), 7.34-7.32 (m, 2H), 6.85-6.83 (m, 2H), 4.21-4.19 (m, 1H), 4.07-4.00 (m, 2H), 3.54-3.49 (m, 1H), 3.14-3.11 (m, 2H), 3.01-2.85 (m, 3H), 2.73-2.66 (m, 1H), 2.61 (dd, J=14, 4.4 Hz, 3H), 1.95-1.83 (m, 1H), 1.69-1.57 (m, 2H), 1.54-1.43 (m, 1H).

LCMS: Rt=3.480 min, [M+H]$^+$=506.0.

Example 37 Preparation of Compound I-037

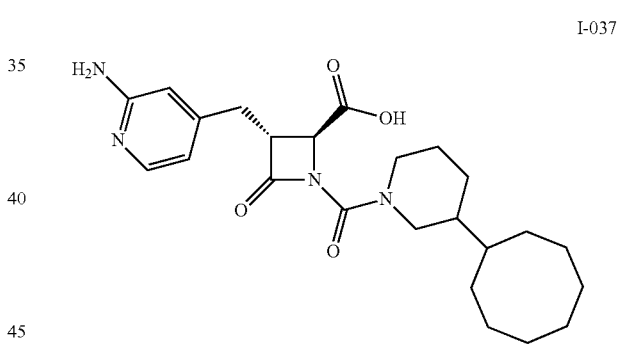

I-037

Compound I-037 was reared according to the following scheme and method.

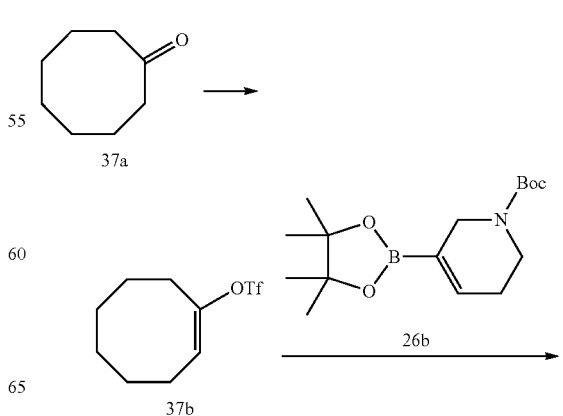

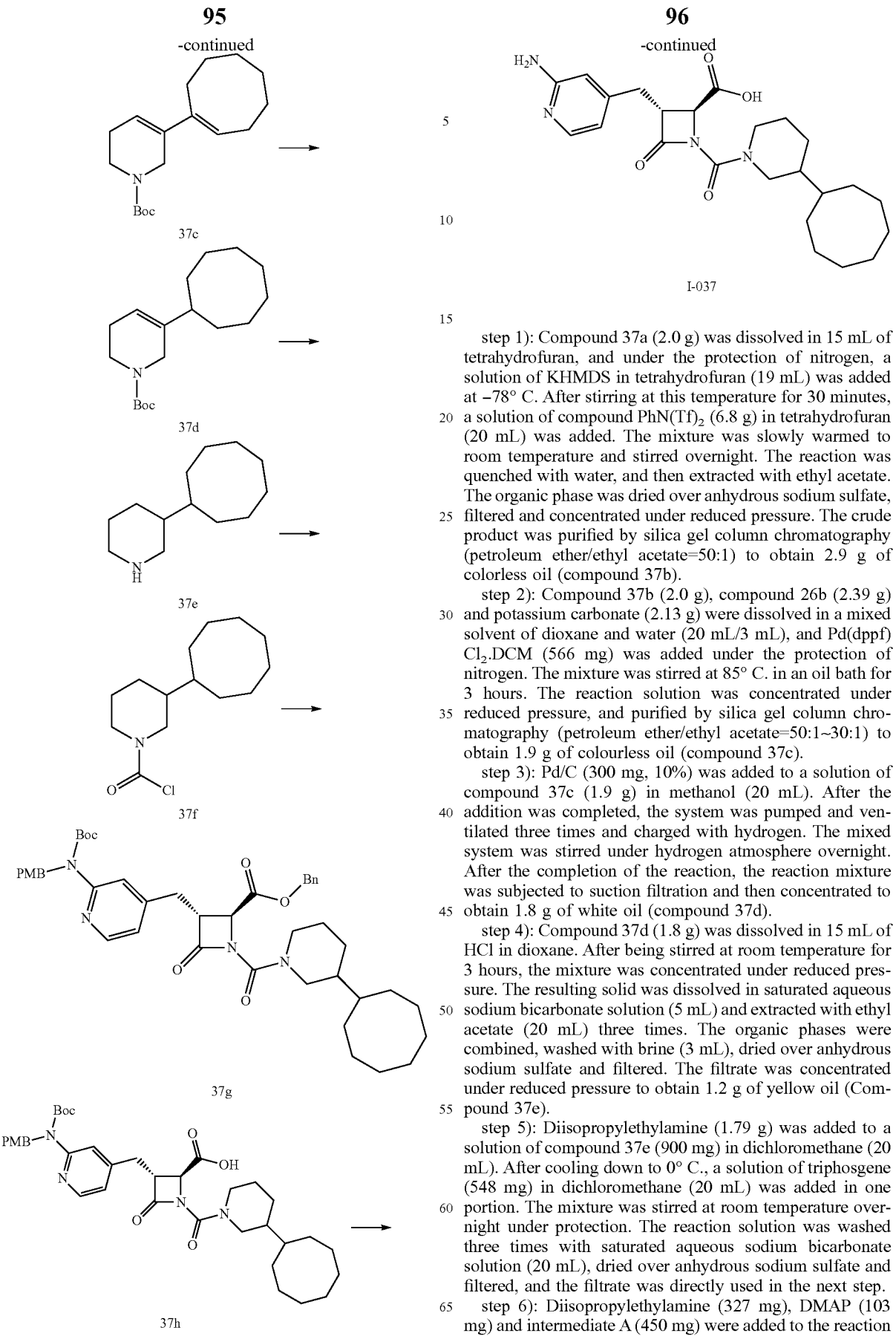

step 1): Compound 37a (2.0 g) was dissolved in 15 mL of tetrahydrofuran, and under the protection of nitrogen, a solution of KHMDS in tetrahydrofuran (19 mL) was added at −78° C. After stirring at this temperature for 30 minutes, a solution of compound PhN(Tf)$_2$ (6.8 g) in tetrahydrofuran (20 mL) was added. The mixture was slowly warmed to room temperature and stirred overnight. The reaction was quenched with water, and then extracted with ethyl acetate. The organic phase was dried over anhydrous sodium sulfate, filtered and concentrated under reduced pressure. The crude product was purified by silica gel column chromatography (petroleum ether/ethyl acetate=50:1) to obtain 2.9 g of colorless oil (compound 37b).

step 2): Compound 37b (2.0 g), compound 26b (2.39 g) and potassium carbonate (2.13 g) were dissolved in a mixed solvent of dioxane and water (20 mL/3 mL), and Pd(dppf)Cl$_2$.DCM (566 mg) was added under the protection of nitrogen. The mixture was stirred at 85° C. in an oil bath for 3 hours. The reaction solution was concentrated under reduced pressure, and purified by silica gel column chromatography (petroleum ether/ethyl acetate=50:1~30:1) to obtain 1.9 g of colourless oil (compound 37c).

step 3): Pd/C (300 mg, 10%) was added to a solution of compound 37c (1.9 g) in methanol (20 mL). After the addition was completed, the system was pumped and ventilated three times and charged with hydrogen. The mixed system was stirred under hydrogen atmosphere overnight. After the completion of the reaction, the reaction mixture was subjected to suction filtration and then concentrated to obtain 1.8 g of white oil (compound 37d).

step 4): Compound 37d (1.8 g) was dissolved in 15 mL of HCl in dioxane. After being stirred at room temperature for 3 hours, the mixture was concentrated under reduced pressure. The resulting solid was dissolved in saturated aqueous sodium bicarbonate solution (5 mL) and extracted with ethyl acetate (20 mL) three times. The organic phases were combined, washed with brine (3 mL), dried over anhydrous sodium sulfate and filtered. The filtrate was concentrated under reduced pressure to obtain 1.2 g of yellow oil (Compound 37e).

step 5): Diisopropylethylamine (1.79 g) was added to a solution of compound 37e (900 mg) in dichloromethane (20 mL). After cooling down to 0° C., a solution of triphosgene (548 mg) in dichloromethane (20 mL) was added in one portion. The mixture was stirred at room temperature overnight under protection. The reaction solution was washed three times with saturated aqueous sodium bicarbonate solution (20 mL), dried over anhydrous sodium sulfate and filtered, and the filtrate was directly used in the next step.

step 6): Diisopropylethylamine (327 mg), DMAP (103 mg) and intermediate A (450 mg) were added to the reaction solution (~50 mL) obtained by the above post-treatment.

After the addition was completed, the mixture was stirred overnight at room temperature under the protection of argon atmosphere. The reaction was completed as detected by LC MS, and then quenched with water and extracted with dichloromethane. The organic phases were combined, dried over anhydrous sodium sulfate, filtered, and concentrated under reduced pressure. The resulting crude product was purified by silica gel column chromatography (petroleum ether/ethyl acetate=1:3) to obtain 570 mg of white solid (compound 37g).

step 7): Pd/C (250 mg, 10%) was added to a solution of compound 37g (570 mg) in ethyl acetate/methanol (20 mL/20 mL). After the addition was completed, the system was pumped and ventilated three times and charged with hydrogen, and stirred for 1 hour under hydrogen atmosphere. After the reaction was completed, the reaction mixture was subjected to suction filtration and then concentrated to obtain 500 mg of white solid (compound 37h).

step 8): Compound 37h (150 mg) was added to a solution of TFA/DCM (4 mL/2 mL), and the mixture was stirred for 4 hours at 25° C. After the reaction was completed as detected by LC MS, the reaction solution was concentrated at room temperature. The crude product was purified by C-18 reverse-phase column chromatography to obtain 68.1 mg of white solid (i.e., compound I-037).

$^1$H NMR (400 MHz, DMSO-$d_6$): (7.79 (d, J=5.6 Hz, 1H), 6.43 (s, 1H), 6.34 (s, 1H), 5.93 (s, 2H), 4.13 (d, J=11.6 Hz, 1H), 4.00-3.90 (m, 2H), 3.57-3.51 (m, 1H), 2.88 (d, J=6.8 Hz, 2H), 2.76-2.63 (m, 1H), 2.58-2.51 (m, 2H), 1.77-1.73 (m, 1H), 1.65-1.53 (m, 8H), 1.44-1.19 (m, 10H).

LCMS: Rt=3.453 min, [M+H]$^+$=443.1.

Example 38 Preparation of Compound I-038 Trifluoroacetate

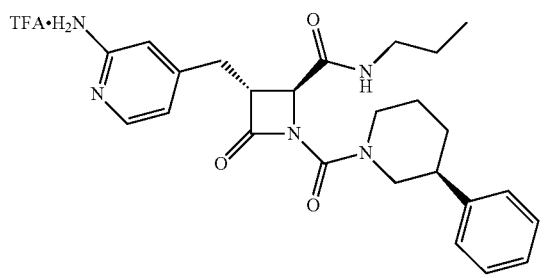

I-038

Compound I-038 trifluoroacetate was prepared according to the following scheme and method.

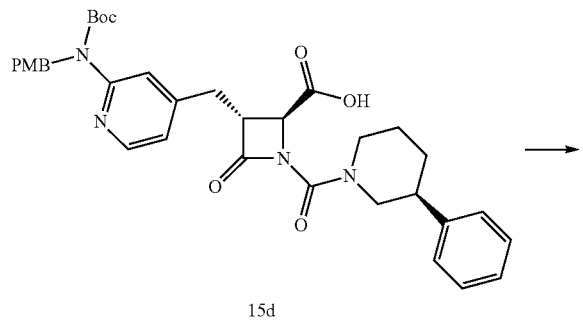

15d

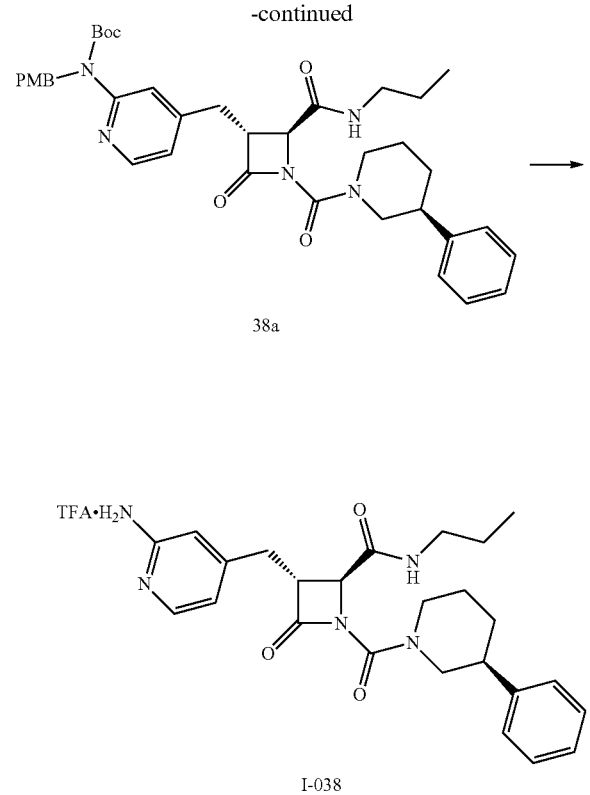

step 1): Under the protection of nitrogen, diisopropylethylamine (93 mg) and HATU (137 mg) were added to a solution (3 mL) of compound 15d (150 mg) in dichloromethane. After stirring at 0° C. for 20 min, n-propylamine (29 mg) was added, and the mixture was further stirred at 0° C. for 4 hours. The reaction solution was diluted with dichloromethane, and washed successively with aqueous ammonium chloride solution (10 mL) and saturated brine (10 mL). The organic phase was dried, and filtered. The crude product was purified by silica gel column chromatography (dichloromethane/methanol=25/1) to obtain 150 mg of white solid (compound 38a).

step 2): Compound 38a (150 mg) was added to a solution of TFA/DCM (3 mL/1.5 mL), and the mixture was stirred at 30° C. for 2 hours. After the action was completed as detected by LCMS, the action solution was concentrated at room temperature. The crude product was purified by reversed-phase preparative HPLC to obtain 67 mg of white solid (i.e., compound I-038 trifluoroacetate).

$^1$H NMR (400 MHz, DMSO-$d_6$): δ 13.43 (brs, 13.43), 8.23-8.21 (m, 1H), 7.97 (s, 2H), 7.87-7.85 (m, 1H), 7.35-7.29 (m, 4H), 7.25-7.21 (m, 1H), 6.86-6.85 (m, 2H), 4.23 (d, J=3.6 Hz, 1H), 4.07-4.00 (m, 2H), 3.52-3.47 (m, 1H), 3.13-3.11 (m, 2H), 3.08-3.01 (m, 1H), 2.98-2.89 (m, 3H), 2.84-2.74 (m, 1H), 1.95-1.88 (m, 1H), 1.84-1.69 (m, 2H), 1.54-1.43 (m, 1H), 1.37-1.31 (m, 2H), 0.76 (t, J=7.2 Hz, 3H).

LCMS: Rt=2.901 min, [M+H]$^+$=450.1.

Example 39 Preparation of Compound I-039

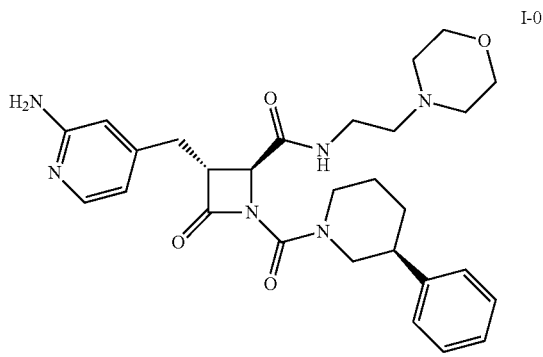

Compound I-039 was prepared according to the following scheme and method.

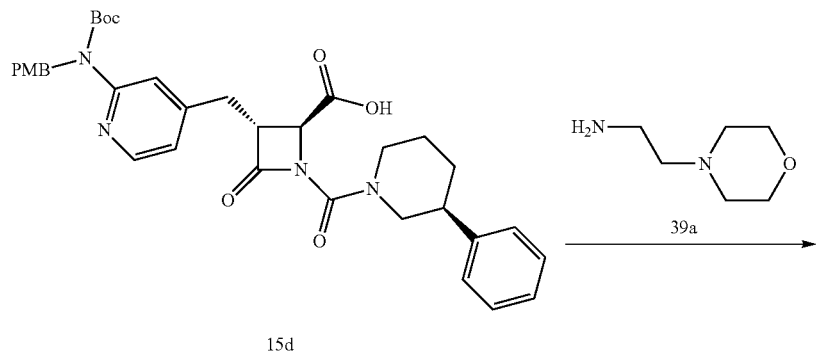

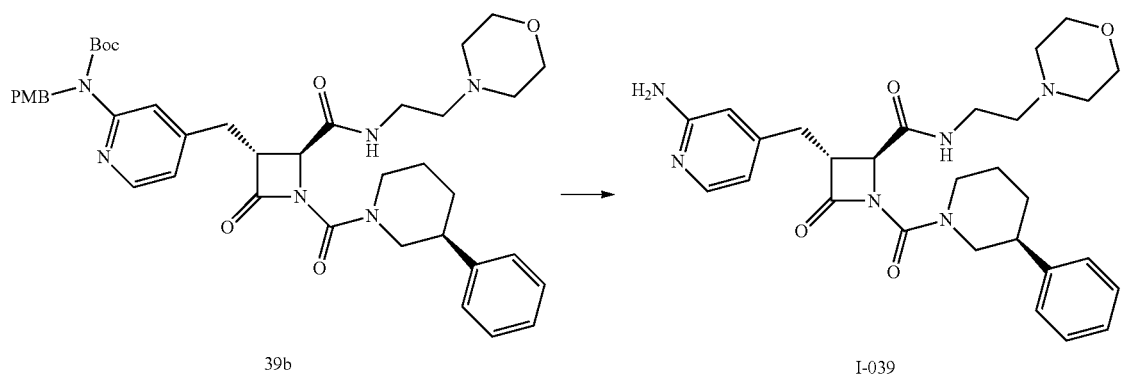

step 1): Under the protection of nitrogen, diisopropylethylamine (98 mg) and HATU (127 mg) were added to a solution (6 mL) of compound 15d (140 mg) in dichloromethane. After stirring at 0° C. for 10 min, compound 39a (58 mg) was added. The reaction solution was stirred at 0° C. for 3 hours, and then quenched with saturated aqueous ammonium chloride solution (4 mL) and extracted three times with dichloromethane (4 mL). The organic phases were combined and washed with water (2 mL), dried over anhydrous sodium sulfate, and filtered. The filtrate was concentrated, and the residue was purified by thin-layer chromatography preparation plate (methanol/dichloromethane=1/16) to obtain 140 mg of white solid (compound 39b).

step 2): Compound 39b (140 mg) was added to a solution of TFA/DCM (4 mL/2 mL), and the mixture was stirred at 25° C. for 2 hours. After the reaction was completed as detected by LC MS, the solution was concentrated at room temperature, and then purified by reversed-phase preparative HPLC to obtain 31.8 mg of white solid (i.e., compound I-039).

$^1$H NMR (400 MHz, DMSO-$d_6$): (8.13 (t, 1H), 7.78 (d, J=5.2 Hz, 1H), 7.34-7.28 (m, 4H), 7.25-7.21 (m, 1H), 6.43 (d, J=6.4 Hz, 1H), 6.32 (s, 1H), 5.84 (s, 2H), 4.23 (d, J=3.2 Hz, 1H), 4.02 (t, 2H), 3.52 (t, 4H), 3.31 (s, 1H), 3.25-3.20 (m, 1H), 3.16-3.09 (m, 1H), 2.93-2.86 (m, 4H), 2.81-2.76 (m, 1H), 2.33-2.30 (m, 4H), 2.28-2.26 (m, 2H), 1.93-1.89 (m, 1H), 1.81-1.72 (m, 2H), 1.53-1.43 (m, 1H).

LCMS: Rt=3.135 min, [M+H]$^+$=521.2.

Example 40 Preparation of Compound I-040

Compound I-040 was prepared according to the following scheme and method.

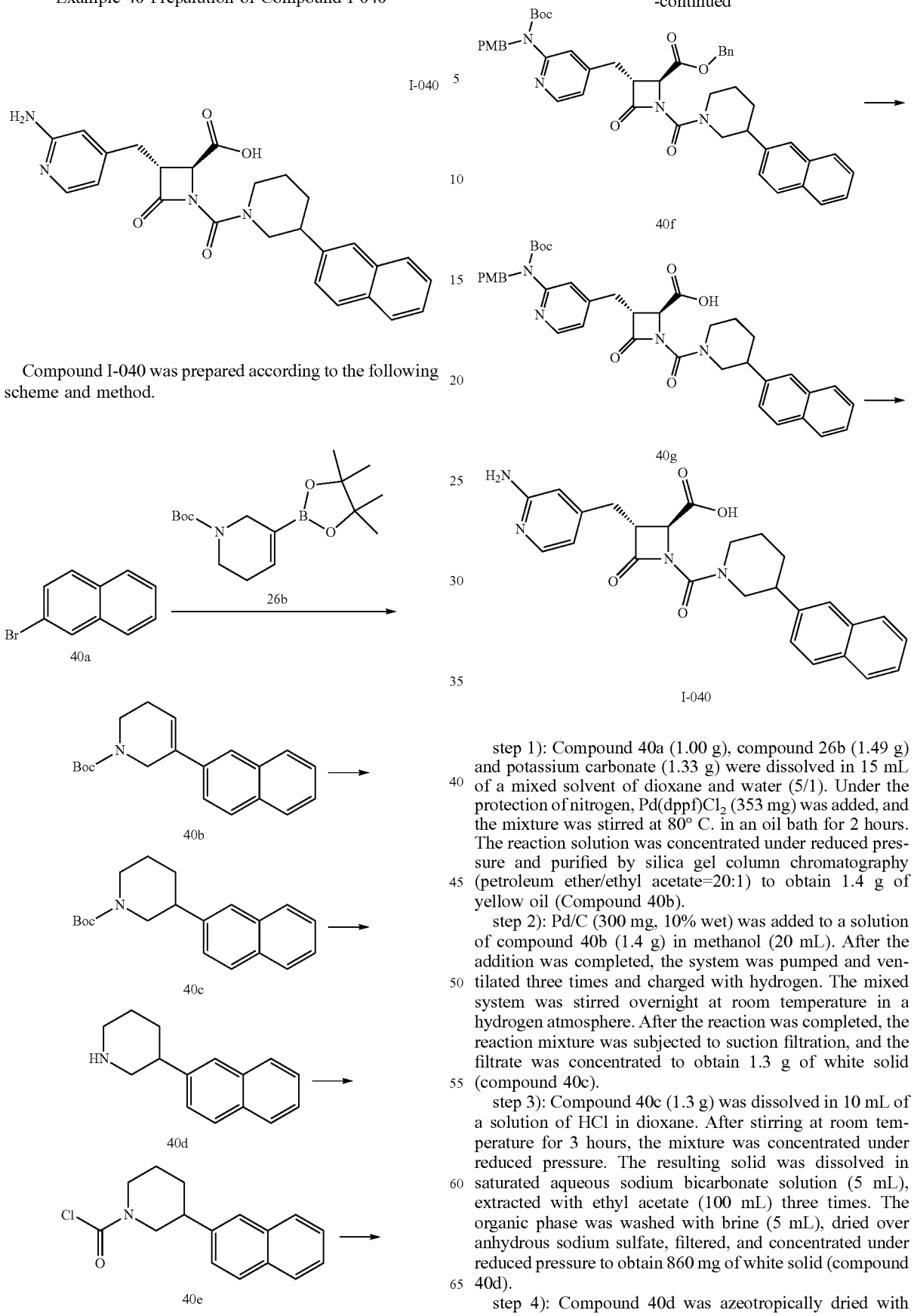

step 1): Compound 40a (1.00 g), compound 26b (1.49 g) and potassium carbonate (1.33 g) were dissolved in 15 mL of a mixed solvent of dioxane and water (5/1). Under the protection of nitrogen, Pd(dppf)Cl$_2$ (353 mg) was added, and the mixture was stirred at 80° C. in an oil bath for 2 hours. The reaction solution was concentrated under reduced pressure and purified by silica gel column chromatography (petroleum ether/ethyl acetate=20:1) to obtain 1.4 g of yellow oil (Compound 40b).

step 2): Pd/C (300 mg, 10% wet) was added to a solution of compound 40b (1.4 g) in methanol (20 mL). After the addition was completed, the system was pumped and ventilated three times and charged with hydrogen. The mixed system was stirred overnight at room temperature in a hydrogen atmosphere. After the reaction was completed, the reaction mixture was subjected to suction filtration, and the filtrate was concentrated to obtain 1.3 g of white solid (compound 40c).

step 3): Compound 40c (1.3 g) was dissolved in 10 mL of a solution of HCl in dioxane. After stirring at room temperature for 3 hours, the mixture was concentrated under reduced pressure. The resulting solid was dissolved in saturated aqueous sodium bicarbonate solution (5 mL), extracted with ethyl acetate (100 mL) three times. The organic phase was washed with brine (5 mL), dried over anhydrous sodium sulfate, filtered, and concentrated under reduced pressure to obtain 860 mg of white solid (compound 40d).

step 4): Compound 40d was azeotropically dried with toluene, and was reserved for use after removing all the water. Diisopropylethylamine (550 mg) was added to a solution of compound 40d (300 mg) in dichloromethane (10 mL). After cooling down to 0° C., a solution of triphosgene (168 mg) in dichloromethane (10 mL) was added in one portion. Under the protection of nitrogen, the mixture was stirred at room temperature overnight. The reaction solution was washed three times with saturated aqueous sodium bicarbonate solution (10 mL), dried over anhydrous sodium sulfate, and directly used in the next step.

step 5): Diisopropylethylamine (109 mg), DMAP (34.5 mg) and intermediate A (150 mg) were added to the reaction solution (containing 40e) (~25 mL) obtained by the above post-treatment. After the addition was completed, under the protection of nitrogen, the mixture was stirred at room temperature for 5 hours. After the reaction was completed as detected by LC MS, 20 mL of water was added to the reaction system. The organic phase was separated, and the aqueous phase was extracted with dichloromethane (30 mL). The organic phases were combined, dried over anhydrous sodium sulfate, and filtered; and the filtrate was concentrated under reduced pressure. The obtained crude product was purified by silica gel column chromatography (petroleum ether/ethyl acetate=3:1~2:1) to obtain 140 mg of white solid (compound 40f).

step 6): Pd/C (100 mg, 10% wet) was added to a solution of compound 40f (140 mg) in ethyl acetate/methanol (10 mL/10 mL). After the addition was completed, the mixed system was pumped and ventilated three times and charged with hydrogen, and then stirred at room temperature for 1 hour under hydrogen atmosphere. After the reaction was completed, the reaction mixture was subjected to suction filtration, and the filtrate was concentrated to obtain 160 mg of white solid (compound 40g).

step 7): Compound 40g (160 mg) was added to a solution of TFA/DCM (4 mL/2 mL), and the mixture was stirred at 25° C. for 3 hours. After the reaction was completed as detected by LC MS, the reaction solution was concentrated at room temperature. The resulting solid was dissolved in 1 mL of DMF, and purified by C-18 reverse-phase column chromatography (5-95% acetonitrile/water) to obtain 67.2 mg of white solid (i.e., compound I-040).

$^1$H NMR (400 MHz, DMSO-d$_6$) δ 7.88 (d, J=8.0 Hz, 3H), 7.78 (dd, J=11.0, 5.1 Hz, 2H), 7.54-7.40 (m, 3H), 6.44 (dd, J=9.5, 4.0 Hz, 1H), 6.35 (d, J=4.3 Hz, 1H), 5.97 (s, 2H), 4.18 (dd, J=22.2, 3.3 Hz, 1H), 4.15-4.08 (m, 2H), 3.63-3.54 (m, 1H), 3.11-3.06 (m, 1H), 2.98-2.91 (m, 1H), 2.90 (t, J=6.9 Hz, 3H), 2.08-1.98 (m, 1H), 1.88-180 (m, 2H), 1.72-1.48 (m, 1H).

LCMS: Rt=3.030, [M+H]$^+$=459.0.

Example 41 Preparation of Compound I-041

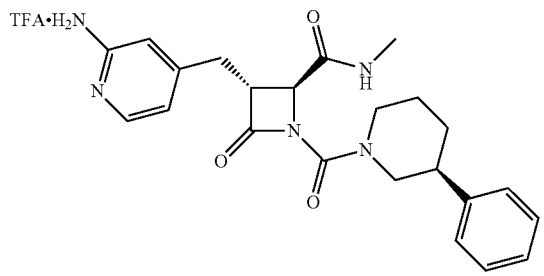

Compound I-041 trifluoroacetate was reared according to the following scheme and method.

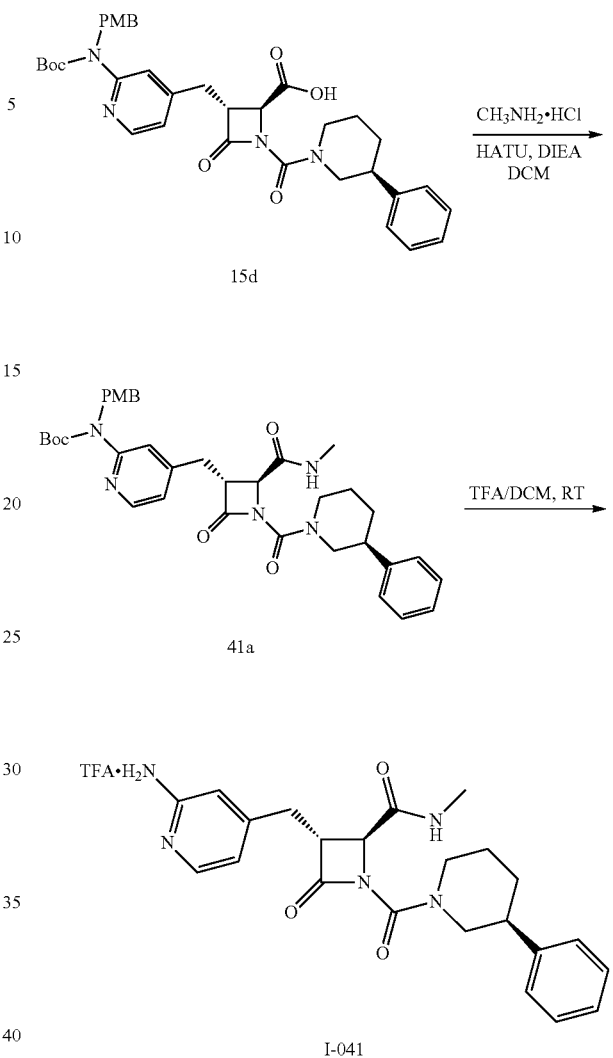

step 1): DIEA (14 mg) and HATU (18 mg) were added to a solution (5 mL) of compound 15d (20 mg) in dichloromethane, and the mixture was stirred for 10 min. After the addition of methylamine hydrochloride, the mixture was stirred at room temperature for 1 hour. The reaction mixture was purified by silica gel preparation plate to obtain 18 mg of colorless solid (i.e., compound 41a).

step 2): Compound 41a (37 mg) was added to a solution of TFA/DCM (1.5/1.5 mL), and the mixture was stirred at room temperature for about 3 hours. After the reaction was completed as detected by LCMS, the reaction solution was concentrated at room temperature and purified by reverse-phase preparative HPLC to obtain 13 mg of white solid (i.e., compound I-041 trifluoroacetate).

$^1$H NMR (400 MHz, DMSO-d$_6$): δ 8.19 (m, 1H), 7.91 (brs, 2H), 7.86 (d, 1H), 7.34-7.21 (m, 5H), 6.84-6.82 (m, 2H), 4.21 (d, 2H), 4.07-4.00 (m, 2H), 3.53-3.48 (m, 1H), 3.11 (d, J=7.2, 2H), 2.95-2.76 (m, 3H), 2.58 (d, 3H), 1.93-1.90 (m, 1H), 1.82-1.71 (m, 2H), 1.53-1.47 (m, 1H).

LCMS: Rt=1.273 min, [M+H]$^+$=422.0.

Example 42 Preparation of Compound I-042 Trifluoroacetate
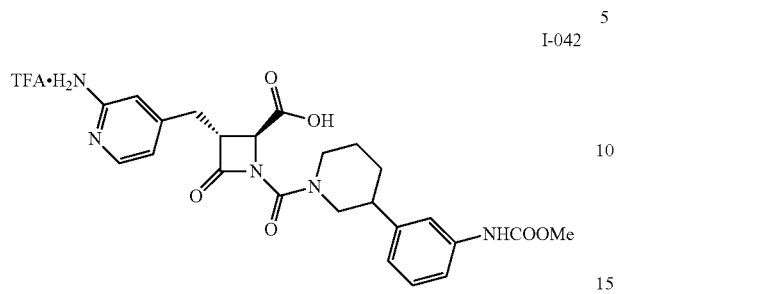
Compound I-042 trifluoroacetate was prepared according to the following scheme and method.
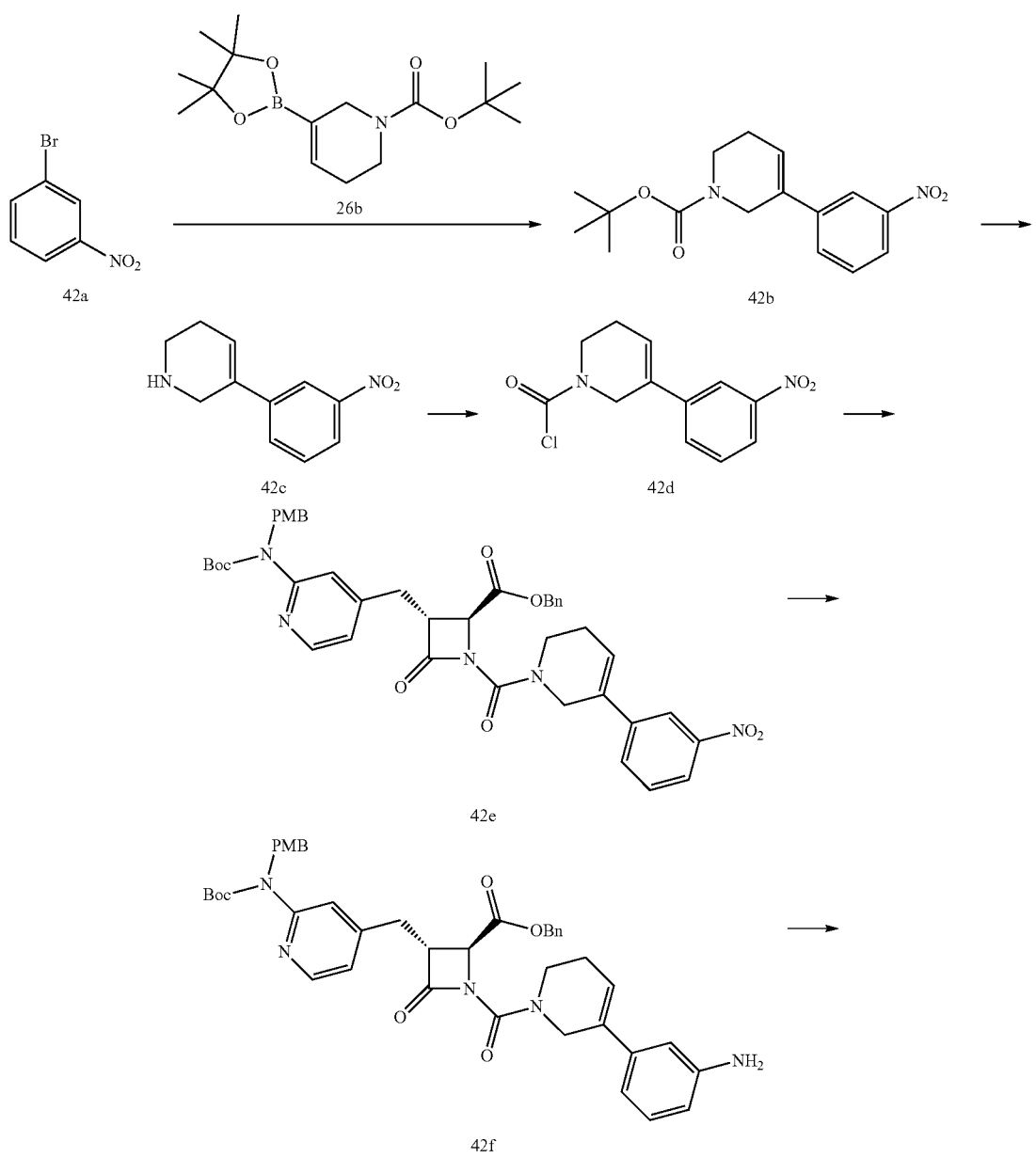

-continued

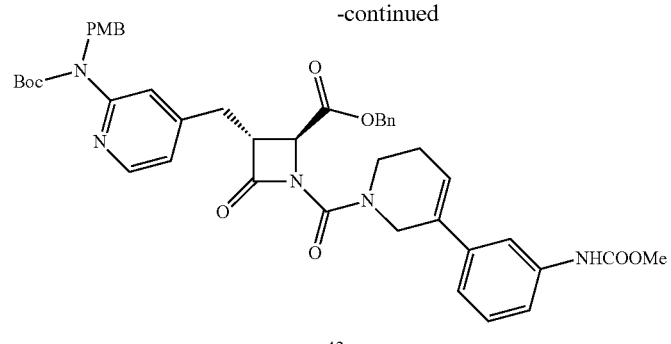

42g

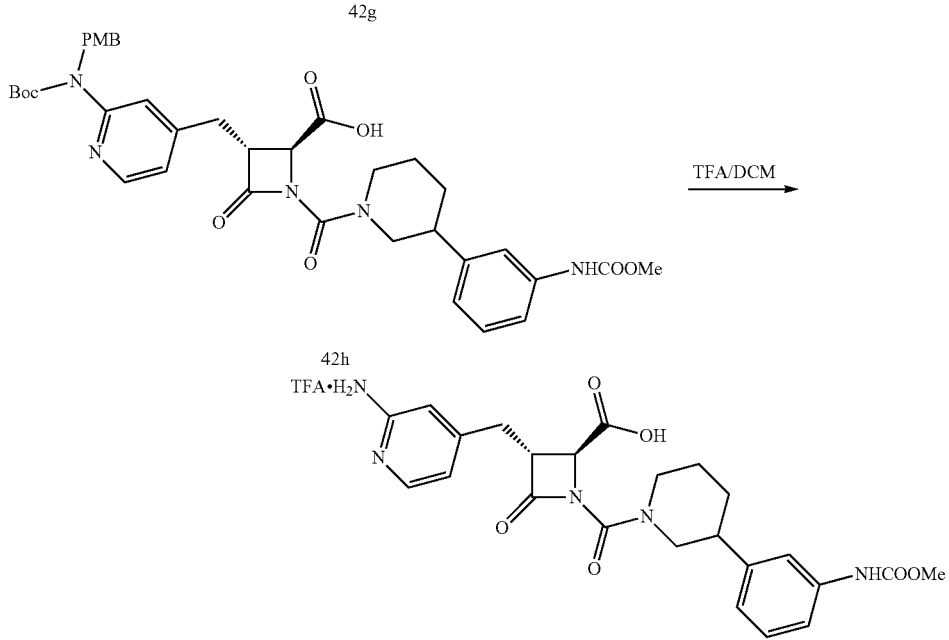

1) Compound 42a (1.5 g), compound 26b (2.5 g) and potassium carbonate (2.1 g) were dissolved in a mixed solvent of dioxane and water (11 mL, 10/1), and Pd(dppf)Cl$_2$ (910 mg) was added under the protection of nitrogen. The mixture was stirred at 80° C. in an oil bath for 2 hours. The reaction solution was concentrated under reduced pressure, and purified by silica gel column chromatography (petroleum ether/ethyl acetate=10:1) to obtain 2.2 g of yellow oil (compound 42b).

2) Compound 42b (1.2 g) was dissolved in 10 mL of a solution of HCl in dioxane, and the mixture was stirred overnight at room temperature and concentrated under reduced pressure. The resulting solid was dissolved in 10 mL of saturated aqueous sodium bicarbonate solution and extracted with ethyl acetate (20 mL×2). The organic phase was dried over anhydrous sodium sulfate, filtered, and concentrated under reduced pressure to obtain 750 mg of yellow oil (compound 42c).

3) Compound 42c was azeotropically dried with toluene, and was reserved for use after removing all the water. Diisopropylethylamine (569 mg) was added to a solution of compound 42c (300 mg) in dichloromethane (10 mL). After cooling down to 0° C., triphosgene (218 mg) was added in one portion. The reaction solution was stirred at room temperature overnight under the protection of nitrogen, and then washed three times with saturated aqueous sodium bicarbonate solution (20 mL), dried over anhydrous sodium sulfate, and directly used in the next step.

4) Diisopropylethylamine (190 mg), DMAP (62 mg) and intermediate A (260 mg) were added to the reaction solution obtained by the above post-treatment. After the addition was completed, the mixture was stirred at room temperature for 3 hours under the protection of nitrogen. 20 mL of water was added to the reaction system, the organic phase was separated, and the aqueous phase was extracted with dichloromethane (30 mL). The organic phases were combined, dried over anhydrous sodium sulfate, filtered, and concentrated under reduced pressure. The resulting crude product was purified by silica gel column chromatography (petroleum ether/ethyl acetate=3:1) to obtain 200 mg of white solid (compound 42c).

5) Ra—Ni (1.0 g) was added to a solution of compound 42e (200 mg) in tetrahydrofuran (5 mL). After the addition was completed, the mixed system was pumped and ventilated three times and charged with hydrogen. The mixed system was stirred at room temperature for 3 hours under hydrogen atmosphere. After the reaction was completed, the reaction mixture was subjected to suction filtration and then concentrated to obtain 168 mg of white solid (Compound 42f).

6) Under ice-water bath conditions, diisopropylethylamine (148 mg) and methyl chloroformate (86 mg) were added to a solution (10 mL) of compound 42f (168 mg) in dichloromethane, and the mixture was stirred at room temperature overnight. The reaction solution was quenched with water. The organic phase was separated, dried over anhydrous sodium sulfate and filtered, and the filtrate was concentrated under reduced pressure. The resulting crude product was purified by silica gel column chromatography (ethyl acetate/petroleum ether=2:1) to obtain 153 mg of white solid (compound 42g).

7) Pd/C (50 mg, 10% wet) was added to a solution of compound 42g (153 mg) in tetrahydrofuran (10 mL). After the addition was completed, the mixed system was pumped and ventilated three times and charged with hydrogen. The mixed system was stirred overnight at room temperature under hydrogen atmosphere. After the reaction was completed, the reaction mixture was subjected to suction filtration and then concentrate to obtain 136 mg of white solid (compound 42h).

Example 43 Preparation of Compound I-043 Trifluoroacetate

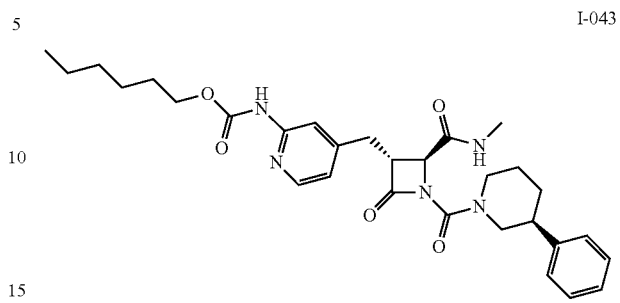

I-043

Compound I-043 was prepared according to the following scheme and method.

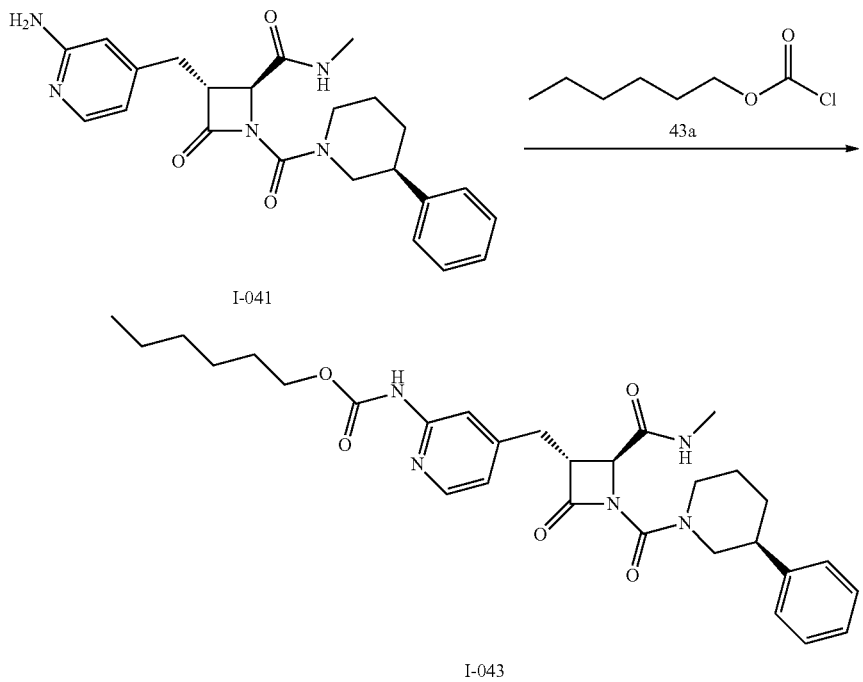

8) Compound 42h (136 mg) was added to a solution of TFA/DCM (6 mL/2 mL), and the mixture was stirred at 30° C. for 3 hours. After the reaction was completed as detected by LC MS, the reaction solution was concentrated at room temperature. The residue was dissolved in 1 mL of DMF, and purified by reverse-phase preparative HPLC to obtain 32 mg of white solid (i.e., compound I-042 trifluoroacetate).

$^1$H NMR (400 MHz, DMSO-d$_6$) δ 13.35 (brs, 1H), 9.61 (d, J=4.0 Hz, 1H), 7.97 (brs, 2H), 7.89-7.87 (m, 1H), 7.39-7.38 (m, 1H), 7.32-7.30 (m, 1H), 7.25-7.20 (m, 1H), 6.95-6.87 (m, 3H), 4.31 (d, J=3.6 Hz, 0.5H), 4.28 (d, J=3.2 Hz, 0.5H), 4.07-3.98 (m, 2H), 3.74-3.70 (m, 1H), 3.65 (s, 3H), 3.14-3.12 (m, 2H), 3.04-2.85 (m, 2H), 2.78-2.67 (m, 0.5H), 2.63-2.54 (m, 0.5H), 1.97-1.87 (m, 1H), 1.85-1.77 (m, 1H), 1.73-1.64 (m, 1H), 1.52-1.42 (m, 1H).

LCMS: Rt=3.562 min, [M+H]$^+$=482.0.

Under the protection of nitrogen, pyridine (64 mg) and compound 43a (81 mg) were successively added to a solution of compound I-041 (90 mg) in tetrahydrofuran (4 mL). After being stirred at 0° C. for 10 minutes, the mixture was further stirred at room temperature overnight. The reaction was quenched with five drops of water, and then purified by C-18 reverse-phase column chromatography (40-95% acetonitrile/water) to obtain 15.2 mg of colorless solid (i.e., compound I-043). The raw material I-041 in the reaction solution was recovered and concentrated to obtain 60 mg of white solid.

$^1$H NMR (400 MHz, DMSO-d$_6$): (8.18 (d, J=4.8 Hz, 1H), 7.83 (s, 1H), 7.64 (s, 1H), 7.35-7.30 (m, 4H), 7.24-7.21 (m, 1H), 6.91 (d, J=5.2 Hz, 1H), 6.54 (brs, 1H), 4.37 (s, 1H), 4.36-4.22 (m, 1H), 4.18 (t, 3H), 3.72-3.67 (m, 1H), 3.18-3.13 (m, 1H), 3.02-2.96 (m, 2H), 2.89-2.83 (m, 2H), 2.10-2.06 (m, 1H), 1.90-1.87 (m, 1H), 1.76-1.65 (m, 4H), 1.41-1.37 (m, 2H), 1.34-1.25 (m, 4H), 0.90 (t, 3H).

LCMS: Rt=4.375 min, [M+H]$^+$=550.4.

Example 44 Preparation of Compound I-044 Trifluoroacetate

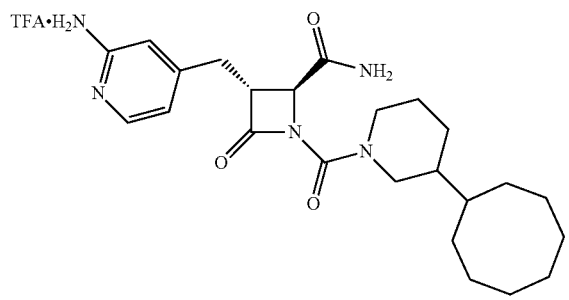

I-044

Compound I-044 trifluoroacetate was prepared according to the following scheme and method.

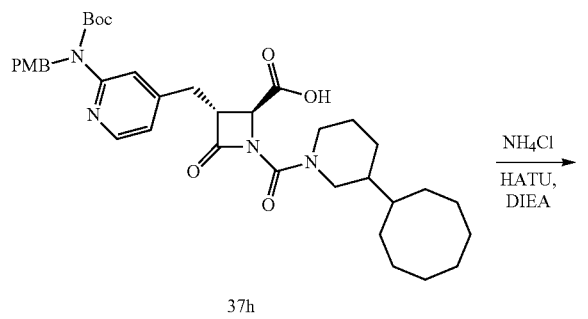

37h

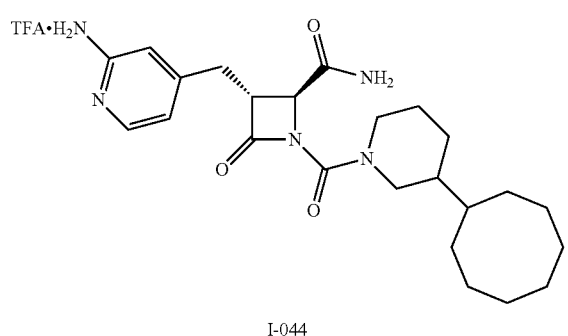

44a

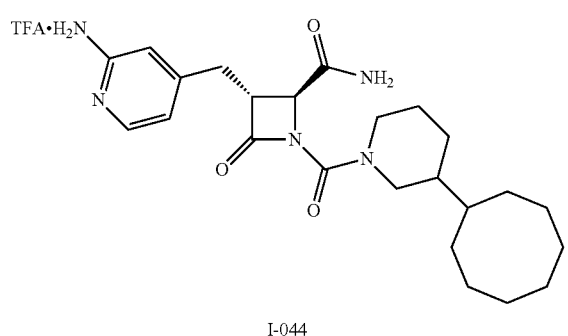

I-044

Under the protection of nitrogen, diisopropylethylamine (93.5 mg) and HATU (137 mg) were added to a solution of compound 37h (160 mg) in dichloromethane (5 mL). After stirring at 0° C. for 10 min, ammonium chloride (25.8 mg) was added. The mixture was stirred at 0° C. for 2 hours. The reaction was quenched with saturated aqueous sodium bicarbonate solution and then extracted with dichloromethane. The organic phases were combined, concentrated and purified by silica gel column chromatography (methanol/dichloromethane=1/40) to obtain 160 mg of white solid (compound 44a).

Compound 44a (160 mg) was added to a solution of TFA/DCM (4 mL/2 mL), and the mixture was stirred at 25° C. for 3 hours. After the reaction was completed as detected by LC MS, the reaction solution was concentrated at room temperature. The crude product was purified by C-18 reverse-phase column chromatography (5-95% acetonitrile/water (containing 0.1% TFA)) to obtain 57.2 mg of white solid (i.e., compound I-044 trifluoroacetate).

$^1$H NMR (400 MHz, DMSO-d): (13.25 (brs, 1H), 7.87-7.85 (m, 3H), 7.66 (s, 1H), 7.29-7.27 (m, 1H), 6.87-6.84 (m, 2H), 4.17 (d, J=2.8 Hz, 1H), 3.96-3.91 (m, 2H), 3.53-3.50 (m, 1H), 3.11-3.09 (m, 2H), 2.83-2.76 (m, 0.5H), 2.63-2.59 (m, 2.5H), 1.77-1.69 (m, 4H), 1.64-1.54 (m, 5H), 1.44-1.21 (m, 10H).

LCMS: Rt=3.233 min, [M+H]$^+$=442.1.

Example 45 Preparation of Compound I-045

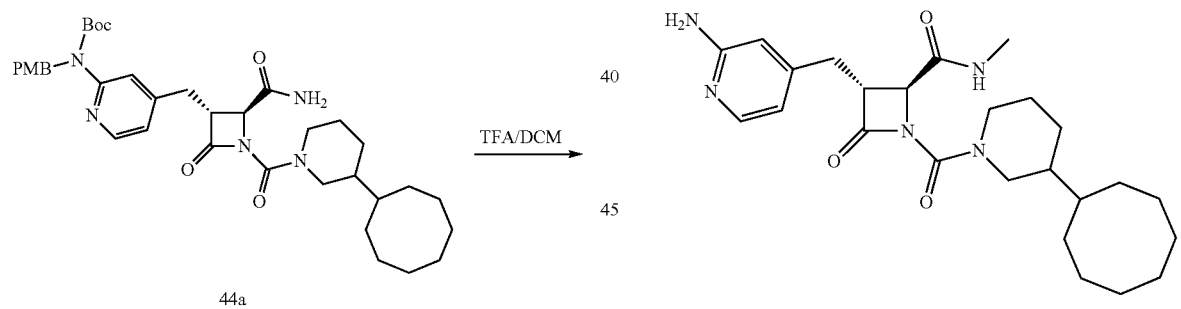

I-045

Compound I-045 was prepared according to the following scheme and method.

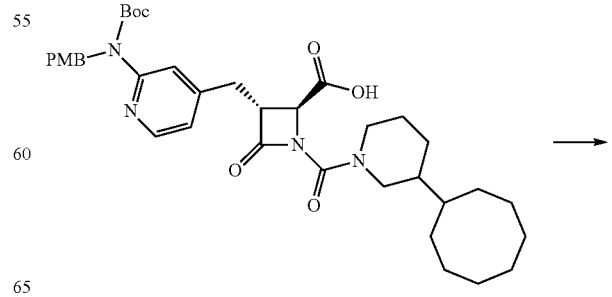

37h

113

-continued

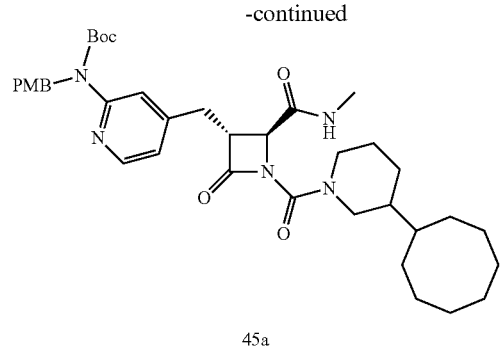

45a

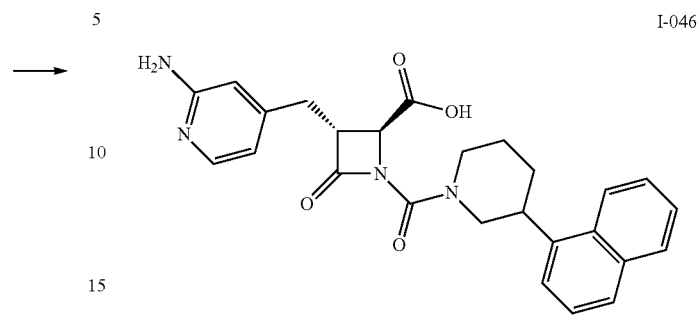

I-045

Under the protection of nitrogen, diisopropylethylamine (166 mg) and HATU (305 mg) were added to a solution of compound 37h (200 mg) in dichloromethane (8 mL). After stirring at 0° C. for 10 min, a solution of methylamine in tetrahydrofuran (2.0 M, 0.33 mL) was added. The mixture was stirred at 0° C. for 2 hours. The reaction was quenched with saturated aqueous sodium bicarbonate solution and then extracted with dichloromethane. The organic phases were combined, concentrated, and purified by silica gel column chromatography (methanol/dichloromethane=1/40) to obtain 180 mg of white solid (compound 45a).

Compound 45a (180 mg) was added to a solution of TFA/DCM (4 mL/2 mL), and the mixture was stirred at 25° C. for 3 hours. After the reaction was completed as detected by LC MS, the reaction solution was concentrated at room temperature. The crude product was purified by C-18 reverse-phase column chromatography (10-95% acetonitrile/water) to obtain 34.2 mg of white solid (i.e., compound I-045).

$^1$HNMR (400 MHz, DMSO-d$_6$): (8.22-21 (m, 1H), 7.79 (d, J=5.2 Hz, 1H), 6.42 (d, J=5.2 Hz, 1H), 6.31 (s, 1H), 5.88 (brs, 2H), 4.14 (d, J=3.2 Hz, 0.5H), 4.12 (d, J=3.2 Hz, 0.5H), 4.02-3.87 (m, 2H), 3.32-3.30 (m, 1H), 2.88-2.84 (m, 2H), 2.80-2.72 (m, 1H), 2.60-2.57 (m, 3H), 2.56-2.51 (m, 2H), 1.65-1.55 (m, 4H), 1.46-1.43 (m, 5H), 1.40-1.21 (m, 10H).

LCMS: Rt=3.328 min, [M+H]$^+$=456.1.

114

Example 46 Preparation of Compound I-046

Compound I-046 was prepared according to the following scheme and method.

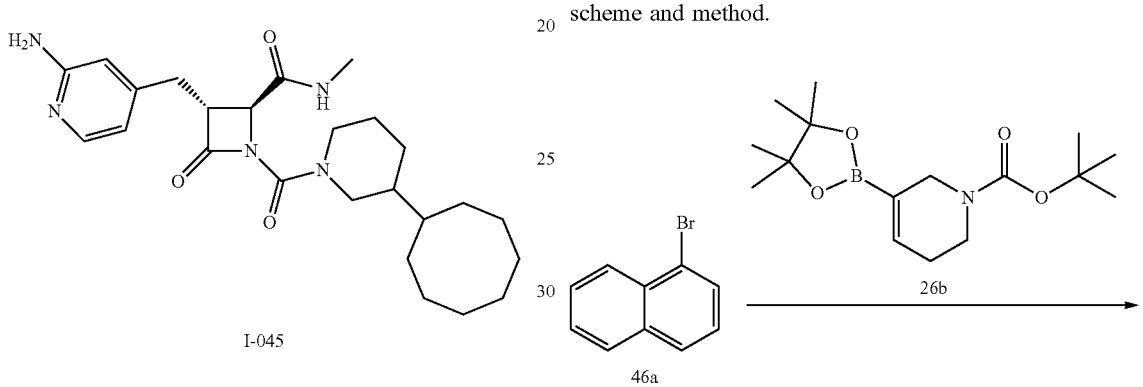

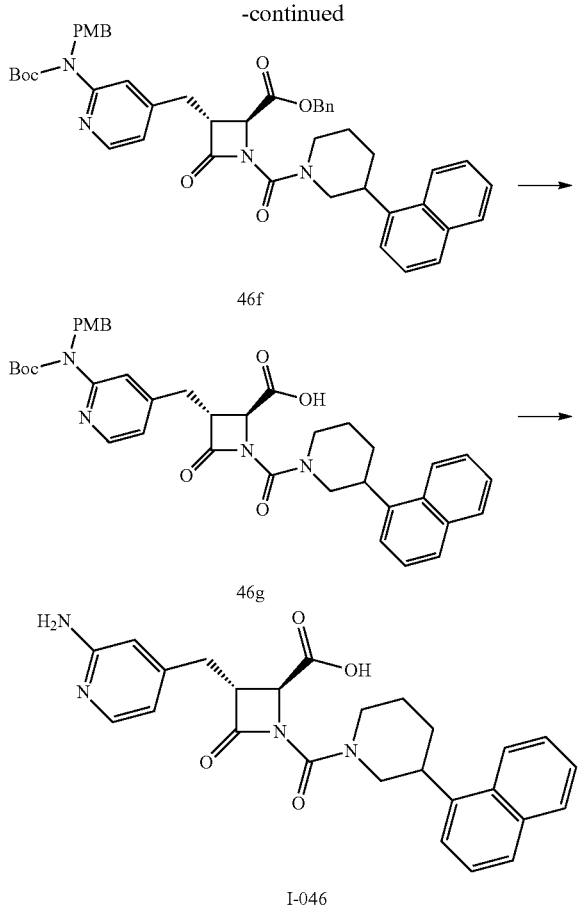

46f

46g

I-046

Compound 46a (1.00 g), compound 26b (1.65 g) and potassium carbonate (1.3 g) were dissolved in 20 mL of a mixed solvent of dioxane and water (10/1), and add Pd(dppf)Cl$_2$ (590 mg) was added under the protection of nitrogen. The mixture was stirred at 80° C. in an oil bath was stirred for 2 hours. The reaction solution was concentrated under reduced pressure, and purified by silica gel column chromatography (petroleum ether/ethyl acetate=10:1) to obtain 1.18 g of yellow oil (compound 46b).

Pd/C (200 mg, 10% wet) was added to a solution of compound 46b (1.18 g) in methanol (20 mL). After the addition was completed, the system was pumped and ventilated three times and charged with hydrogen. The mixed system was stirred at room temperature under hydrogen atmosphere overnight. LC MS showed a conversion rate of ~50%, and the reaction solution was stirred at 50° C. under hydrogen atmosphere of 3.5 atm for 4 hours. After the reaction was completed, the reaction mixture was subjected to suction filtration and concentrated to obtain 1.2 g of brown oil (Compound 46c).

Compound 46c (1.2 g) was dissolved in 10 mL of a solution of HCl in dioxane. After stirring at room temperature for 3 hours, the mixture was concentrated under reduced pressure. The resulting solid was dissolved in 10 mL of saturated aqueous sodium bicarbonate solution and extracted with ethyl acetate (20 mL×2). The organic phase was dried over anhydrous sodium sulfate, filtered, and concentrated under reduced pressure to obtain 600 mg of yellow oil (compound 46d).

Compound 46d was azeotropically dried with toluene, and was reserved for use after removing all the water.

Diisopropylethylamine (734 mg) was added to a solution of compound 46d (400 mg) in dichloromethane (10 mL), and after cooling down to 0° C., triphosgene (282 mg) was added in one portion. The mixture was stirred at room temperature overnight under the protection of nitrogen. The reaction solution was washed three times with saturated aqueous sodium bicarbonate solution (10 mL), dried over anhydrous sodium sulfate, and directly used in the next step.

Diisopropylethylamine (245 mg), DMAP (46 mg) and intermediate A (202 mg) were added to the reaction solution obtained by the above post-treatment. After the addition was completed, the mixture was stirred at room temperature under the protection of nitrogen for 5 hours. After the reaction was completed as detected by LC MS, 20 ml water was added to the reaction system, the organic phase was separated, and the aqueous phase was extracted with dichloromethane (30 mL). The organic phases were combined, dried over anhydrous sodium sulfate, filtered, and concentrated under reduced pressure. The crude product obtained was purified by C-18 reversed-phase column chromatography (40-95% acetonitrile/water) to obtain 140 mg of white solid (compound 46f).

Pd/C (42 mg, 10% wet) was added to a solution of compound 46f (140 mg) in ethyl acetate/methanol (3 mL/3 mL). After the addition was completed, the system was pumped and ventilated three times and charged with hydrogen, and then stirred at room temperature for 1 hour under hydrogen atmosphere. After the reaction was completed, the reaction mixture was subjected to suction filtration and then concentrated to obtain 123 mg of white solid (compound 46g).

Compound 46g (123 mg) was added to a solution of TFA/DCM (6 mL/2 mL), and the mixture was stirred at 30° C. for 3 hours. After the reaction was completed as detected by LC MS, the reaction solution was concentrated at room temperature. The residue was dissolved in 1 mL of DMF, and purified by reverse-phase preparative HPLC to obtain 30.9 mg of white solid (compound I-046).

$^1$H NMR (400 MHz, DMSO-d$_6$) δ 8.32-8.30 (m, 1H), 7.94-7.92 (m, 1H), 7.82 (d, J=7.6 Hz, 1H), 7.77 (d, J=5.6 Hz, 1H), 7.58-7.46 (m, 4H), 6.41 (d, J=4.8 Hz, 1H), 6.33 (s, 1H), 5.89 (brs, 2H), 4.25-4.08 (m, 3H), 3.57-3.54 (m, 1H), 3.47-3.45 (m, 2H), 3.06-2.95 (m, 1H), 2.91-2.81 (m, 2H), 2.05-1.89 (m, 2H), 1.87-1.81 (m, 1H), 1.76-1.65 (m, 1H).

LCMS: Rt=2.934, [M+H]$^+$=459.3.

Example 47 Preparation of Compound I-047 Trifluoroacetate

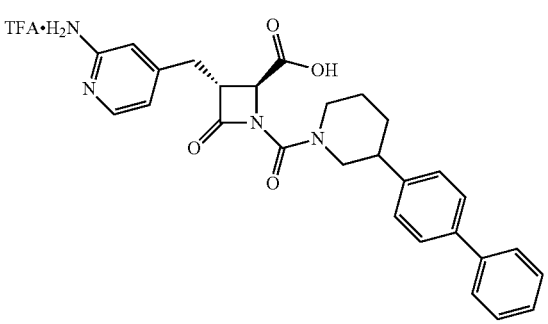

I-047

Compound I-047 trifluoroacetate was prepared according to the following scheme and method.

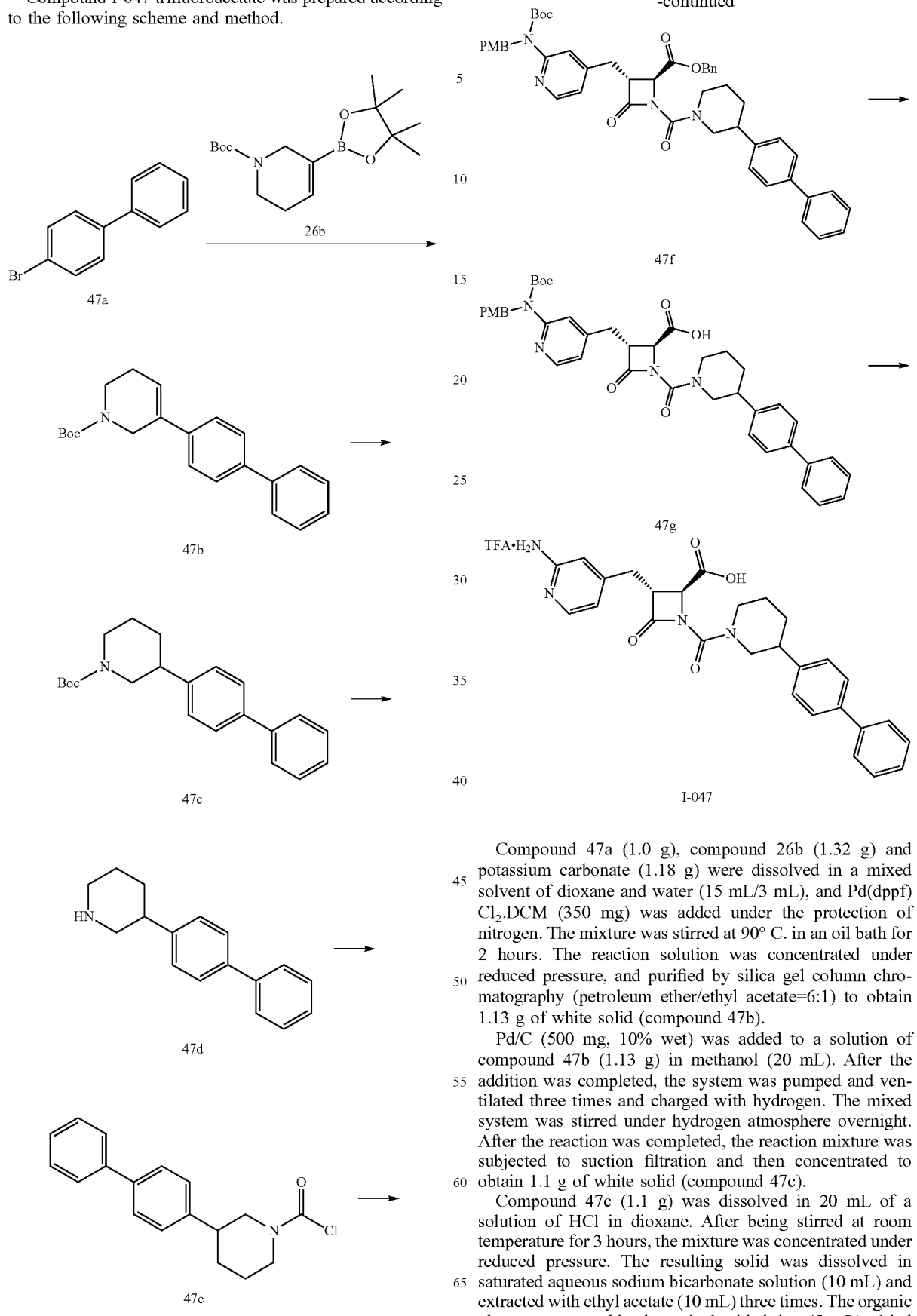

Compound 47a (1.0 g), compound 26b (1.32 g) and potassium carbonate (1.18 g) were dissolved in a mixed solvent of dioxane and water (15 mL/3 mL), and Pd(dppf)Cl$_2$·DCM (350 mg) was added under the protection of nitrogen. The mixture was stirred at 90° C. in an oil bath for 2 hours. The reaction solution was concentrated under reduced pressure, and purified by silica gel column chromatography (petroleum ether/ethyl acetate=6:1) to obtain 1.13 g of white solid (compound 47b).

Pd/C (500 mg, 10% wet) was added to a solution of compound 47b (1.13 g) in methanol (20 mL). After the addition was completed, the system was pumped and ventilated three times and charged with hydrogen. The mixed system was stirred under hydrogen atmosphere overnight. After the reaction was completed, the reaction mixture was subjected to suction filtration and then concentrated to obtain 1.1 g of white solid (compound 47c).

Compound 47c (1.1 g) was dissolved in 20 mL of a solution of HCl in dioxane. After being stirred at room temperature for 3 hours, the mixture was concentrated under reduced pressure. The resulting solid was dissolved in saturated aqueous sodium bicarbonate solution (10 mL) and extracted with ethyl acetate (10 mL) three times. The organic phases were combined, washed with brine (5 mL), dried over anhydrous sodium sulfate and filtered. The filtrate was concentrated under reduced pressure to obtain 750 mg of yellow solid (Compound 47d).

Diisopropylethylamine (489 mg) was added to a solution of compound 47d (300 mg) in dichloromethane (10 mL). After cooling down to 0° C., a solution of triphosgene (150 mg) in dichloromethane (10 mL) was added in one portion, and the mixture was stirred at room temperature overnight under the protection of nitrogen. The reaction solution was washed three times with saturated aqueous sodium bicarbonate solution (10 mL), dried over anhydrous sodium sulfate and filtered, and the filtrate was directly used in the next step.

Diisopropylethylamine (109 mg), DMAP (34.5 mg) and intermediate A (150 mg) were added to the reaction solution obtained by the above post-treatment. After the addition was completed, the mixture was stirred overnight at room temperature under the protection of argon. The reaction was completed as detected by LC MS, quenched with water and then extracted with dichloromethane. The organic phases were combined, dried over anhydrous sodium sulfate, filtered, and concentrated under reduced pressure. The resulting crude product was purified by silica gel column chromatography (petroleum ether/ethyl acetate=40:1) to obtain 200 mg of white solid (crude product, ~80% purity, compound 47f).

Pd/C (100 mg, 10% wet) was added to a solution of compound 47f (200 mg, crude product) in ethyl acetate/methanol (20 mL/20 mL). The mixed system was stirred for 1 hour under hydrogen atmosphere. After the reaction was completed, the reaction mixture was subjected to suction filtration and then concentrated to obtain 200 mg of yellow oil (crude product, ~80% purity, compound 47g).

Compound 47g (200 mg, crude) was added to a solution of TFA/DCM (3 mL/3 mL), and the mixture was stirred at 25° C. for 3 hours. After the reaction was completed as detected by LC MS, the reaction solution was concentrated at room temperature. The crude product was dissolved in DMF (1 mL), purified by C-18 reverse-phase column chromatography (5-95% acetonitrile/water (containing 0.1% TFA)) to obtain 111.2 mg of white solid (i.e., compound I-047 trifluoroacetate).

$^1$H NMR (400 MHz, DMSO-$d_6$): (13.32 (brs, 2H), 7.96 (brs, 2H), 7.90-7.87 (m, 1H), 7.65-7.61 (m, 4H), 7.48-7.44 (m, 2H), 7.41-7.34 (m, 3H), 6.89-6.86 (m, 2H), 4.33 (d, J=3.6 Hz, 0.5H), 4.29 (d, J=3.2 Hz, 0.5H), 4.08-4.02 (m, 2H), 3.76-3.70 (m, 1H), 3.16-3.13 (m, 2H), 3.05-2.92 (m, 2H), 2.90-2.82 (m, 0.5H), 2.73-2.65 (m, 0.5H), 2.00-1.92 (m, 1H), 1.96-1.75 (m, 2H), 1.67-1.59 (m, 0.5H), 1.55-1.46 (m, 0.5H).

LCMS: Rt=3.408 min, [M+H]$^+$=485.0.

Example 48 Preparation of Compound I-048 Trifluoroacetate

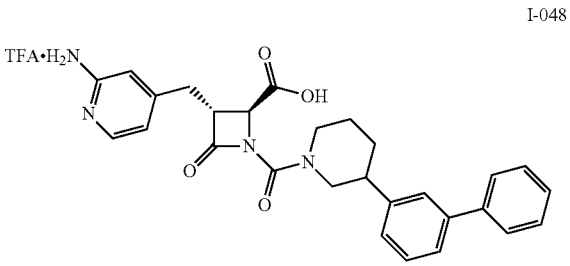

Compound I-048 trifluoroacetate was prepared according to the following scheme and method.

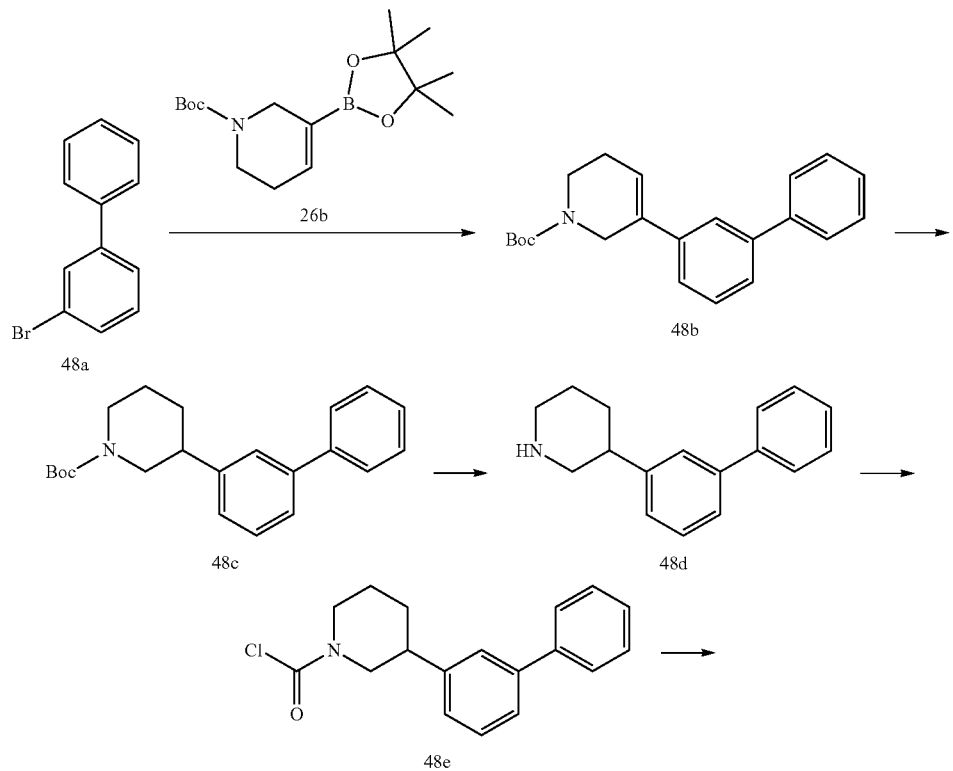

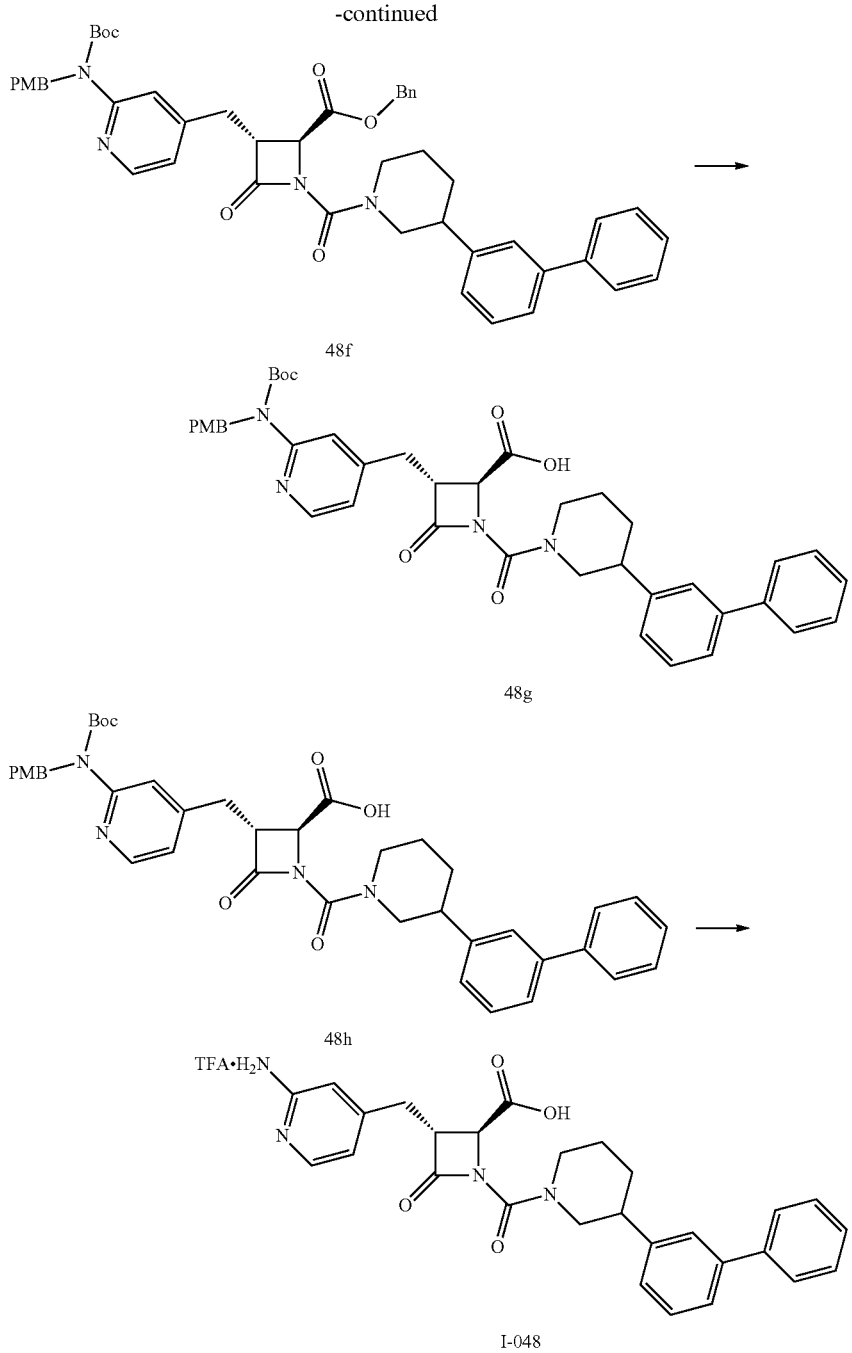

Compound 48a (1.0 g), compound 26b (1.46 g) and potassium carbonate (1.18 g) were dissolved in a mixed solvent (10 mL/1 mL) of dioxane and water. Pd(dppf)Cl₂ (523 mg) was added under the protection of nitrogen, and the mixture was stirred at 80° C. in an oil bath for 3 hours. The reaction solution was concentrated under reduced pressure, and the resulting crude product was purified by silica gel column chromatography (petroleum ether/ethyl acetate=20:1) to obtain 1.21 g of colorless oil (Compound 48b).

Pd/C (240 mg, 10% wet) was added to a solution of compound 48b (1.21 g) in methanol (15 mL). After the addition was completed, the system was pumped and ventilated three times and charged with hydrogen. The mixed system was stirred overnight at room temperature under hydrogen atmosphere. After the reaction was completed, the reaction mixture was subjected to suction filtration. The filtrate was concentrated to obtain 1.22 g of colorless oil (crude product), which was directly used in the next step.

Compound 48c (1.22 g, crude product) was dissolved in 10 mL of a solution of HCl in dioxane. After being stirred at room temperature overnight, the reaction solution was concentrated under reduced pressure. The resulting solid was dissolved in saturated aqueous sodium bicarbonate solution (20 mL), and extracted with ethyl acetate (50 mL). The organic phase was dried over anhydrous sodium sulfate and filtered. The filtrate was concentrated under reduced pressure to obtain 760 mg of yellow oil (compound 48d).

Diisopropylethylamine (364 mg) was added to a solution of compound 48d (230 mg) in dichloromethane (5 mL). After cooling down to 0° C., triphosgene (140 mg) was added in one portion, and the mixture was stirred overnight at room temperature under the protection of nitrogen. The reaction solution was washed with saturated aqueous sodium bicarbonate solution (10 mL), dried over anhydrous sodium sulfate, filtered, and concentrated to obtain 281 mg of yellow oil (crude product), which was directly used in the next step.

Compound 48e (281 mg, crude) obtained from the above reaction was dissolved in dichloromethane (5 mL). Intermediate A (150 mg), diisopropylethylamine (110 mg) and DMAP (35 mg) were added successively. After the addition was completed, the mixture was stirred at room temperature for three hours. After the reaction was completed as detected by LC MS, the reaction solution was washed with saturated brine (10 mL). The organic phase was separated, dried over anhydrous sodium sulfate, and filtered. The filtrate was concentrated under reduced pressure, and the resulting crude product was purified by silica gel column chromatography (petroleum ether/ethyl acetate=4:1) to obtain 180 mg of white solid (compound 48f).

Pd/C (63 mg, 10% wet) was added to a solution of compound 48f (180 mg) in ethyl acetate/methanol (2 mL/2 mL). After the addition was completed, the system was pumped and ventilated three times and charged with hydrogen, and then stirred for 1 hour under hydrogen atmosphere. After the completion of the reaction, the reaction mixture was subjected to suction filtration. The filtrate was concentrated to obtain 164 mg of white solid (crude product, compound 48g).

Compound 48h (164 mg, crude) was added to a solution of TFA/DCM (3 mL/1.5 mL), and the mixture was stirred at 30° C. for 3 hours. After the reaction was completed as detected by LC MS, the reaction solution was concentrated at room temperature. The crude product was purified by reverse-phase preparative HPLC to obtain 80.0 mg of white solid (compound I-048 trifluoroacetate).

$^1$H NMR (400 MHz, DMSO-$d_6$) δ 13.39 (brs, 1H), 7.96 (brs, 2H), 7.89-7.86 (m, 1H), 7.66 (d, J=8.4 Hz, 2H), 7.58-7.52 (m, 2H), 7.47 (t, J=8.0 Hz, 2H), 7.42 (t, J=7.6 Hz, 1H), 7.39-7.35 (m, 1H), 7.31-7.26 (m, 1H), 6.89-6.86 (m, 2H), 4.32 (d, J=3.6 Hz, 0.5H), 4.29 (d, J=3.6 Hz, 0.5H), 4.09-4.01 (m, 2H), 3.75-3.70 (m, 1H), 3.15-3.12 (m, 2H), 3.05-3.00 (m, 1H), 3.00-2.82 (m, 1.5H), 2.78-2.68 (m, 0.5H), 2.02-1.93 (m, 1H), 1.89-1.79 (m, 2H), 1.70-1.60 (m, 0.5H), 1.56-1.45 (m, 0.5H).

LCMS: Rt=2.610 min, [M+H]$^+$=485.3.

Example 49 Preparation of Compound I-049 Trifluoroacetate

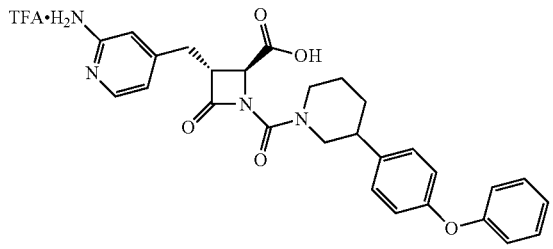

I-049

Compound I-049 trifluoroacetate was prepared according to the following scheme and method.

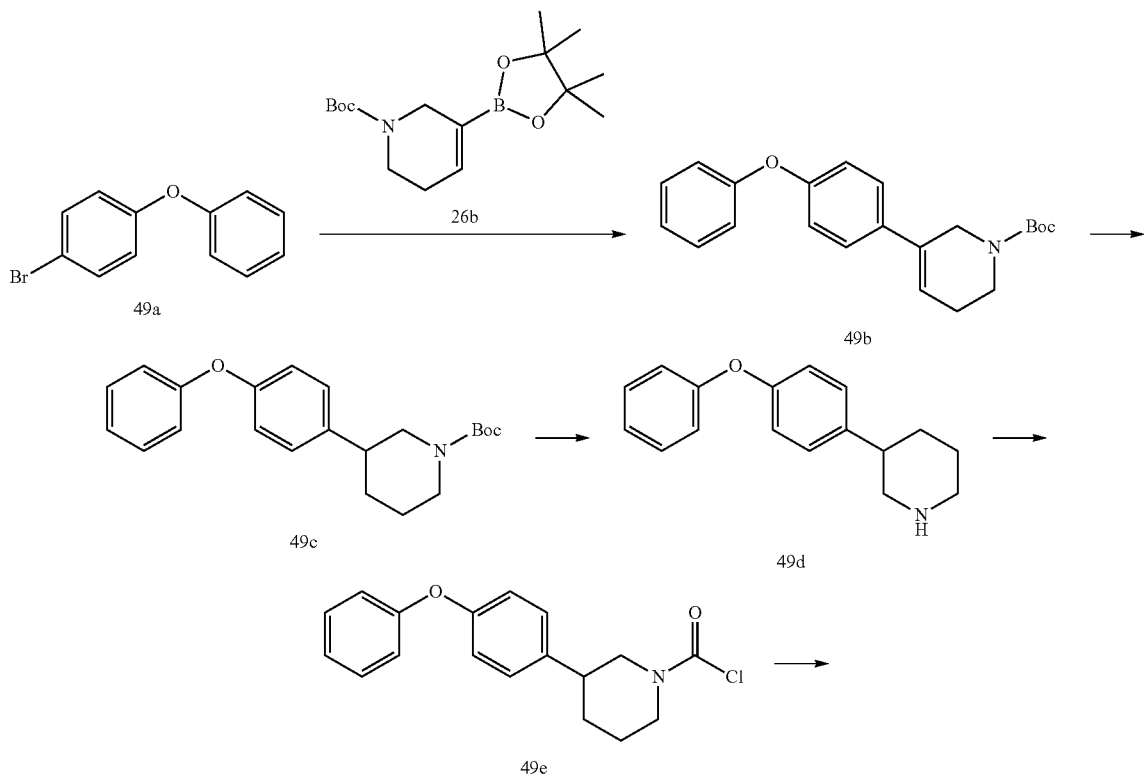

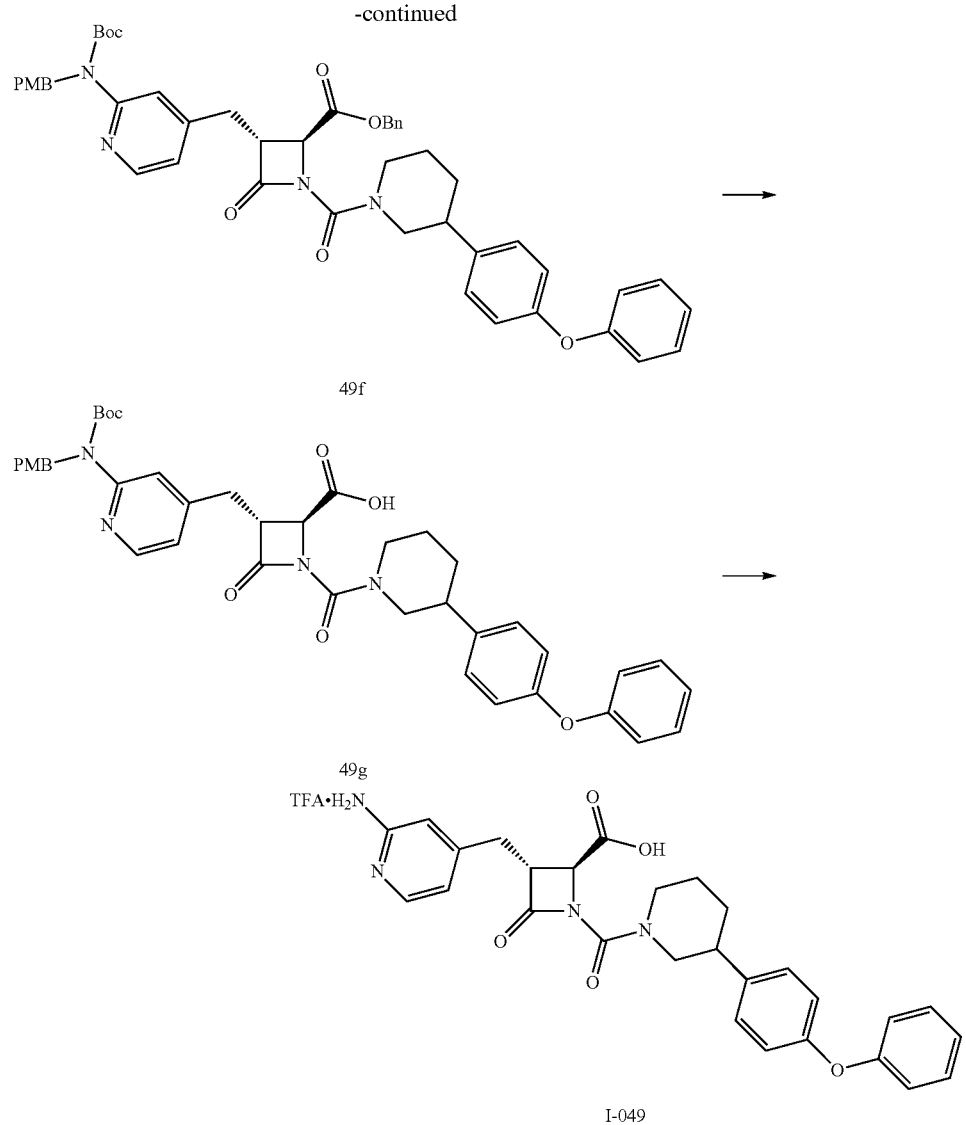

49f

49g

I-049

Compound 49a (1.0 g), compound 26b (1.24 g) and potassium carbonate (1.11 g) were dissolved in a mixed solvent of dioxane and water (15 mL/3 mL), and Pd(dppf)Cl$_2$.DCM (327 mg) was added under the protection of nitrogen. The mixture was stirred at 90° C. in an oil bath for 3 hours. The reaction solution was concentrated under reduced pressure, and purified by silica gel column chromatography (petroleum ether/ethyl acetate=20:1) to obtain 1.3 g of colorless oil (compound 49b).

Pd/C (350 mg, 10% wet) was added to a solution of compound 49b (1.3 g) in methanol (20 mL). After the addition was completed, the mixed system was pumped and ventilated three times and charged with hydrogen, and then stirred overnight under hydrogen atmosphere. After the reaction was completed, the reaction mixture was subjected to suction filtration and then concentrated to obtain 1.2 g of white oil (compound 49c).

Compound 49c (1.2 g) was dissolved in 20 mL of a solution of HCl in dioxane. After being stirred at room temperature for 3 hours, the mixture was concentrated under reduced pressure. The resulting solid was dissolved in saturated aqueous sodium bicarbonate solution (5 mL) and extracted with ethyl acetate (20 mL) three times. The organic phases were combined, washed with brine (3 mL), dried over anhydrous sodium sulfate and filtered. The filtrate was concentrated under reduced pressure to obtain 850 mg of colorless oil (Compound 49d).

Diisopropylethylamine (611 mg) was added to a solution of compound 49d (400 mg) in dichloromethane (20 mL), and after cooling down to 0° C., a solution of triphosgene (187 mg) in dichloromethane (20 mL) was added in one portion. The mixture was stirred at room temperature overnight under the protection of nitrogen. The reaction solution was washed three times with saturated aqueous sodium bicarbonate solution (10 mL), dried over anhydrous sodium sulfate and filtered, and the filtrate was directly used in the next step.

Diisopropylethylamine (131 mg), DMAP (41.3 mg) and intermediate A (180 mg) were added to the reaction solution obtained by the above post-treatment. After the addition was completed, the mixture was stirred at room temperature overnight under the protection of argon. After the reaction was completed as detected by LC MS, the reaction was quenched with water and then extracted with dichloromethane. The organic phases were combined, dried over anhydrous sodium sulfate, filtered, and concentrated under reduced pressure. The resulting crude product was purified by silica gel column chromatography (petroleum ether/ethyl acetate=2.5:1) to obtain 220 mg of white solid (crude, ~70% purity, compound 49f).

Pd/C (100 mg, 10% wet) was added to a solution of compound 49f (220 mg, crude product) in ethyl acetate/methanol (20 mL/20 mL). The mixed system was stirred for 1 hour under hydrogen atmosphere. After the reaction was completed, the reaction mixture was subjected to suction filtration and then concentrated to obtain 200 mg of white solid (crude product, ~70% purity, compound 49g).

Compound 49g (200 mg, crude) was added to a solution of TFA/DCM (4 mL/2 mL), and the mixture was stirred at 25° C. for 4 hours. After the reaction was completed as detected by LC MS, the reaction solution was concentrated at room temperature. The crude product was purified by C-18 reverse-phase column chromatography (5-95% acetonitrile/water (containing 0.1% TFA)) to obtain 58.3 mg of white solid (compound I-049 trifluoroacetate).

$^1$H NMR (400 MHz, DMSO-$d_6$): (13.30 (brs, 1H), 7.97 (brs, 2H), 7.88 (d, J=11.2 Hz, 1H), 7.41-7.37 (m, 2H), 7.33-7.27 (m, 2H), 7.15-7.11 (m, 1H), 7.00-6.96 (m, 4H), 6.89-6.87 (m, 2H), 4.32 (d, J=3.6 Hz, 0.5H), 4.29 (d, J=3.2 Hz, 0.5H), 4.07-3.98 (m, 2H), 3.76-3.71 (m, 1H), 3.15-3.13 (m, 2H), 3.02-2.88 (m, 2H), 2.86-2.74 (m, 0.5H), 2.69-2.61 (m, 0.5H), 1.96-1.89 (m, 1H), 1.84-1.68 (m, 2H), 1.65-1.56 (m, 0.5H), 1.53-1.44 (m, 0.5H).

LCMS: Rt=3.372 min, [M+H]$^+$=501.0.

Example 50 Preparation of Compound I-050 Trifluoroacetate

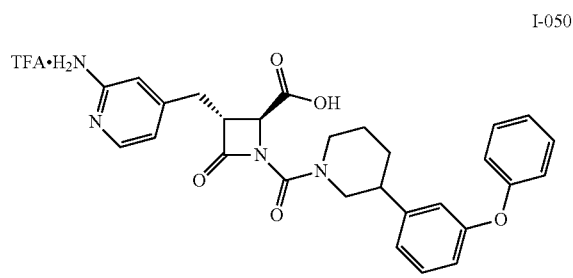

Referring to the synthesis method of compound I-049, compound I-050 trifluoroacetate was prepared by replacing raw material 49a with raw material 50a.

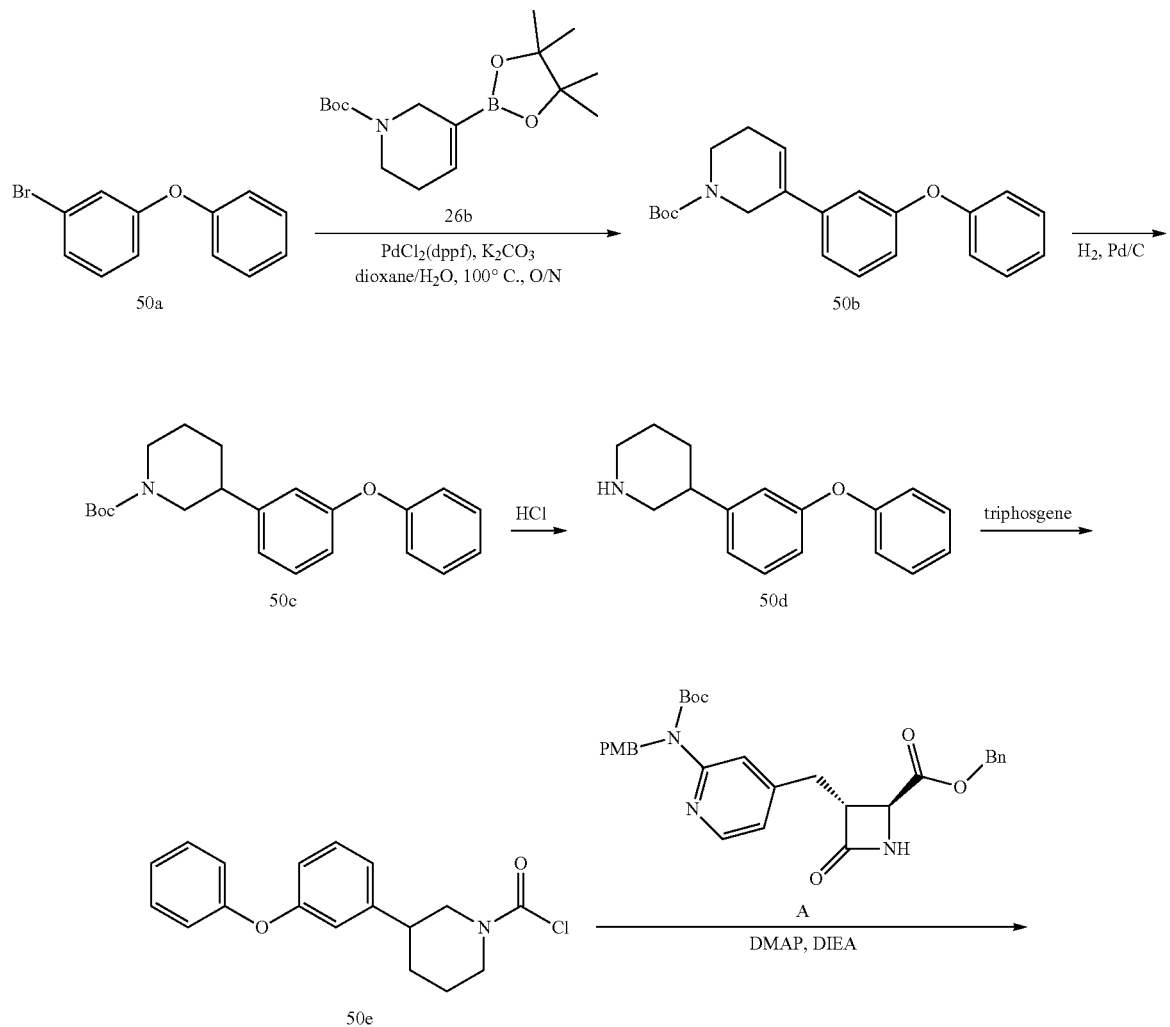

-continued
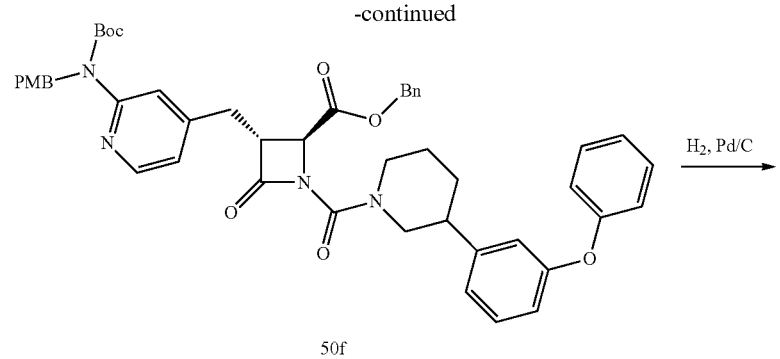
50f
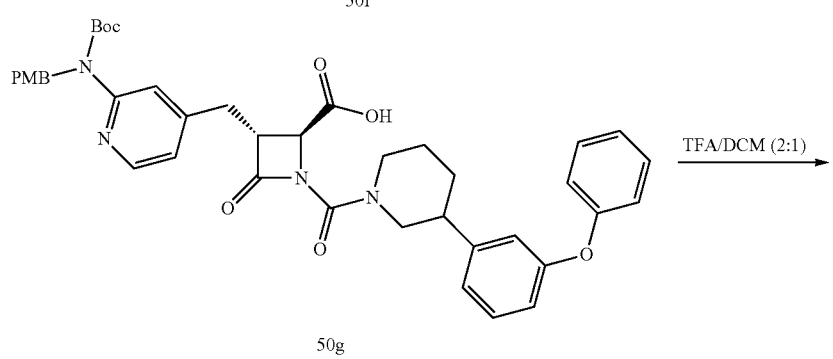
50g
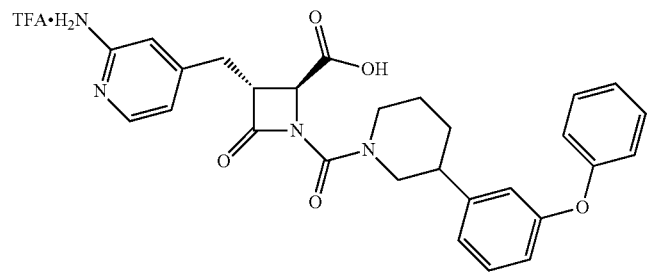
I-050
¹H NMR (400 MHz, DMSO-d₆) δ 13.37 (brs, 1H), 8.00 (brs, 2H), 7.90-7.88 (m, 1H), 7.42-7.31 (m, 3H), 7.16-6.97 (m, 5H), 6.88-6.82 (m, 3H), 4.31 (d, J=3.6 Hz, 0.5H), 4.27 (d, J=3.2 Hz, 0.5H), 4.03-3.98 (m, 2H), 3.73-3.70 (m, 1H), 3.13 (d, J=8.0 Hz, 2H), 3.01-2.88 (m, 2H), 2.85-2.77 (m, 0.51-1), 2.69-2.60 (m, 0.5H), 1.95-1.89 (m, 1H), 1.82-1.68 (m, 2H), 1.64-1.55 (m, 0.5H), 1.51-1.42 (m, 0.5H).
LCMS: Rt=3.108 min, [M+H]⁺=501.3.
Example 51 Preparation of Compound I-051 Trifluoroacetate
Compound I-051 trifluoroacetate was prepared according to the following scheme and method.
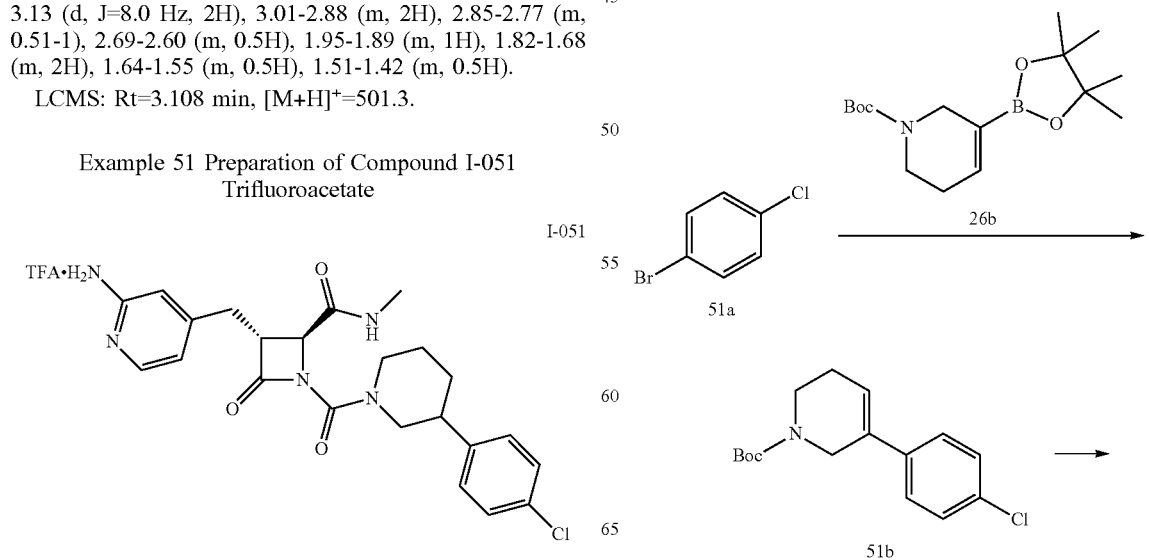
I-051
51a
51b

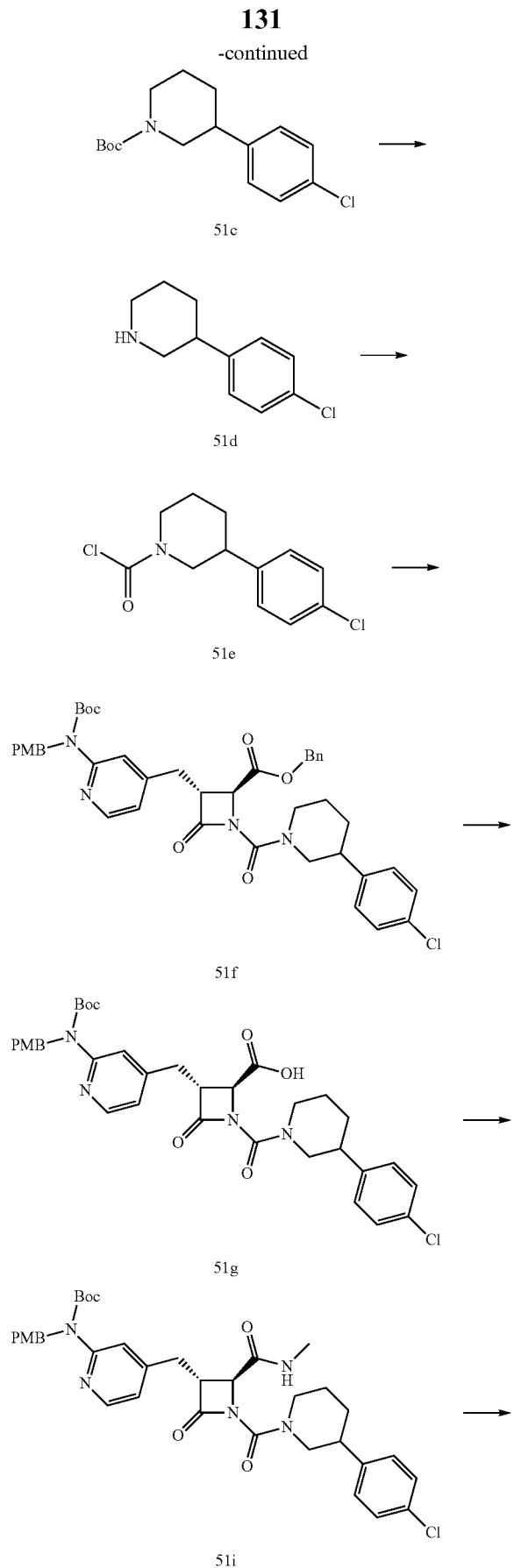

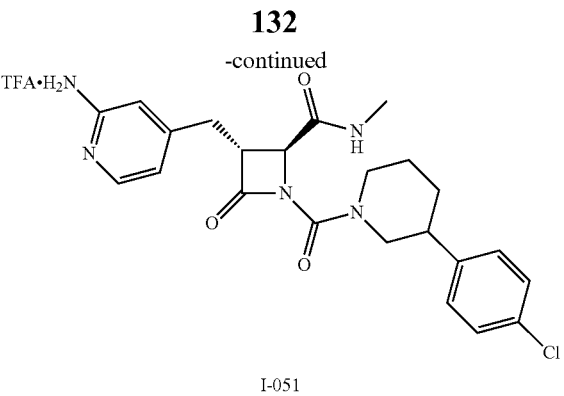

I-051

Compound 51a (1.0 g), compound 26b (1.77 g) and potassium carbonate (1.44 g) were dissolved in a mixed solvent of dioxane and water (11 mL, 10/1). Pd(dppf)Cl$_2$ (637 mg) was added under the protection of nitrogen, and the mixture was stirred at 80° C. in an oil bath for 3 hours. The reaction solution was concentrated under reduced pressure, and the resulting crude product was purified by silica gel column chromatography (petroleum ether/ethyl acetate=10:1) to obtain 1.57 g of colorless oil (Crude product, compound 51b). The crude product was directly used in the next step.

Pd/C (314 mg, 10% wet) was added to a solution of compound 51b (1.57 g, crude product) and 1,2-dichlorobenzene (2.36 g) in methanol (30 mL). After the addition was completed, the mixed system was pumped and ventilated three times and charged with hydrogen, and then stirred at room temperature for three hours under hydrogen atmosphere. After the reaction was completed, the reaction mixture was subjected to suction filtration. The filtrate was concentrated, and the resulting crude product was purified by reverse-phase column chromatography (acetonitrile/water=20-95%) to obtain 523 mg of yellow oil (Compound 51c).

Compound 51c (523 mg) was dissolved in 5 mL of a solution of HCl in dioxane. After being stirred at room temperature overnight, the reaction solution was concentrated under reduced pressure. The resulting solid was dissolved in saturated aqueous sodium bicarbonate solution (10 mL) and then extracted with ethyl acetate (25 mL). The organic phase was dried over anhydrous sodium sulfate and filtered. The filtrate was concentrated under reduced pressure to obtain 321 mg of white solid (compound 51d).

Diisopropylethylamine (639 mg) was added to a solution of compound 51d (321 mg) in dichloromethane (8 mL). After cooling down to 0° C., triphosgene (247 mg) was added in one portion. Under the protection of nitrogen, the mixture was stirred at room temperature overnight. The reaction solution was washed with saturated aqueous sodium bicarbonate solution (10 mL), dried over anhydrous sodium sulfate, filtered and concentrated to obtain 486 mg of yellow oil (crude product, compound 51e), which was directly used in the next step.

Compound 51e (486 mg, crude product) obtained from the above reaction was dissolved in dichloromethane (10 mL). Intermediate A (350 mg), diisopropylethylamine (255 mg) and DMAP (81 mg) were added successively. After the addition was completed, the mixture was stirred at room temperature for three hours under the protection of argon. The reaction was completed as detected by LC MS, and then washed with saturated brine (10 mL). The organic phase was separated, dried over anhydrous sodium sulfate, and filtered. The filtrate was concentrated under reduced pressure, and the resulting crude product was purified by silica gel column chromatography (petroleum ether/ethyl acetate=2:1) to obtain 450 mg of white solid (compound 51f).

Pd/C (158 mg, 10% wet) was added to a solution of compound 51f (450 mg) and 1,2-dichlorobenzene (265 mg) in ethyl acetate/methanol (5 mL/5 mL). After the addition was completed, the mixed system was pumped and ventilated three times and charged with hydrogen, and then stirred under hydrogen atmosphere for 1 hour. After the reaction was completed, the reaction mixture was subjected to suction filtration. The filtrate was concentrated, and the resulting crude product was purified by reverse-phase column chromatography (acetonitrile/water=20%-95%) to obtain 290 mg of white solid (compound 51g).

Under the protection of nitrogen, diisopropylethylamine (135.5 mg) and HATU (266 mg) were added to a solution of compound 51g (230 mg) in dichloromethane (5 mL). After stirring at 0° C. for 50 min, a solution (0.35 mL) of methylamine in tetrahydrofuran was added. The reaction solution was further stirred at 0° C. for 3 hours. The reaction was quenched with 5 mL of aqueous ammonium chloride solution and then extracted with dichloromethane. The organic phases were combined, dried over anhydrous sodium sulfate, filtered and concentrated. The crude product was purified by silica gel column chromatography (dichloromethane/methanol=100/1) to obtain 324 mg of yellow oil (crude product, compound 51i), which was directly used in the next step.

Compound 51i (324 mg, crude product) was added to a solution of TFA/DCM (3 mL/1.5 mL), and the mixture was stirred at 30° C. for 3 hours. After the reaction was completed as detected by LC MS, the reaction solution was concentrated at room temperature. The crude product was purified by reversed-phase preparative HPLC to obtain 32.0 mg of white solid (compound I-051 trifluoroacetate).

$^1$H NMR (400 MHz, DMSO-d$_6$) δ 13.47 (brs, 1H), 8.25 (d, J=4.8 Hz, 0.5H), 8.21 (d, J=4.8 Hz, 0.5H), 7.98 (brs, 2H), 7.88-7.85 (m, 1H), 7.40-7.38 (m, 2H), 7.34-7.31 (m, 2H), 6.85-6.83 (m, 2H), 4.21 (d, J=2.8 Hz, 0.5H), 4.19 (d, J=2.8 Hz, 0.5H), 4.06-3.98 (m, 2H), 3.52-3.49 (m, 1H), 3.14-3.11 (m, 2H), 2.95-2.82 (m, 2H), 2.82-2.77 (m, 0.5H), 2.70-2.66 (m, 0.5H), 2.62 (d, J=4.8 Hz, 1.5H), 2.59 (d, J=4.8 Hz, 15H) 1.93-1.86 (m, 1H), 1.82-1.67 (m, 2H), 1.63-1.56 (m, 0.5H), 1.53-1.43 (m, 0.5H).

LCMS: Rt=3.324 min, [M+H]$^+$=456.0.

Example 52 Preparation of Compound I-052

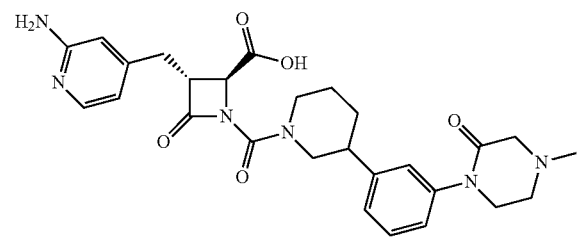

Compound I-052 was prepared according to the following scheme and method.

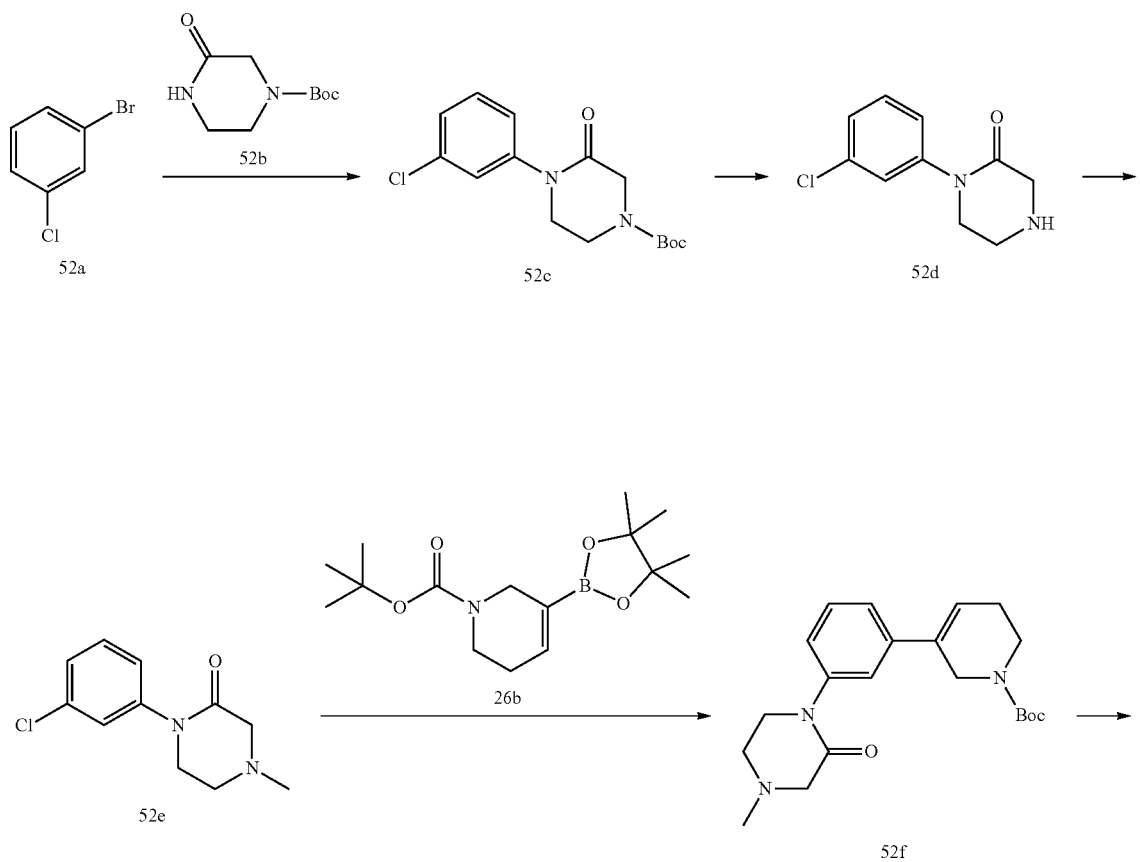

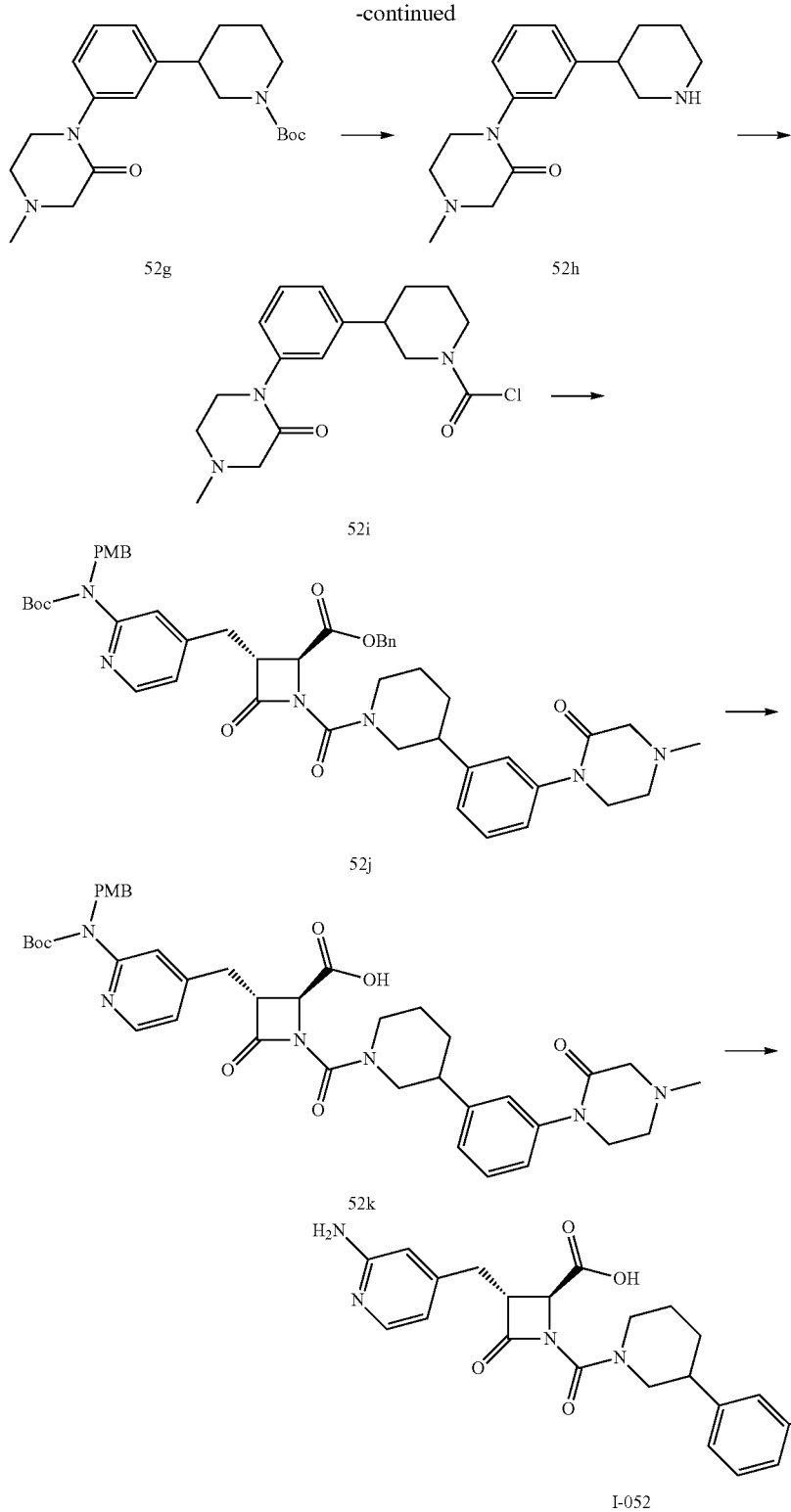

Compound 52a (1.5 g), compound 52b (1.57 g), Xantphos (681 mg) and cesium carbonate (7.7 g) were mixed in 20 mL of dioxane, and then Pd(OAc)$_2$ (264 mg) was added under the protection of nitrogen. The mixture was stirred at 90° C. in an oil bath for 4 hours. The reaction solution was concentrated under reduced pressure, purified by silica gel column chromatography (petroleum ether/ethyl acetate=1:1) to obtain 420 mg of yellow solid (compound 52c).

Compound 52c (660 mg) was dissolved in 20 mL of a solution of HCl in dioxane. The mixture was stirred at room temperature overnight and concentrated under reduced pressure. The resulting solid was dissolved in 10 mL of saturated aqueous sodium bicarbonate solution and then extracted with ethyl acetate (20 mL×5). The organic phase was dried over anhydrous sodium sulfate, filtered, and concentrated under reduced pressure to obtain 440 mg of yellow oil (compound 52d).

In a nice-water bath, 37 wt % aqueous formaldehyde solution (314 mg) was added to a solution of compound 52d (440 mg) in methanol (10 mL). After stirring for 30 minutes, sodium cyanoborohydride (198 mg) was added and the mixture was further stirred overnight. The reaction solution was purified by C18 reverse-phase column chromatography (5-95% acetonitrile/water) to obtain 343 mg of white solid (compound 52e).

Compound 52e (343 mg), compound 26b (520 mg) and potassium carbonate (423 mg) were dissolved in a mixed solvent of dioxane and water (22 mL, 10/1), and Pd (amphos)$_2$Cl$_2$ (217 mg) was added under the protection of nitrogen. The mixture was stirred at 100° C. in an oil bath for 3 hours. The reaction solution was concentrated under reduced pressure, and purified by silica gel column chromatography (dichloromethane/methanol=30:1) to obtain 600 mg of yellow oil (crude product), which was used directly in the next step.

Pd/C (200 mg, 10% wet) was added to a solution of compound 52f (600 mg, crude product) in methanol (20 mL). After the addition was completed, the mixed system was pumped and ventilated three times and charged with hydrogen, and then stirred at 25° C. under hydrogen atmosphere for 3 hours. LC MS showed a conversion rate of ~80%, and the reaction solution was further stirred at room temperature (15° C.) overnight, subjected to suction filtration, and then concentrated to obtain 603 mg of brown oil (crude product), which was directly used in the next step.

Compound 52g (603 mg, crude product) was dissolved in 20 mL of a solution of HCl in dioxane. After being stirred at room temperature for 3 hours, the mixture was concentrated under reduced pressure to obtain 620 mg crude product of white solid (crude product), which was directly used in the next step.

Compound 52h was azeotropically dried with toluene, and was reserved for use after removing all the water. Diisopropylethylamine (1.9 g) was added to a solution of compound 52h (620 mg, crude) in dichloromethane (10 mL), and after cooling down to 0° C., triphosgene (223 mg) was added in one portion. The reaction solution was stirred at room temperature overnight under the protection of nitrogen, and then washed once with saturated aqueous sodium bicarbonate solution (10 mL), dried over anhydrous sodium sulfate, and then directly used in the next step.

Diisopropylethylamine (194 mg), DMAP (92 mg) and intermediate A (400 mg) was added to the reaction solution obtained by the above post-treatment. After the addition was completed, the mixture was stirred at room temperature overnight under the protection of nitrogen. After the reaction was completed as detected by LC MS, 20 ml of water was to the reaction system, the organic phase was separated, and the aqueous phase was extracted with dichloromethane (30 mL). The organic phases were combined, dried over anhydrous sodium sulfate, filtered, and concentrated under reduced pressure. The resulting crude product was purified by C-18 reverse-phase column chromatography (10-95% acetonitrile/water) to obtain 450 mg of white solid (compound 52j).

Pd/C (80 mg, 10% wet) was added to a solution of compound 52j (230 mg) in ethyl acetate/methanol (3 mL/3 mL). After the addition was completed, the mixed system was pumped and ventilated three times and charged with hydrogen, and then stirred at room temperature for 1 hour under hydrogen atmosphere. After the reaction was completed, the reaction mixture was subjected to suction filtration and then concentrated to obtain 205 mg of white solid (compound 52k).

Compound 52k (205 mg) was added to a solution of TFA/DCM (6 mL/2 mL) and the mixture was stirred at 30° C. for 3 hours. After the reaction was completed as detected by LC MS, the reaction solution was concentrated at room temperature, and the residue was dissolved in 1 mL of DMF and purified by reverse-phase preparative HPLC to obtain 54.8 mg of white solid (compound I-052).

$^1$H NMR (400 MHz, DMSO-d$_6$) δ 7.79-7.76 (m, 1H), 7.34 (t, J=7.6 Hz, 1H), 7.25-7.24 (m, 1H), 7.18 (t, J=8.0 Hz, 2H), 6.42 (t, J=5.2 Hz, 1H), 6.34 (d, J=3.6 Hz, 1H), 5.97 (brs, 2H), 4.18 (d, J=2.8 Hz, 0.5H), 4.12 (d, J=2.8 Hz, 0.5H), 4.04-3.95 (m, 2H), 3.65-3.62 (m, 2H), 3.56-3.52 (m, 1H), 3.11 (d, J=4.8 Hz, 2H), 3.05-2.95 (m, 2H), 2.89-2.87 (m, 2H), 2.74-2.68 (m, 3H), 2.29 (d, J=2.8 Hz, 3H), 1.92-1.85 (m, 1H), 1.80-1.68 (m, 2H), 1.62-1.43 (m, 1H).

LCMS: Rt=3.064, [M+H]$^+$=521.1.

Example 53 Preparation of Compound I-053 Trifluoroacetate

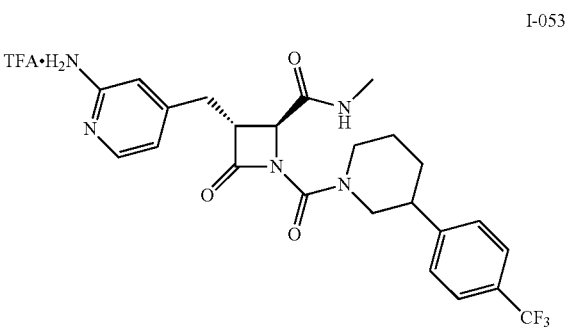

I-053

Compound I-053 trifluoroacetate was prepared according to the following scheme and method.

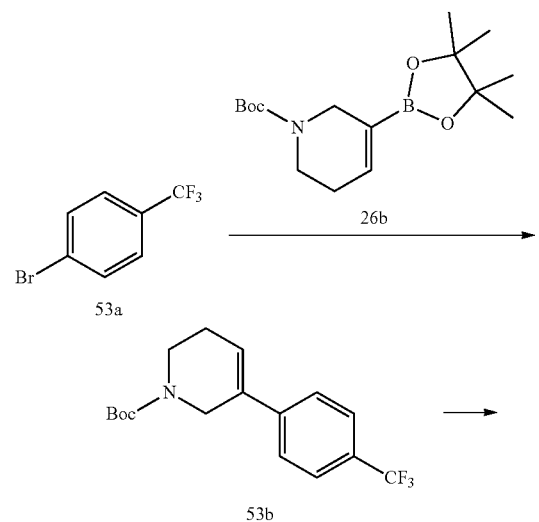

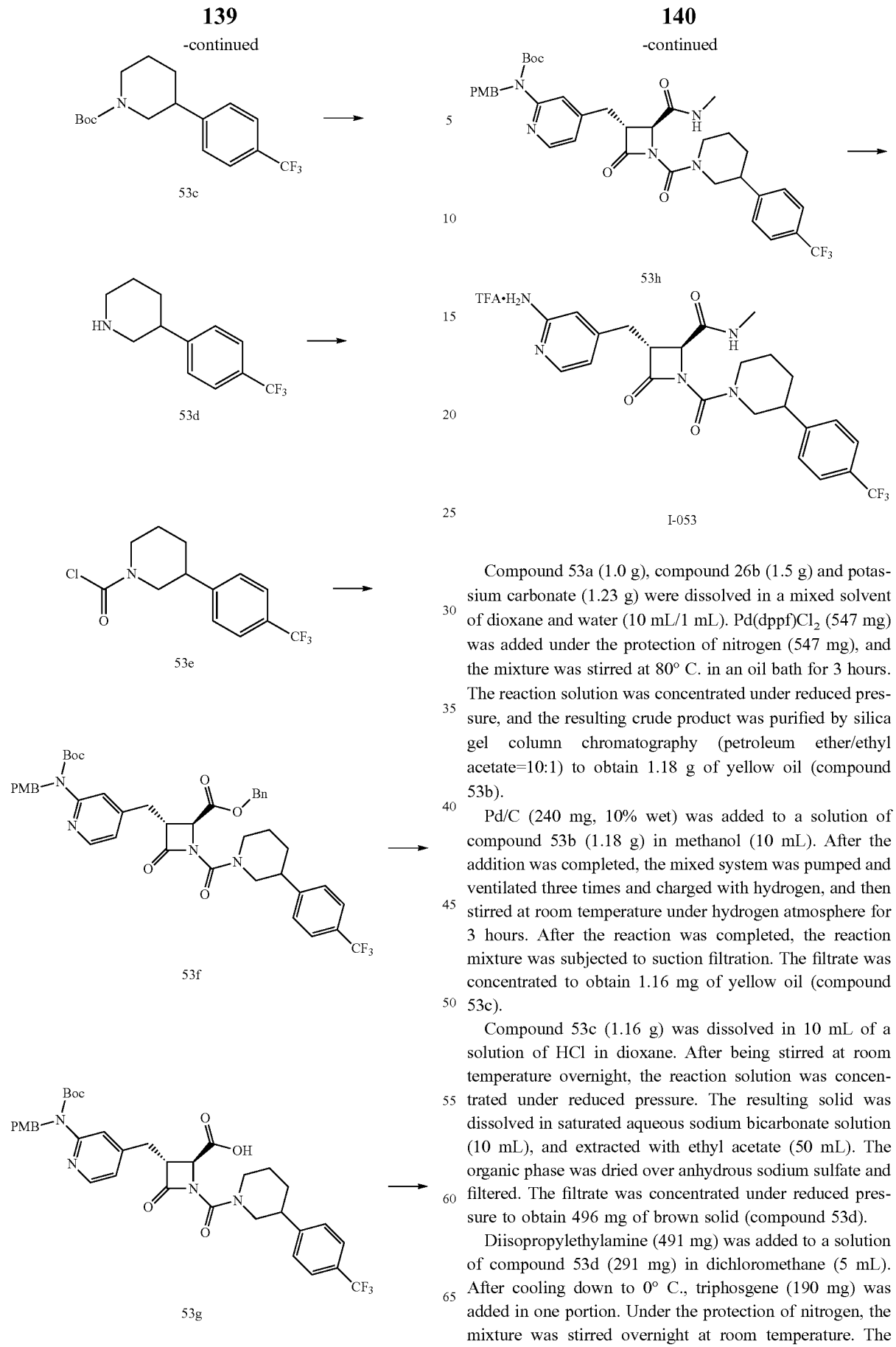

Compound 53a (1.0 g), compound 26b (1.5 g) and potassium carbonate (1.23 g) were dissolved in a mixed solvent of dioxane and water (10 mL/1 mL). Pd(dppf)Cl$_2$ (547 mg) was added under the protection of nitrogen (547 mg), and the mixture was stirred at 80° C. in an oil bath for 3 hours. The reaction solution was concentrated under reduced pressure, and the resulting crude product was purified by silica gel column chromatography (petroleum ether/ethyl acetate=10:1) to obtain 1.18 g of yellow oil (compound 53b).

Pd/C (240 mg, 10% wet) was added to a solution of compound 53b (1.18 g) in methanol (10 mL). After the addition was completed, the mixed system was pumped and ventilated three times and charged with hydrogen, and then stirred at room temperature under hydrogen atmosphere for 3 hours. After the reaction was completed, the reaction mixture was subjected to suction filtration. The filtrate was concentrated to obtain 1.16 mg of yellow oil (compound 53c).

Compound 53c (1.16 g) was dissolved in 10 mL of a solution of HCl in dioxane. After being stirred at room temperature overnight, the reaction solution was concentrated under reduced pressure. The resulting solid was dissolved in saturated aqueous sodium bicarbonate solution (10 mL), and extracted with ethyl acetate (50 mL). The organic phase was dried over anhydrous sodium sulfate and filtered. The filtrate was concentrated under reduced pressure to obtain 496 mg of brown solid (compound 53d).

Diisopropylethylamine (491 mg) was added to a solution of compound 53d (291 mg) in dichloromethane (5 mL). After cooling down to 0° C., triphosgene (190 mg) was added in one portion. Under the protection of nitrogen, the mixture was stirred overnight at room temperature. The reaction solution was washed with saturated aqueous sodium bicarbonate solution (10 mL), dried over anhydrous sodium sulfate, filtered, and concentrated to obtain 450 mg of yellow oil (compound 53e, crude product), which was directly used in the next step.

Compound 53e (450 mg, crude product) obtained from the above reaction was dissolved in dichloromethane (5 mL). Intermediate A (200 mg), diisopropylethylamine (147 mg) and DMAP (46 mg) were added successively. After the addition was completed, the mixture was stirred at room temperature under the protection of argon for 3 hours. The reaction was completed as detected by LC MS, and then was washed with saturated brine (10 mL). The organic phase was separated, dried over anhydrous sodium sulfate, and filtered. The filtrate was concentrated under reduced pressure, and the resulting crude product was purified by silica gel column chromatography (petroleum ether/ethyl acetate=2:1) to obtain 297 mg of white solid (compound 53f, crude product). The crude product was directly used in the next step.

Pd/C (104 mg, 10% wet) was added to a solution of compound 53f (297 mg, crude product) in ethyl acetate/methanol (3 mL/3 mL). After the addition was completed, the mixed system was pumped and ventilated three times and charged with hydrogen, and then stirred under hydrogen atmosphere for 1 hour. After the reaction was completed, the reaction mixture was subjected to suction filtration. The filtrate was concentrated to obtain 259 mg of white solid (compound 53g).

Under the protection of nitrogen, diisopropylethylamine (143 mg) and HATU (281 mg) were added to a solution of compound 53g (259 mg) in dichloromethane (5 mL). After stirring at 0° C. for 50 min, a solution (0.37 mL) of methylamine in tetrahydrofuran was added. The reaction solution was further stirred at 0° C. for 3 hours, and then was quenched with 5 mL of aqueous ammonium chloride solution and extracted with dichloromethane. The organic phases were combined, dried over anhydrous sodium sulfate, filtered and concentrated. The crude product was purified by silica gel column chromatography (petroleum ether/ethyl acetate=1/1) to obtain 216 mg of yellow oil (compound 53h).

Compound 53h (216 mg) was added to a solution of TFA/DCM (3 mL/1.5 mL), and the mixture was stirred at 30° C. for 3 hours. After the reaction was completed as detected by LC MS, the reaction solution was concentrated at room temperature. The crude product was purified by reverse-phase preparative HPLC to obtain 108.8 mg of white solid (compound I-053 trifluoroacetate).

$^1$H NMR (400 MHz, DMSO-$d_6$) δ 13.34 (brs, 1H), 8.26 (m, 0.5H), 8.21 (m, 0.5H), 7.97 (brs, 2H), 7.88-7.85 (m, 1H), 7.71-7.69 (m, 2H), 7.55-7.52 (m, 2H), 6.86-6.83 (m, 2H), 4.21 (d, J=3.2 Hz, 0.51), 4.19 (d, J=3.2 Hz, 0.5H), 4.07-4.01 (m, 2H), 3.54-3.49 (m, 1H), 3.14-3.11 (m, 2H), 3.08-2.85 (m, 2.5H), 2.81-2.71 (m, 0.5H), 2.62 (d, J=4.4 Hz, 1.5H), 2.59 (d, J=4.4 Hz, 1.5H), 1.96-1.93 (m, 1H), 1.91-1.75 (m, 2H), 1.66-1.58 (m, 0.5H), 1.54-1.44 (m, 0.5H).

LCMS: Rt=3.460 min, [M+H]$^+$=490.0.

Example 54-55 Preparation of Compound I-054 Trifluoroacetate and Compound I-055 Trifluoroacetate

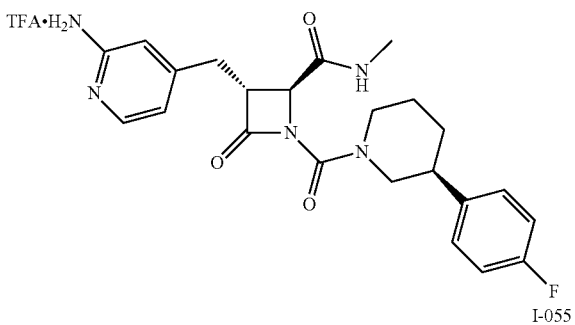

I-054

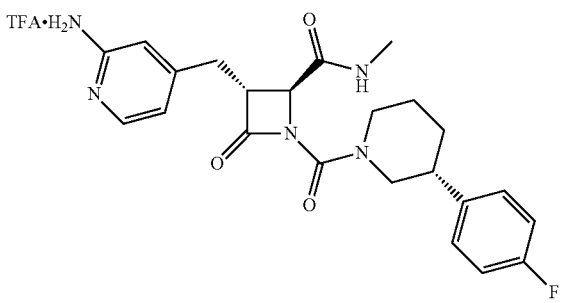

I-055

Compound I-054 trifluoroacetate and compound I-055 trifluoroacetate were prepared according to the following scheme and method.

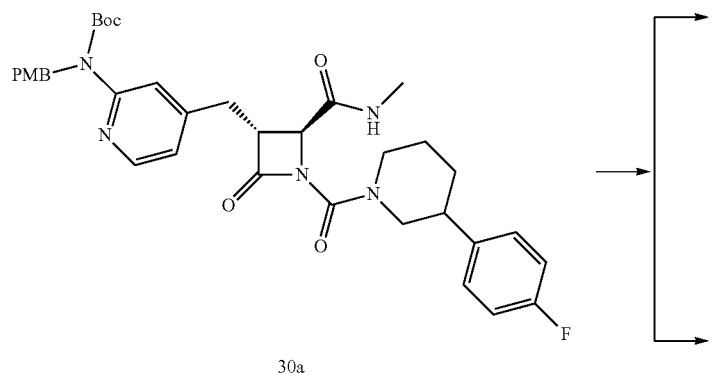

30a

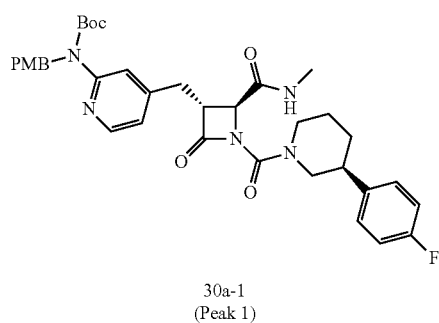

30a-1
(Peak 1)

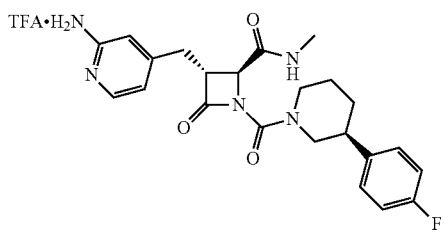

I-054

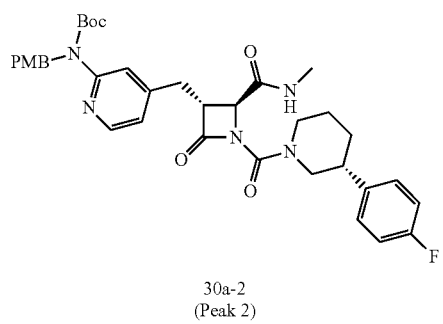

30a-2
(Peak 2)

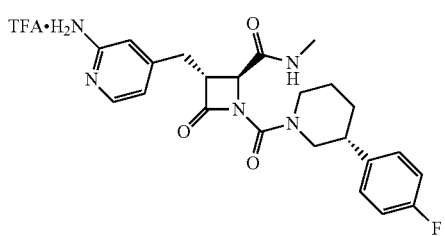

I-055

Compound 30a (277 mg, ~90% purity) was resolved by chiral SFC to obtain Peak 1: 80 mg (30a-1) and Peak 2: 60 mg (30a-2).

Compound 30a-1 (80 mg) was added to a solution of TFA/DCM (3 mL/1.5 mL), and the mixture was stirred at 30° C. for 3 hours. After the reaction was completed as detected by LC MS, the reaction solution was concentrated at room temperature. The crude product was purified by reverse-phase preparative HPLC to obtain 50.1 mg of white solid (trifluoroacetate salt of compound I-054).

$^1$H NMR (400 MHz, DMSO-d$_6$) δ 13.39 (brs, 1H), 8.21-8.20 (m, 1H), 7.98 (brs, 2H), 7.87 (d, J=6.8 Hz, 1H), 7.35-7.32 (m, 2H), 7.15 (m, 2H), 6.86-6.84 (m, 2H), 4.21 (d, J=3.2 Hz, H), 4.07-3.98 (m, 2H), 3.54-3.49 (m, 1H), 3.13 (d, J=8.0 Hz, 2H), 2.93-2.81 (m, 3H), 2.59 (d, J=4.8 Hz, 3H), 1.93-1.88 (m, 1H), 1.83-1.67 (m, 2H), 1.52-1.43 (m, 1H).

LCMS: Rt=3.113 min, [M+H]$^+$=440.1.

Compound 30a-2 (60 mg) was added to a solution of TFA/DCM (3 mL/1.5 mL), and the mixture was stirred at 30° C. for 3 hours. After the reaction was completed as detected by LC MS, the reaction solution was concentrated at room temperature. The crude product was purified by reverse-phase preparative HPLC to obtain 21.3 mg of white solid (trifluoroacetate salt of compound I-055).

$^1$H NMR (400 MHz, DMSO-d) δ 13.40 (brs, 1H), 8.27-8.25 (m, 1H), 7.96 (brs, 2H), 7.86 (d, J=6.4 Hz, 1H), 7.34-7.31 (m, 2H), 7.18-7.14 (m, 2H), 6.84-6.83 (m, 2H), 4.19 (d, J=3.2 Hz, 1H), 4.05-3.98 (m, 2H), 3.53-3.48 (m, 1H), 3.12 (d, J=8.0 Hz, 2H), 3.00-2.85 (m, 2H), 2.71-2.65 (m, 1H), 2.62 (d, J=4.8 Hz, 3H), 1.91-1.88 (m, 1H), 1.78-1.67 (m, 2H), 1.64-1.55 (m, 1H).

LCMS: Rt=3.062 min, [M+H]$^+$=440.1.

Pharmacological Evaluation

1. Determination of Activated Partial Thromboplastin Time (APTT)

Method:

1. Preparation of human plasma: human venous whole blood was collected and placed in 3.2% sodium citrate anticoagulation tube (human blood: sodium citrate=9:1 (V/V)). The tube was centrifuged at ~1560 g for 8 min, to obtain human plasma.

2. Preparation of the test sample: the test compound was dissolved in DMSO, and diluted in gradient to obtain 3000, 600, 120, 24, 4.8 μM stock solutions; each stock solution was mixed with the human plasma as prepared under item 1 at a ratio of 1:49 (V/V).

3. Negative control: DMSO solvent without the test compound was diluted in gradient to obtain 3000, 600, 120, 24, 4.8 μM stock solutions; each stock solution was mixed with the human plasma as prepared under item 1 at a ratio of 1:49 (V/V).

4. Test: After mixing the test solution of the above test sample and that of the negative control separately for 3 to 5 minutes, 30 μL of the test solution was added to the machine (MC-2000 coagulometer), and pre-warmed at 37° C. for 2 min; 30 μL of APTT reagent (MDC Hemostasis, Cat: 300025) was added and incubated at 37° C. for 5 min; and then 30 μL CaCl$_2$ was added to initiate the APTT measurement.

Calculation:

According to the measured APTT result, APTT ratio was calculated according to the following formula.

$$\text{APTT ratio}=(\text{APTT}_{test\ compound}/\text{APTT}_{negative\ control}).$$

Exponential equation was used to fit the Lg (concentration) to APTT ratio (Origin Pro 8.5.1 SR2), the drug working concentrations at 1.5 times APTT ratio and 2 times APTT ratio were calculated, namely EC$_{150}$ and EC$_{200}$. The results are shown in Table 1.

TABLE 1

| Example | EC$_{150}$ (μM) | EC$_{200}$ (μM) |
|---|---|---|
| 16 | 1.41 | 6.99 |
| 23 | 1.48 | 4.40 |
| 41 | 2.18 | 8.22 |

The APTT of other exemplary compounds of the invention was tested according to the same method as described above, and it was found that the $EC_{150}$ of other exemplary compounds of the invention or their salts were basically in the range of 1.41~30.0 μM, and the $EC_{200}$ were in the range of 4.4~60.00 μM. Other exemplary compounds of the invention show very good coagulation activity.

II. Enzyme Activity Assay In Vitro

Method: the test compound was dissolved in 10 mM mother liquor with DMSO, and stored at −80° C. until use. The frozen mother liquor was diluted with DMSO to 2 mM as the initial reaction concentration, and then diluted with DMSO in 4-fold gradient to 9 concentrations as the working solution, 1 μl/well; the preparation of 2× buffer: 200 mM tris-HCl, 400 mM NaCl, 0.04% TWEEN20, pH 7.4; 2 human FXIa protein (hFXIa), the reaction solution was prepared by diluting the FXIa protein (Cat #ab62411) with 2× buffer to the required concentration of the reaction 0.25 ng/μl, 10 μl/well; 2×S-2366 reaction solution was prepared by diluting the S-2366 reaction solution with deionized water to 2 mM, 10 μl/well; the enzyme reaction solution was first added to the 384-well plate, and then the diluted test compound reaction solution was added to the corresponding wells in sequence; the negative control was DMSO solvent; the blank was buffer solution: the plate was centrifuged at 1000 rpm for 1 min at room temperature, and after 30 min of reaction in the dark, S-2366 reaction solution was added to each well; after being shaked and mixed for 30 s, the wells were allowed to react at 37° C. for 20 min; then, the absorbance at $OD_{405nm}$ was measured and analyzed by prism curve, and the $IC_{50}$ values were calculated.

The results are shown in Table 2.

TABLE 2

| Example | $IC_{50}$ (nM) |
|---|---|
| 13 | 23.21 |
| 16 | 1.89 |
| 18 | 10.71 |
| 19 | 5.99 |
| 20 | 10.81 |
| 23 | 1.5 |
| 24 | 3.6 |
| 25 | 3.2 |
| 26 | 11.1 |
| 28 | 23.14 |
| 30 | 2.4 |
| 31 | 2.8 |
| 32 | 4.1 |
| 33 | 3.5 |
| 41 | 4.1 |
| 42 | 9.1 |
| 44 | 3.8 |
| 45 | 5.3 |
| 46 | 7.7 |
| 51 | 3.3 |
| 55 | 1.7 |

The enzyme activity of other exemplary compounds of the invention was tested according to the same method as described above, and as a result, it was found that the $IC_{50}$ values of other exemplary compounds of the invention or salts thereof were basically in the range of 1.5 to 50.00 nM, exhibiting excellent enzyme activity.

The embodiments of the invention have been described above. However, the invention is not limited to the above-mentioned embodiments. Any modification, equivalent replacement, improvement, etc. made within the spirit and principle of the invention should be included within the scope of protection of the invention.

What is claimed is:

1. A compound of formula (I), a solvate, mixtures thereof, and pharmaceutically acceptable salts thereof,

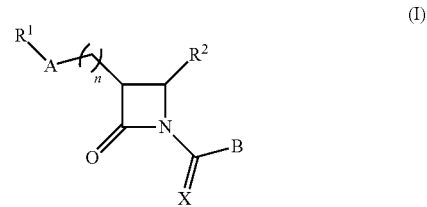

wherein, $R^1$ is selected from halogen, $C_{1-10}$ alkyl, —$(CH_2)_tNR^6R^7$, —$COR^{5a}$, —$COOR^{5b}$, —$C(O)_m(CH_2)_tNR^6R^7$, —$(CH_2)_tNHC(O)_mC_{1-10}$ alkyl, —NHC$(O)_m(CH_2)_nC(O)_mC_{1-6}$ alkyl, —$S(O)_m(CH_2)_tNR^6R^7$, —$NH(CH_2)_tS(O)_mR^{5a}$, —$NH(CH_2)_tS(O)_m$—$OR^{5b}$, —$OR^{5b}$, —$SR^{5b}$, —$(CH_2)_tCN$, and —$O(CH_2)_nNR^6R^7$;

$R^2$ is selected from the group consisting of hydrogen, halogen, hydroxyl, $C_{1-10}$ alkyl, $C_{1-10}$ alkoxy, —$(CH_2)_tX(CH_2)_nNR^6R^7$, —$(CH_2)_tCN$, —$(CH_2)_tCOR^{5a}$, —$(CH_2)_tCOOR^{5b}$, —$(CH_2)_tNR^6R^7$, —$C(O)_m(CH_2)_tNR^6R^7$, —$CONHS(O)_mR^{5a}$, and —$CONHS(O)_m$—$OR^{5b}$;

X is O or S;

A is heteroaryl;

B is selected from benzopyrrolidinyl, benzopiperidinyl, benzopiperazinyl, and triazolopiperazinyl, and the fused bicyclic group in B is optionally further substituted with 1 to 3 $R^{4b}$;

$R^{4b}$ is the same or different and are independently selected from hydrogen, oxo, halogen, —$(CH_2)_tCN$, $C_{1-10}$ alkyl, $C_{1-10}$ alkoxy, halogenated $C_{1-10}$ alkyl, halogenated $C_{1-10}$ alkoxy, $C_{3-10}$ cycloalkyl, $C_{3-10}$ cycloalkyloxy, aryl, amino, nitro, —$(CH_2)_tNR^6R^7$, —$(CH_2)_tNHC(O)_mC_{1-10}$ alkyl, —$(CH_2)_tCONR^6R^7$, —$(CH_2)_tCOR^{5a}$, —$(CH_2)_tCOOR^{5b}$, —$SR^{5b}$, and —$OR^{5b}$; and $R^{4b}$ is optionally substituted with one or more of the following groups: hydrogen, =O, halogen, $C_{1-10}$ alkyl, $C_{1-10}$ alkoxy, and aryl;

in the above groups, each $R^{5a}$ is the same or different and is independently selected from hydrogen, halogen, $C_{1-10}$ alkyl, halogenated $C_{1-10}$ alkyl, and aryl;

in the above groups, $R^{5b}$, $R^6$, and $R^7$ are the same or different and are independently selected from hydrogen, $C_{1-10}$ alkyl, halogenated $C_{1-10}$ alkyl, $C_{3-10}$ cycloalkyl, heterocyclyl, aryl, and heteroaryl;

in the above groups, each n is the same or different and is independently selected from integers from 1 to 10;

in the above groups, each m is the same or different and is independently 1 or 2; and in the above groups, each t is the same or different and is independently selected from integers from 0 to 10.

2. The compound of claim 1, wherein $R^1$ is selected from halogen, $C_{1-10}$ alkyl, $C_{1-10}$ alkoxy, —$(CH_2)_tNR^6R^7$, —$COR^{5a}$, —$COOR^{5b}$, —$C(O)(CH_2)_tNR^6R^7$, —$(CH_2)_tNHC(O)_mC_{1-10}$ alkyl, —$NHC(O)_m(CH_2)_nC(O)_mC_{1-6}$ alkyl, —$S(O)_m(CH_2)_tNR^6R^7$, —$NH(CH_2)_tS(O)_mR^{5a}$, —$SR^{5b}$, —$(CH_2)_tCN$, and —$O(CH_2)_nNR^6R^7$.

3. The compound of claim 1, wherein the compound has the following structure:

4. A compound selected from

5. A preparation method of the compound of formula (I) of claim 1, comprising the following steps:

-continued

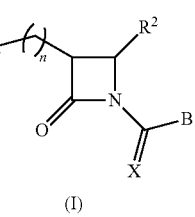

(I)

1) reacting compound (e) with triphosgene or sulfur dichloride under alkaline condition to obtain compound (f); and
2) reacting compound (f) with compound ($A_0$) under alkaline condition to obtain compound (I).

6. A pharmaceutical composition, comprising at least one selected from the compound of formula (I), the solvate, mixtures thereof, and pharmaceutically acceptable salts thereof of claim 1, and an optional pharmaceutically acceptable carrier and/or excipient.

7. A pharmaceutical preparation, comprising the pharmaceutical composition of claim 6, wherein the pharmaceutical preparation includes tablet, pill, granule, capsule, injection, suspension, drop, extract, ointment, patch, emulsion, film, suppository, paste, gel, or spray.

8. A combined preparation, comprising combining the pharmaceutical composition of claim 6 with at least one of other anticoagulant drugs, antithrombotic drugs or antivenous thromboembolic drugs; wherein the anticoagulant drugs, antithrombotic drugs or antivenous thromboembolic drugs are selected from heparin, low molecular weight heparin LMWH, enoxaparin, warfarin, rivaroxaban, apixaban, edoxaban, betrixaban, omisaraban, aspirin, ticlopidine, clopidogrel, tirofiban, coumarin, urokinase, and platelet protein IIb/IIIa receptor antagonist.

9. A method of treating disorders related to thrombosis or thromboembolism, comprising administering an effective amount of the pharmaceutical composition of claim 6 to a subject in need thereof, wherein the disorders related to thrombosis or thromboembolism are selected from arterial cardiovascular thromboembolic disorders, venous cardiovascular thromboembolic disorders, thromboembolic disorders in the cardiac chamber or peripheral circulation, unstable angina, acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, renal embolism, pulmonary embolism, and thrombosis due to medical implants, devices, or processes in which blood is exposed to artificial surfaces that promote thrombosis.

10. The compound of claim 1, wherein B is

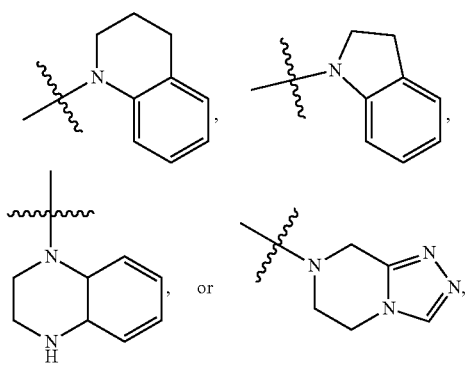

and is optionally substituted with 1 to 3 $R^{4b}$.

11. The compound of claim 1, wherein A is heteroaryl.

12. The compound of claim 1, wherein $R^2$ is selected from —(CH$_2$)$_t$X(CH$_2$)$_n$NR$^6$R$^7$, —(CH$_2$)$_t$CN, —(CH$_2$)$_t$NR$^6$R$^7$, —(CH$_2$)$_t$COR$^{5a}$, —(CH$_2$)$_t$COOR$^{5b}$, —C(O)$_m$(CH$_2$)$_t$NR$^6$R$^7$, and —CONHS(O)$_m$R$^{5a}$.

13. The compound of claim 1, wherein each $R^{5a}$ is the same or different and is independently selected from hydrogen, halogen, $C_{1-4}$ alkyl, halogenated $C_{1-4}$ alkyl, and aryl.

14. The compound of claim 1, wherein $R^{5b}$, $R^6$, and $R^7$ are the same or different and are independently selected from hydrogen, $C_{1-4}$ alkyl, halogenated $C_{1-4}$ alkyl, and aryl.

* * * * *